United States Patent
Kobayashi et al.

(10) Patent No.: US 8,481,725 B2
(45) Date of Patent: *Jul. 9, 2013

(54) CYCLOALKYLCARBONYLAMINO ACID DERIVATIVE AND PROCESS FOR PRODUCING THE SAME

(75) Inventors: Nobuo Kobayashi, Higashiyamato (JP); Tsuneo Koji, Higashiyamato (JP); Hisatomo Kunii, Higashiyamato (JP)

(73) Assignee: Seikagaku Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/087,688

(22) PCT Filed: Jan. 10, 2007

(86) PCT No.: PCT/JP2007/050153
§ 371 (c)(1), (2), (4) Date: Jul. 10, 2008

(87) PCT Pub. No.: WO2007/080883
PCT Pub. Date: Jul. 19, 2007

(65) Prior Publication Data
US 2009/0111983 A1 Apr. 30, 2009

(30) Foreign Application Priority Data

Jan. 11, 2006 (JP) .................. 2006-003593
Dec. 20, 2006 (JP) .................. 2006-343594

(51) Int. Cl.
*C07C 229/48* (2006.01)
*C07D 307/77* (2006.01)
*C07D 213/81* (2006.01)
*C07D 241/04* (2006.01)
*C07D 413/14* (2006.01)

(52) U.S. Cl.
USPC .............. 544/129; 544/388; 546/323; 560/43

(58) Field of Classification Search
None
See application file for complete search history.

(56) References Cited

U.S. PATENT DOCUMENTS

| | | | |
|---|---|---|---|
| 5,837,807 A | 11/1998 | Abrecht et al. | |
| 6,117,870 A | 9/2000 | Hosoda et al. | |
| 6,162,828 A | 12/2000 | Fukuda et al. | |
| 2005/0192279 A1* | 9/2005 | Barbay et al. | 514/247 |
| 2005/0197299 A1* | 9/2005 | Babine et al. | 514/18 |
| 2009/0137799 A1* | 5/2009 | Kobayashi et al. | 544/130 |
| 2009/0156805 A1 | 6/2009 | Kobayashi et al. | |

FOREIGN PATENT DOCUMENTS

| | | |
|---|---|---|
| EP | 0 393 457 | 10/1990 |
| JP | 59-89671 | 5/1984 |
| JP | 2-256654 | 10/1990 |
| JP | 2-268145 | 11/1990 |
| JP | 4-202170 | 7/1992 |
| JP | 9-165360 | 6/1997 |
| JP | 2000-204071 | 7/2000 |
| JP | 2001-139534 | 5/2001 |
| JP | 2002-513029 | 5/2002 |
| JP | 2002-513032 | 5/2002 |
| JP | 2004-517047 | 6/2004 |
| JP | 2005-504099 | 2/2005 |
| JP | 2005-520171 | 7/2005 |
| WO | WO-97/16177 | 5/1997 |
| WO | WO-98/01133 | 1/1998 |
| WO | WO-0037429 | 6/2000 |
| WO | WO 0037429 A2 * | 6/2000 |
| WO | WO 0218369 A2 * | 3/2002 |

OTHER PUBLICATIONS

STN preliminary 12087688 01272010.*
Christensen et al., QSAR & Combinatorial Science (2003), 22(7), p. 754-766 (Abstract from STN search report).*
Babu et al., Indian Journal of Chemistry, Section B: Organic Chemistry Including Medicinal Chemistry (2005), 44B(11), p. 2328, from STN search report.*
Apr. 25, 2003 "Peptide backbone folding induced by the C-alpha-tetrasubstituted cyclic alpha-amino acids 4-amino-1,2-dithiolane-4-carboxylic acid (Adt) and 1-aminocyclopentane-1-carboxylic acid (Ac₅c). A joint computational and experimental study", Massimiliano Aschi et al., Organic and Biomolecular Chemistry, vol. 1, No. 11, pp. 1980-1988.
1961 "Synthèses de courts peptides renfermant des acides amino-1 cycloalkyl carboxyliques", Tailleur, Patrice and Louis Berlinguet, Canadian Journal of Chemistry, vol. 39, pp. 1309-1320.
Jan. 1, 2001 "Synthesis and Biological Activity of Novel Potent Endothelin-Converting Enzyme-1 Inhibitors", Firooznia et al., Bioorganic & Medicinal Chemistry Letters, vol. 11, No. 3 pp. 375-378.
Christine E. Garrett, et al., "New observation on peptide bond formation using CDMT", Tetrahedron Letters, 2002, vol. 43, No. 23, pp. 4161-4165, Scheme 2.
Tetsuya Inaoka, et al., "Molecular Cloning of Human cDNA for Cathespin K: Novel Cysteine Proteinase Predominantly Expressed in Bone", Biochemical and Biophysical Research Communications, vol. 2006, No. 1, Jan. 5, 1995, pp. 89-96.

(Continued)

*Primary Examiner* — Yong Chu
(74) *Attorney, Agent, or Firm* — Jordan and Hamburg LLP

(57) ABSTRACT

Cycloalkylcarbonylamino acid derivatives, which are raw material intermediates of a novel cycloalkane carboxamide derivative that selectively inhibits cathepsin K, and a production process thereof, are provided.

A cycloalkylcarbonylamino acid derivative represented by the following general formula (I), or a pharmaceutically acceptable salt thereof:

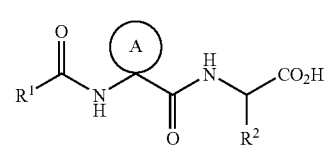

(I)

(wherein, $R^1$ and $R^2$ represent alkyl groups, alkenyl groups, alkynyl groups, aromatic hydrocarbon groups, heterocyclic groups or the like, and ring A represents a cyclic alkylidene group having 5, 6 or 7 carbon atoms).

11 Claims, No Drawings

OTHER PUBLICATIONS

Fred H. Drake, et al., "Cathespin K, but Not Cathespins B, L, or S, Is Abundantly Expressed in Human Osteoclasts", The Journal of Biological Chemistry, vol. 271, No. 21, May 24, 1996, pp. 12511-12516.

Bruce D. Gelb, et al., "Pycnodysostosis, a Lysosomal Disease Caused by Cathespin K Deficiency", Science, vol. 273, Aug. 30, 1996, pp. 1236-1238.

Dieter Broemme, et al., "Human Cathespin O2, a Matrix Protein-degrading Cysteine Protease Expressed in Osteoclasts, Functional Expression of Human Cathespin O2 in *Spodoptera frugiperda* and Characterization of the Enzyme", The Journal of Biological Chemistry, vol. 271, No. 4, Jan. 26, 1996, pp. 2126-2132.

Kazuhiko Aibe, et al., "Substrate Specificity of Recombinant Osteoclast-Specific Cathespin K from Rabbits", Biol. Pharm. Bull., vol. 19, No. 8, 1996, pp. 1026-1031.

Mary E. McGrath, et al., "Crystal structure of human cathespin K complexed with a potent inhibitor, the high resolution structure of the new therapeutic target, cathespin K. complexed with the ptent mechanism-based inhibitor, APC 3328, reveals the substrate-binding sites of this cysteine proteinase and validates the binding mode for this inhibitor class", Nature Structural Biology, vol. 4, No. 2, Feb. 1997, pp. 105-109.

James T. Palmer, et al., "Vinyl Sulfones as Mechanism-Based Cysteine Protease Inhibitors", J. Med. Chem., vol. 38, 1995, pp. 3193-3196.

Dieter Broemme, et al., "Peptide Methyl Ketones as Reversible Inhibitors of Cysteine Proteinases", J. Enzyme Inhibition, 1989, vol. 3, pp. 13-21.

Toshimasa Tsujinaka, et al., "Synthesis of a New Cell Penetrating Calpain Inhibitor (Calpeptin)", Biochemical and Biophysical Research Communications, vol. 153, No. 3, Jun. 30, 1988, pp. 1201-1208.

Seiichi Hashida, et al., "Inhibitions by E-64 Derivatives of Rat Liver Cathespin B and Cathespin L In Vitro and In Vivo", J. Biochem, vol. 88, No. 6, 1980, pp. 1805-1811.

Scott K. Thompson, et al., "Design of potent and selective human cathespin K inhibitors that span the active site", Proc. Natl. Acad. Sci. USA, vol. 94, Dec. 1997, pp. 14249-14254.

Baoguang Zhao, et al., "Crystal structure of human osteoclast cathespin K complex with E-64, The structure of human cathespin K, a potential target for treatment of osteoporosis, reveals active site differences with homologous cysteine proteinases that should enable the design of cathespin K selective inhibitors", Nature Structural Biology, vol. 4, No. 2, Feb. 1997, pp. 109-111.

Renee L. Desjarlais, et al., "Use of X-ray Co-crystal Structures and Molecular Modeling to Design Potent and Selective Non-peptide Inhibitors of Cathespin K", J. Am. Chem. Soc., vol. 120, 1998, vol. 120, pp. 9114-9115.

Robert W. Marquis, et al., "Conformationally Constrained 1,3-Diamino Ketones: A Series of Potent Inhibitors of the Cysteine Protease Cathespin K", J. Med. Chem. vol. 41, 1998, pp. 3563-3567.

David H. Sun, et al., "P4 cap modified tetrapeptidyl α-ketoamides as potent HCB NS3 protease inhibitors", Bioorganic & Medical Chemistry Letters 14, (2004), pp. 4333-4338.

David G. Barrett, et al., "Potent and selective $P^2$-$P^3$ ketoamide inhibitors of cathespin K with good pharmacokinetic properties via favorable $P^1$, $P^{1'}$, and/or $P^3$ substitutions", Bioorganic & Medicinal Chemistry Letters 14, (2004), pp. 4897-4902.

Min Yang, et al., "Impact of methanol and acetonitrile on separations based on π-π interactions with a reserved-phase phenyl column", Journal of Chromatography A, vol. 1097, 2005, pp. 124-129.

Christine E. Garrett et al., "New observations on peptide bond formation using CDMT", Tetrahedron Letters, vol. 43, 2002, pp. 4161-4165.

Fariborz Firooznia, et al., "Synthesis and Biological Activity of Potent Heterocyclic Thiol-Based Inhibitors of Endothelin-Converting Enzyme-1", Bioorganic & Medicinal Chemistry Letters, vol. 12, 2002, pp. 3059-3062.

"Design and Synthesis of 1-Aminocycloalkane-l-carboxylic Acid-Substituted Deltorphin Analogues: Unique δ and μ Opioid Activity in Modified Peptides"; Angela Breveglieri, et al.; Journal of Medicinal Chemistry (1996) vol. 39, pp. 773-780.

"New α-Thiol Dipeptide Dual Inhibitors of Angiotensin-I Converting Enzyme and Neutral Endopeptidase EC 3.4.24.11"; Cynthia A. Fink, et al.; Journal of Medicinal Chemistry (1995) vol. 38, pp. 5023-5030.

"Utilization of a β-Aminophosphotyrosyl Mimetic in the Design and Synthesis of Macrocyclic Grb2 SH2 Domain-Binding Peptides"; Keyong Lee, et al.; Journal of Medicinal Chemistry (2003) vol. 46, pp. 2621-2630.

"Synthesis Approach to Peptides derived from α-Alkyl-serines involving Conversion of C-Terminal Amino-Acids", CODEN:SYNTBF ISSN: 0039-7881; J. Kaminski, et al.; Synthesis (1975) vol. 9, pp. 593-596.

"Solid Phase Combinatorial Library of 1,3-Azole Containing Peptides for the Discovery of Matrix Metallo Proteinase Inhibitors"; Caspar Christensen, et al.; QSAR & Combinatorial Science (2003) vol. 22(7), pp. 754-766.

"Conformational Behaviour of a Cyclolinopeptide A Analogue: Two-dimensional NMR study of cyclo($Pro^1$-Pro-Phe-Phe-$Ac_6c$-Ile-ala-$Val^8$)"; Marco Mazzeo, et al.; Journal of Peptide Science (1995) vol. 1(5), pp. 330-340.

"Proctolin and its Analogues, Structure/Biological Function Relationship Studies"; D. Konopińska, et al.; Polish Journal of Chemistry (1994) vol. 68(7), pp. 1437-1439.

"New Proctolin Analogues Modified in Position 4 of the Peptide Chain and Their Influence on the Heart-Beat Frequency of Insects"; Danuta Konopińska, et al.; Bulletin of the Polish Academy of Sciences, Chemistry (1994), Volume Date 1993 vol. 41(1), pp. 27-39.

"Subtle Differences between Human and Rabbit Neutrophil Receptors Shown by the Secretagogue Activity of Constrained Formyl Peptides"; Andrew R. Dentino, et al.; Archives of Biochemistry and Biophysics (1997) vol. 337(2), pp. 267-274.

"A computergraphic Determination of the Chemotactic Peptide Preferred Conformation"; S.F. Semus, et al.; Biochemical and Biophysical Research Communications (1988) vol. 157(2), pp. 569-574.

"Conformation-Biological Activity Relationships of Conformationally Constrained Delta Specific Cyclic Enkephalins"; Victor J. Hruby, et al.; Pept.: Struct. Funct., Proc. Am. Pept. Symp., (1985) vol. 9, pp. 487-490.

"Synthesis and CCK-B Binding Affinities of Cyclic Analogues of the Potent and Selective CCK-B Receptor Antagonist CI-988"; Eric Didier, et al.; Tetrahedron (1992) vol. 48(39), pp. 8471-8490.

Bratkovic, et al. "Affinity selection to papain yields potent peptide inhibitors of cathepsins L, B, H, and K." Biochem Biophys Res Communi. U.S. National Library of Medicine National Institutes of Health. Jul. 8, 2005. Abstract Only.

Aug. 2, 1996 "Mercaptoacyl Dipeptides as Orally Active Dual Inhibitors of Angiotensin-Converting Enzyme and Neutral Endopeptidase" Cynthia A. Fink et al. Journal of Medicinal Chemistry vol. 39, No. 16 pp. 3158-3168.

Oct. 10, 1997 "Conformational restriction through $C^{\alpha}_i \leftrightarrows C^{\alpha}_j$ cyclization: 1-aminocycloheptane-l-carboxylic acid ($Ac_7c$)" Ettore Benedetti et al. Journal of the Chemical Society: Perkin Transactions 2 vol. 1997, No. 10 pp. 2023-2032.

Aug. 1, 1971 "Peptides with Terminal Tyrosyl and Phenylalanyl Groups" Joseph A Skorcz Journal of Medicinal Chemistry vol. 14, No. 8 pp. 775-776.

H. Lynn, et al. "Angiotensin converting enzyme inhibitor use is associated with higher bone mineral density in elderly Chinese." Bone. 2006. pp. 584-588.

* cited by examiner

CYCLOALKYLCARBONYLAMINO ACID DERIVATIVE AND PROCESS FOR PRODUCING THE SAME

TECHNICAL FIELD

The present invention relates to a novel cycloalkylcarbonylamino acid derivative, a salt thereof, and to a process for producing the same. More particularly, the present invention relates to a novel cycloalkylcarbonylamino acid derivative, useful as a raw material intermediate for producing a cycloalkane carboxamide derivative having an action that selectively inhibits cathepsin K, an important cysteine protease involved especially in bone resorption, and a pharmaceutically acceptable salt thereof, and a process for producing the same.

BACKGROUND ART

Accompanying the rapid progression to an elderly society in recent years, the number of patients with geriatric diseases, and particularly those with bone diseases, is continuing to increase. In particular, osteoporosis, which is prevalent among women and especially postmenopausal women, is becoming a serious problem. Since accelerated bone resorption brought about by hormonal imbalance and aging phenomena in postmenopausal women is intimately related to the onset and progression of bone disease, bone resorption inhibitors have been used during the course of ordinary drug therapy for osteoporosis. However, drugs currently in use that demonstrate bone resorption inhibitory action, such as calcitonin preparations, estrogen preparations, vitamin K preparations and bisphosphonate preparations, have problems in terms of their therapeutic effects, rapid-acting, adverse side effects and patient compliance, thus desiring the development of a bone resorption inhibitor capable of being used as a more effective drug for the treatment or prevention of osteoporosis.

In the living body, bone calcium concentrations and blood calcium concentrations are in a state of equilibrium, and calcium is constantly migrating between the bone and blood. This migration of calcium between bone and blood is governed by dynamic shifts between bone formation and bone resorption. In the process of bone resorption, bone resorption is known to be accelerated as a result of activated osteoclasts eluting bone inorganic substances such as calcium simultaneous to cysteine proteases secreted from osteoclasts decomposing bone organic substances such as collagen. Cysteine proteases such as cathepsin B, cathepsin H, cathepsin L and cathepsin S are present in osteoclast lysosomes, and osteoclast-localized human cathepsin K was isolated in 1995, which was demonstrated to be expressed in osteoclasts in larger amounts than other cathepsins (Biochem. Biophys. Res. Commun., 206, 89 (1995); J. Biol. Chem., 271, 12511 (1996)). Moreover, the cathepsin K gene was demonstrated to mutate in patients with dwarfism presenting with bone resorption abnormalities (Science, 273, 1236 (1997)).

In this manner, attention has been focused on cathepsin K as the main cysteine protease involved in bone resorption, and considerable expectations are being placed on cathepsin K inhibitors as inhibitors of bone resorption. Previously reported examples of compounds having cathepsin K inhibitory action include aldehyde derivatives, epoxy succinic acid derivatives (J. Biol. Chem., 271, p. 2126 (1996); Biol. Pharm. Bull., 19, p. 1026 (1996)) and vinylsulfonic acid derivatives (Nature Structural Biology, 4, p. 105 (1997); J. Med. Chem., 38, p. 3139 (1995)), and these derivatives have low selectivity and are known to strongly inhibit other cysteine proteases in addition to cathepsin K (J. Enzyme Inhibition, 3, p. 13 (1989); Biochem. Biophys. Res. Commun., 153, p. 1201 (1988); J. Biochem., 87, p. 39 (1980); J. Biochem., 88, p. 1805 (1980)).

Moreover, accompanying the growing interest in cathepsin K as described above, research has also been actively conducted in the area of X-ray crystal analyses of cathepsin K and inhibitors (Nature Structural Biology, 4, p. 105 (1997); Nature Structural Biology, 4, p. 109 (1997)), and compounds are known that have a selective inhibitory action on cathepsin K (Proc. Natl. Acad. Sci. USA, 94, 142, p. 49 (1997); WO9801133; J. Am. Chem. Soc., 120, 9, p. 114 (1998); J. Med. Chem., 41, p. 3563 (1988); Japanese Unexamined Patent Publication No. 2000-204071; Bioorg. Med. Chem., 14, p. 4333 (2004); Bioorg. Med. Chem., 14, p. 4897 (2004)). In addition, WO971677 identifies the catalyst active site of cathepsin K and discloses a method for inhibiting cathepsin K using a compound that interacts with this active site.

Moreover, although not containing descriptions of inhibition of cathepsin K, Japanese Unexamined Patent Publication Nos. H2-256654 and H2-268145 disclose various types of protease inhibitors as aldehyde derivatives.

[Non-Patent Document 1] Proc. Natl. Acad. Sci. USA, 94, 142, 49 (1997).
[Non-Patent Document 2] J. Am. Chem. Soc., 120, 9, 114 (1998)
[Non-Patent Document 3] J. Med. Chem., 41, 3563 (1998)
[Non-Patent Document 4] Bioorg. Med. Chem., 14, 4333 (2004)
[Non-Patent Document 5] Bioorg. Med. Chem., 14, 4897 (2004)
[Patent Document 1] WO9801133
[Patent Document 2] WO971677
[Patent Document 3] Japanese Unexamined Patent Publication No. 2000-204071
[Patent Document 4] Japanese Unexamined Patent Publication No. H2-256654
[Patent Document 5] Japanese Unexamined Patent Publication No. H2-268145

DISCLOSURE OF THE INVENTION

Problems to be Solved by the Invention

As has been described above, compounds that inhibit cathepsin K have attracted attention as bone resorption inhibitors, and although numerous derivatives have been reported, none has yet been able to be used practically as a therapeutic drug for metabolic bone diseases. As a result of conducting extensive studies on novel compounds having potent and selective cathepsin K inhibitory action, the inventors of the present invention found that novel cycloalkylcarbonylamino aldehyde derivatives represented by a specific structural formula indicated by formula (XII) to be described later selectively inhibit cathepsin K as compared with conventional aldehyde derivatives known to be protease inhibitors. An object of the present invention is to provide a novel cycloalkylcarbonylamino acid derivative, which is a useful raw material compound for producing said cycloalkylcarbonylamino aldehyde derivatives, and a process for producing the same.

Means for Solving the Problems

The present invention relates to a novel cycloalkylcarbonyl-amino acid derivative represented by formula (I) having a non-naturally-occurring amino acid structure, which is a raw material compound for producing cycloalkylcarbonylamino aldehyde derivatives represented by formula (XII) to be described later having selective inhibitory activity against cathepsin K, and to a process for producing the same, and the gist thereof lies in the cycloalkylcarbonylamino acid derivatives described in 1 to 11 below, pharmaceutically acceptable salts thereof, and a process for producing the same.

1. A cycloalkylcarbonylamino acid derivative represented by formula (I) or a pharmaceutically acceptable salt thereof:

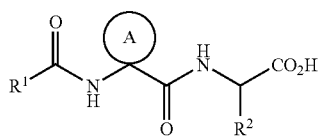
(I)

[wherein, $R^1$ represents a substituted or unsubstituted alkyl group, substituted or unsubstituted alkenyl group, substituted or unsubstituted alkynyl group, substituted or unsubstituted aromatic hydrocarbon group, substituted or unsubstituted heterocyclic group, group represented by $R^4O$—, group represented by $R^5S$— (wherein $R^4$ and $R^5$ respectively and independently represent a substituted or unsubstituted alkyl group, substituted or unsubstituted alkenyl group, substituted or unsubstituted alkynyl group, substituted or unsubstituted aromatic hydrocarbon group or substituted or unsubstituted heterocyclic group), or group represented by $R^6(R^7)N$— (wherein, $R^6$ and $R^7$ respectively and independently represent a substituted or unsubstituted alkyl group, substituted or unsubstituted alkenyl group, substituted or unsubstituted alkynyl group, substituted or unsubstituted aromatic hydrocarbon group, or substituted or unsubstituted heterocyclic group, furthermore $R^6$ and $R^7$ may together form a ring); $R^2$ represents a primary or secondary substituted or unsubstituted alkyl group, substituted or unsubstituted alkenyl group, substituted or unsubstituted alkynyl group, substituted or unsubstituted aromatic hydrocarbon group, or substituted or unsubstituted heterocyclic group; and, ring A represents a cyclic alkylidene group having 5, 6 or 7 carbon atoms;

provided that, in the case $R^2$ is a 2,2-dimethylpropyl group or 2-(methylthio)ethyl group, $R^4$ is not a t-butyl group, in the case $R^2$ is a methyl group, $R^4$ is not a benzyl group, in the case $R^2$ is a 4,5-dichlorophenyl group, $R^4$ is not a methyl group, and in the case $R^2$ is a phenylmethyl group or pyridylmethyl group, said phenyl or pyridyl group does not have a substituted methoxy group (—$OCH_2$— group) or substituted carbonylamino group (—NHC(=O)— group);

a substituent of an alkyl group in the groups represented by $R^1$ is a group selected from a hydroxyl group, alkenyl group, alkynyl group, bromine atom, fluorine atom, iodine atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, ureido group, carboxyl group, carbamoyl group, oxo group, sulfamoyl group, sulfo group, cyano group, nitro group, acyloxy group, azido group, sulfonamido group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group);

a substituent of an alkyl group in the groups represented by $R^2$, $R^4$, $R^5$, $R^6$ and $R^7$ is a group selected from a hydroxyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group, provided that Rx and Ry are not simultaneously hydrogen atoms); and, a substituent of an alkenyl group, alkynyl group, aromatic hydrocarbon group or heterocyclic group in the groups represented by $R^1$, $R^2$, $R^4$, $R^5$, $R^6$ and $R^7$ is a group selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group)].

2. The cycloalkylcarbonylamino acid derivative or pharmaceutically acceptable salt thereof according to 1 above, wherein the alkyl group in the groups represented by $R^1$, $R^2$, $R^4$, $R^5$, $R^6$ and $R^7$ in the formula (I) is a linear, branched or cyclic alkyl group having 1 to 12 carbon atoms, the alkenyl group is a linear, branched or cyclic alkenyl group having 2 to 12 carbon atoms, the alkynyl group is a linear, branched or cyclic alkynyl group having 2 to 12 carbon atoms, the aromatic hydrocarbon group is a monocyclic or polycyclic aromatic hydrocarbon group having 6 to 18 carbon atoms, and the heterocyclic group is a heterocyclic group of a 3- to 7-membered ring containing at least one nitrogen atom, oxygen atom or sulfur atom as a ring-composing atom.

3. A cycloalkylcarbonylamino acid derivative represented by formula (I') or a pharmaceutically acceptable salt thereof:

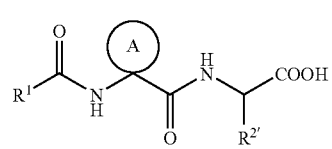
(I')

[wherein, $R^1$ represents a substituted or unsubstituted alkyl group, substituted or unsubstituted alkenyl group, substituted or unsubstituted alkynyl group, substituted or unsubstituted aromatic hydrocarbon group, substituted or unsubstituted heterocyclic group, group represented by $R^4O$—, group represented by $R^5S$— (wherein $R^1$ and $R^5$ respectively and independently represent a substituted or unsubstituted alkyl group, substituted or unsubstituted alkenyl group, substituted or unsubstituted alkynyl group, substituted or unsubstituted aromatic hydrocarbon group, or substituted or unsubstituted heterocyclic group), or group represented by $R^6(R^7)N$— (wherein, $R^6$ and $R^7$ respectively and independently represent a substituted or unsubstituted alkyl group, substituted or unsubstituted alkenyl group, substituted or unsubstituted alkynyl group, substituted or unsubstituted aromatic hydrocarbon group, or substituted or unsubstituted heterocyclic group, furthermore $R^6$ and $R^7$ may together form a ring); $R^{2'}$ represents an alkyl group represented by Ra(Rb)CH— (wherein, Ra and Rb respectively and independently represent a hydrogen atom, substituted or unsubstituted alkyl group, substituted or unsubstituted aromatic hydrocarbon group, or substituted or unsubstituted heterocyclic group), substituted or unsubstituted alkenyl group, substituted or unsubstituted alkynyl group, substituted or unsubstituted aromatic hydrocarbon group or substituted or unsubstituted heterocyclic group; and, ring A represents a cyclic alkylidene group having 5, 6 or 7 carbon atoms;

provided that, in the case $R^{2'}$ is a 2,2-dimethylpropyl group or 2-(methylthio)ethyl group, $R^4$ is not a t-butyl group, in the case $R^{2'}$ is a methyl group, $R^4$ is not a benzyl group, and in the case $R^{2'}$ is a 4,5-dicyclophenyl group, $R^4$ is not a methyl group;

a substituent of an alkyl group in the groups represented by $R^1$ is a group selected from a hydroxyl group, alkenyl group, alkynyl group, bromine atom, fluorine atom, iodine atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, ureido group, carboxyl group, carbamoyl group, oxo group, sulfamoyl group, sulfo group, cyano group, nitro group, acyloxy group, azido group, sulfonamido group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group, provided that both Rx and Ry are not simultaneously hydrogen atoms);

a substituent of an alkyl group in the groups represented by $R^4$, $R^5$, $R^6$, $R^7$, Ra and Rb is a group selected from a hydroxyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group);

a substituent of an alkenyl group, alkynyl group, aromatic hydrocarbon group or heterocyclic group in the groups represented by $R^1$, $R^{2'}$, $R^4$, $R^5$, $R^6$ and $R^7$ is a group selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group); and, a substituent of an aromatic hydrocarbon group or heterocyclic group in the groups represented by Ra and Rb is a group selected from a hydroxyl group, alkyl group, alkenyl group, alkynyl group, halogen atom, aromatic hydrocarbon group, heterocyclic group, guanidino group, alkylthio group, alkoxycarbonyl group, aryloxy group, arylthio group, acyl group, sulfonyl group, heterocyclyloxy group, heterocyclylthio group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group)].

4. The cycloalkylcarbonylamino acid derivative or pharmaceutically acceptable salt thereof according to 3 above, wherein the alkyl group in the groups represented by $R^1$, $R^4$, $R^5$, $R^6$, $R^7$, Ra, Rb, Rx and Ry in the formula (I') above is a linear, branched or cyclic alkyl group having 1 to 12 carbon atoms, the aromatic hydrocarbon group in the groups represented by $R^1$, $R^{2'}$, $R^4$, $R^5$, $R^6$, $R^7$, Ra, Rb, Rx and Ry is a monocyclic or polycyclic aromatic hydrocarbon group having 6 to 18 carbon atoms, the heterocyclic group is a heterocyclic group of a 3- to 7-membered ring containing at least one nitrogen atom, oxygen atom or sulfur atom as a ring-composing atom, the alkenyl group in the groups represented by $R^1$, $R^{2'}$, $R^4$, $R^5$, $R^6$, $R^7$, Rx and Ry is a linear, branched or cyclic alkenyl group having 2 to 12 carbon atoms, and the alkynyl group is a linear, branched or cyclic alkynyl group having 2 to 12 carbon atoms.

5. A cycloalkylcarbonylamino acid derivative represented by formula (I") or a pharmaceutically acceptable salt thereof:

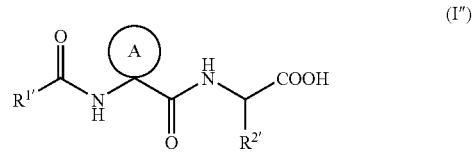

(I")

[wherein, $R^{1'}$ represents a substituted or unsubstituted alkyl group, substituted or unsubstituted alkenyl group, substituted or unsubstituted alkynyl group, substituted or unsubstituted aromatic hydrocarbon group, substituted or unsubstituted heterocyclic group, group represented by $R^5S$— (wherein $R^5$ represents a substituted or unsubstituted alkyl group, substituted or unsubstituted alkenyl group, substituted or unsubstituted alkynyl group, substituted or unsubstituted aromatic hydrocarbon group or substituted or unsubstituted heterocyclic group), group represented by $R^6(R^7)N$— (wherein, $R^6$ and $R^7$ respectively and independently represent a substituted or unsubstituted alkyl group, substituted or unsubstituted alkenyl group, substituted or unsubstituted alkynyl group, substituted or unsubstituted aromatic hydrocarbon group, or substituted or unsubstituted heterocyclic group, furthermore $R^6$ and $R^7$ may together form a ring) or group represented by Rc(Rd)CHO— (wherein, Rc and Rd respectively and independently represent a hydrogen atom, substituted or unsubstituted alkyl group, substituted or unsubstituted alkenyl group, substituted or unsubstituted alkynyl group, substituted or unsubstituted aromatic hydrocarbon group, or substituted or unsubstituted heterocyclic group, provided that Rc and Rd are not both simultaneously hydrogen atoms); $R^{2'}$ represents an alkyl group represented by Ra(Rb)CH— (wherein Ra and Rb respectively and independently represent a hydrogen atom, substituted or unsubstituted alkyl group, substituted or unsubstituted aromatic hydrocarbon group, or substituted or unsubstituted heterocyclic group), substituted or unsubstituted alkenyl group, substituted or unsubstituted alkynyl group, substituted or unsubstituted aromatic hydrocarbon group, or substituted or unsubstituted heterocyclic group; and, ring A represents a cyclic alkylidene group having 5, 6 or 7 carbon atoms;

provided that, a substituent of an alkyl group in the groups represented by $R^{1'}$ is a group selected from a hydroxyl group, alkenyl group, alkynyl group, bromine atom, fluorine atom, iodine atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, ureido group, carboxyl group, carbamoyl group, oxo group, sulfamoyl group, sulfo group, cyano group, nitro group, acyloxy group, azido group, sulfonamido group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group, provided that both Rx and Ry are not simultaneously hydrogen atoms);

a substituent of an alkyl group in the groups represented by $R^{2'}$, $R^5$, $R^6$, $R^7$, Ra, Rb, Rc and Rd is a group selected from a hydroxyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group);

a substituent of an alkenyl group, alkynyl group or aromatic hydrocarbon group in the groups represented by $R^{1'}$, $R^{2'}$, $R^5$, $R^6$, $R^7$, Rc and Rd is a group selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group);

a substituent of an aromatic hydrocarbon group in the groups represented by Ra and Rb is a group selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group);

a substituent of a heterocyclic group in the groups represented by $R^{1'}$ is a group selected from a hydroxyl group, primary or secondary alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group); and, a substituent of a heterocyclic group in the groups represented by $R^{2'}$, $R^5$, $R^6$, $R^7$, Ra, Rb, Rc and Rd is a group selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group (wherein, Rx and Ry respectively and independently represent a hydrogen atom, alkyl group, alkenyl group, alkynyl group, aromatic hydrocarbon group or heterocyclic group)].

6. The cycloalkylcarbonylamino acid derivative or pharmaceutically acceptable salt thereof according to 5 above, wherein the alkyl group in the groups represented by $R^{1'}$, $R^5$, $R^6$, $R^7$, Ra, Rb, Rc and Rd in the formula (I") above is a linear, branched or cyclic alkyl group having 1 to 12 carbon atoms, the aromatic hydrocarbon group in the groups represented by $R^{1'}$, $R^{2'}$, $R^5$, $R^6$, $R^7$, Ra, Rb, Rc and Rd is a monocyclic or polycyclic aromatic hydrocarbon group having 6 to 18 carbon atoms, the heterocyclic group is a heterocyclic group of a 3- to 7-membered ring containing at least one nitrogen atom, oxygen atom or sulfur atom as a ring-composing atom, the alkenyl group in the groups represented by $R^{1'}$, $R^{2'}$, $R^5$, $R^6$, $R^7$, Rc and Rd is a linear, branched or cyclic alkenyl group having 2 to 12 carbon atoms, and the alkynyl group is a linear, branched or cyclic alkynyl group having 2 to 12 carbon atoms.

7. The cycloalkylcarbonylamino acid derivative or pharmaceutically acceptable salt thereof according to any one of 3 to 6 above, wherein in the formula (I') or (I") above, $R^1$ or $R^{1'}$ represents a substituted or unsubstituted alkyl group, substituted or unsubstituted alkenyl group, substituted or unsubstituted aromatic hydrocarbon group, or substituted or unsubstituted heterocyclic group, and $R^{2'}$ represents an alkyl group represented by Ra(Rb)CH— (wherein, Ra and Rb respectively and independently represent a hydrogen atom, substituted or unsubstituted alkyl group, substituted or unsubstituted aromatic hydrocarbon group, or substituted or unsubstituted heterocyclic group), or substituted or unsubstituted aromatic hydrocarbon group.

8. The cycloalkylcarbonylamino acid derivative or pharmaceutically acceptable salt thereof according to any one of 1 to 7 above, wherein in the formula (I), (I') or (I") above, the primary or secondary substituted or unsubstituted alkyl group represented by $R^2$ or $R^{2'}$ or alkyl group represented by Ra(Rb)CH— (wherein Ra and Rb respectively and independently represent a hydrogen atom, substituted or unsubstituted alkyl group, substituted or unsubstituted aromatic hydrocarbon group or substituted or unsubstituted heterocyclic group), substituted or unsubstituted alkenyl group, substituted or unsubstituted alkynyl group, substituted or unsubstituted aromatic hydrocarbon group, or substituted or unsubstituted heterocyclic group is a group derived from an α-amino acid, and said α-amino acid is an α-amino acid selected from alanine, arginine, asparagine, aspartic acid, isoasparagine, γ-carboxyglutamic acid, cysteine, cystine, glutamine, glutamic acid, histidine, homoarginine, homocysteine, homocystine, homoserine, homophenylalanine, isoleucine, leucine, lysine, methionine, norleucine, norvaline, ornithine, phenylalanine, phenylglycine, serine, threonine, tryptophan, tyrosine, valine, 3,4-dihydroxyphenylalanine, allylglycine, neopentylglycine, allothreonine, homolysine, naphthylalanine, α-aminoadipic acid, thienylglycine, pyridylalanine and cyclohexylalanine.

9. The cycloalkylcarbonylamino acid derivative or pharmaceutically acceptable salt thereof according to any one of 1 to 8 above, wherein in the formula (I), (I') or (I''), $R^1$ or $R^{1'}$ represents a 3- to 7-membered heterocyclic group, containing at least one nitrogen atom, oxygen atom or sulfur atom as a ring-composing atom, or a substituted aromatic hydrocarbon group, $R^2$ or $R^{2'}$ represents an alkyl group having 1 to 4 carbon atoms, and ring A represents a cyclohexylidene group.

10. A process for producing a cycloalkylcarbonylamino acid derivative represented by formula (I) comprising: condensing an oxazolone derivative represented by formula ($I_o$) with an amino alcohol derivative represented by formula (VII):

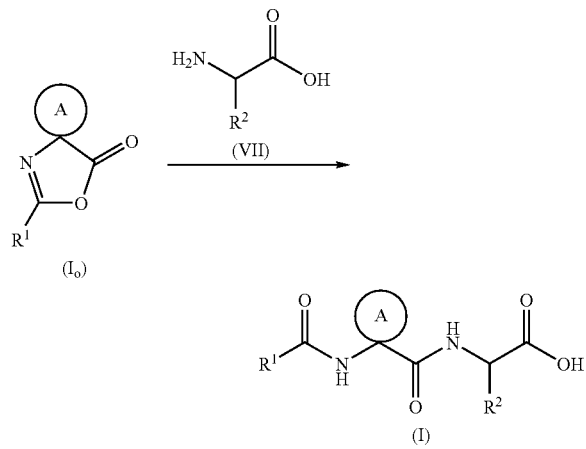

[wherein, $R^1$, $R^2$ and ring A are the same as in 1 above].

Effects of the Invention

A novel cycloalkylcarbonylamino aldehyde derivative derived from the novel cycloalkylcarbonylamino acid derivative of the present invention has highly active and highly selective cathepsin K inhibitory activity. Thus, compounds of the present invention are useful as intermediates of drugs for the prevention and treatment of diseases such as osteoporosis, hypercalcemia, Paget's disease, bone resorption diseases, osteogenesis imperfecta, osteoarthrosis, rheumatoid arthritis, arthritis, Klinefelter's syndrome, hereditary hyperphosphatasemia, Charcot's neuroarthopathy, mastocytosis, Gaucher's disease, cancer metastasis and multiple myeloma, and the contribution thereof to the medicine is considerable.

BEST MODE FOR CARRYING OUT THE INVENTION

The cycloalkylcarbonylamino acid derivatives of the present invention are compounds represented by the aforementioned formula (I), (I') or (I'') and pharmaceutically acceptable salts thereof, and specific examples of alkyl groups, alkenyl groups, alkynyl groups, aromatic hydrocarbon groups and heterocyclic groups included by the groups represented by substituents $R^1$, $R^{1'}$, $R^2$, $R^{2'}$, $R^4$, $R^5$, $R^6$, $R^7$, Ra, Rb, Rc and Rd in these derivatives are listed below.

The alkyl group may be a linear, branched or cyclic alkyl group having 1 to 12 carbon atoms, examples of which include a methyl group, ethyl group, n-propyl group, 2-propyl group, cyclopropyl group, n-butyl group, 2-methylpropyl group, 2-butyl group, 1,1-dimethylethyl group, cyclobutyl group, n-pentyl group, 3-methylbutyl group, cyclopentyl group, 2,2-dimethylpropyl group, 1-methylcyclobutyl group, cyclobutylmethyl group, n-hexyl group, 4-methylpentyl group, cyclohexyl group, 1-methylcyclopentyl group, cyclopentylmethyl group, (1-methylcyclobutyl)methyl group, n-heptyl group, 5-methylhexyl group, 4,4-dimethylpentyl group, cycloheptyl group, cyclohexylmethyl group, (1-methylcyclopentyl)methyl group, n-octyl group, 6-methylheptyl group, 5,5-dimethylhexyl group, (1-methylcyclohexyl)methyl group, n-nonyl group, 7-methyloctyl group, 6,6-dimethylheptyl group, n-decyl group, 8-methylnonyl group, n-dodecacyl group, 10-methylundecacyl group and 9,9-dimethyldecacyl group.

The alkenyl group may be a linear, branched or cyclic alkenyl group having 2 to 12 carbon atoms, examples of which include a vinyl group, 1-propenyl group, 2-propenyl group, 1-methylethenyl group, 1-methyl-1-propenyl group, 1-methyl-2-propenyl group, 2-methyl-2-propenyl group, 1-propenyl group, 2-propenyl group, 1-butenyl group, 2-butenyl group, 2-pentenyl group, 1-pentenyl group, 1-hexenyl group and 2-hexenyl group.

The alkynyl group may be a linear, branched or cyclic alkynyl group having 2 to 12 carbon atoms and may be substituted, examples of which include an ethynyl group, 1-propynyl group, 2-propynyl group and 2-butynyl group.

The aromatic hydrocarbon group may be a monocyclic or polycyclic group having 6 to 18 carbon atoms, examples of which include a phenyl group, naphthyl group and anthranyl group.

The heterocyclic group may be a 3- to 7-membered ring group containing at least one heteroatom such as a nitrogen atom, oxygen atom or sulfur atom as a ring-composing atom, and these may condense with heterocyclic groups, aliphatic rings or aromatic rings and may form a spiro ring, examples of which include a furanyl group, thienyl group, pyrrolyl group, pyrazolyl group, thiazolyl group, oxazolyl group, isoxazolyl group, pyridinyl group, pyrazinyl group, pyrimidinyl group, pyridazinyl group, pyranyl group, indolyl group, benzofuranyl group, benzimidazolyl group, benzoxazolyl group, quinolyl group, isoquinolyl group, pyrrolidinyl group, piperizinyl group, piperadinyl group, morpholinyl group, indolinyl group and benzodioxolyl group. Preferable examples include a furanyl group and morpholinyl group.

In addition, examples of substituents which can be possessed by the alkyl groups include groups selected from a hydroxyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and an Rx(Ry)N group (wherein, Rx and Ry respectively and independently represent a hydrogen atom, alkyl group, alkenyl group, alkynyl group, aromatic hydrocarbon group or heterocyclic group).

Moreover, examples of substituents which can be possessed by the alkenyl groups, alkynyl groups, aromatic hydrocarbon groups and heterocyclic groups above include groups selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and an Rx(Ry)N group (wherein, Rx and Ry respectively and independently represent a hydrogen atom, alkyl group, alkenyl group, alkynyl group, aromatic hydrocarbon group or heterocyclic group).

Furthermore, the alkyl groups, alkenyl groups, alkynyl groups, aromatic hydrocarbon groups and heterocyclic groups listed as Rx, Ry and substituents include the same types of groups as the groups represented by $R^1$, $R^{1'}$, $R^2$, $R^{2'}$, $R^4$, $R^5$, $R^6$, $R^7$, Ra, Rb, Rc and Rd. In addition, the alkyl groups in the alkoxy groups, alkylthio groups, alkoxycarbonyl groups and alkoxycarbonylamino groups as substituent group are also the same as the previously described alkyl groups having 1 to 12 carbon atoms, and the aryl groups of aryloxy groups and arylthio groups are also the same as the previously described aromatic hydrocarbon groups having 6 to 18 carbon atoms.

In addition, examples as substituents of guanidino groups, acyl groups, sulfonyl groups, heterocyclyloxy groups, heterocyclylthio groups, amido groups, ureido groups, carbamoyl groups, sulfamoyl groups, acyloxy groups, sulfonamido groups and alkoxycarbonylamino groups are indicated below.

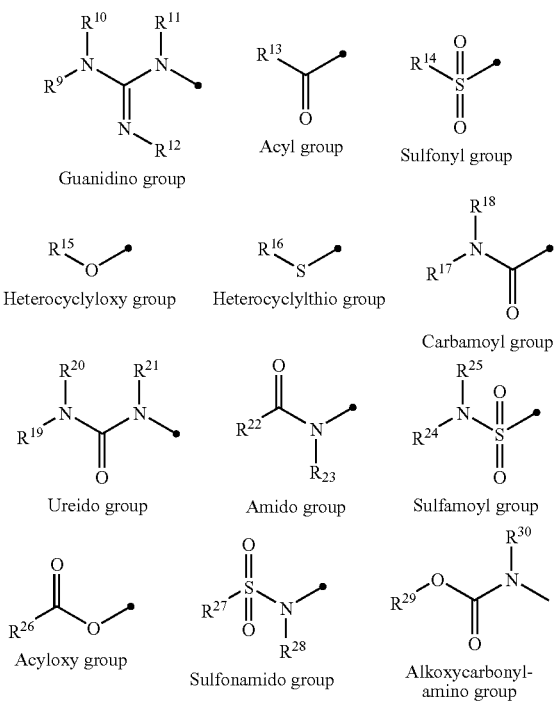

(In the examples of groups indicated above, $R^9$ to $R^{12}$, $R^{17}$ to $R^{21}$, $R^{23}$ to $R^{25}$, $R^{28}$ and $R^{30}$ represent hydrogen atoms, substituted or unsubstituted alkyl groups, substituted or unsubstituted alkenyl groups, substituted or unsubstituted alkynyl groups, substituted or unsubstituted aromatic hydrocarbon groups or substituted or unsubstituted heterocyclic groups. $R^{13}$, $R^{14}$, $R^{22}$, $R^{26}$, $R^{27}$ and $R^{29}$ substituted or unsubstituted alkyl groups, substituted or unsubstituted alkenyl groups, substituted or unsubstituted alkynyl groups, substituted or unsubstituted aromatic hydrocarbon groups or substituted or unsubstituted heterocyclic groups. $R^{15}$ and $R^{16}$ represent substituted or unsubstituted heterocyclic groups.

In addition, examples of substituents of these substituted alkyl groups, substituted alkenyl groups, substituted alkynyl groups, substituted aromatic hydrocarbon groups and substituted heterocyclic groups include the same groups as the substituents of these groups listed for $R^1$ in 13 above).

However, in the case $R^2$ is a 2,2-dimethylpropyl group or 2-(methylthio)ethyl group, $R^4$ is not a t-butyl group, in the case $R^2$ is a methyl group, $R^4$ is not a benzyl group, in the case $R^2$ is a 4,5-dichlorophenyl group, $R^4$ is not a methyl group, and in the case $R^2$ is a phenylmethyl group or pyridylmethyl group, said phenyl or pyridyl group does not have a substituted methoxy group (—OCH$_2$— group) or substituted carbonylamino group (—NHC(=O)— group). In addition, in the case $R^{2'}$ is a 2,2-dimethylpropyl group or 2-(methylthio) ethyl group, $R^4$ is not a t-butyl group, in the case $R^{2'}$ is a methyl group, $R^4$ is not a benzyl group, and in the case $R^{2'}$ is a 4,5-dichlorophenyl group, $R^4$ is not a methyl group.

In a cycloalkylcarbonylamino acid derivative represented by formula (I), (I') or (I'') of the present invention, ring A is a cyclopentylidene group, cyclohexylidene group or cycloheptylidene group, and preferably a cyclohexylidene group.

In formula (I), (I') or (I''), compound in which $R^1$ or $R^{1'}$ is a 3- to 7-membered heterocyclic group or substituted aromatic hydrocarbon group containing at least one nitrogen atom, oxygen atom or sulfur atom as a ring-composing atom, $R^2$ or $R^{2'}$ is an alkyl group having 1 to 4 carbon atoms, and ring A is a cyclohexylidene group is preferred.

In the case a cycloalkylcarbonylamino acid derivative represented by formula (I), (I') or (I'') of the present invention has a basic site in a molecule thereof, a salt can be formed with an inorganic acid or organic acid, and examples of inorganic acids include hydrochloric acid, sulfuric acid, nitric acid, phosphoric acid and hydrobromic acid. In addition, examples of organic acids include acetic acid, propionic acid, benzoic acid, oxalic acid, malonic acid, succinic acid, phthalic acid, glycolic acid, lactic acid, glyceric acid, malic acid, tartaric acid, gallic acid, citric acid, maleic acid, fumaric acid, methanesulfonic acid, benzenesulfonic acid and toluenesulfonic acid.

Moreover, in the case the cycloalkylcarbonylamino acid derivative has an acidic site in a molecule thereof, a salt can be formed with an alkaline metal such as lithium, sodium or potassium, an alkaline earth metal such as magnesium or calcium, aluminum salt or zinc salt. In addition, a salt can also be formed with an organic base, and examples of such an organic base include primary amines such as methylamine, ethylamine or aniline, secondary amines such as diethylamine, pyrrolidine, piperidine, morpholine, piperazine or dicyclohexylamine, tertiary amines such as trimethylamine, triethylamine, N,N-diisopropylethylamine or pyridine, and ammonia.

The following indicates an example of the production of a cycloalkylcarbonylamino acid derivative represented by formula (I) of the present invention.

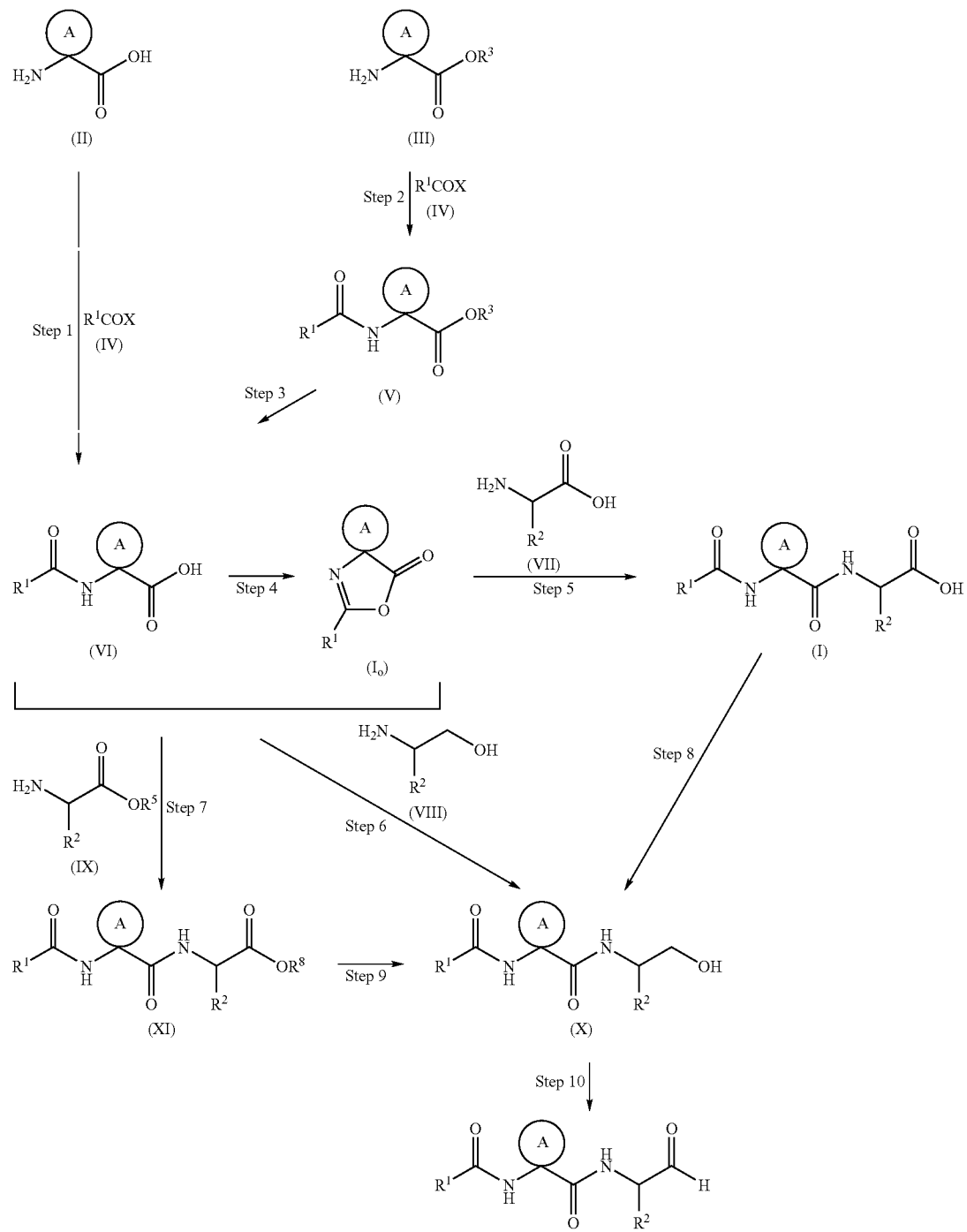

(In the above formulas, $R^1$, $R^2$ and ring A are the same as previously defined in the formula (I), $R^3$ and $R^8$ represent substituted or unsubstituted alkyl groups having 1 to 6 carbon atoms, and X represents a hydroxyl group or a leaving group).

Step 1:

This step is a step for producing a cycloalkylcarboxylic acid derivative represented by formula (VI) above by condensing an amino acid represented by formula (II) above with a carboxylic acid derivative represented by formula (IV) above. Examples of carboxylic acid derivatives used include acid halides, active esters and acid anhydrides. In addition, this step can be carried out by adding a base as necessary. Examples of bases that can be used include pyridine, triethylamine, N,N-diisopropylethylamine, 4-(dimethylamino)pyridine, N-methylmorpholine, sodium carbonate, potassium carbonate, sodium bicarbonate, sodium hydroxide and potassium hydroxide.

This step is preferably carried out in a solvent, examples of solvents that can be used include water and organic solvents such as methylene chloride, chloroform, dichloroethane, ethyl acetate, acetone, benzene, toluene, xylene, dimethylformamide, acetonitrile, tetrahydrofuran, dioxane, diethyl ether, isopropyl ether or dimethoxyethane, and a mixed solvent of an organic solvent and water can be used as necessary. The reaction is normally carried out at a reaction temperature within the range of −30 to 200° C. and is preferably allowed to proceed within the range of −15 to 100° C.

Step 2:

This step is a step for producing a cycloalkyl ester derivative represented by formula (V) above by a condensation reaction between an amino acid ester represented by formula (III) above and a carboxylic acid or carboxylic acid derivative represented by formula (IV) above. Examples of carboxylic acid derivatives used include acid halides, active esters and acid anhydrides. In this step, the reaction can be carried out by adding a condensation agent or base as necessary. Examples of condensation agents that can be used include dicyclohexylcarbodiimide, 1-ethyl-3-(3-dimethylaminopropyl)carbodiimide hydrochloride, diisopropylcarbodiimide and carbonyldiimidazole. Here, an activator such as 1-hydroxybenzotriazole can also be added as necessary. Examples of bases that can be used include pyridine, triethylamine, N,N-diisopropylethylamine, 4-(dimethylamino)pyridine, N-methylmorpholine, sodium carbonate, potassium carbonate and sodium bicarbonate.

This step is preferably carried out in a solvent, examples of solvents that can be used include water and organic solvents such as methylene chloride, chloroform, dichloroethane, ethyl acetate, acetone, benzene, toluene, xylene, dimethylformamide, acetonitrile, tetrahydrofuran, dioxane, diethyl ether, isopropyl ether or dimethoxyethane, and a mixed solvent of an organic solvent and water can be used as necessary. The reaction is normally carried out at a reaction temperature within the range of −30 to 200° C. and is preferably allowed to proceed within the range of −15 to 100° C.

Step 3:

This step is a step for producing a compound of formula (VI) above by a hydrolysis reaction, or a hydrogenation reaction by catalytic reduction using a metal catalyst, of the cycloalkyl ester derivative represented by formula (V) above. Hydrolysis can be carried out in the presence of an acid or base. Examples of acids that can be used include hydrochloric acid, sulfuric acid, nitric acid and acetic acid. Examples of bases that can be used include sodium hydroxide, potassium hydroxide, lithium hydroxide, sodium carbonate and potassium carbonate. This step is preferably carried out in water or in a mixed solvent of an organic solvent and water, and examples of organic solvents that can be used include methanol, ethanol, isopropyl alcohol, tetrahydrofuran and dimethoxyethane. The reaction is normally carried out at a reaction temperature within the range of −20 to 200° C. and is preferably allowed to proceed within the range of 0 to 180° C. In addition, examples of metal catalysts that can be used in the catalytic hydrogenation reaction include platinum, palladium, nickel, rhodium, ruthenium and copper. This step is preferably carried out in a solvent, and examples of solvents that can be used include methanol, ethanol, isopropyl alcohol, isopropyl ether, tetrahydrofuran, benzene, toluene, xylene, dimethylformamide, dioxane and water. The reaction is normally carried out at a reaction temperature of −50 to 200° C. and is preferably allowed to proceed within the range of 10 to 100° C.

Examples of the carboxylic acid or carboxylic acid derivative represented by formula (IV) above include the compounds listed below.

Carboxylic acids: acetic acid, isobutyric acid, acrylic acid, propionic acid, cyclohexane carboxylic acid, benzoic acid, cinnamic acid, 2-furan carboxylic acid, nicotinic acid, tetrahydrofuran-2-carboxylic acid, 1-acetyl-piperidine-2-carboxylic acid, 2-pyrrole carboxylic acid, 5-indole carboxylic acid;

Acid halides: acetyl chloride, benzoyl chloride, pivaloyl chloride, 2-furan carbonyl chloride, 4-morpholine carbonyl chloride, 2-thiophene carbonyl chloride;

Active esters: 1-acetylimidazole, benzoic acid p-nitrophenyl esters, benzoic acid N-hydroxysuccinimide esters, benzoic acid 1-hydroxybenzotriazole esters; and Acid anhydrides: acid anhydrides of benzoic acid and methyl carbonate, acid anhydrides of benzoic acid and isobutyl carbonate, acid anhydrides of benzoic acid and pivalic acid, acid anhydrides of benzoic acid and methanesulfonic acid.

Examples of the cycloalkylcarboxylic acid derivatives represented by formula (VI) above include the compounds listed below:

1-[(phenylacetyl)amino]cyclohexanecarboxylic acid, 1-[(1-oxo-3-phenylpropyl)amino]cyclohexanecarboxylic acid, 1-(benzoylamino)cyclohexanecarboxylic acid, 1-[(4-biphenylcarbonyl)amino]cyclohexanecarboxylic acid, 1-[(2-naphthylcarbonyl)amino]cyclohexanecarboxylic acid, 1-[(1-naphthylcarbonyl)amino]cyclohexanecarboxylic acid, 1-[[[(RS)-2,3-tetrahydrobenzofuran-2-yl]carbonyl]amino]cyclohexanecarboxylic acid, 1-[(2-furanylcarbonyl)amino]cyclohexanecarboxylic acid, 1-[(3-furanylcarbonyl)amino]cyclohexanecarboxylic acid, 1-[[(E)-3-(2-furanyl)-1-oxo-2-propenyl]amino]cyclohexanecarboxylic acid, 1-[(2-benzofuranylcarbonyl)amino]cyclohexanecarboxylic acid, 1-[(cyclohexylcarbonyl)amino]cyclohexanecarboxylic acid, 1-[(6-benzothiazolylcarbonyl)amino]cyclohexanecarboxylic acid, 1-[[(6-hydroxy-3-pyridinyl)carbonyl]amino]cyclohexanecarboxylic acid, 1-[(2-thienylcarbonyl)amino]cyclohexanecarboxylic acid, 1-[(2-pyridinylcarbonyl)amino]cyclohexanecarboxylic acid, 1-[(3-thienylcarbonyl)amino]cyclohexanecarboxylic acid, 1-[[(3-ethoxy-2-thienyl)carbonyl]amino]cyclohexanecarboxylic acid, 1-[[(S)-1-oxo-2-phenylpropyl]amino]cyclohexanecarboxylic acid, 1-[(2-pyrazinylcarbonyl)amino]cyclohexanecarboxylic acid, 1-[[(5-methyl-2-thienyl)carbonyl]amino]cyclohexanecarboxylic acid, 1-[[(4-methoxyphenyl)carbonyl]amino]cyclohexanecarboxylic acid, 1-[[(3-methyl-2-thienyl)carbonyl]amino]cyclohexanecarboxylic acid, 1-[[(3-methyl-2-furanyl)carbonyl]amino]cyclohexanecarboxylic acid, 1-[(3-pyridinylcarbonyl)amino]cyclohexanecarboxylic acid, 1-[[(1-methyl-1H-pyrrol-2-yl)carbonyl]amino]cyclohexanecarboxylic acid, 1-[((R)-1-oxo-2-phenylpropyl)amino]cyclohexanecarboxylic acid, 1-[(1H-indol-5-ylcarbonyl)amino]cyclohexanecarboxylic acid, 1-[(1-cyclopentenylcarbonyl)amino]cyclohexanecarboxylic acid, 1-[(4-pyridinylcarbonyl)amino]cyclohexanecarboxylic acid, 1-[[(1H-pyrrol-2-yl)carbonyl]amino]cyclohexanecarboxylic acid, 1-[[(6-hydroxy-2-pyridinyl)carbonyl]amino]cyclohexanecarboxylic acid, 1-[[(2-hydroxy-3-pyridinyl)carbonyl]amino]cyclohexanecarboxylic acid, 1-[[(6-hydroxy-3-pyridinyl)carbonyl]amino]cyclohexanecarboxylic acid, 1-[[[1-(2-propoxycarbonyl)piperidin-4-yl]carbonyl]amino]cyclohexanecarboxylic acid, 1-[[[1-(ethoxycarbonyl)piperidin-4-yl]carbonyl]amino]cyclohexanecarboxylic acid, 1-[[[1-(2-furanylcarbonyl)piperidin-4-yl]carbonyl]amino]cyclohexanecarboxylic acid, 1-[[[(2-furanylcarbonyl)amino]acetyl]amino]cyclohexanecarboxylic acid, 1-[[(benzoylamino)acetyl]amino]cyclohexanecarboxylic acid, 1-[[(2-oxo-2H-pyran-5-yl)carbonyl]amino]cyclohexanecarboxylic acid, 1-[(4-fluorobenzoyl)amino]cyclohexanecarboxylic acid, 1-[[[4-(4-propylpiperazine-1-yl)phenyl]carbonyl]

amino]cyclohexanecarboxylic acid, 1-[[[4-(4-propylpiperazine-1-yl)phenyl]carbonyl]amino]cyclohexanecarboxylic acid hydrochloride,

[[(2,3-dihydro-2-oxo-5-benzoxazole)carbonyl]amino]cyclohexanecarboxylic acid, [[(2,3-dihydro-1,4-benzodioxin-6-yl)carbonyl]amino]cyclohexanecarboxylic acid, [[(2,4-dioxo-3-thiazolidinyl)acetyl]amino]cyclohexanecarboxylic acid, [(1-oxo-3-phenyl-2-propenyl)amino]cyclohexanecarboxylic acid, [[1-oxo-3-(2-chlorophenyl)-2-propenyl]amino]cyclohexanecarboxylic acid, [[1-oxo-3-(4-chlorophenyl)-2-propenyl]amino]cyclohexanecarboxylic acid, [[1-oxo-3-(dichlorophenyl)-2-propenyl]amino]cyclohexanecarboxylic acid, [[1-oxo-3-(2-bromophenyl)-2-propenyl]amino]cyclohexanecarboxylic acid, [[1-oxo-3-(4-bromophenyl)-2-propenyl]amino]cyclohexanecarboxylic acid, [[1-oxo-3-(dibromophenyl)-2-propenyl]amino]cyclohexanecarboxylic acid, [[1-oxo-3-(2-fluorophenyl)-2-propenyl]amino]cyclohexanecarboxylic acid,

[[1-oxo-3-(2-iodophenyl)-2-propenyl]amino]cyclohexanecarboxylic acid, [[oxo-3-(4-fluorophenyl)-2-propenyl]amino]cyclohexanecarboxylic acid, [[oxo-3-(difluorophenyl)-2-propenyl]amino]cyclohexanecarboxylic acid, [[1-oxo-3-(4-iodophenyl)-2-propenyl]amino]cyclohexanecarboxylic acid, [[1-oxo-3-(diiodophenyl)-2-propenyl]amino]cyclohexanecarboxylic acid, [[oxo-3-(trifluorophenyl)-2-propenyl]amino]cyclohexanecarboxylic acid, [[1-oxo-3-(2-methylphenyl)-2-propenyl]amino]cyclohexanecarboxylic acid, [[1-oxo-3-(3-methylphenyl)-2-propenyl]amino]cyclohexanecarboxylic acid, [[1-oxo-3-(4-methylphenyl)-2-propenyl]amino]cyclohexanecarboxylic acid, [[1-oxo-3-(dimethylphenyl)-2-propenyl]amino]cyclohexanecarboxylic acid, [[1-oxo-3-(2-methoxyphenyl)-2-propenyl]amino]cyclohexanecarboxylic acid,

[[1-oxo-3-(4-methoxyphenyl)-2-propenyl]amino]cyclohexanecarboxylic acid, [[1-oxo-3-(dimethoxyphenyl)-2-propenyl]amino]cyclohexanecarboxylic acid, [[1-oxo-3-(nitrophenyl)-2-propenyl]amino]cyclohexanecarboxylic acid, [[1-oxo-3-(dinitrophenyl)-2-propenyl]amino]cyclohexanecarboxylic acid, [[1-oxo-3-(acetaminophenyl)-2-propenyl]amino]cyclohexanecarboxylic acid, [[1-oxo-3-(2-pyridinyl)-2-propenyl]amino]cyclohexanecarboxylic acid, [(1-oxo-3-cyclohexyl-2-propenyl)amino]cyclohexanecarboxylic acid, [(1-oxo-3-cyclopentyl-2-propenyl)amino]cyclohexanecarboxylic acid, [(1-oxo-3-phenyl-2-propynyl)amino]cyclohexanecarboxylic acid, [[1-oxo-3-(fluorophenyl)-2-propynyl]amino]cyclohexanecarboxylic acid, [[1-oxo-3-(chlorophenyl)-2-propynyl]amino]cyclohexanecarboxylic acid, [[1-oxo-3-(bromophenyl)-2-propynyl]amino]cyclohexanecarboxylic acid, [[1-oxo-3-(iodophenyl)-2-propynyl]amino]cyclohexanecarboxylic acid,

[[1-oxo-3-(difluorophenyl)-2-propynyl]amino]cyclohexanecarboxylic acid, [[1-oxo-3-(dibromophenyl)-2-propynyl]amino]cyclohexanecarboxylic acid, [[1-oxo-3-(diiodophenyl)-2-propynyl]amino]cyclohexanecarboxylic acid, [[1-oxo-3-(trifluorophenyl)-2-propynyl]amino]cyclohexanecarboxylic acid, [(1-oxo-3-cyclohexyl-2-propynyl)amino]cyclohexanecarboxylic acid, [(1-oxo-3-cyclopentyl-2-propynyl)amino]cyclohexanecarboxylic acid, [[3-(2-furanyl)-1-oxo-2-propynyl]amino]cyclohexanecarboxylic acid, 1-[[[4-(4-propylpiperazine-1-yl)phenyl]carbonyl]amino]cyclohexanecarboxylic acid acetate, 1-[[[4-(4-propylpiperazine-1-yl)phenyl]carbonyl]amino]cyclohexanecarboxylic acid hydrobromide, 1-[[[4-(4-propylpiperazine-1-yl)phenyl]carbonyl]amino]cyclohexanecarboxylic acid benzenesulfonate, 1-[[[4-(4-propylpiperazine-1-yl)phenyl]carbonyl]amino]cyclohexanecarboxylic acid toluenesulfonate, 1-[[[4-(4-propylpiperazine-1-yl)phenyl]carbonyl]amino]cyclohexanecarboxylic acid phthalate, 1-[[[4-(4-propylpiperazine-1-yl)phenyl]carbonyl]amino]cyclohexanecarboxylic acid fumarate, and 1-[[[4-(4-propylpiperazine-1-yl)phenyl]carbonyl]amino]cyclohexanecarboxylic acid citrate.

Step 4:

This step is a step for producing an oxazolone derivative represented by formula ($I_o$) above by ring-closing the cycloalkylcarboxylic acid derivative represented by formula (VI) above by a dehydration reaction. The dehydration reaction of this step is preferably carried out in the presence of a condensation agent, halogenating agent, acid, acid anhydride or acid chloride and the like, and examples of condensation agents that can be used include dicyclohexylcarbodiimide, 1-ethyl-3-(3-dimethylaminopropyl)carbodiimide hydrochloride, diisopropylcarbodiimide and carbonyldiimidazole. Examples of halogenating agents that can be used include chlorine, bromine, iodine, phosphorous pentachloride, thionyl chloride, oxalyl chloride and thionyl bromide. Examples of acids that can be used include acetic acid, sulfuric acid, hydrochloric acid, methanesulfonic acid and toluenesulfonic acid. Examples of acid anhydrides that can be used include acetic anhydride, methanesulfonic anhydride, toluenesulfonic anhydride and trifluoromethanesulfonic anhydride. Examples of acid chlorides that can be used include acetyl chloride, pivaloyl chloride, methanesulfonyl chloride, toluenesulfonyl chloride, methyl chloroformate, ethyl chloroformate, propyl chloroformate and isobutyl chloroformate.

In addition, the reaction of this step can also be carried out by adding a base as necessary, and examples of bases that can be used include pyridine, triethylamine, N,N-diisopropylethylamine, 4-(dimethylamino)pyridine, N-methylmorpholine, sodium carbonate, potassium carbonate and sodium bicarbonate.

This step is preferably carried out in a solvent, and examples of solvents that can be used include methylene chloride, chloroform, dichloroethane, ethyl acetate, acetone, benzene, toluene, xylene, dimethylformamide, acetonitrile, tetrahydrofuran, dioxane, diethyl ether, diisopropyl ether and dimethoxyethane.

The reaction is normally carried out at a reaction temperature within the range of −30 to 200° C. and is preferably allowed to proceed within the range of 0 to 100° C.

Step 5:

This step is a step for producing a cycloalkylcarbonylamino acid derivative of the present invention represented by formula (I) above by reacting the oxazolone derivative represented by formula ($I_o$) above with the amino acid derivative represented by formula (VII) above.

This step can be carried out in the presence of a base and in the presence or absence of a solvent, and examples of solvents that can be used include methylene chloride, chloroform, dichloroethane, ethyl acetate, acetone, benzene, toluene, xylene, dimethylformamide, acetonitrile, tetrahydrofuran, dioxane, diethyl ether, diisopropyl ether, dimethoxyethane, dimethylsulfoxide, methanol, ethanol and 2-propanol. In addition, examples of bases that can be used include pyridine, triethylamine, N,N-diisopropylethylamine, 4-(dimethylamino)pyridine, N-methylmorpholine, sodium carbonate, potassium carbonate, sodium bicarbonate, sodium hydroxide and potassium hydroxide. The reaction is normally carried out at a reaction temperature within the range of −30 to 200° C. and can be preferably allowed to proceed within the range of 20 to 200° C.

Examples of oxazolone derivatives represented by formula ($I_O$) above include the compounds listed below: 2-phenylmethyl-3-oxa-1-azaspiro[4.5]dec-1-en-4-one, 2-phenylethyl- 3-oxa-1-azaspiro[4.5]dec-1-en-4-one, 2-(4-biphenyl)-3-oxa-1-azaspiro[4.5]dec-1-en-4-one, 2-(2-naphthyl)-3-oxa-1-azaspiro[4.5]dec-1-en-4-one, 2-[(RS)-2,3-tetrahydrobenzofuran-2-yl]-3-oxa-1-azaspiro[4.5]dec-1-en-4-one, 2-(6-benzothiazolyl)-3-oxa-1-azaspiro[4.5]dec-1-en-4-one, 2-(2-thienyl)-3-oxa-1-azaspiro[4.5]dec-1-en-4-one, 2-(1,3-benzoxol-5-yl)-3-oxa-1-azaspiro[4.5]dec-1-en-4-one, 2-(2-benzofuranyl)-3-oxa-1-azaspiro[4.5]dec-1-en-4-one, 2-(2-pyridinyl)-3-oxa-1-azaspiro[4.5]dec-1-en-4-one, 2-(3-ethoxy-2-thienyl)-3-oxa-1-azaspiro[4.5]dec-1-en-4-one, 2-(2-pyrazinyl)-3-oxa-1-azaspiro[4.5]dec-1-en-4-one, 2-(5-methylisoxazol-4-yl)-3-oxa-1-azaspiro[4.5]dec-1-en-4-one, 2-cyclopentyl-3-oxa-1-azaspiro[4.5]dec-1-en-4-one, 2-(5-methyl-2-thienyl)-3-oxa-1-azaspiro[4.5]dec-1-en-4-one, 2-(4-methoxyphenyl)-3-oxa-1-azaspiro[4.5]dec-1-en-4-one, 2-(3-methyl-2-furanyl)-3-oxa-1-azaspiro[4.5]dec-1-en-4-one, 2-(1-methyl-1H-pyrrol-2-yl)-3-oxa-1-azaspiro[4.5]dec-1-en-4-one, 2-(1H-indol-5-yl)-3-oxa-1-azaspiro[4.5]dec-1-en-4-one, 2-(1-cyclopentenyl)-3-oxa-1-azaspiro[4.5]dec-1-en-4-one, 2-(6-hydroxy-2-pyridinyl)-3-oxa-1-azaspiro[4.5]dec-1-en-4-one, 2-[2-(furanyl)ethyl]-3-oxa-1-azaspiro[4.5]dec-1-en-4-one, 2-[1-[(2-propoxy)carbonyl]piperidin-4-yl]-3-oxa-1-azaspiro[4.5]dec-1-en-4-one, 2-[1-(ethoxycarbonyl)piperidin-4-yl]-3-oxa-1-azaspiro[4.5]dec-1-en-4-one, 2-[1-(2-furanylcarbonyl)piperidin-4-yl]-3-oxa-1-azaspiro[4.5]dec-1-en-4-one, 2-[(2-furanylcarbonyl)amino]methyl]-3-oxa-1-azaspiro[4.5]dec-1-en-4-one, 2-[(benzoylamino)methyl]-3-oxa-1-azaspiro[4.5]dec-1-en-4-one, 2-(4-fluorophenyl)-3-oxa-1-azaspiro[4.5]dec-1-en-4-one, 2-[[4-[(1-propyl)piperazin-1-yl]phenyl]-3-oxa-1-azaspiro[4.5]dec-1-en-4-one, 2-(2-furyl)-3-oxa-1-azaspiro[4.5]dec-1-en-4-one, 2-cyclohexyl-3-oxa-1-azaspiro[4.5]dec-1-en-4-one, 2-(2-propyl)-3-oxa-1-azaspiro[4.5]dec-1-en-4-one, 2-(1-acetyl-piperidin-4-yl)-3-oxa-1-azaspiro[4.5]dec-1-en-4-one, 2-[4-[2-(4-methyl-1-piperazinyl)-4-thiazolyl]phenyl]-3-oxa-1-azaspiro[4.5]dec-1-en-4-one, 2-[4-[2-[4-(4-morpholinyl)-1-piperidinyl]-4-thiazolyl]phenyl]-3-oxa-1-azaspiro[4.5]dec-1-en-4-one, 2-[4-(2-[1,4-bipiperidine]-1'-yl-4-thiazolyl)phenyl]-3-oxa-1-azaspiro[4.5]dec-1-en-4-one, 2-[4-[2-[4-(1,1-dimethylethyl)-1-piperazinyl]-4-thiazolyl]phenyl]-3-oxa-1-azaspiro[4.5]dec-1-en-4-one, 2-([1,1'-biphenyl]-3-yl)-3-oxa-1-azaspiro[4.5]dec-1-en-4-one, 2-[2-(4-pyridinyl)-4-thiazolyl]-3-oxa-1-azaspiro[4.5]dec-1-en-4-one, 2-(4-aminophenyl)-3-oxa-1-azaspiro[4.5]dec-1-en-4-one, 2-[4-(4-morpholinyl)phenyl]-3-oxa-1-azaspiro[4.5]dec-1-en-4-one, 2-(5-bromo-2-thienyl)-3-oxa-1-azaspiro[4.5]dec-1-en-4-one, 2-[4-[(4-methyl-1-piperazinyl)carbonyl]phenyl]-3-oxa-1-azaspiro[4.5]dec-1-en-4-one, 2-[4-[(4-methyl-1-piperazinyl)sulfonyl]phenyl]-3-oxa-1-azaspiro[4.5]dec-1-en-4-one, 2-(4-dimethylamino)phenyl]-3-oxa-1-azaspiro[4.5]dec-1-en-4-one, 2-(4-ethynylphenyl)-3-oxa-1-azaspiro[4.5]dec-1-en-4-one, 2-[4'-(dimethylamino)[1,1'-biphenyl]-4-yl]-3-oxa-1-azaspiro[4.5]dec-1-en-4-one, 2-[4-(4-methyl-1-piperazinyl)phenyl]-3-oxa-1-azaspiro[4.5]dec-1-en-4-one, 2-[4'-(1-piperazinyl)[1,1'-biphenyl]-4-yl]-3-oxa-1-azaspiro[4.5]dec-1-en-4-one, 2-[4'-[[1-(2-hydroxyethyl)-4-piperidinyl]oxy][1,1'-biphenyl]-4-yl]-3-oxa-1-azaspiro[4.5]dec-1-en-4-one, 2-[4'-[(1-methyl-4-piperidinyl)oxy][1,1'-biphenyl]-4-yl]-3-oxa-1-azaspiro[4.5]dec-1-en-4-one, 2-[4'-[methyl(1-methyl-3-pyrrolidinyl)amino][1,1'-biphenyl]-4-yl]-3-oxa-1-azaspiro[4.5]dec-1-en-4-one, 2-[4'-[4-(1,1-dimethylethyl)-1-piperidinyl][1,1'-biphenyl]-4-yl]-3-oxa-1-azaspiro[4.5]dec-1-en-4-one, 2-[4'-(1-piperazinylsulfonyl)[1,1'-biphenyl]-4-yl]-3-oxa-1-azaspiro[4.5]dec-1-en-4-one, 2-[4'-(4-fluoro-4-piperidinyl)[1,1'-biphenyl]-4-yl]-3-oxa-1-azaspiro[4.5]dec-1-en-4-one, 2-[4'-[[4-(2,2,2-trifluoroethyl)-1-piperazinyl]sulfonyl][1,1'-biphenyl]-4-yl]-3-oxa-1-azaspiro[4.5]dec-1-en-4-one, 2-[4'-[(1-methyl-3-piperidinyl)oxy][1,1'-biphenyl]-4-yl]-3-oxa-1-azaspiro[4.5]dec-1-en-4-one, 2-[4'-[[1-(2-methoxyethyl)-4-piperidinyl]oxy][1,1'-biphenyl]-4-yl]]-3-oxa-1-azaspiro[4.5]dec-1-en-4-one, 2-[4'-[[(2S)-1-methyl-2-pyrrolidinyl]methoxy][1,1'-biphenyl]-4-yl]-3-oxa-1-azaspiro[4.5]dec-1-en-4-one, 2-[4'-[4-[(1,1-dimethylethyl)amino]-1-piperidinyl][1,1'-biphenyl]-4-yl]-3-oxa-1-azaspiro[4.5]dec-1-en-4-one, 2-[4'-(5-isoxazolyl)[1,1'-biphenyl]-4-yl]-3-oxa-1-azaspiro[4.5]dec-1-en-4-one, 2-[4-[2-(4-morpholinylmethyl)-4-thiazolyl]phenyl]-3-oxa-1-azaspiro[4.5]dec-1-en-4-one, 2-[4-[2-[3-(dimethylamino)-1-pyrrolidinyl]-4-thiazolyl]phenyl]-3-oxa-1-azaspiro[4.5]dec-1-en-4-one, 2-[4-[2-(4-methyl-1-piperazinylmethyl)-4-thiazolyl]phenyl]-3-oxa-1-azaspiro[4.5]dec-1-en-4-one, 2-[4-[2-(1,4-dimethyl-4-piperidinyl)-4-thiazolyl]phenyl]-3-oxa-1-azaspiro[4.5]dec-1-en-4-one, 2-[4-[2-(1-methyl-4-piperidinyl)-4-thiazolyl]phenyl]-3-oxa-1-azaspiro[4.5]dec-1-en-4-one, 2-[4-[2-[(3R)-3-amino-1-pyrrolidinyl]-4-thiazolyl]phenyl]-3-oxa-1-azaspiro[4.5]dec-1-en-4-one, 2-[4-[2-(4-piperidinyloxy)-4-thiazolyl]phenyl]-3-oxa-1-azaspiro[4.5]dec-1-en-4-one, 2-[4-[2-(4-morpholinyl)-4-thiazolyl]phenyl]-3-oxa-1-azaspiro[4.5]dec-1-en-4-one, 2-[4-[2-[4-[(1-methylethyl)amino]-1-piperidinyl]-4-thiazolyl]phenyl]-3-oxa-1-azaspiro[4.5]dec-1-en-4-one, 2-[4-[2-[methyl(4-methyl-1-piperazinyl)amino]-4-thiazolyl]phenyl]-3-oxa-1-azaspiro[4.5]dec-1-en-4-one, 2-[4-[2-[4-[methyl(1-methylethyl)amino]-1-piperidinyl]-4-thiazolyl]phenyl]-3-oxa-1-azaspiro[4.5]dec-1-en-4-one, 2-[4-[2-[4-(tetrahydro-2H-pyran-4-yl)-1-piperazinyl]-4-thiazolyl]phenyl]-3-oxa-1-azaspiro[4.5]dec-1-en-4-one, 2-[4-[2-[4-(2-methoxyethyl)-1-piperazinyl]-4-thiazolyl]phenyl]-3-oxa-1-azaspiro[4.5]dec-1-en-4-one, 2-[3-(4-morpholinyl)-1-propynyl]-3-oxa-1-azaspiro[4.5]dec-1-en-4-one, 2-cycloheptyl-3-oxa-1-azaspiro[4.5]dec-1-en-4-one, 2-[4-(4-morpholinylmethyl)phenyl]-3-oxa-1-azaspiro[4.5]dec-1-en-4-one, 2-cyclopropyl-3-oxa-1-azaspiro[4.5]dec-1-en-4-one, 2-[2-(diethylamino)ethyl]-3-oxa-1-azaspiro[4.5]dec-1-en-4-one, 2-[4-[(dimethylamino)methyl]phenyl]-3-oxa-1-azaspiro[4.5]dec-1-en-4-one, 2-(2-benzothienyl)-3-oxa-1-azaspiro[4.5]dec-1-en-4-one, 2-(1-methyl-4-piperazinyl)-3-oxa-1-azaspiro[4.5]dec-1-en-4-one, 2-[2-(1-piperazinyl)ethyl]-3-oxa-1-azaspiro[4.5]dec-1-en-4-one, 2-[3-(trifluoromethyl)phenyl]-3-oxa-1-azaspiro[4.5]dec-1-en-4-one, 2-[4-(trifluoromethoxy)phenyl]-3-oxa-1-azaspiro[4.5]dec-1-en-4-one, 2-[4-(trifluoromethyl)phenyl]-3-oxa-1-azaspiro[4.5]dec-1-en-4-one, 2-[2-(trifluoromethyl)phenyl]-3-oxa-1-azaspiro[4.5]dec-1-en-4-one, 2-[3-(trifluoromethoxy)phenyl]-3-oxa-1-azaspiro[4.5]dec-1-en-4-one, 2-(4-pyridinyl)-3-oxa-1-azaspiro[4.5]dec-1-en-4-one, 2-(3-fluorophenyl)-3-oxa-1-azaspiro[4.5]dec-1-en-4-one, 2-(2-fluorophenyl)-3-oxa-1-azaspiro[4.5]dec-1-en-4-one, 2-[2-(trifluoromethoxy)phenyl]-3-oxa-1-azaspiro[4.5]dec-1-en-4-one, 2-(3-methylphenyl)-3-oxa-1-azaspiro[4.5]dec-1-en-4-one, 2-[4-[(methoxymethylamino)methyl]phenyl]-3-oxa-1-azaspiro[4.5]dec-1-en-4-one, 2-(3-methoxyphenyl)-3-oxa-1-azaspiro[4.5]dec-1-en-4-one, 2-(4-chlorophenyl)-3-oxa-1-azaspiro[4.5]dec-1-en-4-one, 2-(4-cyanophenyl)-3-oxa-1-azaspiro[4.5]dec-1-en-4-one, 2-[3-(4-morpholinylmethyl)phenyl]-3-oxa-1-azaspiro[4.5]dec-1-en-4-one, 2-(phenoxymethyl)-3-oxa-1-azaspiro[4.5]dec-1-en-4-one, 2-(2-chlorophenyl)-3-oxa-1-azaspiro[4.5]dec-1-en-4-one, 2-(2-thienylmethyl)-3-oxa-1-azaspiro[4.5]

dec-1-en-4-one, 2-(2-methylphenyl)-3-oxa-1-azaspiro[4.5]dec-1-en-4-one, 2-(4-hydroxyphenyl)-3-oxa-1-azaspiro[4.5]dec-1-en-4-one, 2-[3-[(dimethylamino)methyl]phenyl]-3-oxa-1-azaspiro[4.5]dec-1-en-4-one, 2-(4-methyl-1,2,3-thiadiazol-5-yl)-3-oxa-1-azaspiro[4.5]dec-1-en-4-one, and 2-(2,5-dimethyl-3-furanyl)-3-oxa-1-azaspiro[4.5]dec-1-en-4-one.

Examples of amino acid derivatives represented by formula (VII) above include the compounds listed below: alanine, arginine, $N^\omega$-nitro-arginine, asparagine, aspartic acid, β-benzyl ester, isoasparagine, γ-carboxyglutamic acid, cysteine, S-acetamide-cysteine, S-trityl-cysteine, cystine, glutamine, glutamic acid, glutamic acid γ-t-butyl ester, histidine, homoarginine, homocysteine, homocystine, homoserine, homophenyl alanine, isoleucine, leucine, t-leucine, lysin, $N^\varepsilon$-t-butoxycarbonyl-lysin, methionine, norleucine, norvaline, ornithine, $N^\delta$-carbobenzoxy-ornithine, phenylalanine, phenylglycine, serine, O-benzyl-serine, threonine, O-t-butylthreonine, tryptophan, tyrosine, O-benzyl-tyrosine, valine, 3,4-dihydroxyphenylalanine, allylglycine, neopentyl glycine, allothreonine, homolysin, naphthylalanine, α-aminoadipic acid, thienylglycine, pyridylalanine, and cyclohexylalanine.

Step 6:

This step is a step for producing a cycloalkylcarbonylamino alcohol derivative represented by formula (X) above. In this step, a cycloalkylcarbonylamino alcohol derivative represented by formula (X) above can be produced by two types of methods consisting of a method that uses a cycloalkylcarboxylic acid derivative represented by formula (VI) above for the starting raw material (Step 6-A), and a method using an oxazolone derivative represented by formula ($I_o$) above for the starting raw material (Step 6-B).

Step 6-A:

This step is a step for producing a cycloalkylcarbonylamino alcohol derivative represented by formula (X) above by condensing a cycloalkylcarboxylic acid derivative represented by formula (VI) above with an amino alcohol derivative represented by formula (VIII) above.

Examples of condensation agents that can be used in this step include dicyclohexylcarbodiimide, 1-ethyl-3-(3-dimethylaminopropyl)carbodiimide hydrochloride, diisopropylcarbodiimide and carbonyldiimidazole. Here, an activator such as 1-hydroxybenzotriazole or N-hydroxysuccinimide can be added as necessary.

In addition, this step can also be carried out by condensing in the presence of a base according to a mixed acid anhydride method with an acid chloride. Examples of acid chlorides that can be used include pivaloyl chloride, isobutyl chloroformate, methyl chloroformate, ethyl chloroformate, methanesulfonyl chloride and toluenesulfonyl chloride. Examples of bases that can be used include pyridine, triethylamine, N,N-diisopropylethylamine, 4-(dimethylamino)pyridine and N-methylmorpholine.

This step is preferably carried out in a solvent, and examples of solvents that can be used include methylene chloride, chloroform, dichloroethane, ethyl acetate, acetone, benzene, toluene, xylene, dimethylformamide, acetonitrile, tetrahydrofuran, dioxane, diethyl ether, diisopropyl ether and dimethoxyethane.

The reaction is normally carried out at a reaction temperature within the range of −30 to 200° C. and can be preferably allowed to proceed within the range of 0 to 100° C.

Step 6-B:

This step is a step for producing a cycloalkylcarbonylamino alcohol derivative represented by formula (X) above by reacting an oxazolone derivative represented by formula ($I_o$) above with an amino alcohol derivative represented by formula (VIII) above.

This step can be carried out in the presence or absence of solvent, and examples of solvents that can be used include methylene chloride, chloroform, dichloroethane, ethyl acetate, acetone, benzene, toluene, xylene, dimethylformamide, acetonitrile, tetrahydrofuran, dioxane, diethyl ether, diisopropyl ether, dimethoxyethane, dimethylsulfoxide, methanol, ethanol and 2-propanol. In addition, in this step, a base can be added as necessary. Examples of bases that can be used include pyridine, triethylamine, N,N-diisopropylethylamine, 4-(dimethylamino)pyridine and N-methylmorpholine. The reaction is normally carried out at a reaction temperature within the range of −30 to 200° C. and can be preferably allowed to proceed within the range of 20 to 200° C.

Step 7:

This step is a step for producing a cycloalkylcarbonylamino acid ester derivative represented by formula (XI) above. In this step, a cycloalkylcarbonylamino acid ester derivative represented by formula (XI) above can be produced by two types of methods consisting of a method that uses a cycloalkylcarboxylic acid derivative represented by formula (VI) above for the starting raw material (Step 7-A), and a method that uses an oxazolone derivative represented by formula ($I_o$) above for the starting raw material (Step 7-B).

Step 7-A:

This step is a step for producing a cycloalkylcarbonylamino acid ester derivative represented by formula (XI) above by condensing a cycloalkylcarboxylic acid derivative represented by formula (VI) above with an amino acid ester derivative represented by formula (IX) above.

Examples of condensation agents that can be used in this step include dicyclohexylcarbodiimide, 1-ethyl-3-(3-dimethylaminopropyl)carbodiimide hydrochloride, diisopropylcarbodiimide and carbonyldiimidazole. Here, an activator such as 1-hydroxybenzotriazole or N-hydroxysuccinimide can be added as necessary.

In addition, this step can also be carried out by condensing in the presence of a base according to a mixed acid anhydride method with an acid chloride. Examples of acid chlorides that can be used include pivaloyl chloride, isobutyl chloroformate, methyl chloroformate, ethyl chloroformate, methanesulfonyl chloride and toluenesulfonyl chloride. Examples of bases that can be used include pyridine, triethylamine, N,N-diisopropylethylamine, 4-(dimethylamino)pyridine and N-methylmorpholine.

This step is preferably carried out in a solvent, and examples of solvents that can be used include methylene chloride, chloroform, dichloroethane, ethyl acetate, acetone, benzene, toluene, xylene, dimethylformamide, acetonitrile, tetrahydrofuran, dioxane, diethyl ether, diisopropyl ether and dimethoxyethane.

The reaction is normally carried out at a reaction temperature within the range of −30 to 200° C. and can be preferably allowed to proceed within the range of 0 to 100° C.

Step 7-B:

This step is a step for producing a cycloalkylcarbonylamino acid ester derivative represented by formula (XI) above by reacting an oxazolone derivative represented by formula ($I_o$) above with an amino acid ester derivative represented by formula (IX) above.

This step can be carried out in the presence or absence of solvent, and examples of solvents that can be used include methylene chloride, chloroform, dichloroethane, ethyl acetate, acetone, benzene, toluene, xylene, dimethylformamide, acetonitrile, tetrahydrofuran, dioxane, diethyl ether, diisopropyl ether, dimethoxyethane, dimethylsulfoxide, methanol, ethanol and 2-propanol. In addition, in this step, a base can be added as necessary. Examples of bases that can be used include pyridine, triethylamine, N,N-diisopropylethylamine, 4-(dimethylamino)pyridine and N-methylmorpholine. The reaction is normally carried out at a reaction temperature within the range of −30 to 200° C. and can be preferably allowed to proceed within the range of 20 to 200° C.

Step 8:

This step is a step for producing a cycloalkylcarbonylamino alcohol derivative represented by formula (X) above by carrying out a reduction reaction after activating a cycloalkylcarbonylamino acid represented by formula (I) above by a mixed acid anhydride method.

Examples of acid chlorides used in the reaction for forming a mixed acid anhydride in this step include pivaloyl chloride, isobutyl chloroformate, methyl chloroformate, ethyl chloroformate, methanesulfonyl chloride and toluenesulfonyl chloride. Examples of bases that can be used include pyridine, triethylamine, N,N-diisopropylethylamine, 4-(dimethylamino)pyridine and N-methylmorpholine.

This reaction is preferably carried out in a solvent, and examples of solvents that can be used include methylene chloride, chloroform, dichloroethane, benzene, toluene, xylene, dimethylformamide, acetonitrile, tetrahydrofuran, dioxane, diethyl ether, diisopropyl ether and dimethoxyethane.

The reaction is normally carried out at a reaction temperature within the range of −50 to 200° C. and can be preferably allowed to proceed within the range of −20 to 50° C.

In addition, examples of reducing agents that can be used in this step include sodium borohydride, lithium aluminum hydride, diisobutyl aluminum hydride, and sodium dihydrobis(2-methoxyethoxy)aluminate (Red-Al).

This step is preferably carried out in a solvent, and examples of solvents that can be used include methylene chloride, chloroform, dichloroethane, benzene, toluene, xylene, dimethylformamide, acetonitrile, tetrahydrofuran, dioxane, diethyl ether, diisopropyl ether, dimethoxyethane, ethanol, 2-propanol and water. The reaction is normally carried out at a reaction temperature within the range of −30 to 200° C. and can be preferably allowed to proceed within the range of −20 to 80° C.

Step 9:

This step is a step for producing a cycloalkylcarbonylamino alcohol derivative represented by formula (X) above by reducing a cycloalkylcarbonylamino acid ester derivative represented by formula (XI) above.

Examples of reducing agents that can be used in this step include sodium borohydride, lithium aluminum hydride, diisobutyl aluminum hydride, and Red-Al.

This reaction is preferably carried out in a solvent, and examples of solvents that can be used include methylene chloride, chloroform, dichloroethane, benzene, toluene, xylene, dimethylformamide, acetonitrile, tetrahydrofuran, dioxane, diethyl ether, diisopropyl ether and dimethoxyethane.

The reaction is normally carried out at a reaction temperature within the range of −100 to 200° C. and can be preferably allowed to proceed within the range of −80 to 100° C.

Step 10:

This step is a step for producing a cycloalkylcarbonylamino aldehyde derivative represented by formula (XII) by oxidizing a cycloalkylcarbonylamino alcohol derivative represented by formula (X) above.

The oxidation reaction used in this step can use activated DMSO (dimethylsulfoxide) oxidation. Examples of electrophilic activating reagents used here include dicyclohexylcarbodiimide, phosphorous pentoxide, pyridine-sulfur trioxide complex, acetic anhydride, silver (II) acetate and oxalyl chloride. A hydrogen donor such as phosphoric acid, trifluoroacetic acid, dichloroacetic acid, pyridine-phosphoric acid or pyridine-trifluoroacetic acid can also be added in this step as necessary. In addition, an amine such as triethylamine, N,N-diisopropylethylamine or N-methylmorpholine can also be added as necessary.

This step can be carried out in dimethylsulfoxide, and a solvent such as methylene chloride, chloroform, dichloroethane, toluene, acetone or tetrahydrofuran can also be added as necessary.

The reaction is normally carried out at a reaction temperature within the range of −80 to 200° C. and can be preferably allowed to proceed within the range of −40 to 40° C.

In addition, in this step, an oxidation reaction can also be carried out by preparing an active species having a structure resembling an activated DMSO reaction from a sulfide and halogenating agent.

Examples of sulfides that can be used in this step include dimethyl sulfide and methyl phenyl sulfide. Examples of halogenating agents that can be used include N-chlorosuccinimide and chlorine.

In this step, an amine such as triethylamine, N,N-diisopropylethylamine, N-methylmorpholine or 1,8-diazabicyclo[5.4.0]undec-7-ene (DBU) can also be added as necessary.

This step is preferably carried out in a solvent, and examples of solvents that can be used include methylene chloride, chloroform, dichloroethane, toluene and tetrahydrofuran.

The reaction is normally carried out at a reaction temperature within the range of −80 to 200° C. and can be preferably allowed to proceed within the range of −40 to 40° C.

In addition, oxidation can also be carried out in this step using a hypervalent iodine compound reagent. Examples of hypervalent iodine compounds that can be used in this step include Dess-Martin reagent (1,1,1-tris(acetoxy)-1,1-dihydro-1,2-benziodoxol-3-(1H)-one) and IBX (1-hydroxy-1,2-benziodoxol-3-(1H)-1-oxide).

A base such as pyridine or sodium bicarbonate can be added in this step as necessary.

This step is preferably carried out in a solvent, and examples of solvents that can be used include methylene chloride, chloroform, dichloroethane, benzene, toluene, xylene, dimethylformamide, acetonitrile, tetrahydrofuran, dioxane and dimethoxyethane.

The reaction is normally carried out at a reaction temperature within the range of −20 to 200° C. and can be preferably allowed to proceed within the range of 0 to 40° C.

In addition, this step can also be carried out using oxidation (Oppenauer's oxidation) with aluminum alkoxide and a hydrogen acceptor. Examples of aluminum alkoxides that can be used include aluminum isopropoxide and aluminum t-butoxide.

Examples of hydrogen acceptors that can be used include benzoquinone, benzophenone, acetone, cyclohexanone and benzaldehyde.

This step is preferably carried out in a solvent, and examples of solvents that can be used include benzene, toluene and xylene.

The reaction is normally carried out at a reaction temperature within the range of −20 to 200° C. and can be preferably allowed to proceed within the range of 0 to 150° C.

In addition, this step can also be carried out using an oxidation reaction with tetrapropylammonium perruthenate (TPAP). N-methylmorpholine-N-oxide or molecular oxygen can be used for the oxidizing agent.

This step is preferably carried out in a solvent, and examples of solvents that can be used include methylene chloride, acetonitrile and toluene.

A type 4A molecular sieve can be added in this step as necessary.

The reaction is normally carried out at a reaction temperature within the range of −20 to 200° C. and can be preferably allowed to proceed within the range of 0 to 40° C.

In addition, this step can also use an oxidation reaction with 2,2,6,6-tetramethyl-1-piperidinyloxy radical (TEMPO) or derivative thereof.

The oxidizing agent is preferably hypochlorous acid, while other examples of oxidizing agents that can be used include bromous acid and N-chlorosuccinimide.

This step is preferably carried out in a solvent, and examples of solvents that can be used include dimethylsulfoxide, N,N-dimethylformamide, methylene chloride, acetonitrile, toluene and ethyl acetate.

In addition, sodium bromide or water can also be added in this step as necessary.

The reaction is normally carried out at a reaction temperature within the range of −20 to 200° C. and can be preferably allowed to proceed within the range of 0 to 40° C.

Specific examples of cycloalkylcarbonylamino acid derivatives represented by formula (I) of the present invention include the compounds listed below.

N-[[1-[[(phenylmethoxy)carbonyl]amino]cyclohexyl]carbonyl]-L-valine, N-[[1-[[(phenylmethoxy)carbonyl]amino]cyclohexyl]carbonyl]-L-norleucine, N-[[1-[(2-furanylcarbonyl)amino]cyclohexyl]carbonyl]-L-valine, N-[[1-[(4-morpholinylcarbonyl)amino]cyclohexyl]carbonyl]-L-norleucine, N-[[1-[[(phenylmethoxy)carbonyl]amino]cyclohexyl]carbonyl]-L-methionine, N-[[1-[(2-furanylcarbonyl)amino]cyclohexyl]carbonyl]-L-phenylalanine, N-[[1-[(4-morpholinylcarbonyl)amino]cyclohexyl]carbonyl]-L-tryptophan, N-[[1-[[(phenylmethoxy)carbonyl]amino]cyclohexyl]carbonyl]-L-tyrosine, N-[[1-[(2-furanylcarbonyl)amino]cyclohexyl]carbonyl]-L-phenylglycine, N-[[1-[(4-morpholinylcarbonyl)amino]cyclohexyl]carbonyl]-L-histidine, N-[[1-[[(phenylmethoxy)carbonyl]amino]cyclohexyl]carbonyl]-L-pyridyl glycine, N-[[1-(acetamide)cyclohexyl]carbonyl]-L-valine, N-[[1-[[(phenylmethylthio)carbonyl]amino]cyclohexyl]carbonyl]-L-valine, N-[[1-[(1-oxo-3-phenyl-2-propenyl)amino]cyclohexyl]carbonyl]-L-valine, N-[[1-[(1-oxo-3-phenyl-2-propynyl)amino]cyclohexyl]carbonyl]-L-valine, N-[[1-[(1-oxo-3-phenyl-2-propynyl)amino]cyclohexyl]carbonyl]-L-allylglycine, N-[[1-[(2-benzothienylcarbonyl)amino]cyclohexyl]carbonyl]-L-phenylglycine, N-[[1-[(2-benzothienylcarbonyl)amino]cyclohexyl]carbonyl]-L-methionine, N-[[[1-[(1H-pyrrol-2-yl)carbonyl]amino]cyclohexyl]carbonyl]-L-phenylglycine, N-[[[1-[(1H-pyrrol-2-yl)carbonyl]amino]cyclohexyl]carbonyl]-L-methionine, N-[[[1-[(4-methoxyphenyl)carbonyl]amino]cyclohexyl]carbonyl]-L-phenylglycine, N-[[1-[[(4-methoxyphenyl)carbonyl]amino]cyclohexyl]carbonyl]-L-methionine, and N-[[1-[[(E)-3-(2-furanyl)-1-oxo-2-propenyl]amino]cyclohexyl]carbonyl]-L-methionine.

As will be clear from the forthcoming test examples, a cycloalkylcarbonylamino aldehyde derivative derived from a cycloalkylcarbonylamino acid derivative represented by formula (I) of the present invention has highly active and highly selective inhibitory activity against cathepsin K, and as a result of having this selective inhibitory activity against cathepsin K, it is expected to be used as a useful drug for prevention or treatment of such diseases as osteoporosis, hypercalcemia, osteoarthrosis and rheumatoid arthritis.

Although the following provides a more detailed explanation of the present invention through reference examples and examples, the present invention is not limited to these examples provided they do not exceed the gist thereof.

Furthermore, "%" refers to "% by weight" unless specifically indicated otherwise.

In addition, synthesis examples of cycloalkylcarboxylic acids represented by formula (VI) above and esters thereof, synthesis examples of oxazolone derivatives represented by formula (I$_o$), as well as synthesis examples of cycloalkylcarbonylamino alcohol derivatives, cycloalkylcarbonylamino acid ester derivatives and cycloalkylcarbonylamino aldehyde derivatives represented by formulas (X), (XI) and (XII), respectively, which are intermediates for producing the cycloalkylcarbonylamino acid derivatives of the present invention, are indicated as reference examples.

Reference Example 1

1-[(Phenylacetyl)amino]cyclohexanecarboxylic acid phenylmethyl ester

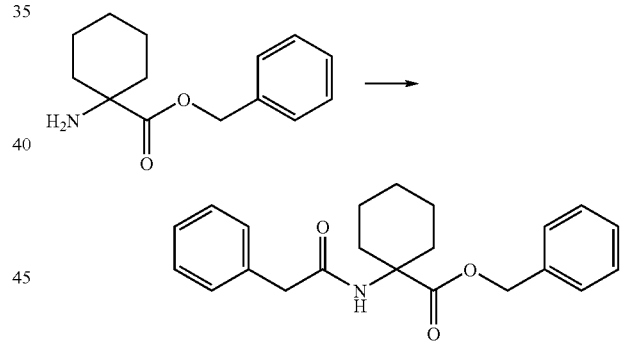

1.21 g (12 mmol) of triethylamine was added to a solution of 2.33 g (10 mmol) of 1-aminocyclohexanecarboxylic acid phenylmethyl ester in 100 ml of tetrahydrofuran, and 1.55 g (10 mmol) of phenylacetyl chloride was added dropwise to the mixture under ice-cooling, followed by stirring of the mixture overnight. Under reduced pressure, the reaction solution was concentrated, ethyl acetate was added thereto, and the mixture was successively washed with water, a 10% aqueous potassium hydrogensulfate solution, a saturated aqueous sodium hydrogencarbonate solution and saturated brine, followed by drying with anhydrous sodium sulfate. After the solvent was distilled off under reduced pressure, the residue was purified by silica gel chromatography to obtain 3.21 g (91%) of the title compound.

1H-NMR (CDCl$_3$, δ): 1.10-1.23 (3H, m), 1.50-1.58 (3H, m), 1.74-1.80 (2H, m), 1.95-1.98 (2H, m), 3.57 (2H, s), 5.12 (2H, s), 5.48 (1H, br-s), 7.24-7.38 (10H, m)

Reference Example 2

1-[(Phenylacetyl)amino]cyclohexanecarboxylic acid

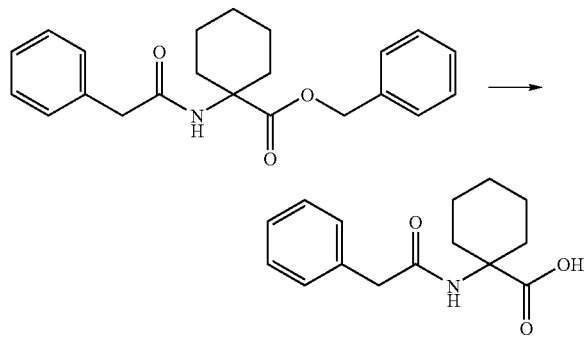

2.69 g (9.1 mmol) of 1-[(phenylacetyl)amino]cyclohexanecarboxylic acid phenylmethyl ester obtained in Reference Example 1 was dissolved in 100 ml of methanol, and 300 mg of 10% palladium-carbon was added thereto, followed by stirring of the mixture under a hydrogen atmosphere at room temperature overnight. After the reaction solution was filtered, the filtrate was concentrated under reduced pressure to obtain 1.96 g (98%) of the title compound.

1H-NMR (CDCl$_3$, δ): 1.01-1.10 (2H, m), 1.18-1.26 (1H, m), 1.49-1.59 (3H, m), 1.75-1.82 (2H, m), 1.97-2.00 (2H, m), 3.66 (2H, s), 5.67 (1H, br-s), 7.29-7.34 (3H, m), 7.37-7.40 (2H, m)

Reference Example 3

1-[(1-Oxo-3-phenylpropyl)amino]cyclohexanecarboxylic acid phenylmethyl ester

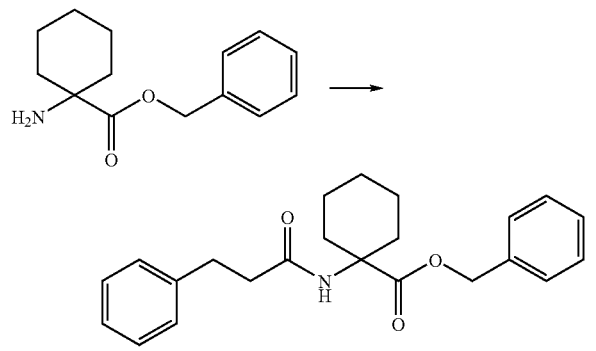

1.68 g (10 mmol) of 3-phenylpropionyl chloride was used instead of phenylacetyl chloride in the process according to Reference Example 1 to obtain 3.47 g (95%) of the title compound.

1H-NMR (CDCl$_3$, δ): 1.19-1.26 (3H, m), 1.50-1.61 (3H, m), 1.78-1.84 (2H, m), 1.96-2.05 (2H, m), 2.50 (2H, t, J=7 Hz), 2.93 (2H, t, J=7 Hz), 5.13 (2H, s), 5.45 (1H, br-s), 7.18-7.21 (4H, m), 7.26-7.37 (6H, m)

Reference Example 4

1-[(1-Oxo-3-phenylpropyl)amino]cyclohexanecarboxylic acid

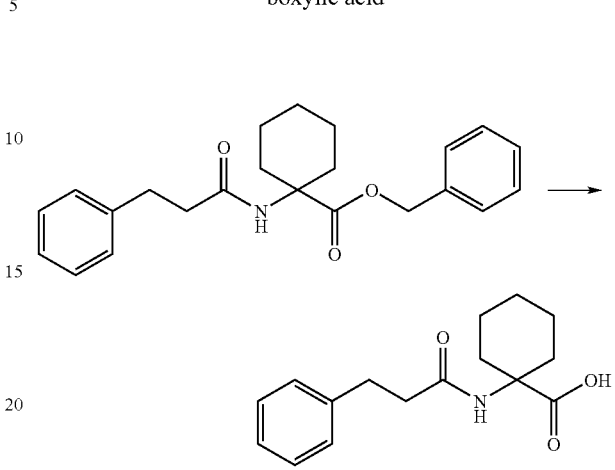

3.47 g (9.5 mmol) of 1-[(1-oxo-3-phenylpropyl)amino]cyclohexanecarboxylic acid phenylmethyl ester was used instead of 1-[(phenylacetyl)amino]cyclohexanecarboxylic acid phenylmethyl ester in the process according to Reference Example 2 to obtain 2.35 g (90%) of the title compound.

1H-NMR (CDCl$_3$, δ): 1.16-1.25 (3H, m), 1.48-1.51 (1H, m), 1.52-1.62 (2H, m), 1.84-1.97 (4H, m), 2.62 (2H, t, J=7 Hz), 3.00 (2H, t, J=7 Hz), 5.43 (1H, br-s), 7.21-7.26 (3H, m), 7.29-7.33 (2H, m)

Reference Example 5

1-(Benzoylamino)cyclohexanecarboxylic acid phenylmethyl ester

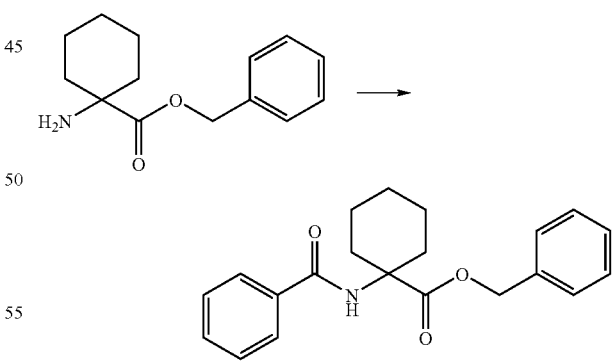

1.41 g (10 mmol) of benzoyl chloride was used instead of phenylacetyl chloride in the process according to Reference Example 1 to obtain 3.39 g (quantitative) of the title compound.

1H-NMR (CDCl$_3$, δ): 1.33-1.40 (1H, m), 1.45-1.54 (2H, m), 1.62-1.76 (3H, m), 1.93-1.99 (2H, m), 2.19-2.22 (2H, m), 5.17 (2H, s), 6.25 (1H, br-s), 7.25-7.32 (4H, m), 7.41-7.45 (3H, m), 7.49-7.52 (1H, m), 7.75-7.77 (2H, m)

Reference Example 6

1-(Benzoylamino)cyclohexanecarboxylic acid

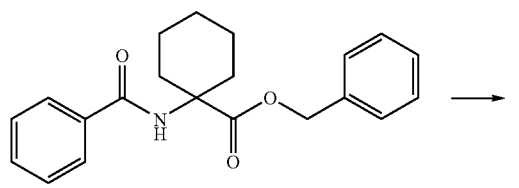

3.39 g (10 mmol) of 1-(benzoylamino)cyclohexanecarboxylic acid phenylmethyl ester was used instead of 1-[(phenylacetyl)amino]cyclohexanecarboxylic acid phenylmethyl ester in the process according to Reference Example 2 to obtain 2.44 g (99%) of the title compound.

1H-NMR (CDCl$_3$, δ): 1.38-1.55 (3H, m), 1.67-1.71 (1H, m), 1.75-1.79 (2H, m), 1.98-2.04 (2H, m), 2.24-2.27 (2H, m), 6.26 (1H, br-s), 7.46 (1H, td, J=7 Hz, 1 Hz), 7.48 (1H, td, J=7 Hz, 1 Hz), 7.57 (1H, td, 7 Hz, 1 Hz), 7.79-7.82 (2H, m)

Reference Example 7

1-[(4-Biphenylcarbonyl)amino]cyclohexanecarboxylic acid phenylmethyl ester

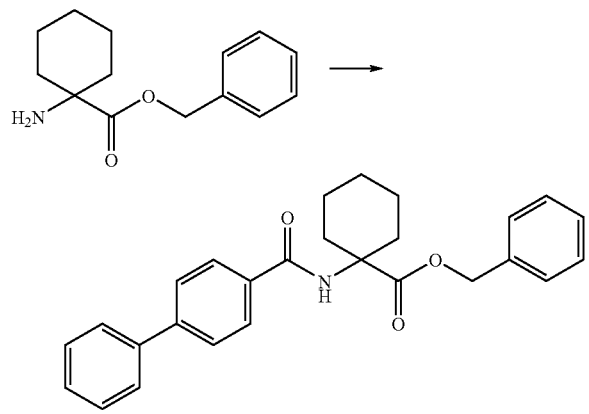

2.11 g (11 mmol) of 1-ethyl-3-(3-dimethylaminopropyl) carbodiimide hydrochloride was added to a solution of 2.33 g (10 mmol) of 1-aminocyclohexanecarboxylic acid phenylmethyl ester, 1.68 g (11 mmol) of 1-hydroxybenzotriazole and 3.23 g (10 mmol) of 4-biphenylcarboxylic acid in 120 ml of methylene chloride under ice-cooling. After the mixture was stirred at room temperature overnight, the reaction solution was concentrated under reduced pressure, ethyl acetate was added thereto, and the mixture was successively washed with water, a 10% aqueous potassium hydrogensulfate solution, a saturated aqueous sodium hydrogencarbonate solution and saturated brine, followed by drying with anhydrous sodium sulfate. After the solvent was distilled off under reduced pressure, the residue was purified by silica gel chromatography to obtain 3.51 g (85%) of the title compound.

1H-NMR (CDCl$_3$, δ): 1.38-1.41 (1H, m), 1.51-1.61 (2H, m), 1.66-1.80 (3H, m), 1.95-2.05 (2H, m), 2.23-2.31 (2H, m), 5.20 (2H, s), 6.38 (1H, br-s), 7.24-7.34 (7H, m), 7.55-7.60 (2H, m), 7.81 (1H, dd, J=8 Hz, 1 Hz), 7.87-7.91 (3H, m), 8.26 (1H, d, J=1 Hz)

Reference Example 8

1-[(4-Biphenylcarbonyl)amino]cyclohexanecarboxylic acid

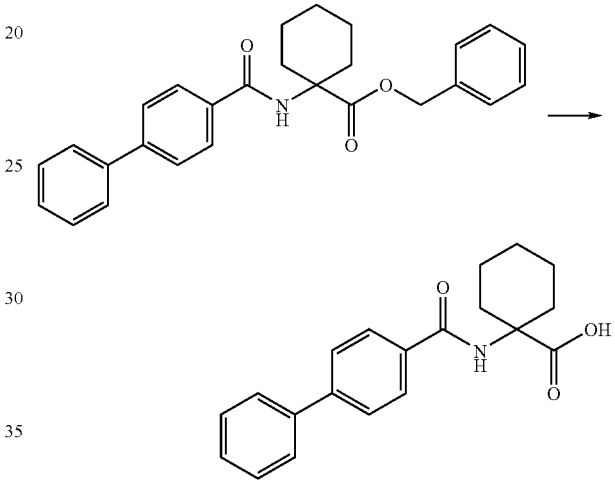

3.51 g (8.5 mmol) of 1-[(4-biphenylcarbonyl)amino]cyclohexanecarboxylic acid phenylmethyl ester was used instead of 1-[(phenylacetyl)amino]cyclohexanecarboxylic acid phenylmethyl ester in the process according to Reference Example 2 to obtain 2.75 g (quantitative) of the title compound.

1H-NMR (CDCl$_3$, δ): 1.37-1.48 (1H, m), 1.48-1.60 (2H, m) 1.66-1.73 (1H, m), 1.73-1.82 (2H, m), 2.00-2.10 (2H, m), 2.27-2.35 (2H, m), 6.32 (1H, br-s), 7.39-7.43 (1H, m), 7.46-7.49 (2H, m), 7.61-7.66 (2H, m), 7.68-7.70 (2H, m), 7.87-7.89 (2H, m)

Reference Example 9

1-[(2-Naphthylcarbonyl)amino]cyclohexanecarboxylic acid phenylmethyl ester

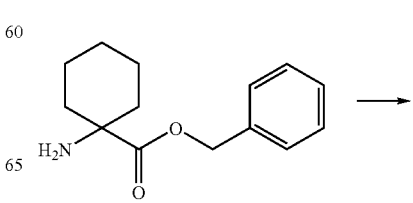

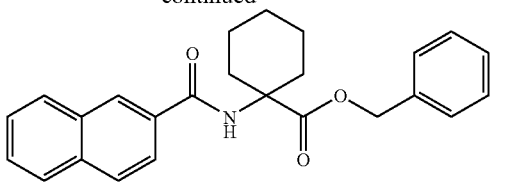

1.28 g (7.4 mmol) of 2-naphthoeic acid was used instead of 4-biphenylcarboxylic acid in the process according to Reference Example 7 to obtain 2.12 g (74%) of the title compound.

1H-NMR (CDCl$_3$, δ): 1.32-1.41 (1H, m), 1.48-1.61 (2H, m) 1.64-1.78 (3H, m), 1.95-2.01 (2H, m), 2.21-2.24 (2H, m), 5.19 (2H, s), 6.27 (1H, br-s), 7.27-7.36 (3H, m), 7.40 (1H, td, J=7 Hz, 1 Hz), 7.46-7.49 (2H, m), 7.61-7.63 (2H, m), 7.65-7.67 (2H, m), 7.83-7.85 (2H, m)

Reference Example 10

1-[(2-Naphthylcarbonyl)amino]cyclohexanecarboxylic acid

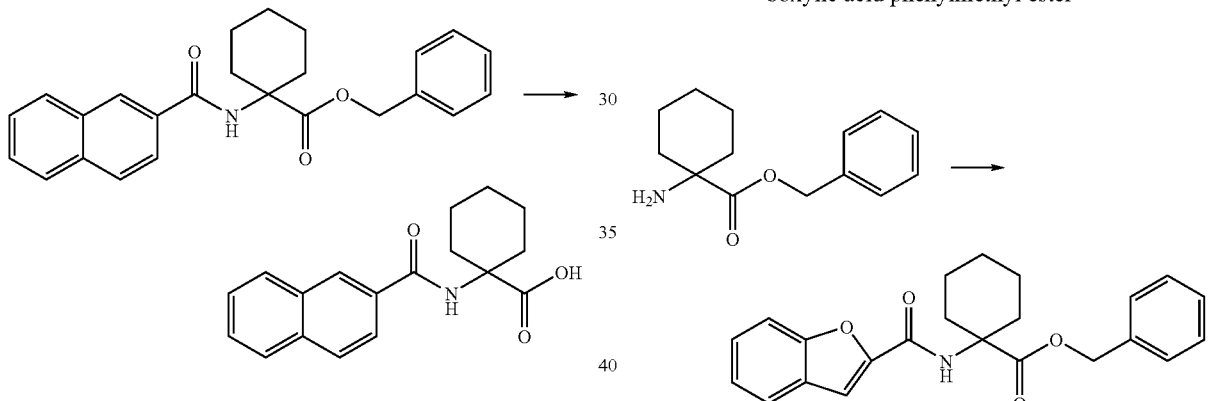

2.12 g (5.5 mmol) of 1-[(2-naphthylcarbonyl)amino]cyclohexanecarboxylic acid phenylmethyl ester was used instead of 1-[(phenylacetyl)amino]cyclohexanecarboxylic acid phenylmethyl ester in the process according to Reference Example 2 to obtain 1.63 g (quantitative) of the title compound.

1H-NMR (CDCl$_3$, δ): 1.41-1.45 (1H, m), 1.52-1.60 (2H, m), 1.70-1.74 (1H, m), 1.77-1.82 (2H, m), 2.03-2.09 (2H, m), 2.29-2.32 (2H, m), 6.41 (1H, br-s), 7.56-7.63 (2H, m), 7.83 (1H, dd, J=8 Hz, 2 Hz), 7.89-7.96 (3H, m), 8.33 (1H, s)

Reference Example 11

1-[(1-Naphthylcarbonyl)amino]cyclohexanecarboxylic acid phenylmethyl ester

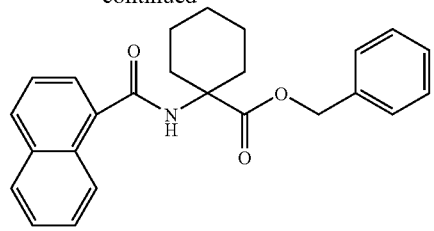

1.72 g (10 mmol) of 1-naphthoeic acid was used instead of 4-biphenylcarboxylic acid in the process according to Reference Example 7 to obtain 3.87 g (quantitative) of the title compound.

1H-NMR (CDCl$_3$, δ): 1.31-1.42 (1H, m), 1.45-1.60 (2H, m), 1.65-1.71 (1H, m), 1.71-1.80 (2H, m), 1.98-2.05 (2H, m), 2.24-2.32 (2H, m), 5.26 (2H, s), 6.10 (1H, br-s), 7.32-7.37 (3H, m), 7.40-7.45 (4H, m), 7.48-7.52 (1H, m), 7.57 (1H, dd, J=7 Hz, 1 Hz), 7.85 (1H, dd, J=7 Hz, 1 Hz), 7.91 (1H, dd, J=7 Hz, 1 Hz), 8.25 (1H, dd, J=7 Hz, 1 Hz)

Reference Example 12

1-[(2-Benzofuranylcarbonyl)amino]cyclohexanecarboxylic acid phenylmethyl ester 12.22 g (75.4 mmol) of benzofuran-2-carboxylic acid was used instead of 4-biphenylcarboxylic acid in the process according to Reference Example 7 to obtain 21.3 g (75%) of the title compound.

1H-NMR (CDCl$_3$, δ): 1.26-1.42 (1H, m), 1.50-1.61 (2H, m) 1.64-1.77 (3H, m), 1.95-2.04 (2H, m), 2.21-2.28 (2H, m), 5.19 (2H, s), 6.77 (1H, br-s), 7.25-7.34 (6H, m), 7.44 (1H, td, J=8 Hz, 2 Hz), 7.52 (1H, dd, J=8 Hz, 2 Hz), 7.57 (1H, dd, J=8 Hz, 2 Hz), 7.68 (1H, dd, J=8 Hz, 2 Hz)

Reference Example 13

1-[[[(RS)-2,3-Tetrahydrobenzofuran-2-yl]carbonyl]amino]cyclohexanecarboxylic acid

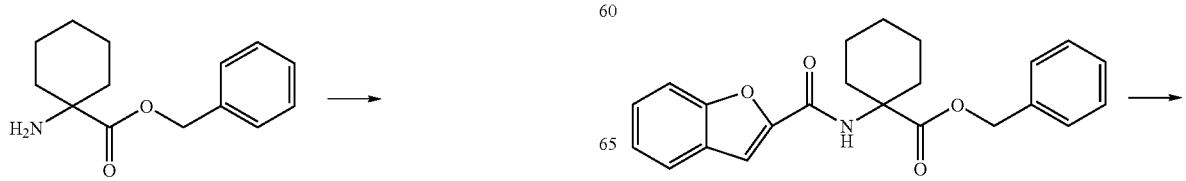

-continued

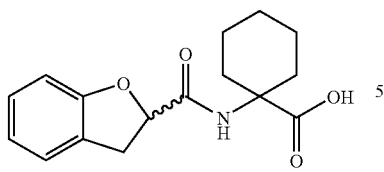

1.5 g of 10% palladium-carbon was added to a solution of 15 g (40 mmol) of 1-[(2-benzofuranylcarbonyl)amino]cyclohexanecarboxylic acid phenylmethyl ester in 300 ml of 2-propanol, and the mixture was stirred under a hydrogen atmosphere at 60° C. for 20 hours. After the reaction solution was filtered, the filtrate was concentrated under reduced pressure to obtain 11.57 g (quantitative) of the title compound.

1H-NMR (CDCl$_3$, δ): 1.07-1.19 (1H, m), 1.21-1.36 (2H, m) 1.50-1.63 (2H, m), 1.65-1.71 (1H, m), 1.80-1.88 (1H, m), 1.89-1.95 (1H, m), 2.04-2.15 (2H, m), 3.42 (1H, dd, J=17 Hz, 7 Hz), 3.60 (1H, dd, J=17 Hz, 7 Hz), 5.18 (1H, dd, J=7 Hz, 7 Hz), 6.84 (1H, br-s), 6.91 (1H, d, J=8 Hz), 6.96 (1H, dd, J=8 Hz, 1 Hz), 7.18 (1H, td, J=8 Hz, 1 Hz), 7.22 (1H, dd, J=8 Hz, 1 Hz)

Reference Example 14

1-[(2-Furanylcarbonyl)amino]cyclohexanecarboxylic acid

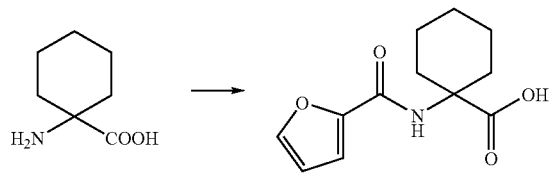 [SMILES: NC1(C(=O)O)CCCCC1 ; O=C(NC1(C(=O)O)CCCCC1)c1ccco1]

71.6 g (0.5 mol) of 1-aminocyclohexanecarboxylic acid was added to a solution of 20 g (0.5 mol) of sodium hydroxide in 250 ml of water, and the mixture was stirred at 80° C. for 2 hours. The mixture solution was cooled by ice-water, and 71.8 g (0.2 mol) of 2-furancarbonyl chloride and a solution of 24 g (0.6 mol) of sodium hydroxide in 100 ml in water were simultaneously added thereto for approximately 1 hour. The reaction solution was slowly returned to room temperature, and it was stirred overnight. After 80 ml of ethyl acetate was added to the reaction solution and the mixture was stirred for 1 hour, the insolubles were removed by filtration. The aqueous layer was separately collected, and 49 ml of concentrated hydrochloric acid was added thereto under ice-cooling. The precipitated crystal was collected by filtration and dried under reduced pressure to obtain 112.6 g (95%) of the title compound.

1H-NMR (CDCl$_3$, δ): 1.35-1.41 (1H, m), 1.48-1.53 (2H, m) 1.64-1.67 (1H, m), 1.71-1.76 (2H, m), 1.96-2.02 (2H, m), 2.20-2.24 (2H, m), 6.48 (1H, br-s), 6.55 (1H, dd, J=4 Hz, 2 Hz), 7.19 (1H, dd, J=4 Hz, 1 Hz), 7.50 (1H, dd, J=2 Hz, 1 Hz)

Reference Example 15

1-[(3-Furanylcarbonyl)amino]cyclohexanecarboxylic acid methyl ester

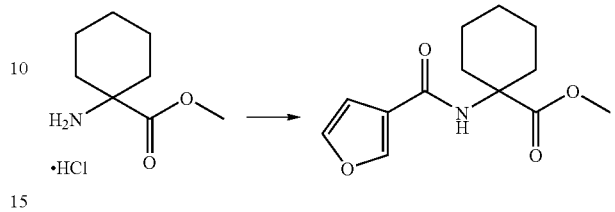

105 g (550 mmol) of 1-ethyl-3-(3-dimethylaminopropyl)carbodiimide hydrochloride was added to a solution of 98.8 g (500 mmol) of 1-aminocyclohexanecarboxylic acid methyl ester hydrochloride, 84.2 g (550 mmol) of 1-hydroxybenzotriazole, 56.0 g (500 mmol) of 3-furancarboxylic acid and 152 g (1.5 mol) of triethylamine in 1000 ml of methylene chloride under ice-cooling. After the mixture was stirred at room temperature overnight, the reaction solution was concentrated under reduced pressure. Ethyl acetate was added to the residue, and the mixture was successively washed with water, a 10% aqueous potassium hydrogensulfate solution, a saturated aqueous sodium hydrogencarbonate solution and saturated brine, followed by drying with anhydrous sodium sulfate. After the solvent was distilled off under reduced pressure, the obtained crystal was washed with diisopropyl ether to obtain 114 g (91%) of the title compound.

1H-NMR (CDCl$_3$, δ): 1.34-1.40 (1H, m), 1.43-1.44 (2H, m) 1.62-1.73 (3H, m), 1.90-1.96 (2H, m), 2.10-2.14 (2H, m), 3.73 (3H, s), 5.87 (1H, br-s), 6.23 (1H, dd, J=2 Hz, 1 Hz), 7.44 (1H, dd, J=2 Hz, 1 Hz), 7.94 (1H, dd, J=2 Hz, 1 Hz)

Reference Example 16

1-[(3-Furanylcarbonyl)amino]cyclohexanecarboxylic acid

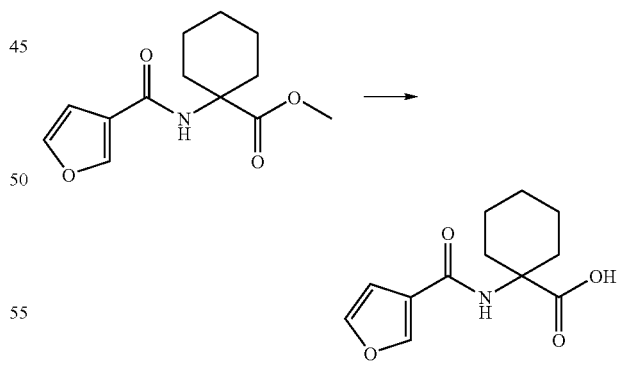

450 ml of 2N aqueous sodium hydroxide solution was added to a solution of 75.4 g (300 mmol) of 1-[(3-furanylcarbonyl)amino]cyclohexanecarboxylic acid methyl ester in 450 ml of tetrahydrofuran, and the mixture was heated under reflux for 3 hours. After ether was added to the reaction solution to wash it, the aqueous layer was neutralized by concentrated hydrochloric acid, it was extracted with ethyl acetate. After the obtained organic layer was washed with saturated brine, it was dried with anhydrous sodium sulfate.

The solvent was distilled off under reduced pressure to obtain 68.8 g (97%) of the title compound.

1H-NMR (CDCl₃, δ): 1.37-1.50 (3H, m), 1.58-1.64 (1H, m) 1.68-1.80 (2H, m), 1.98-2.05 (2H, m), 2.14-2.23 (2H, m), 5.87 (1H, s), 6.63 (1H, d, J=2 Hz), 7.49 (1H, d, J=2 Hz), 8.00 (1H, s)

Reference Example 17

1-[[(E)-3-(2-Furanyl)-1-oxo-2-propenyl]amino]cyclohexanecarboxylic acid methyl ester

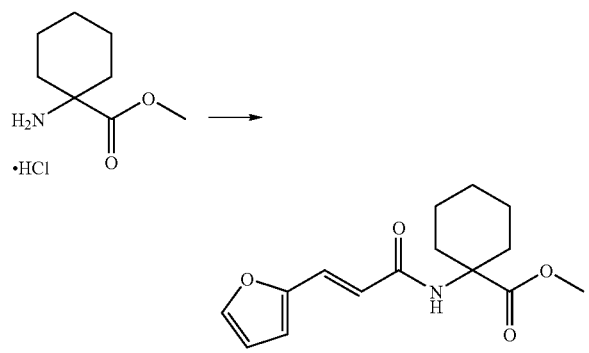

80 g (362 mmol) of 2-furanacrylic acid was used instead of 3-furancarboxylic acid in the process according to Reference Example 15 to obtain 89 g (89%) of the title compound.

1H-NMR (CDCl₃, δ): 1.29-1.39 (1H, m), 1.40-1.51 (2H, m), 1.58-1.71 (3H, m), 1.88-1.95 (2H, m), 2.05-2.14 (2H, m), 3.73 (3H, s), 5.67 (1H, br-s), 6.35 (1H, d, J=16 Hz), 6.45 (1H, dd, J=3 Hz, 2 Hz), 6.54 (1H, d, J=3 Hz), 7.37 (1H, d, J=16 Hz), 7.40 (1H, d, J=2 Hz)

Reference Example 18

1-[[(E)-3-(2-Furanyl)-1-oxo-2-propenyl]amino]cyclohexanecarboxylic acid

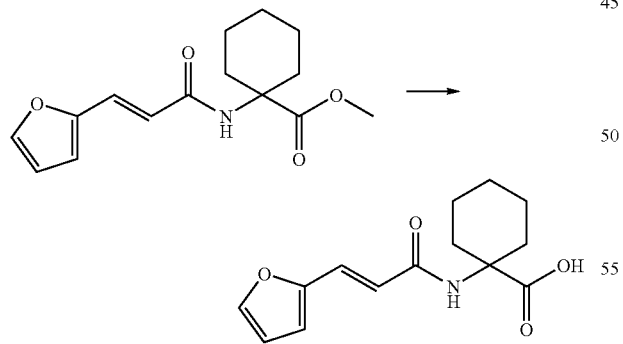

44.9 g (162 mmol) of 1-[[(E)-3-(2-furanyl)-1-oxo-2-propenyl]amino]cyclohexanecarboxylic acid methyl ester was used instead of 1-[(3-furanylcarbonyl)amino]cyclohexanecarboxylic acid methyl ester in the process according to Reference Example 16 to obtain 37.5 g (quantitative) of the title compound.

1H-NMR (CDCl₃, δ): 1.32-1.85 (6H, m), 1.96-2.05 (2H, m) 2.15-2.18 (2H, m), 5.66 (1H, br-s), 6.36 (1H, d, J=15 Hz), 6.49 (1H, dd, J=3 Hz, 2 Hz), 6.64 (1H, d, J=3 Hz), 7.48 (1H, d, J=15 Hz), 7.49 (1H, d, J=2 Hz)

Reference Example 19

1-[(2-Benzofuranylcarbonyl)amino]cyclohexanecarboxylic acid ethyl ester

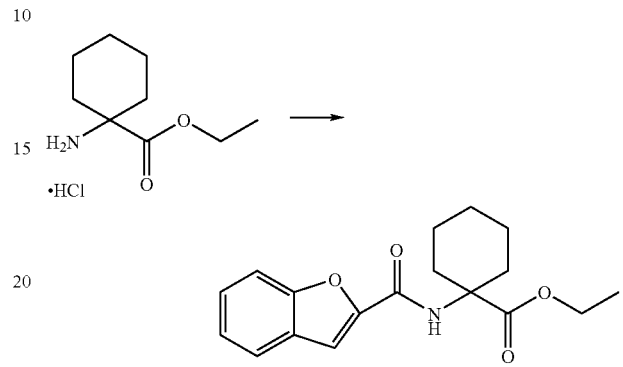

3.11 g (15 mmol) of 1-aminocyclohexanecarboxylic acid ethyl ester hydrochloride was used instead of 1-aminocyclohexanecarboxylic acid methyl ester hydrochloride, and 2.43 g (15 mmol) of benzofuran-2-carboxylic acid was used instead of 3-furancarboxylic acid in the process according to Reference Example 15 to obtain 3.80 g (80%) of the title compound.

1H-NMR (CDCl₃, δ): 1.26 (3H, t, J=7 Hz), 1.33-1.42 (1H, m), 1.50-1.62 (2H, m), 1.65-1.78 (3H, m), 1.94-2.02 (2H, m), 2.19-227 (2H, m), 4.21 (2H, q, J=7 Hz), 6.75 (1H, br-s), 7.30 (1H, td, J=8 Hz, 1 Hz), 7.43 (1H, td, J=8 Hz, 1 Hz), 7.45 (1H, d, J=1 Hz), 7.53 (1H, dd, J=8 Hz, 1 Hz), 7.67 (1H, dd, J=8 Hz, 1 Hz)

Reference Example 20

1-[(2-Benzofuranylcarbonyl)amino]cyclohexanecarboxylic acid

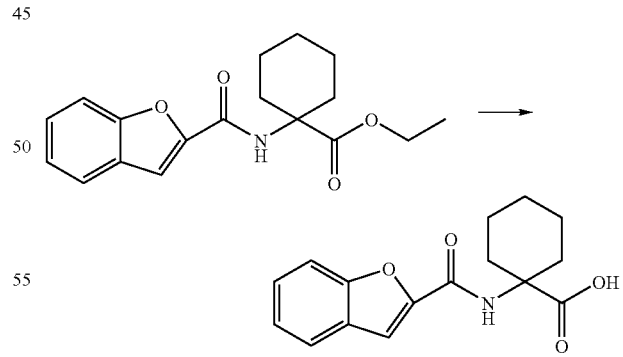

3.80 g (12 mmol) of 1-[(2-benzofuranylcarbonyl)amino]cyclohexanecarboxylic acid ethyl ester was used instead of 1-[(3-furanylcarbonyl)amino]cyclohexanecarboxylic acid methyl ester in the process according to Reference Example 16 to obtain 3.42 g (quantitative) of the title compound.

1H-NMR (CDCl₃, δ): 1.35-1.44 (1H, m), 1.50-1.62 (2H, m), 1.65-1.73 (1H, m), 1.74-1.82 (2H, m), 2.00-2.08 (2H, m), 2.25-2.33 (2H, m), 6.77 (1H, br-s), 7.32 (1H, td, J=8 Hz, 1

Hz), 7.46 (1H, td, J=8 Hz, 1 Hz), 7.53 (1H, d, J=1 Hz), 7.55 (1H, dd, J=8 Hz, 1 Hz), 7.70 (1H, dd, J=8 Hz, 1 Hz)

Reference Example 21

1-[(Cyclohexylcarbonyl)amino]cyclohexanecarboxylic acid phenylmethyl ester

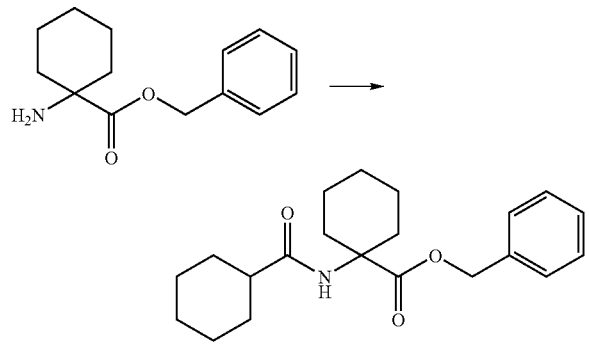

3.85 g (30 mmol) of cyclohexanecarboxylic acid was used instead of 4-biphenylcarboxylic acid in the process according to Reference Example 7 to obtain 4.77 g (46%) of the title compound.

1H-NMR (CDCl$_3$, δ): 1.17-1.45 (8H, m), 1.59-1.77 (4H, m) 1.73-1.88 (6H, m), 2.03-2.11 (3H, m), 5.12 (2H, s), 5.55 (1H, br-s), 7.23-7.36 (5H, m)

Reference Example 22

1-[(Cyclohexylcarbonyl)amino]cyclohexanecarboxylic acid

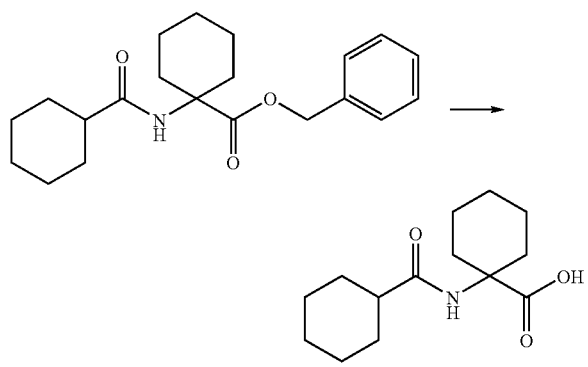

5.62 g (16.3 mmol) of 1-[(cyclohexylcarbonyl)amino]cyclohexanecarboxylic acid phenylmethyl ester was used instead of 1-[(phenylacetyl)amino]cyclohexanecarboxylic acid phenylmethyl ester in the process according to Reference Example 2 to obtain 4.15 g (quantitative) of the title compound.

1H-NMR (CDCl$_3$, δ): 1.18-1.50 (8H, m), 1.60-1.76 (4H, m) 1.78-1.95 (6H, m), 2.06-2.14 (2H, m), 2.16-2.23 (1H, m), 5.58 (1H, br-s)

Reference Example 23

1-[(6-Benzothiazolylcarbonyl)amino]cyclohexanecarboxylic acid phenylmethyl ester

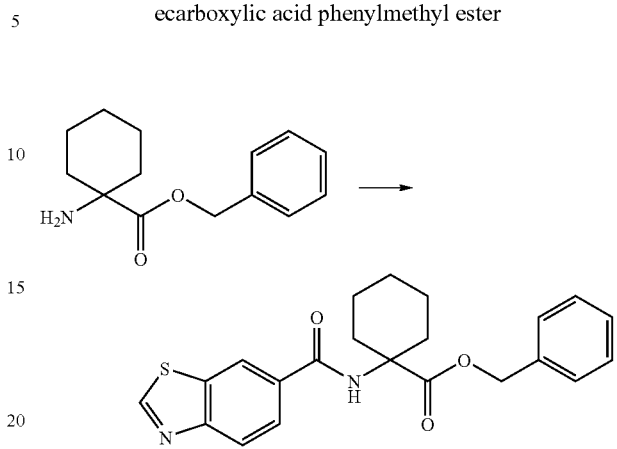

1.15 g (6.4 mmol) of benzothiazole-6-carboxylic acid was used instead of 4-biphenylcarboxylic acid in the process according to Reference Example 7 to obtain 1.58 g (62%) of the title compound.

1H-NMR (CDCl$_3$, δ): 1.35-1.43 (1H, m), 1.49-1.60 (2H, m), 1.61-1.78 (3H, m), 1.96-2.06 (2H, m), 2.20-2.27 (2H, m), 5.19 (2H, s), 6.30 (1H, br-s), 7.28-7.75 (5H, m), 7.86 (1H, dd, J=7 Hz, 2 Hz), 8.17 (1H, dd, J=7 Hz, 1 Hz), 8.41 (1H, dd, J=2 Hz, 1 Hz), 9.12 (1H, s)

Reference Example 24

1-[(6-Benzothiazolylcarbonyl)amino]cyclohexanecarboxylic acid

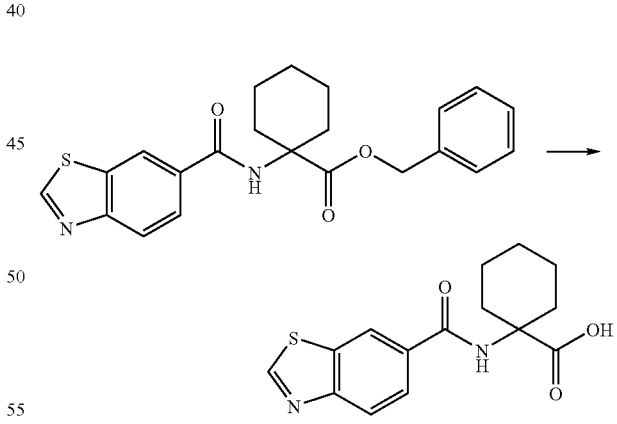

1.18 g (30 mmol) of 1-[(6-benzothiazolylcarbonyl)amino]cyclohexanecarboxylic acid phenylmethyl ester was used instead of 1-[(3-furanylcarbonyl)amino]cyclohexanecarboxylic acid methyl ester in the process according to Reference Example 16 to obtain 0.77 g (84%) of the title compound.

1H-NMR (CD$_3$OD, δ): 1.38-1.46 (1H, m), 1.60-1.76 (5H, m), 1.91-2.01 (2H, m), 2.21-2.28 (2H, m), 7.98 (1H, dd, J=7 Hz, 2 Hz), 8.12 (1H, dd, J=7 Hz, 1 Hz), 8.54 (1H, dd, J=2 Hz, 1 Hz), 9.37 (1H, s)

Reference Example 25

1-[[(6-Hydroxy-3-pyridinyl)carbonyl]amino]cyclo-hexanecarboxylic acid phenylmethyl ester

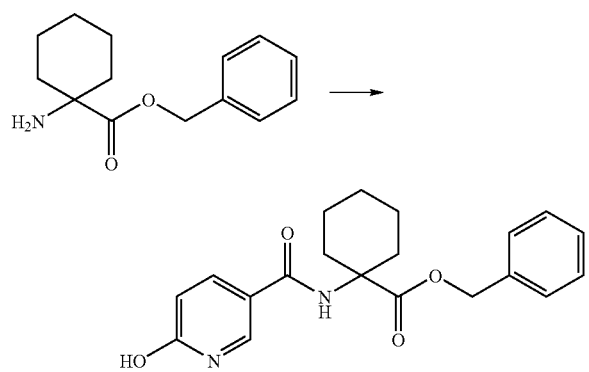

139 mg (1.0 mmol) of 6-hydroxy-3-pyridinecarboxylic acid was used instead of 4-biphenylcarboxylic acid in the process according to Reference Example 7 to obtain 222 mg (62%) of the title compound.

1H-NMR (CDCl$_3$, δ): 1.30-1.40 (1H, m), 1.42-1.54 (2H, m), 1.62-1.73 (3H, m), 1.91-1.98 (2H, m), 2.13-2.20 (2H, m), 5.17 (2H, s), 6.22 (1H, s), 6.54 (1H, d, J=10 Hz), 7.26-7.35 (5H, m), 7.76 (1H, dd, J=10 Hz, 3 Hz), 7.93 (1H, d, J=3 Hz)

Reference Example 26

1-[[(6-Hydroxy-3-pyridinyl)carbonyl]amino]cyclo-hexanecarboxylic acid

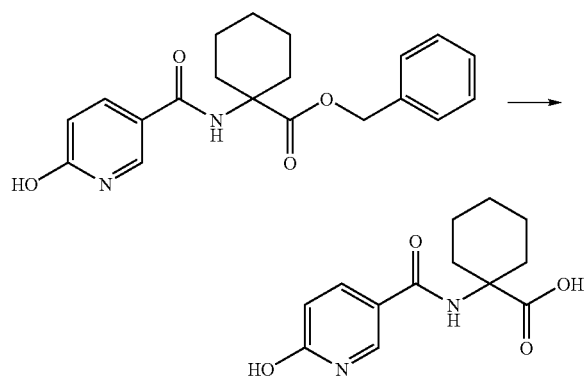

760 mg (2.2 mmol) of 1-[[(6-hydroxy-3-pyridinyl)carbonyl]amino]cyclohexanecarboxylic acid phenylmethyl ester was used instead of 1-[(phenylacetyl)amino]cyclohexanecarboxylic acid phenylmethyl ester in the process according to Reference Example 2 to obtain 565 mg (quantitative) of the title compound.

1H-NMR (CD$_3$OD, δ): 1.21-1.30 (1H, m), 1.43-1.54 (5H, m), 1.67-1.74 (2H, m), 2.03-2.09 (2H, m), 6.33 (1H, d, J=9 Hz), 7.84 (1H, dd, J=9 Hz, 3 Hz), 8.05 (1H, d, J=3 Hz)

Reference Example 27

1-[(2-Thienylcarbonyl)amino]cyclohexanecarboxylic acid

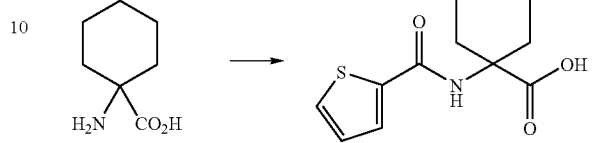

100 g (680 mmol) of 2-thiophenecarbonyl chloride was used instead of 2-furancarbonyl chloride in the process according to Reference Example 14 to obtain 57.6 g (51%) of the title compound.

1H-NMR (CDCl$_3$, δ): 1.35-1.54 (3H, m), 1.65-1.80 (3H, m), 1.98-2.05 (2H, m), 2.21-2.27 (2H, m), 6.06 (1H, br-s), 7.13 (1H, dd, J=5 Hz, 3 Hz), 7.57 (1H, dd, J=5 Hz, 1 Hz), 7.59 (1H, dd, J=3 Hz, 1 Hz)

Reference Example 28

1-[(2-Pyridinylcarbonyl)amino]cyclohexanecarboxylic acid methyl ester

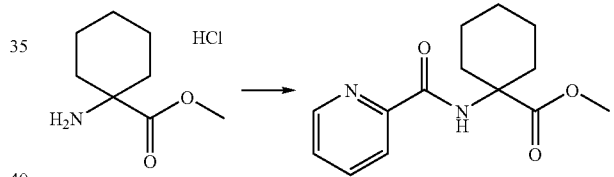

370 mg (3 mmol) of 2-pyridinecarboxylic acid was used instead of 3-furancarboxylic acid in the process according to Reference Example 15 to obtain 600 mg (76%) of the title compound.

1H-NMR (CDCl$_3$, δ): 1.31-1.42 (1H, m), 1.51-1.73 (5H, m), 1.95 (2H, td, J=13 Hz, 4 Hz), 1.99-2.08 (2H, m), 3.73 (3H, s), 7.44 (1H, ddd, J=8 Hz, 5 Hz, 2 Hz), 7.84 (1H, dd, J=8 Hz, 2 Hz), 8.16 (1H, d, J=8 Hz), 8.33 (1H, s), 8.57 (1H, dd, J=5 Hz, 2 Hz)

Reference Example 29

1-[(2-Pyridinylcarbonyl)amino]cyclohexanecarboxylic acid

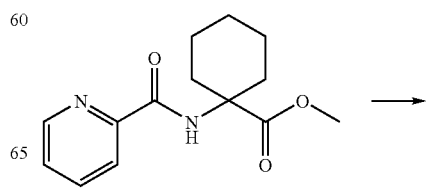

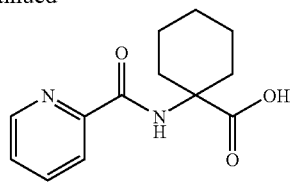

539 mg (2 mmol) of 1-[(2-pyridinylcarbonyl)amino]cyclohexanecarboxylic acid methyl ester was used instead of 1-[(3-furanylcarbonyl)amino]cyclohexanecarboxylic acid methyl ester in the process according to Reference Example 16 to obtain 479 mg (quantitative) of the title compound.

1H-NMR (CDCl$_3$, δ): 1.32-1.41 (1H, m), 1.48-1.57 (2H, m), 1.62-1.78 (3H, m), 1.98 (2H, m), 2.25-2.35 (2H, m), 7.50 (1H, ddd, J=8 Hz, 5 Hz, 2 Hz), 7.89 (1H, dd, J=8 Hz, 2 Hz), 8.19 (1H, d, J=8 Hz), 8.59 (1H, s), 8.60 (1H, dd, J=5 Hz, 2 Hz)

Reference Example 30

1-[(3-Thienylcarbonyl)amino]cyclohexanecarboxylic acid methyl ester

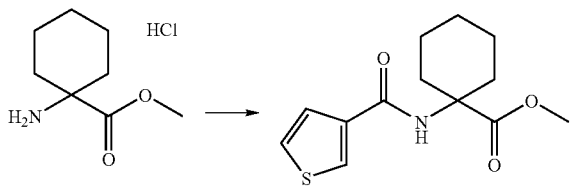 [SMILES: COC(=O)C1(N)CCCCC1 ; Cl ; COC(=O)C1(NC(=O)c2ccsc2)CCCCC1]

384 mg (3 mmol) of 3-thiophenecarboxylic acid was used instead of 3-furancarboxylic acid in the process according to Reference Example 15 to obtain 759 mg (95%) of the title compound.

1H-NMR (CDCl$_3$, δ): 1.32-1.41 (1H, m), 1.42-1.55 (2H, m), 1.61-1.75 (3H, m), 1.90-1.99 (2H, m), 2.11-2.18 (2H, m), 3.74 (3H, s), 6.26 (1H, br-s), 7.35 (1H, dd, J=5 Hz, 2 Hz), 7.39 (1H, dd, J=5 Hz, 2 Hz), 7.88 (1H, dd, J=3 Hz, 2 Hz)

Reference Example 31

1-[(3-Thienylcarbonyl)amino]cyclohexanecarboxylic acid

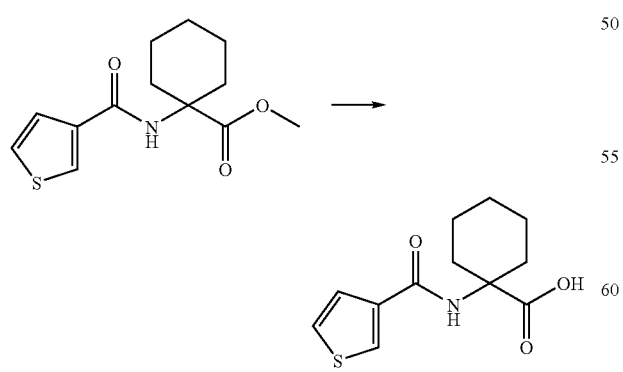

759 mg (2.8 mmol) of 1-[(3-thienylcarbonyl)amino]cyclohexanecarboxylic acid methyl ester was used instead of 1-[(3-furanylcarbonyl)amino]cyclohexanecarboxylic acid methyl ester in the process according to Reference Example 16 to obtain 692 mg (96%) of the title compound.

1H-NMR (DMSO-d$_6$, δ): 1.24-1.32 (1H, m), 1.45-1.55 (5H, m), 1.72-1.78 (2H, m), 2.05-2.12 (2H, m), 7.50 (1H, dd, J=5 Hz, 2 Hz), 7.57 (1H, dd, J=5 Hz, 2 Hz), 7.96 (1H, br-s), 8.21 (1H, dd, J=3 Hz, 2 Hz)

Reference Example 32

1-[[(3-Ethoxy-2-thienyl)carbonyl]amino]cyclohexanecarboxylic acid

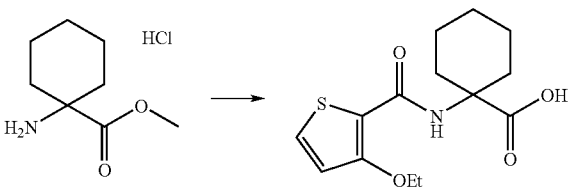 [SMILES: COC(=O)C1(N)CCCCC1 ; Cl ; CCOc1ccsc1C(=O)NC1(C(=O)O)CCCCC1]

633 mg (3.3 mmol) of 1-ethyl-3-(3-dimethylaminopropyl)carbodiimide hydrochloride was added to a solution of 581 mg (3 mmol) of 1-aminocyclohexanecarboxylic acid methyl ester hydrochloride, 482 mg (3.1 mmol) of 1-hydroxybenzotriazole, 517 mg (3 mmol) of 3-ethoxy-2-thiophenecarboxylic acid and 1.16 g (9 mmol) of diisopropylethylamine in 10 ml of methylene chloride under ice-cooling. After the mixture was stirred at room temperature overnight, the reaction solution was concentrated under reduced pressure, ethyl acetate was added thereto, and the mixture was washed with water, a 10% aqueous potassium hydrogensulfate solution, a saturated aqueous sodium hydrogencarbonate solution and then saturated brine, followed by drying with anhydrous sodium sulfate. After the solvent was distilled off under reduced pressure, diisopropyl ether was added to the residue, the mixture was stirred overnight, and the crystal was collected by filtration. Then, the obtained crystal was dissolved in 3 ml of tetrahydrofuran solution, 2.8 ml of 2N aqueous NaOH solution was added thereto, and the mixture was heated under reflux for 3 hours. Ether was added to the reaction solution and the aqueous layer was separated. After the separated aqueous layer was neutralized by concentrated hydrochloric acid, it was extracted with ethyl acetate. After the obtained organic layer was washed with saturated brine, it was dried with anhydrous sodium sulfate. The solvent was distilled off under reduced pressure to obtain 656 mg (73%) of the title compound.

1H-NMR (CDCl$_3$, δ): 1.29-1.40 (1H, m), 1.43-1.54 (2H, m), 1.50 (3H, t, J=7 Hz), 1.62-1.76 (3H, m), 1.90-2.00 (2H, m), 2.22-2.30 (2H, m), 4.30 (2H, q, J=7 Hz), 6.87 (1H, d, J=6 Hz), 7.49 (1H, d, J=6 Hz), 7.60 (1H, s)

Reference Example 33

1-[[(S)-1-Oxo-2-phenylpropyl]amino]cyclohexanecarboxylic acid methyl ester

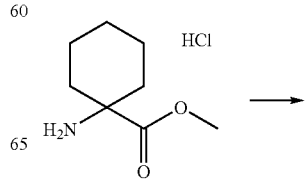

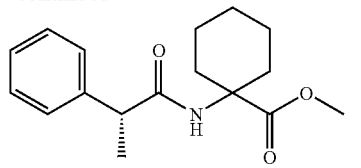

451 mg (3 mmol) of (S)-(+)-2-phenylpropionic acid was used instead of 3-furancarboxylic acid in the process according to Reference Example 15 to obtain 601 mg (69%) of the title compound.

1H-NMR (CDCl$_3$, δ): 1.06-1.22 (2H, m), 1.48-1.61 (7H, m), 1.71-1.77 (2H, m), 1.90-1.96 (2H, m), 3.60 (1H, q, 7 Hz), 3.67 (3H, s), 5.40 (1H, br-s), 7.27-7.39 (5H, m)

Reference Example 34

1-[[(S)-1-Oxo-2-phenylpropyl]amino]cyclohexanecarboxylic acid

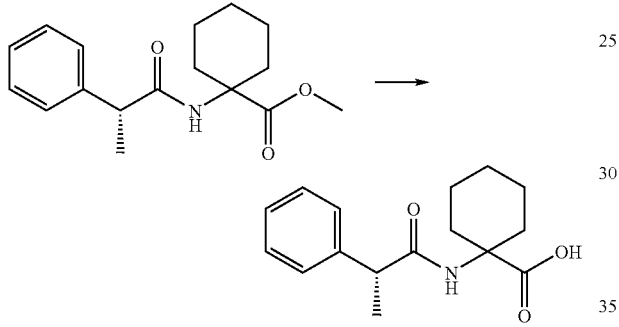

608 mg (2.1 mmol) of 1-[[(S)-1-oxo-2-phenylpropyl]amino]cyclohexanecarboxylic acid methyl ester was used instead of 1-[(3-furanylcarbonyl)amino]cyclohexanecarboxylic acid methyl ester in the process according to Reference Example 16 to obtain 366 mg (63%) of the title compound.

1H-NMR (DMSO-d$_6$, δ): 1.08-1.21 (2H, m), 1.28-1.47 (7H, m), 1.53-1.62 (2H, m), 1.93 (2H, br-s), 3.79 (1H, q, J=7 Hz), 7.18-7.21 (1H, m), 7.27-7.33 (4H, m), 7.90 (1H, s), 12.00 (1H, s)

Reference Example 35

1-[(2-Pyrazinylcarbonyl)amino]cyclohexanecarboxylic acid methyl ester

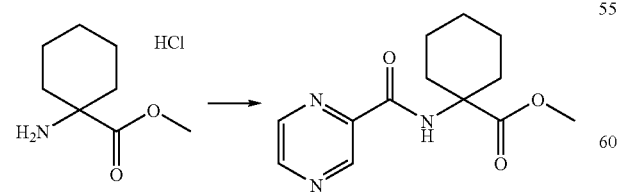

372 mg (3 mmol) of 2-pyrazinecarboxylic acid was used instead of 3-furancarboxylic acid in the process according to Reference Example 15 to obtain 476 mg (60%) of the title compound.

1H-NMR (CDCl$_3$, δ): 1.35-1.40 (1H, m), 1.47-1.59 (2H, m), 1.65-1.75 (3H, m), 1.94-2.00 (2H, m), 2.18-2.29 (2H, m), 3.75 (3H, s), 8.03 (1H, s), 8.55 (1H, dd, J=3 Hz, 1 Hz), 8.77 (1H, d, J=3 Hz), 9.38 (1H, d, J=1 Hz)

Reference Example 36

1-[(2-Pyrazinylcarbonyl)amino]cyclohexanecarboxylic acid

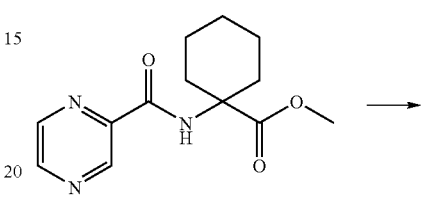

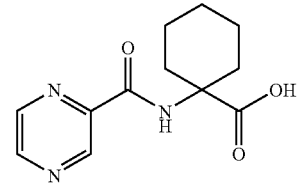

476 mg (1.8 mmol) of 1-[(2-pyrazinylcarbonyl)amino]cyclohexanecarboxylic acid methyl ester was used instead of 1-[(3-furanylcarbonyl)amino]cyclohexanecarboxylic acid methyl ester in the process according to Reference Example 16 to obtain 356 mg (79%) of the title compound.

1H-NMR (DMSO-d$_6$, δ): 1.28-1.59 (6H, m), 1.79 (2H, td, J=12 Hz, 4 Hz), 2.10-2.19 (2H, m), 8.35 (1H, s), 8.75 (1H, d, J=2 Hz), 8.89 (1H, d, J=2 Hz), 9.14 (1H, d, J=2 Hz), 12.42 (1H, s)

Reference Example 37

1-[[(5-Methyl-2-thienyl)carbonyl]amino]cyclohexanecarboxylic acid methyl ester

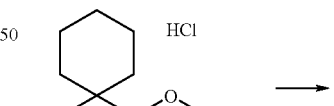

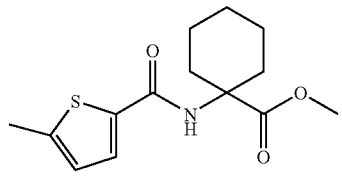

427 mg (3 mmol) of 5-methyl-2-thiophenecarboxylic acid was used instead of 3-furancarboxylic acid in the process according to Reference Example 15 to obtain 812 mg (96%) of the title compound.

1H-NMR (CDCl$_3$, δ): 1.36-1.72 (6H, m), 1.92 (2H, td, J=13 Hz, 4 Hz), 2.11-2.19 (2H, m), 2.51 (3H, s), 3.73 (3H, s), 5.95 (1H, s), 6.74 (1H, d, J=4 Hz), 7.34 (1H, d, J=4 Hz)

Reference Example 38

1-[[(5-Methyl-2-thienyl)carbonyl]amino]cyclohexanecarboxylic acid

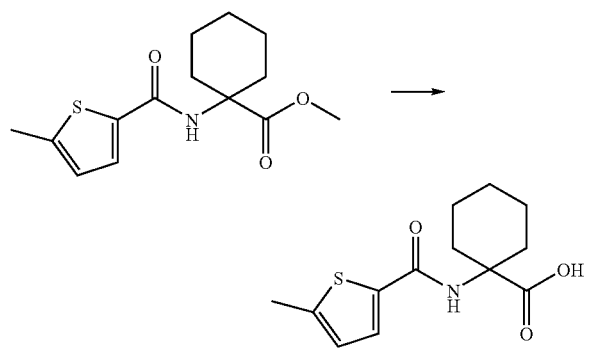

812 mg (2.9 mmol) of 1-[[(5-methyl-2-thienyl)carbonyl]amino]cyclohexanecarboxylic acid methyl ester was used instead of 1-[(3-furanylcarbonyl)amino]cyclohexanecarboxylic acid methyl ester in the process according to Reference Example 16 to obtain 771 mg (99%) of the title compound.

1H-NMR (DMSO-d$_6$, δ): 1.21-1.38 (1H, m), 1.52 (5H, br-s), 1.68-1.80 (2H, m), 2.01-2.12 (2H, m), 2.46 (3H, s), 6.84 (1H, d, J=4 Hz), 7.70 (1H, s), 8.02 (1H, s)

Reference Example 39

1-[[(4-Methoxyphenyl)carbonyl]amino]cyclohexanecarboxylic acid methyl ester

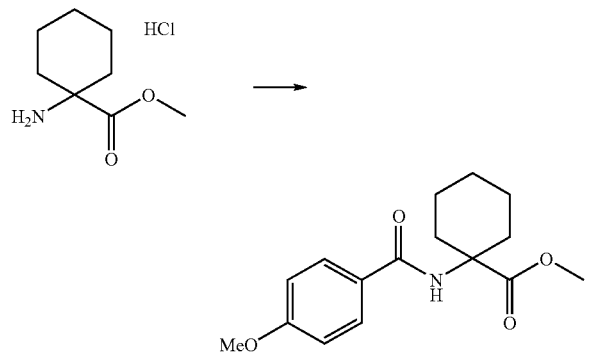

581 mg (3 mmol) of 1-aminocyclohexanecarboxylic acid methyl ester hydrochloride was used instead of 1-aminocyclohexanecarboxylic acid phenylmethyl ester, and 512 mg (3 mmol) of 4-methoxybenzoyl chloride was used instead of phenylacetyl chloride in the process according to Reference Example 1 to obtain 619 mg (71%) of the title compound.

1H-NMR (CDCl$_3$, δ): 1.32-1.41 (1H, m), 1.49-1.74 (5H, m) 1.94 (2H, td, J=13 Hz, 4 Hz), 2.12-2.22 (2H, m), 3.73 (3H, s), 3.85 (3H, s), 6.16 (1H, br-s), 6.92 (2H, dd, J=7 Hz, 2 Hz), 7.76 (2H, dd, J=7 Hz, 2 Hz)

Reference Example 40

1-[[(4-Methoxyphenyl)carbonyl]amino]cyclohexanecarboxylic acid

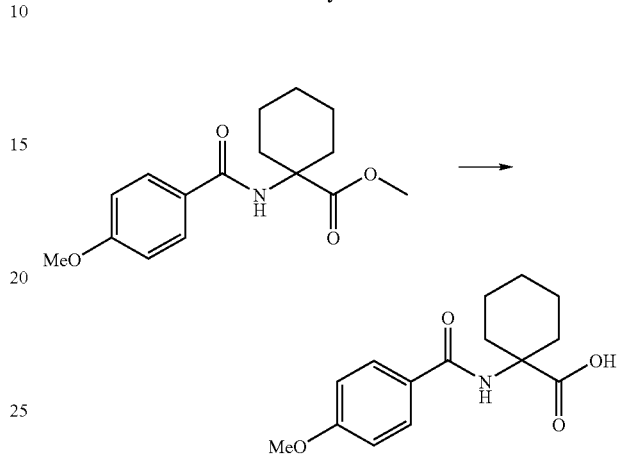

619 mg (2.1 mmol) of 1-[[(4-methoxyphenyl)carbonyl]amino]cyclohexanecarboxylic acid methyl ester was used instead of 1-[(3-furanylcarbonyl)amino]cyclohexanecarboxylic acid methyl ester in the process according to Reference Example 16 to obtain 552 mg (94%) of the title compound.

1H-NMR (DMSO-d$_6$, δ): 1.22-1.38 (1H, m), 1.51-1.60 (5H, br-s), 1.65-1.79 (2H, m), 2.04-2.19 (2H, m), 3.81 (3H, s), 6.98 (2H, d, J=9 Hz), 7.83 (2H, d, J=9 Hz), 8.04 (1H, s), 12.3 (1H, br-s)

Reference Example 41

1-[[(3-Methyl-2-thienyl)carbonyl]amino]cyclohexanecarboxylic acid methyl ester

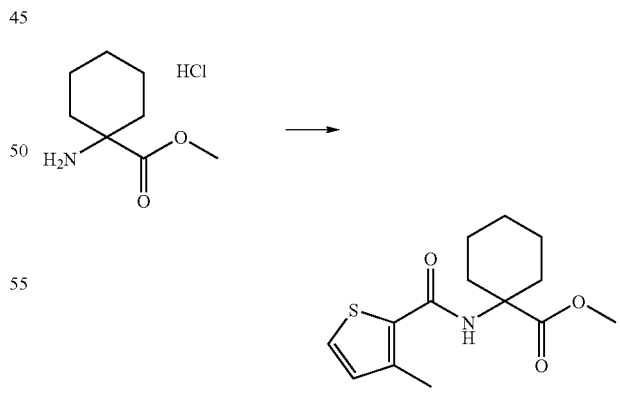

581 mg (3 mmol) of 1-aminocyclohexanecarboxylic acid methyl ester hydrochloride was used instead of 1-aminocyclohexanecarboxylic acid phenylmethyl ester, and 482 mg (3 mmol) of 3-methyl-2-thiophenecarbonyl chloride was used instead of phenylacetyl chloride in the process according to Reference Example 1 to obtain 394 mg (47%) of the title compound.

1H-NMR (CDCl₃, δ): 1.32-1.42 (1H, m), 1.49-1.53 (2H, m), 1.70-1.72 (3H, m), 1.92 (2H, td, J=12 Hz, 4 Hz), 2.11-2.22 (2H, m), 2.36 (3H, s), 3.74 (3H, s), 6.33 (1H, d, J=2 Hz), 6.44 (1H, br-s), 7.30 (1H, d, J=2 Hz)

Reference Example 42

1-[[(3-Methyl-2-thienyl)carbonyl]amino]cyclohexanecarboxylic acid

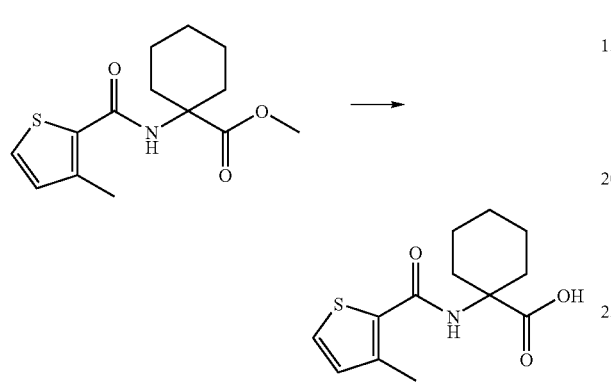

394 mg (1.4 mmol) of 1-[[(3-methyl-2-thienyl)carbonyl]amino]cyclohexanecarboxylic acid methyl ester was used instead of 1-[(3-furanylcarbonyl)amino]cyclohexanecarboxylic acid methyl ester in the process according to Reference Example 16 to obtain 330 mg (88%) of the title compound.

1H-NMR (CDCl₃, δ): 1.36-1.53 (3H, m), 1.68-1.78 (3H, m), 1.96-2.05 (2H, m), 1.99-2.08 (2H, m), 2.55 (3H, s), 5.91 (1H, s), 6.94 (1H, d, J=5 Hz), 7.35 (1H, d J=5 Hz)

Reference Example 43

1-[[(3-Methyl-2-furanyl)carbonyl]amino]cyclohexanecarboxylic acid

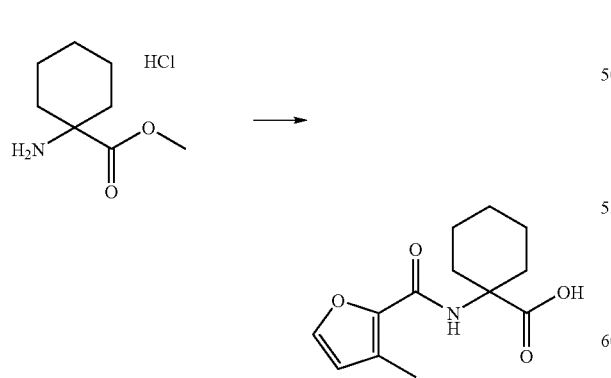

756 mg (6 mmol) of 3-methyl-2-furancarboxylic acid was used instead of 3-ethoxy-2-thiophenecarboxylic acid in the process according to Reference Example 32 to obtain 902 mg (59%) of the title compound.

1H-NMR (DMSO-d₆, δ): 1.20-1.38 (1H, m), 1.40-1.59 (5H, m), 1.70-1.80 (2H, m), 2.02-2.18 (2H, m), 2.25 (3H, s), 6.50 (1H, d, J=1 Hz), 7.67 (1H, s), 7.68 (1H, d, J=1 Hz)

Reference Example 44

1-[(3-Pyridinylcarbonyl)amino]cyclohexanecarboxylic acid methyl ester

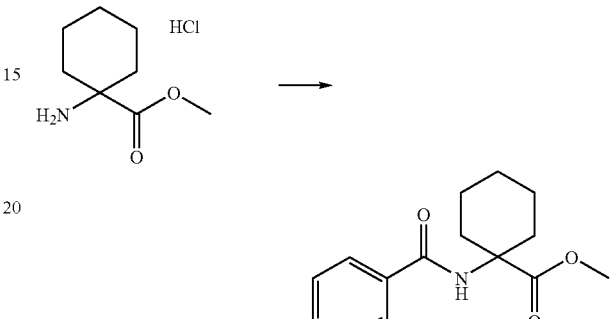

370 mg (3 mmol) of 3-pyridinecarboxylic acid was used instead of 3-furancarboxylic acid in the process according to Reference Example 15 to obtain 539 mg (68%) of the title compound.

1H-NMR (CDCl₃, δ): 1.32-1.42 (1H, m), 1.45-1.55 (2H, m), 1.62-1.78 (3H, m), 1.92-2.01 (2H, m), 2.12-2.21 (2H, m), 3.75 (3H, s), 6.27 (1H, s), 7.40 (1H, dd, J=8 Hz, 5 Hz), 8.12 (1H, d, J=8 Hz), 8.74 (1H, d, J=5 Hz), 9.00 (1H, s)

Reference Example 45

1-[(3-Pyridinylcarbonyl)amino]cyclohexanecarboxylic acid

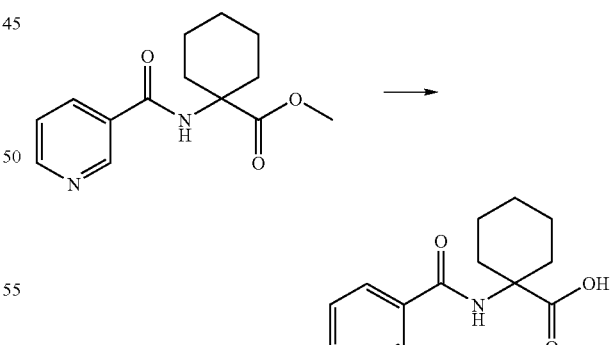

539 mg (2 mmol) of 1-[(3-pyridinylcarbonyl)amino]cyclohexanecarboxylic acid methyl ester was used instead of 1-[(3-furanylcarbonyl)amino]cyclohexanecarboxylic acid methyl ester in the process according to Reference Example 16 to obtain 508 mg (quantitative) of the title compound.

1H-NMR (DMSO-d₆, δ): 1.22-1.35 (1H, m), 1.49-1.62 (5H, m), 1.69-1.82 (2H, m), 2.09-2.17 (2H, m), 7.50 (1H, dd,

J=8 Hz, 5 Hz), 8.16 (1H, d, J=8 Hz), 8.44 (1H, s), 8.71 (1H, d, J=5 Hz), 8.97 (1H, s), 12.24 (1H, br-s)

Reference Example 46

1-[[(1-Methyl-1H-pyrrol-2-yl)carbonyl]amino]cyclohexanecarboxylic acid methyl ester

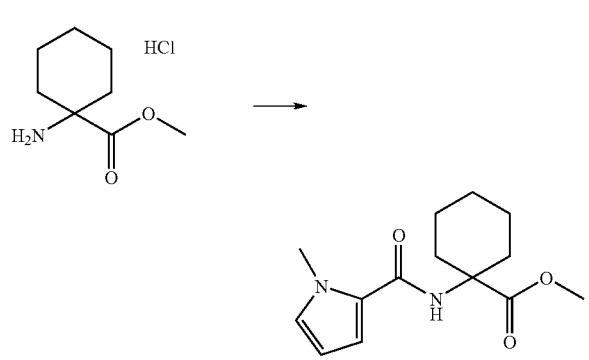

375 mg (3 mmol) of 1-methyl-2-pyrrolecarboxylic acid was used instead of 3-furancarboxylic acid in the process according to Reference Example 15 to obtain 320 mg (40%) of the title compound.

1H-NMR (CDCl$_3$, δ): 1.28-1.40 (1H, m), 1.44-1.55 (2H, m) 1.61-1.74 (3H, m), 1.86-1.95 (2H, m), 2.05-2.16 (2H, m), 3.73 (3H, s), 3.89 (3H, s), 5.97 (1H, s), 6.09 (1H, dd, J=4 Hz, 3 Hz), 6.59 (1H, dd, J=4 Hz, 2 Hz), 6.71 (1H, dd, J=3 Hz, 2 Hz)

Reference Example 47

1-[[(1-Methyl-1H-pyrrol-2-yl)carbonyl]amino]cyclohexanecarboxylic acid

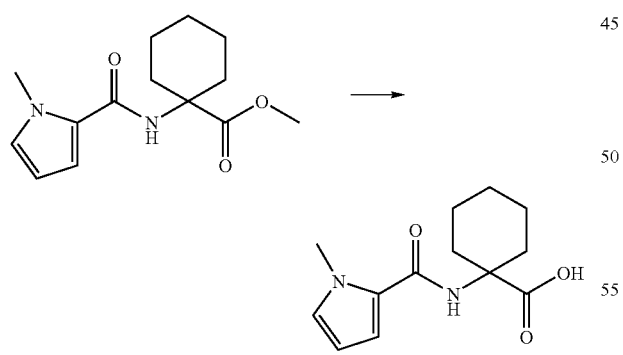

320 mg (1.2 mmol) of 1-[[(1-methyl-1H-pyrrol-2-yl)carbonyl]amino]cyclohexanecarboxylic acid methyl ester was used instead of 1-[(3-furanylcarbonyl)amino]cyclohexanecarboxylic acid methyl ester in the process according to Reference Example 16 to obtain 187 mg (62%) of the title compound.

1H-NMR (CDCl$_3$, δ): 1.31-1.53 (3H, m), 1.62-1.79 (3H, m), 1.91-2.02 (2H, m), 2.18-2.24 (2H, m), 3.93 (3H, s), 5.92 (1H, s), 6.14 (1H, dd, J=4 Hz, 3 Hz), 6.68 (1H, dd, J=4 Hz, 2 Hz), 6.81 (1H, dd, J=3 Hz, 2 Hz)

Reference Example 48

1-[((R)-1-Oxo-2-phenylpropyl)amino]cyclohexanecarboxylic acid methyl ester

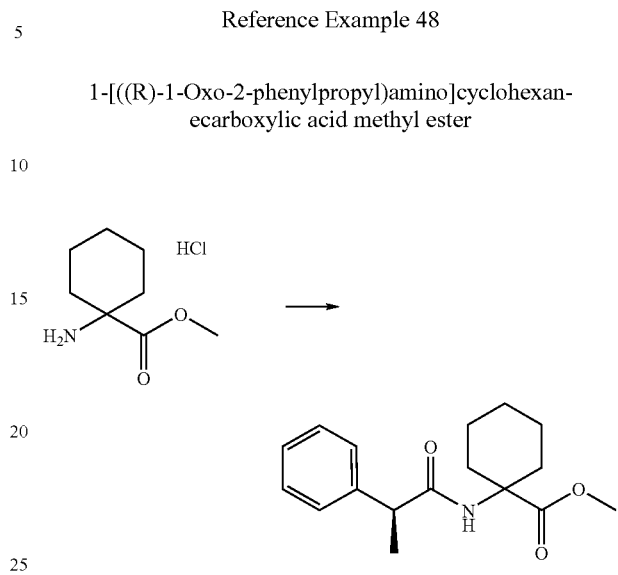

451 mg (3 mmol) of (R)-(−)-2-phenylpropionic acid was used instead of 3-furancarboxylic acid in the process according to Reference Example 15 to obtain 435 mg (50%) of the title compound.

1H-NMR (CDCl$_3$, δ): 1.03-1.22 (3H, m), 1.48-1.62 (6H, m), 1.88-2.00 (2H, m), 3.60 (3H, q, J=7 Hz), 3.68 (3H, s), 5.40 (1H, br-s), 7.27-7.39 (5H, m)

Reference Example 49

1-[((R)-1-Oxo-2-phenylpropyl)amino]cyclohexanecarboxylic acid

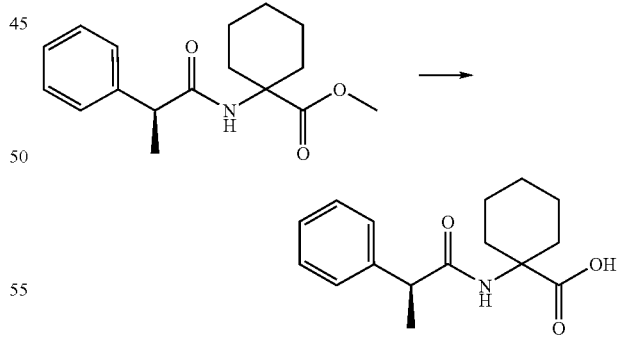

435 mg (1.5 mmol) of 1-[((R)-1-oxo-2-phenylpropyl)amino]cyclohexanecarboxylic acid methyl ester was used instead of 1-[(3-furanylcarbonyl)amino]cyclohexanecarboxylic acid methyl ester in the process according to Reference Example 16 to obtain 349 mg (84%) of the title compound.

1H-NMR (DMSO-d$_6$, δ): 1.15-1.23 (2H, m), 1.29 (3H, d, J=7 Hz), 1.35-1.53 (4H, m), 1.53-1.63 (2H, m), 1.91 (2H, br-s), 3.78 (1H, q, J=7 Hz), 7.18-7.20 (1H, m), 7.21-7.32 (4H, m), 7.90 (1H, s), 12.00 (1H, s)

J=3 Hz), 7.40-7.43 (2H, m), 7.60 (1H, dd, J=3 Hz, 1 Hz), 8.03 (1H, s), 8.14 (1H, s), 11.31 (1H, s), 12.04 (1H, s)

Reference Example 50

1-[(1H-Indol-5-ylcarbonyl)amino]cyclohexanecarboxylic acid methyl ester

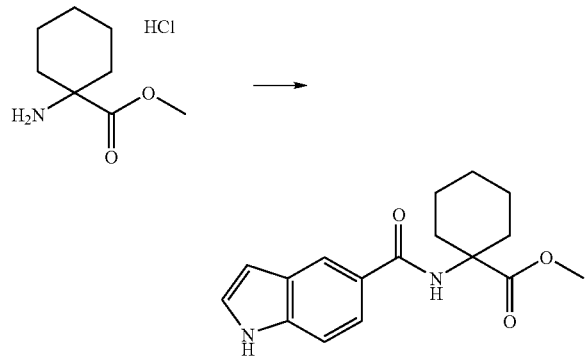

483 mg (3 mmol) of indole-5-carboxylic acid was used instead of 3-furancarboxylic acid in the process according to Reference Example 15 to obtain 766 mg (85%) of the title compound.

1H-NMR (DMSO-$d_6$, δ): 1.16-1.33 (1H, m), 1.54-1.63 (5H, m), 1.75-1.80 (2H, m), 2.04-2.18 (2H, m), 3.33 (3H, s), 6.52-6.56 (1H, m), 7.40 (1H, s), 7.41-7.44 (1H, m), 7.60 (1H, dd, J=9 Hz, 2 Hz), 8.14 (1H, d, J=2 Hz), 8.18 (1H, s), 11.32 (1H, s)

Reference Example 51

1-[(1H-Indol-5-ylcarbonyl)amino]cyclohexanecarboxylic acid

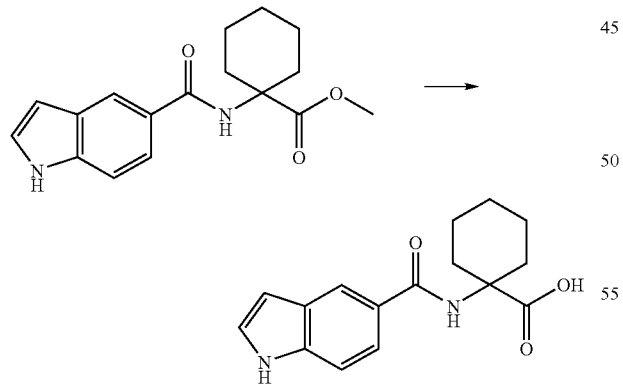

766 mg (2.6 mmol) of 1-[(1H-indol-5-ylcarbonyl)amino]cyclohexanecarboxylic acid methyl ester was used instead of 1-[(3-furanylcarbonyl)amino]cyclohexanecarboxylic acid methyl ester in the process according to Reference Example 16 to obtain 561 mg (77%) of the title compound.

1H-NMR (DMSO-$d_6$, δ): 1.22-1.38 (1H, m), 1.55-1.62 (5H, m), 1.63-1.79 (2H, m), 2.10-2.22 (2H, m), 6.54 (1H, d,

Reference Example 52

1-[(1-Cyclopentenylcarbonyl)amino]cyclohexanecarboxylic acid methyl ester

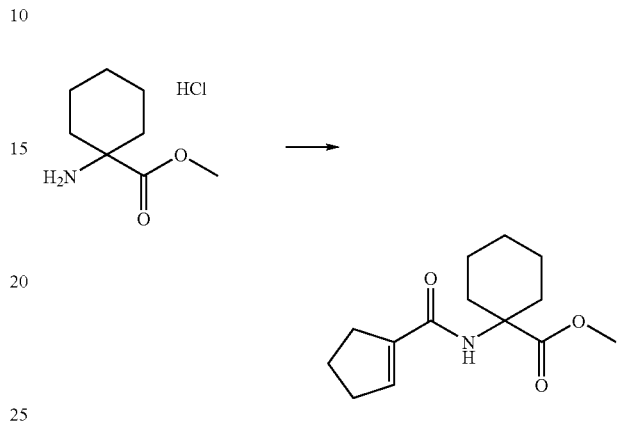

336 mg (3 mmol) of 1-cyclopentenecarboxylic acid was used instead of 3-furancarboxylic acid in the process according to Reference Example 15 to obtain 717 mg (95%) of the title compound.

1H-NMR (CDCl$_3$, δ): 1.34-1.44 (2H, m), 1.60-1.70 (4H, m), 1.87 (2H, td, J=9 Hz, 4 Hz), 1.99-2.09 (4H, m), 2.49 (2H, m), 2.58 (2H, m), 3.72 (3H, s), 5.75 (1H, br-s), 6.55 (1H, t, J=2 Hz)

Reference Example 53

1-[(1-Cyclopentenylcarbonyl)amino]cyclohexanecarboxylic acid

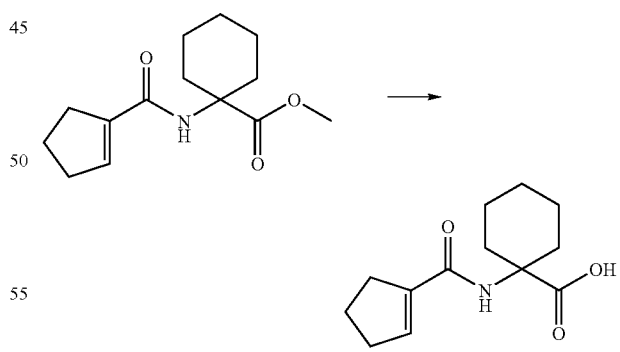

717 mg (2.9 mmol) of 1-[(1-cyclopentenylcarbonyl)amino]cyclohexanecarboxylic acid methyl ester was used instead of 1-[(3-furanylcarbonyl)amino]cyclohexanecarboxylic acid methyl ester in the process according to Reference Example 16 to obtain 588 mg (87%) of the title compound.

1H-NMR (DMSO-$d_6$, δ): 1.24 (1H, d, J=8 Hz), 1.40-1.50 (5H, m), 1.67 (2H, td, J=10 Hz, 9 Hz), 1.81-1.89 (2H, m), 1.91-2.09 (2H, m), 2.40-2.50 (4H, m), 6.53 (1H, t, J=3 Hz), 7.46 (1H, s), 12.03 (1H, s)

Reference Example 54

1-[(4-Pyridinylcarbonyl)amino]cyclohexanecarboxylic acid methyl ester

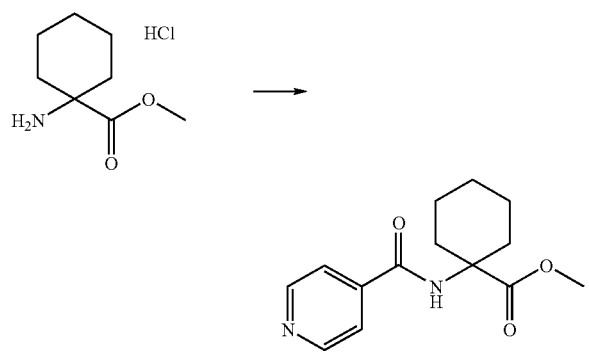

370 mg (3 mmol) of 4-pyridinecarboxylic acid was used instead of 3-furancarboxylic acid in the process according to Reference Example 15 to obtain 609 mg (77%) of the title compound.

1H-NMR (CDCl$_3$, δ): 1.32-1.53 (3H, m), 1.62-1.77 (3H, m), 1.92-2.03 (2H, m), 2.13-2.21 (2H, m), 3.75 (3H, s), 6.29 (1H, br-s), 7.62 (2H, dd, J=5 Hz, 2 Hz), 8.76 (2H, dd, J=5 Hz, 2 Hz)

Reference Example 55

1-[(4-Pyridinylcarbonyl)amino]cyclohexanecarboxylic acid

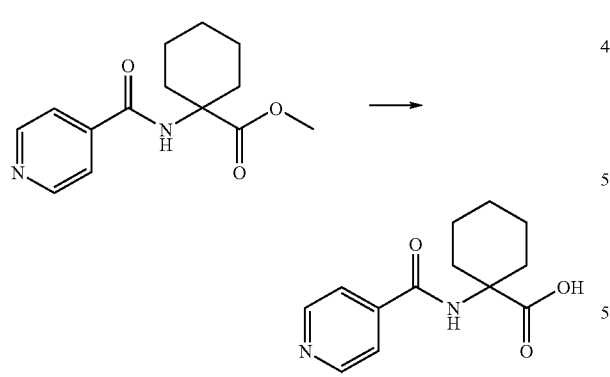

609 mg (2.3 mmol) of 1-[(4-pyridinylcarbonyl)amino]cyclohexanecarboxylic acid methyl ester was used instead of 1-[(3-furanylcarbonyl)amino]cyclohexanecarboxylic acid methyl ester in the process according to Reference Example 16 to obtain 522 mg (97%) of the title compound.

1H-NMR (DMSO-d$_6$, δ): 1.22-1.33 (1H, m), 1.46-1.59 (5H, m), 1.70-1.80 (2H, m), 2.09-2.15 (2H, m), 7.73 (2H, dd, J=5 Hz, 2 Hz), 8.51 (1H, s), 8.72 (2H, dd, J=5 Hz, 2 Hz)

Reference Example 56

1-[(1H-Pyrrol-2-ylcarbonyl)amino]cyclohexanecarboxylic acid methyl ester

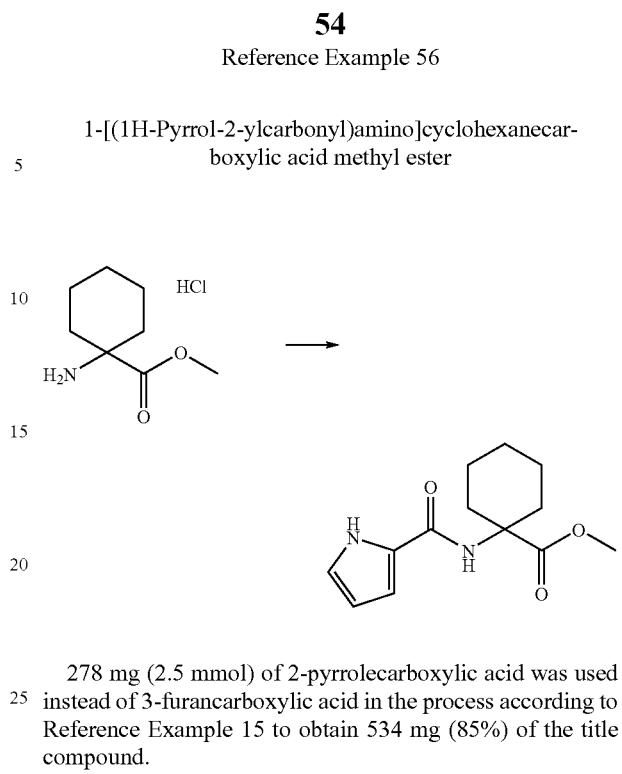

278 mg (2.5 mmol) of 2-pyrrolecarboxylic acid was used instead of 3-furancarboxylic acid in the process according to Reference Example 15 to obtain 534 mg (85%) of the title compound.

1H-NMR (CDCl$_3$, δ): 1.32-1.45 (2H, m), 1.45-1.53 (2H, m) 1.62-1.72 (2H, m), 1.93 (2H td, J=13 Hz, 4 Hz), 2.08-2.19 (2H, m), 3.70 (3H, s), 6.05 (1H, br-s), 6.23-6.25 (1H, m), 6.61 (1H, d, J=2 Hz), 6.94 (1H, d, J=2 Hz)

Reference Example 57

1-[(1H-Pyrrol-2-ylcarbonyl)amino]cyclohexanecarboxylic acid

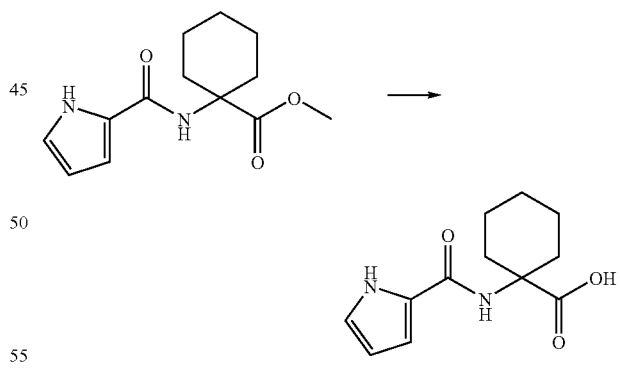

500 mg (2 mmol) of 1-[[(1H-pyrrol-2-yl)carbonyl]amino] cyclohexanecarboxylic acid methyl ester was used instead of 1-[(3-furanylcarbonyl)amino]cyclohexanecarboxylic acid methyl ester in the process according to Reference Example 16 to obtain 338 mg (71%) of the title compound.

1H-NMR (DMSO-d$_6$, δ): 1.20-1.31 (1H, m), 1.52 (5H, br-s), 1.70-1.80 (2H, m), 2.04-2.18 (2H, m), 6.08 (1H, dd, J=4 Hz, 2 Hz), 6.85-6.89 (2H, m), 7.59 (1H, s), 11.39 (1H, s), 12.09 (1H, br-s)

Reference Example 58

1-[[(6-Hydroxy-2-pyridinyl)carbonyl]amino]cyclo-
hexanecarboxylic acid methyl ester

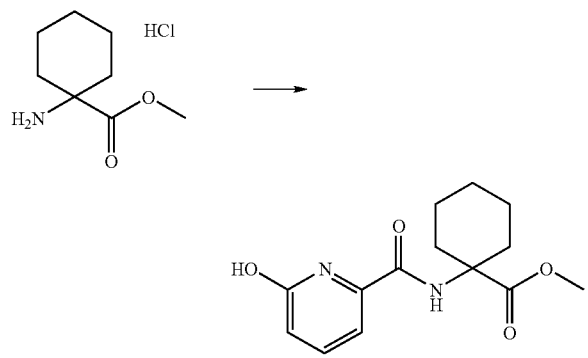

1.39 g (10 mmol) of 6-hydroxy-2-pyridinecarboxylic acid was used instead of 3-furancarboxylic acid in the process according to Reference Example 15 to obtain 1.32 g (47%) of the title compound.

1H-NMR (CDCl$_3$, δ): 1.30-1.42 (1H, m), 1.65 (5H, m), 1.96 (2H, td, J=12 Hz, 4 Hz), 2.10-2.21 (2H, m), 3.73 (3H, s), 6.71 (1H, d, J=9 Hz), 7.20 (1H, d, J=7 Hz), 7.62 (1H, dd, J=9 Hz, 7 Hz), 8.00 (1H, s)

Reference Example 59

1-[[(6-Hydroxy-2-pyridinyl)carbonyl]amino]cyclo-
hexanecarboxylic acid

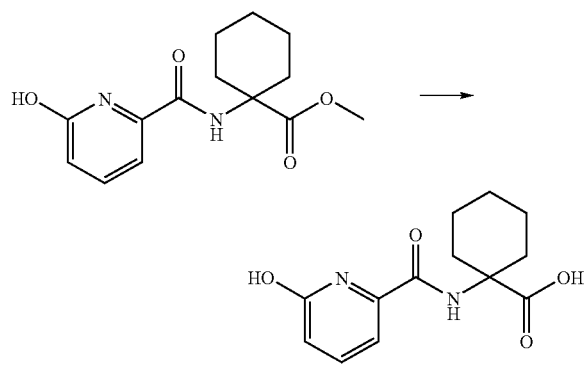

1.32 mg (4.7 mmol) of 1-[[(6-hydroxy-2-pyridinyl)carbonyl]amino]cyclohexanecarboxylic acid methyl ester was used instead of 1-[(3-furanylcarbonyl)amino]cyclohexanecarboxylic acid methyl ester in the process according to Reference Example 16 to obtain 1.16 g (88%) of the title compound.

1H-NMR (DMSO-d$_6$, δ): 1.39-1.50 (1H, m), 1.39-1.50 (2H, m), 1.51-1.63 (3H, m), 1.70-1.82 (2H, m), 2.01-2.12 (2H, d, m), 6.78 (1H, d, J=8 Hz), 7.32 (1H, br-s), 7.74 (1H, t, J=8 Hz), 8.18 (1H, s)

Reference Example 60

1-[[(2-Hydroxy-3-pyridinyl)carbonyl]amino]cyclo-
hexanecarboxylic acid methyl ester

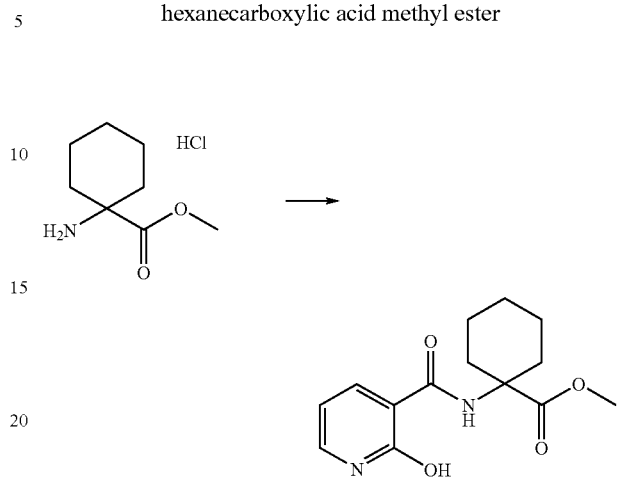

1.39 g (10 mmol) of 2-hydroxynicotinic acid was used instead of 3-furancarboxylic acid in the process according to Reference Example 15 to obtain 697 mg (25%) of the title compound.

1H-NMR (CDCl$_3$, δ): 1.24-1.38 (1H, m), 1.50-1.62 (2H, m), 1.64-1.74 (3H, m), 1.82-1.93 (2H, m), 2.15-2.24 (2H, m), 3.74 (3H, s), 6.53 (1H, t, J=7 Hz), 7.49 (1H, d, J=7 Hz), 8.57 (1H, d, J=7 Hz), 10.04 (1H, s)

Reference Example 61

1-[[(2-Hydroxy-3-pyridinyl)carbonyl]amino]cyclo-
hexanecarboxylic acid

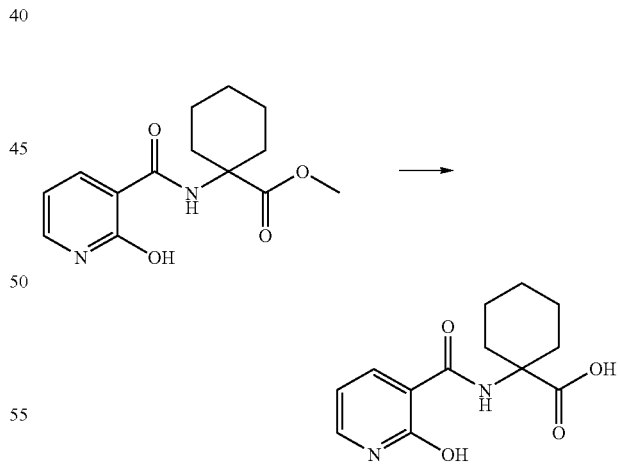

698 mg (2.5 mmol) of 1-[[(2-hydroxy-3-pyridinyl)carbonyl]amino]cyclohexanecarboxylic acid methyl ester was used instead of 1-[(3-furanylcarbonyl)amino]cyclohexanecarboxylic acid methyl ester in the process according to Reference Example 16 to obtain 580 mg (83%) of the title compound.

1H-NMR (DMSO-d$_6$, δ): 1.21-1.31 (1H, m), 1.38-1.41 (2H, m), 1.59 (3H, d, J=10 Hz), 1.67-1.72 (2H, m), 1.98-2.04

(2H, m), 6.49 (1H, t, J=7 Hz), 7.73 (1H, br-s), 8.28 (1H, d, J=7 Hz), 10.21 (1H, s), 12.19 (1H, s), 12.53 (1H, br-s)

Reference Example 62

1-[[(6-Hydroxy-3-pyridinyl)carbonyl]amino]cyclohexanecarboxylic acid methyl ester

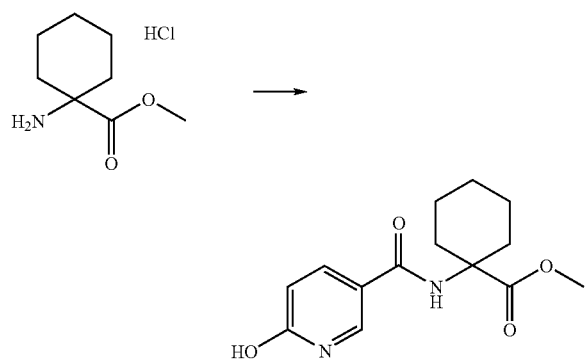

1.39 g (10 mmol) of 6-hydroxynicotinic acid was used instead of 3-furancarboxylic acid in the process according to Reference Example 15 to obtain 869 mg (31%) of the title compound.

1H-NMR (CDCl$_3$, δ): 1.30-1.41 (1H, m), 1.43-1.58 (2H, m), 1.61-1.75 (3H, m), 1.89-1.99 (2H, m), 2.11-2.19 (2H, m), 3.74 (3H, s), 6.43 (1H, s), 6.53 (1H, d, J=10 Hz), 7.82 (1H, dd, J=10 Hz, 2 Hz), 8.05 (1H, d, J=2 Hz)

Reference Example 63

1-[[(6-Hydroxy-3-pyridinyl)carbonyl]amino]cyclohexanecarboxylic acid

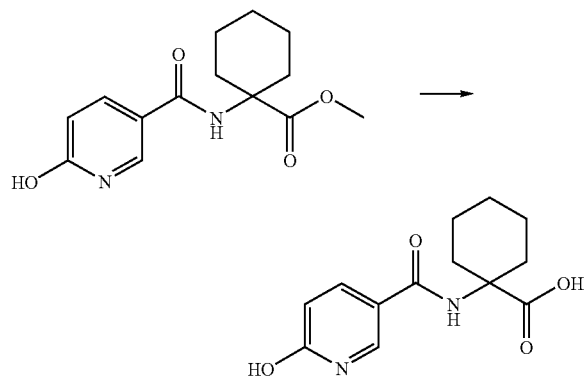

869 mg (3.1 mmol) of 1-[[(6-hydroxy-3-pyridinyl)carbonyl]amino]cyclohexanecarboxylic acid methyl ester was used instead of 1-[(3-furanylcarbonyl)amino]cyclohexanecarboxylic acid methyl ester in the process according to Reference Example 16 to obtain 818 mg (94%) of the title compound.

1H-NMR (DMSO-d$_6$, δ): 1.19-1.31 (1H, m), 1.42-1.57 (5H, m), 1.67-1.78 (2H, m), 2.01-2.11 (2H, m), 6.34 (1H, d, J=10 Hz), 7.84 (1H, dd, J=10 Hz, 2 Hz), 7.95 (1H, s), 8.05 (1H, d, J=2 Hz), 11.90-12.18 (2H, m)

Reference Example 64

1-[[1-Oxo-3-(2-furanyl)propyl]amino]cyclohexanecarboxylic acid methyl ester

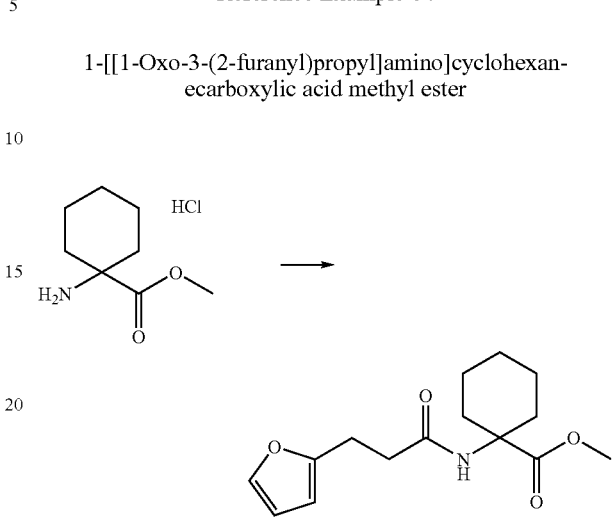

420 mg (3 mmol) of 3-(2-furyl)propionic acid was used instead of 3-furancarboxylic acid in the process according to Reference Example 15 to obtain 478 mg (57%) of the title compound.

1H-NMR (CDCl$_3$, δ): 1.25-1.38 (3H, m), 1.57-1.65 (3H, m) 1.78-1.85 (2H, m), 1.96-2.01 (2H, m), 2.56 (2H, t, J=7 Hz), 2.98 (2H, t, J=7 Hz), 3.69 (3H, s), 5.56 (1H, br-s), 6.06 (1H, dd, J=3 Hz, 2 Hz), 6.29 (1H, dd, J=3 Hz, 2 Hz), 7.31 (1H, dd, J=3 Hz, 2 Hz)

Reference Example 65

1-[[[1-(2-Propoxycarbonyl)piperidin-4-yl]carbonyl]amino]cyclohexanecarboxylic acid methyl ester

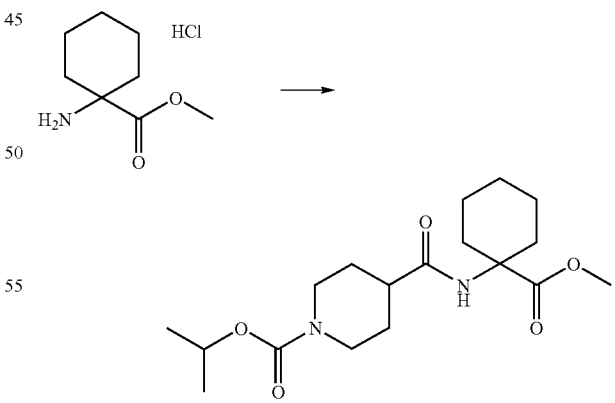

646 mg (3 mmol) of 1-(2-propoxycarbonyl)nipecotinic acid was used instead of 3-furancarboxylic acid in the process according to Reference Example 15 to obtain 979 mg (92%) of the title compound.

1H-NMR (CDCl$_3$, δ): 1.24 (6H, d, J=6 Hz), 1.25-1.44 (3H, m), 1.56-1.70 (5H, m), 1.79-1.90 (4H, m), 1.98-2.07 (2H, m), 2.26-2.34 (1H, m), 2.75-2.88 (2H, m), 3.69 (3H, s), 4.17 (2H, br-s), 4.86-4.96 (1H, m), 5.58 (1H, s)

Reference Example 66

1-[[[1-(2-Propoxycarbonyl)piperidin-4-yl]carbonyl]amino]cyclohexanecarboxylic acid

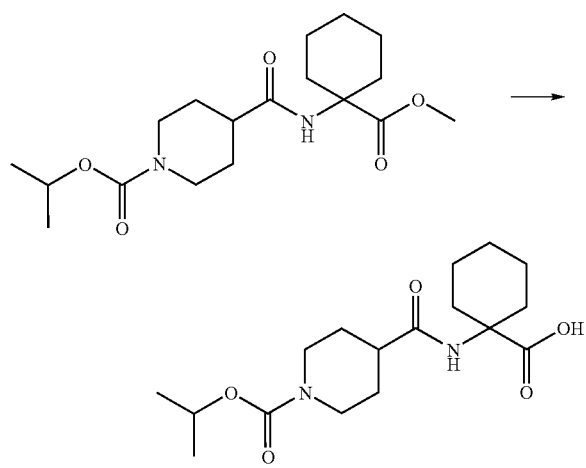

979 mg (2.76 mmol) of 1-[[[1-(2-propoxycarbonyl)piperidin-4-yl]carbonyl]amino]cyclohexanecarboxylic acid methyl ester was used instead of 1-[(3-furanylcarbonyl)amino]cyclohexanecarboxylic acid methyl ester in the process according to Reference Example 16 to obtain 940 mg (quantitative) of the title compound.

1H-NMR (CDCl$_3$, δ): 1.23-1.28 (7H, m), 1.34-1.39 (3H, m), 1.62-1.71 (6H, m), 1.85-1.91 (4H, m), 2.05-2.09 (2H, m), 2.33-2.36 (1H, m), 2.74-2.84 (2H, m), 4.21 (1H, br-s), 4.91 (1H, q, J=7 Hz), 5.67 (1H, s)

Reference Example 67

1-[[[1-(Ethoxycarbonyl)piperidin-4-yl]carbonyl]amino]cyclohexanecarboxylic acid methyl ester

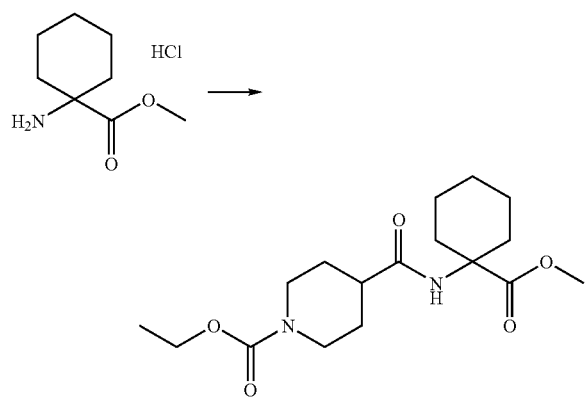

604 mg (3 mmol) of 1-ethoxycarbonylnipecotinic acid was used instead of 3-furancarboxylic acid in the process according to Reference Example 15 to obtain 976 mg (95%) of the title compound.

1H-NMR (CDCl$_3$, δ): 1.26 (3H, t, J=7 Hz), 1.25-1.42 (3H, m) 1.55-1.70 (3H, m), 1.81-1.86 (4H, m), 2.01-2.05 (3H, m), 2.26-2.32 (1H, m), 2.80-2.89 (2H, m), 3.69 (3H, s), 4.08-4.23 (3H, m), 4.13 (2H, q, J=7 Hz), 5.54 (1H, br-s)

Reference Example 68

1-[[[1-(Ethoxycarbonyl)piperidin-4-yl]carbonyl]amino]cyclohexanecarboxylic acid

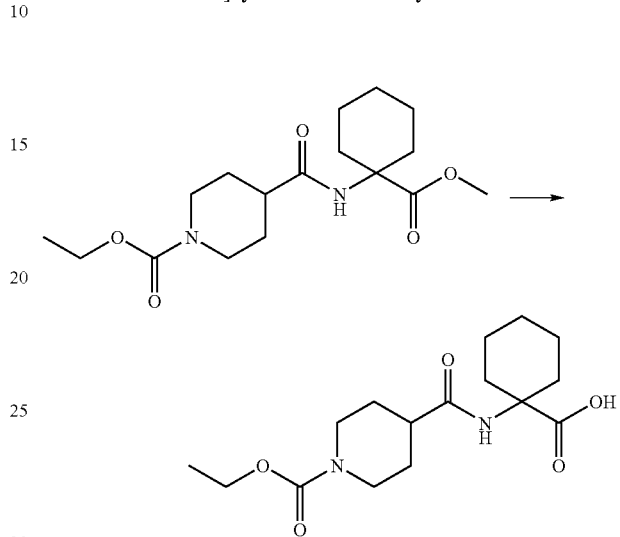

976 mg (2.87 mmol) of 1-[[[1-(ethoxycarbonyl)piperidin-4-yl]carbonyl]amino]cyclohexanecarboxylic acid methyl ester was used instead of 1-[(3-furanylcarbonyl)amino]cyclohexanecarboxylic acid methyl ester in the process according to Reference Example 16 to obtain 935 mg (quantitative) of the title compound.

1H-NMR (CDCl$_3$, δ): 1.25 (3H, t, J=7 Hz), 1.30-1.42 (3H, m), 1.62-1.72 (5H, m), 1.85-1.91 (4H, m), 2.06-2.09 (2H, m), 2.34-2.39 (1H, m), 2.79-2.90 (2H, m), 4.10-4.25 (3H, m), 4.13 (2H, q, J=7 Hz), 5.69 (1H, s)

Reference Example 69

1-[[[1-(2-Furanylcarbonyl)piperidin-4-yl]carbonyl]amino]cyclohexanecarboxylic acid methyl ester

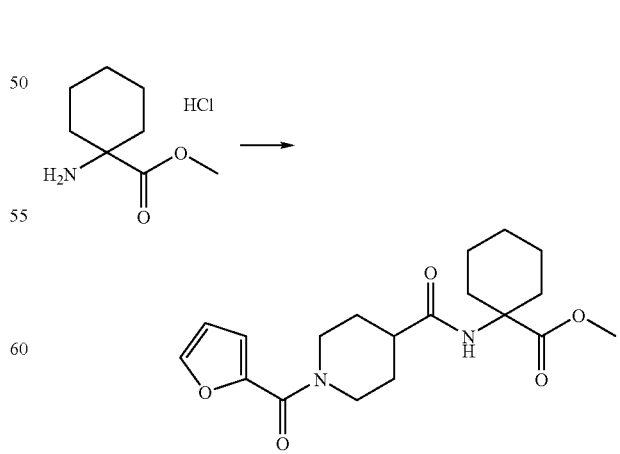

670 mg (3 mmol) of 1-(2-furanylcarbonyl)piperidine-4-carboxylic acid was used instead of 3-furancarboxylic acid in the process according to Reference Example 15 to obtain 910 mg (80%) of the title compound.

1H-NMR (CDCl₃, δ): 1.30-1.43 (3H, m), 1.53-1.69 (3H, m), 1.74-1.90 (4H, m), 1.91-2.05 (4H, m), 2.43-2.48 (1H, m), 2.89-3.21 (2H, m), 3.79 (3H, s), 4.40-4.56 (2H, m), 5.58 (1H, br-s), 6.47 (1H, dd, J=3 Hz, 1 Hz), 6.95 (1H, dd, J=3 Hz, 1 Hz), 7.48 (1H, dd, J=3 Hz, 1 Hz)

Reference Example 70

1-[[[1-(2-Furanylcarbonyl)piperidin-4-yl]carbonyl]amino]cyclohexanecarboxylic acid

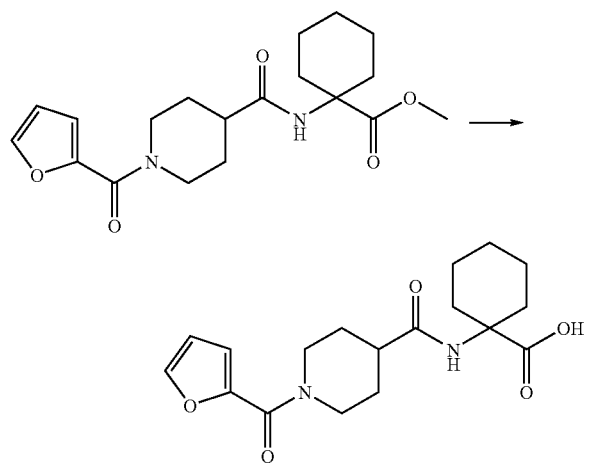

910 mg (2.4 mmol) of 1-[[[1-(2-furanylcarbonyl)piperidin-4-yl]carbonyl]amino]cyclohexanecarboxylic acid methyl ester was used instead of 1-[(3-furanylcarbonyl)amino]cyclohexanecarboxylic acid methyl ester in the process according to Reference Example 16 to obtain 196 mg (23%) of the title compound.

1H-NMR (DMSO-d₆, δ): 1.17-1.25 (1H, m), 1.40-1.58 (7H, m), 1.58-1.62 (2H, m), 1.73-1.76 (2H, m), 1.93-1.96 (2H, m), 2.51-2.61 (1H, m), 2.80-3.11 (2H, m), 4.22-4.33 (2H, m), 6.61 (1H, dd, J=3 Hz, 1 Hz), 6.95 (1H, dd, J=3 Hz, 1 Hz), 7.78 (1H, s), 7.82 (1H, dd, J=3 Hz, 1 Hz)

Reference Example 71

1-[[[(2-Furanylcarbonyl)amino]acetyl]amino]cyclohexanecarboxylic acid methyl ester

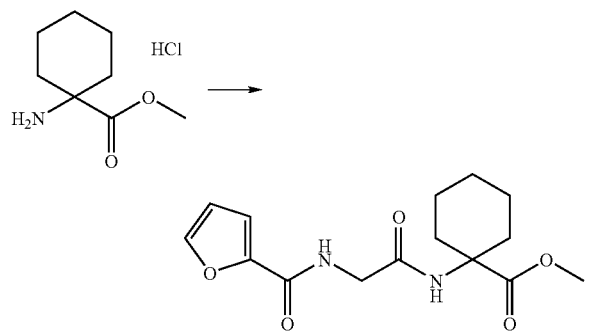

507 mg (3 mmol) of N-(2-furanylcarbonyl)glycine was used instead of 3-furancarboxylic acid in the process according to Reference Example 15 to obtain 781 mg (88%) of the title compound.

1H-NMR (CDCl₃, δ): 1.22-1.38 (1H, m), 1.39-1.50 (2H, m) 1.58-1.69 (3H, m), 1.85 (2H, td, J=9 Hz, 4 Hz), 2.02-2.10 (2H, m), 3.70 (3H, s), 4.15 (2H, d, J=6 Hz), 6.51 (1H, dd, J=2 Hz, 1 Hz), 6.67 (1H, s), 7.13 (2H, m), 7.47 (1H, dd, J=2 Hz, 1 Hz)

Reference Example 72

1-[[[(2-Furanylcarbonyl)amino]acetyl]amino]cyclohexanecarboxylic acid

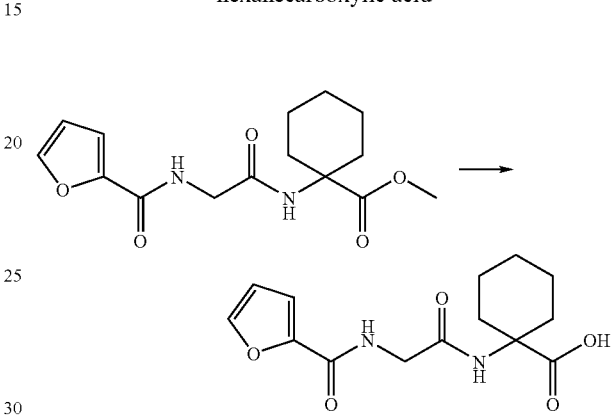

781 mg (2.7 mmol) of 1-[[[(2-furanylcarbonyl)amino]acetyl]amino]cyclohexanecarboxylic acid methyl ester was used instead of 1-[(3-furanylcarbonyl)amino]cyclohexanecarboxylic acid methyl ester in the process according to Reference Example 16 to obtain 320 mg (41%) of the title compound.

1H-NMR (DMSO-d₆, δ): 1.12-1.25 (1H, m), 1.39-1.58 (5H, m), 1.64 (2H, td, J=13 Hz, 4 Hz), 1.90-2.02 (2H, m), 3.88 (2H, d, J=6 Hz), 6.62 (1H, dd, J=3 Hz, 1 Hz), 7.13 (1H, dd, J=3 Hz, 1 Hz), 7.84 (1H, d, J=1 Hz), 7.87 (1H, s), 8.38 (1H, d, J=6 Hz)

Reference Example 73

1-[[(Benzoylamino)acetyl]amino]cyclohexanecarboxylic acid methyl ester

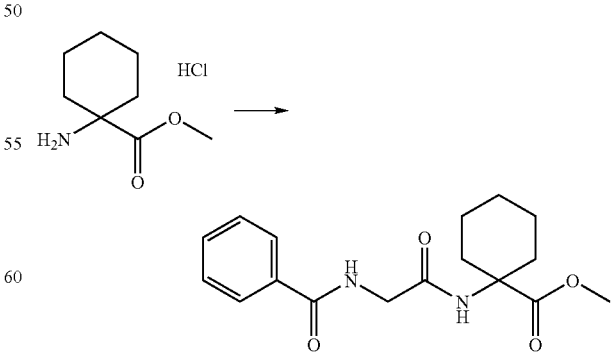

538 mg (3 mmol) of N-benzoylglycine was used instead of 3-furancarboxylic acid in the process according to Reference Example 15 to obtain 812 mg (81%) of the title compound.

1H-NMR (CDCl$_3$, δ): 1.23-1.38 (1H, m), 1.48 (2H, td, J=9 Hz, 4 Hz), 1.58-1.71 (3H, m), 1.84 (2H, dt, J=9 Hz, 4 Hz), 2.02-2.10 (2H, m), 3.70 (3H, s), 4.21 (2H, d, J=7 Hz), 7.08 (1H, br-s), 7.26-7.46 (3H, m), 7.54 (1H, td, J=8 Hz, 1 Hz), 7.84 (2H, dd, J=8 Hz, 1 Hz)

Reference Example 74

1-[[(Benzoylamino)acetyl]amino]cyclohexanecarboxylic acid

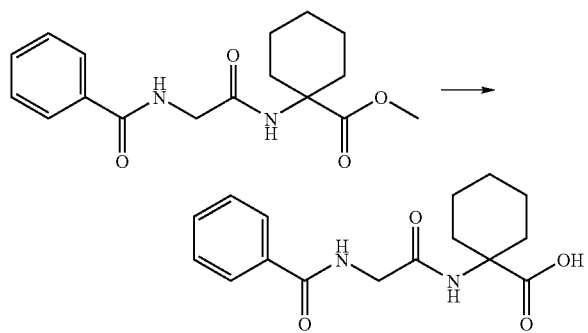

812 mg (2.4 mmol) of 1-[[(benzoylamino)acetyl]amino]cyclohexanecarboxylic acid methyl ester was used instead of 1-[(3-furanylcarbonyl)amino]cyclohexanecarboxylic acid methyl ester in the process according to Reference Example 16 to obtain 724 mg (93%) of the title compound.

1H-NMR (DMSO-d$_6$, δ): 1.09-1.67 (8H, m), 1.96 (2H, d, J=11 Hz), 3.93 (2H, d, J=6 Hz), 7.47 (2H, td, J=6 Hz, 1 Hz), 7.52-7.55 (1H, m), 7.86-7.89 (3H, m), 8.64 (1H, t, J=6 Hz)

Reference Example 75

1-[[(2-Furanylmethoxy)carbonyl]amino]cyclohexanecarboxylic acid methyl ester

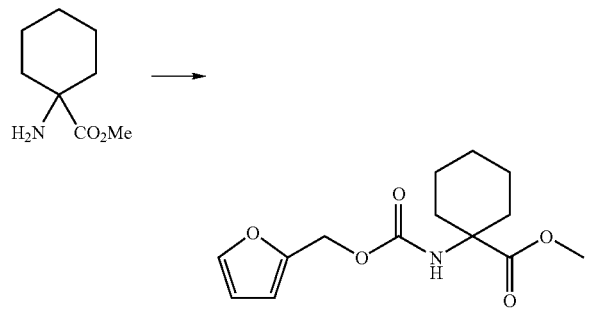

3.67 g (30 mmol) of dimethylaminopyridine was added to a solution of 65.48 g (0.3 mol) of di-t-butyl dicarbonate in 300 ml of anhydrous toluene, and the mixture was stirred at room temperature for 15 minutes. A solution of 47.17 g (0.3 mol) of 1-aminocyclohexanecarboxylic acid methyl ester in 100 ml of anhydrous toluene was added to the reaction solution, and the mixture was stirred at room temperature for 1 hour. Further, after 60.71 g (0.6 mol) of triethylamine and 44.1 g (0.45 mol) of furfuryl alcohol were added, the mixture was heated under reflux for 3 hours. The reaction solution was returned to room temperature and was concentrated under reduced pressure. The obtained residue was crushed by a mortar, and it was stirred in a mixture solution of 5 ml of hydrochloric acid and 3 L of water for 18 hours. The obtained crystal was collected by filtration to obtain 74.37 g (88%) of the title compound.

1H-NMR (CDCl$_3$, δ): 1.23-1.36 (1H, m), 1.38-1.51 (2H, m), 1.55-1.65 (3H, m), 1.80-1.88 (2H, m), 1.93-2.04 (2H, m), 3.71 (3H, br-s), 4.93 (1H, br-s), 5.04 (2H, s), 6.36 (1H, dd, J=3 Hz, 2 Hz), 6.41 (1H, d, J=3 Hz), 7.43 (1H, d, J=2 Hz)

Reference Example 76

1-[[(2-Furanylmethoxy)carbonyl]amino]cyclohexanecarboxylic acid

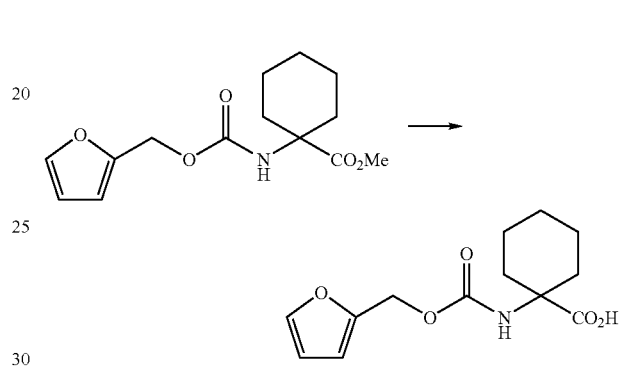

28.13 g (0.1 mol) of 1-[[(2-furanylmethoxy)carbonyl]amino]cyclohexanecarboxylic acid methyl ester was added to a mixture solution of 150 ml of 2N aqueous sodium hydroxide solution and 200 ml of tetrahydrofuran, and the mixture was heated under reflux for 18 hours. After the solvent was distilled off, water was added to the residue and the mixture was washed with diethyl ether. After potassium hydrogensulfate was added to the aqueous layer to acidify it, the mixture was extracted with ethyl acetate twice. After the organic layer was washed with saturated brine, it was dried with anhydrous magnesium sulfate, and thereafter the solvent was distilled off under reduced pressure. Diisopropyl ether was added to the residue, and the mixture was stirred for 18 hours. The obtained crystal was collected by filtration to obtain 19.89 g (74%) of the title compound.

1H-NMR (CDCl$_3$, δ): 1.24-1.37 (1H, m), 1.38-1.52 (2H, m), 1.59-1.71 (3H, m), 1.82-1.93 (2H, m), 1.99-2.12 (2H, m), 4.99 (1H, br-s), 5.07 (2H, s), 6.37 (1H, dd, J=3 Hz, 2 Hz), 6.42 (1H, d, J=3 Hz), 7.43 (1H, d, J=2 Hz)

Reference Example 77

1-[[(4-Phenyl-1-piperazinyl)carbonyl]amino]cyclohexanecarboxylic acid phenylmethyl ester

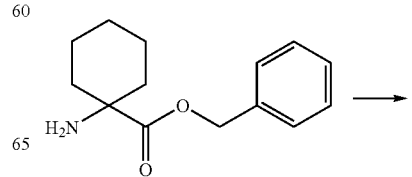

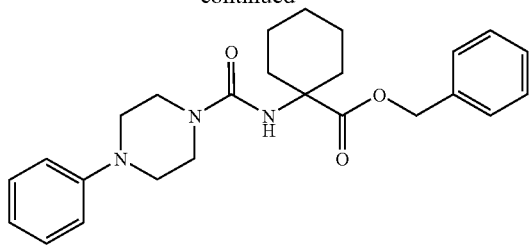

A solution of 366 mg (3 mmol) of N,N-dimethylaminopyridine and 6.99 g (30 mmol) of 1-aminocyclohexanecarboxylic acid phenylmethyl ester in methylene chloride was added to a solution of 6.55 g (30 mmol) of di-t-butyl dicarbonate in 150 ml of methylene chloride, and the mixture was stirred at room temperature for 30 minutes. Thereafter, a solution of 6.07 g (60 mmol) of triethylamine and 5.11 g (33 mmol) of 1-phenylpiperazine in methylene chloride was added, and the mixture was stirred at room temperature overnight. The reaction solution was concentrated, ethyl acetate was added thereto, and the mixture was successively washed with water, a saturated aqueous sodium hydrogencarbonate solution and saturated brine, followed by drying with anhydrous sodium sulfate. After the solvent was distilled off under reduced pressure, the obtained crystal was washed with diethyl ether to obtain 8.88 g (70%) of the title compound.

1H-NMR (CDCl$_3$, δ): 1.25-1.37 (1H, m), 1.42-1.51 (2H, m), 1.50-1.69 (3H, m), 1.82-1.91 (2H, m), 2.03-2.10 (2H, m), 3.17 (4H, t, J=5 Hz), 3.54 (4H, t, J=5 Hz), 4.60 (1H, br-s), 5.15 (2H, s), 6.89-6.94 (3H, m), 7.26-7.35 (7H, m)

Reference Example 78

1-[[(4-Phenyl-1-piperazinyl)carbonyl]amino]cyclohexanecarboxylic acid

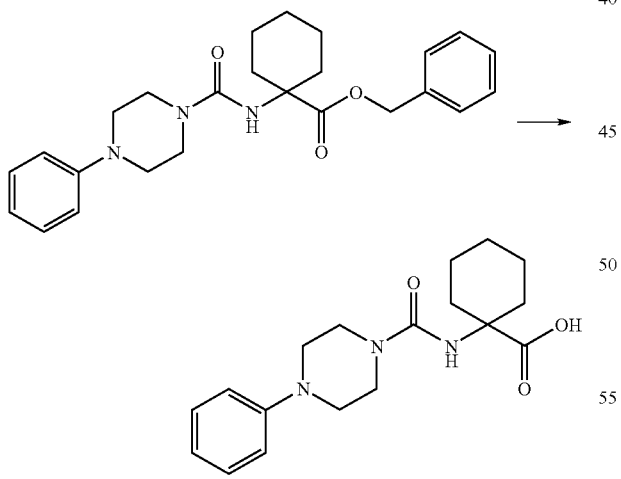

8.88 g (21 mmol) of 1-[[(4-phenyl-1-piperazinyl)carbonyl]amino]cyclohexanecarboxylic acid phenylmethyl ester obtained in Reference Example 77 was dissolved in 200 ml of methanol, 900 mg of 10% palladium-carbon was added thereto, and the mixture was stirred under a hydrogen atmosphere at room temperature overnight. After the reaction solution was filtered, the filtrate was concentrated under reduced pressure to obtain 6.96 g (quantitative) of the title compound.

1H-NMR (CDCl$_3$, δ): 1.22-1.30 (1H, m), 1.36-1.42 (2H, m) 1.50-2.05 (5H, m), 2.06-2.14 (2H, m), 3.24 (4H, t, J=5 Hz), 4.61 (4H, t, J=5 Hz), 4.51 (1H, br-s), 6.92-6.95 (2H, m), 7.28-7.32 (3H, m)

Reference Example 79

1-[[[4-(2-Pyridinyl)-1-piperazinyl]carbonyl]amino]cyclohexanecarboxylic acid phenylmethyl ester

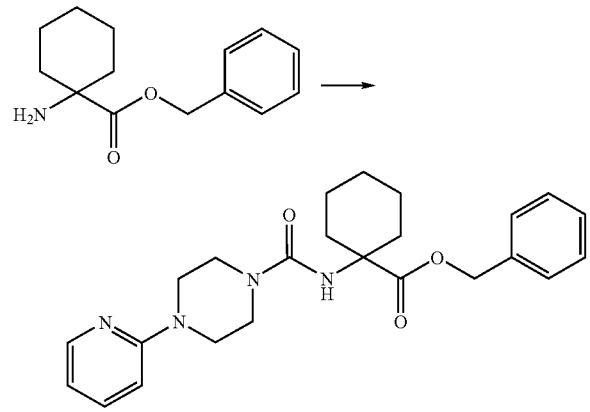

3.43 g (21 mmol) of 1-(2-pyridinyl)piperazine was used instead of 1-phenylpiperazine in the process according to Reference Example 77 to obtain 7.33 g (87%) of the title compound.

1H-NMR (CDCl$_3$, δ): 1.26-1.35 (1H, m), 1.42-1.53 (2H, m), 1.60-1.68 (3H, m), 1.83-1.92 (2H, m), 2.02-2.10 (2H, m), 3.52 (4H, t, J=5 Hz), 3.57 (4H, t, J=5 Hz), 4.58 (1H, br-s), 5.15 (2H, s), 6.63 (1H, d, J=8 Hz), 6.67 (1H, td, J=8 Hz, 1 Hz), 7.25-7.34 (5H, m), 7.51 (1H, td, J=8 Hz, 1 Hz), 8.20 (1H, dd, J=8 Hz, 1 Hz)

Reference Example 80

1-[[[4-(2-Pyridinyl)-1-piperazinyl]carbonyl]amino]cyclohexanecarboxylic acid

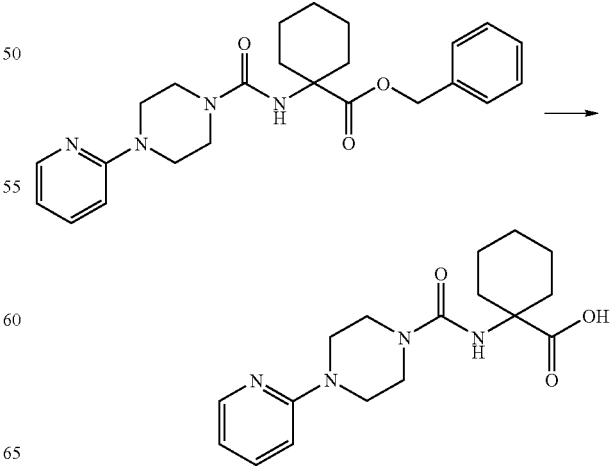

7.33 g (17.4 mmol) of 1-[[[4-(2-pyridinyl)-1-piperazinyl]carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 5.75 g (quantitative) of the title compound.

1H-NMR (CDCl$_3$, δ): 1.30-1.43 (2H, m), 1.60-1.72 (4H, m) 1.89-1.99 (2H, m), 2.06-2.13 (2H, m), 3.61 (4H, t, J=5 Hz), 3.66 (4H, t, J=5 Hz), 4.61 (1H, br-s), 6.65 (1H, dd, J=8 Hz, 1 Hz), 6.69 (1H, td, J=8 Hz, 1 Hz), 7.52 (1H, td, J=8 Hz, 1 Hz), 8.20 (1H, dd, J=8 Hz, 1 Hz)

Reference Example 81

1-[[[4-(4-Fluorophenyl)-1-piperazinyl]carbonyl]amino]cyclohexanecarboxylic acid phenylmethyl ester

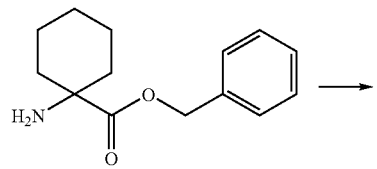

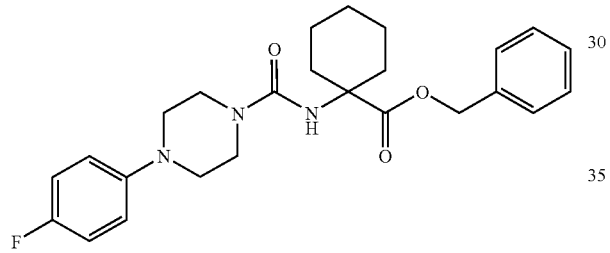

3.78 g (21 mmol) of 1-(4-fluorophenyl)piperazine was used instead of 1-phenylpiperazine in the process according to Reference Example 77 to obtain 4.48 g (51%) of the title compound.

1H-NMR (CDCl$_3$, δ) 1.22-1.35 (1H, m), 1.40-1.51 (2H, m), 1.55-1.70 (3H, m), 1.85-1.93 (2H, m), 2.02-2.09 (2H, m), 3.07 (4H, t, J=5 Hz), 3.53 (4H, t, J=5 Hz), 4.60 (1H, br-s), 5.15 (2H, s), 6.87 (2H, ddd, J=9 Hz, 6 Hz, 2 Hz), 6.98 (2H, ddd, J=9 Hz, 6 Hz, 2 Hz), 7.25-7.35 (5H, m)

Reference Example 82

1-[[[4-(4-Fluorophenyl)-1-piperazinyl]carbonyl]amino]cyclohexanecarboxylic acid

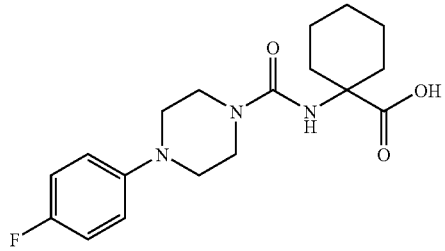

4.48 g (10 mmol) of 1-[[[4-(4-fluorophenyl)-1-piperazinyl]carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 3.56 g (quantitative) of the title compound.

1H-NMR (CDCl$_3$, δ): 1.31-1.43 (3H, m), 1.60-1.75 (3H, m) 1.89-2.01 (2H, m), 2.05-2.13 (2H, m), 3.14 (4H, t, J=5 Hz), 3.61 (4H, t, J=5 Hz), 4.55 (1H, br-s), 6.89 (2H, ddd, J=8 Hz, 5 Hz, 2 Hz), 6.99 (2H, ddd, J=8 Hz, 5 Hz, 2 Hz)

Reference Example 83

1-[[[4-[3-(Trifluoromethyl)phenyl]-1-piperazinyl]carbonyl]amino]cyclohexanecarboxylic acid phenylmethyl ester

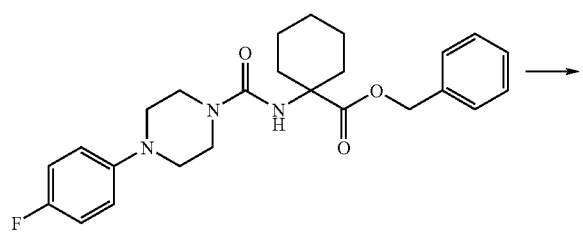

4.83 g (21 mmol) of 1-[3-(trifluoromethyl)phenyl]piperazine was used instead of 1-phenylpiperazine in the process according to Reference Example 77 to obtain 7.54 g (77%) of the title compound.

1H-NMR (CDCl$_3$, δ): 1.23-1.37 (1H, m), 1.42-1.53 (2H, m), 1.59-1.70 (3H, m), 1.85-1.94 (2H, m), 2.02-2.10 (2H, m), 3.21 (4H, t, J=5 Hz), 3.55 (4H, t, J=5 Hz), 4.60 (1H, br-s), 5.15 (2H, s), 7.05 (1H, dd, J=8 Hz, 2 Hz), 7.09 (1H, s), 7.12 (1H, dd, J=8 Hz, 2 Hz), 7.25-7.40 (6H, m)

Reference Example 84

1-[[[4-[3-(Trifluoromethyl)phenyl]-1-piperazinyl]carbonyl]amino]cyclohexanecarboxylic acid

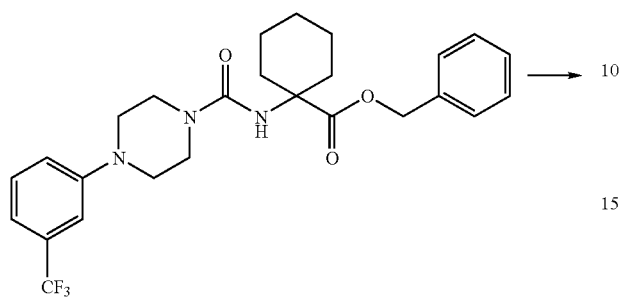

7.54 g (15.4 mmol) of 1-[[[4-[3-(trifluoromethyl)phenyl]-1-piperazinyl]carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 5.92 g (96%) of the title compound.

1H-NMR (CDCl$_3$, δ): 1.36-1.44 (2H, m), 1.60-1.75 (4H, m), 1.91-2.00 (2H, m), 2.05-2.14 (2H, m), 3.30 (4H, t, J=5 Hz), 3.63 (4H, t, J=5 Hz), 4.63 (1H, br-s), 7.07 (1H, d, J=8 Hz), 7.11 (1H, s), 7.15 (1H, d, J=8 Hz), 7.38 (1H, t, J=8 Hz)

Reference Example 85

1-[[(4-Cyclohexyl-1-piperazinyl)carbonyl]amino]cyclohexanecarboxylic acid phenylmethyl ester

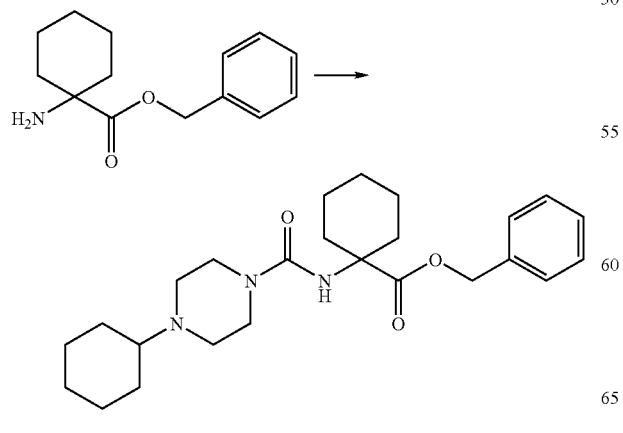

2.66 g (15.8 mmol) of 1-(cyclohexyl)piperazine was used instead of 1-phenylpiperazine in the process according to Reference Example 77 to obtain 3.21 g (50%) of the title compound.

1H-NMR (CDCl$_3$, δ): 1.22-1.45 (3H, m), 1.39-1.50 (3H, m) 1.51-1.67 (6H, m), 1.89-1.90 (6H, m), 2.01-2.07 (2H, m), 2.22-2.30 (1H, m), 2.54 (4H, t, J=5 Hz), 3.38 (4H, t, J=5 Hz), 4.53 (1H, br-s), 5.14 (2H, s), 7.25-7.34 (5H, m)

Reference Example 86

1-[[(4-Cyclohexyl-1-piperazinyl)carbonyl]amino]cyclohexanecarboxylic acid

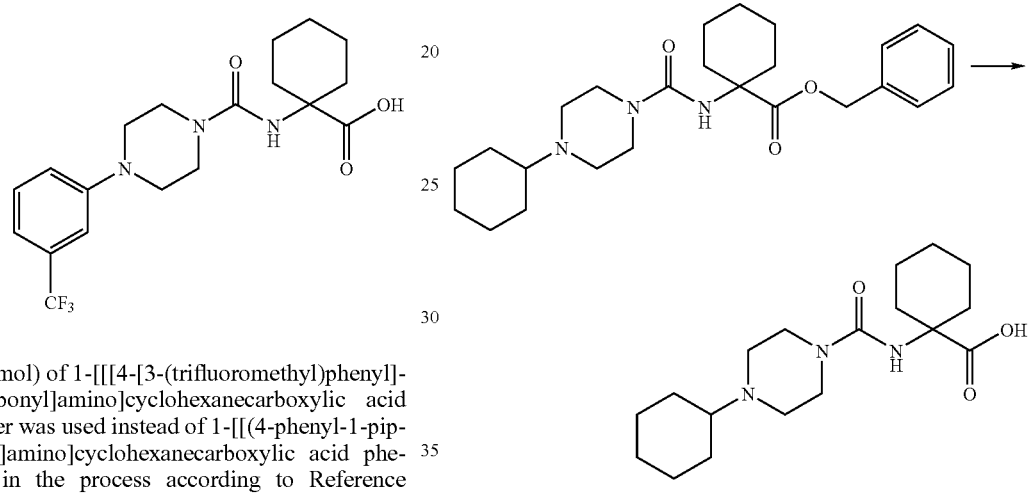

3.21 g (7.5 mmol) of 1-[[(4-cyclohexyl-1-piperazinyl)carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 2.53 g (quantitative) of the title compound.

1H-NMR (CDCl$_3$, δ): 1.05-1.19 (1H, m), 1.10-1.19 (2H, m) 1.20-1.32 (2H, m), 1.58-1.97 (13H, m), 2.03-2.12 (2H, m), 2.35-2.44 (1H, m), 2.67 (4H, t, J=5 Hz), 3.48 (4H, t, J=5 Hz), 4.59 (1H, br-s)

Reference Example 87

1-[[(4-Benzoyl-1-piperazinyl)carbonyl]amino]cyclohexanecarboxylic acid phenylmethyl ester

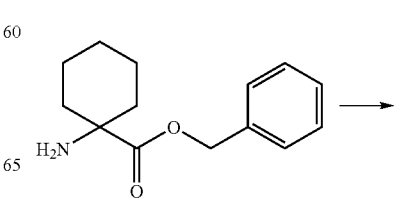

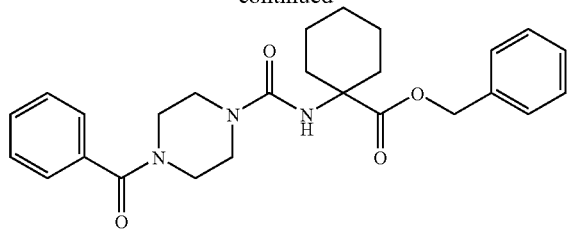

A solution of 114 mg (0.9 mmol) of N,N-dimethylaminopyridine and 2.17 g (9.3 mmol) of 1-aminocyclohexanecarboxylic acid phenylmethyl ester in methylene chloride was added to a solution of 2.03 g (9.3 mmol) of di-t-butyl dicarbonate in 60 ml of methylene chloride, and the mixture was stirred at room temperature for 30 minutes. Thereafter, a solution of 1.88 g (18.6 mmol) of triethylamine and 1.86 g (9.8 mmol) of 1-(benzoyl)piperazine in methylene chloride was added, and the mixture was stirred at room temperature overnight. After the reaction solution was concentrated, the residue was dissolved in ethyl acetate, and the mixture was successively washed with water, a 10% aqueous potassium hydrogensulfate solution, a saturated aqueous sodium hydrogencarbonate solution and saturated brine, followed by drying with anhydrous sodium sulfate. After the solvent was distilled off under reduced pressure, the obtained crystal was washed with diethyl ether to obtain 3.60 g (86%) of the title compound.

1H-NMR (CDCl$_3$, δ): 1.26-1.38 (1H, m), 1.39-1.50 (2H, m), 1.53-1.68 (3H, m), 1.85-1.93 (2H, m), 2.02-2.08 (2H, m), 3.28-3.57 (6H, m), 3.66-3.85 (2H, m), 4.57 (1H, br-s), 5.15 (2H, s), 7.31-7.39 (4H, m), 7.40-7.48 (6H, m)

Reference Example 88

1-[[(4-Benzoyl-1-piperazinyl)carbonyl]amino]cyclohexanecarboxylic acid

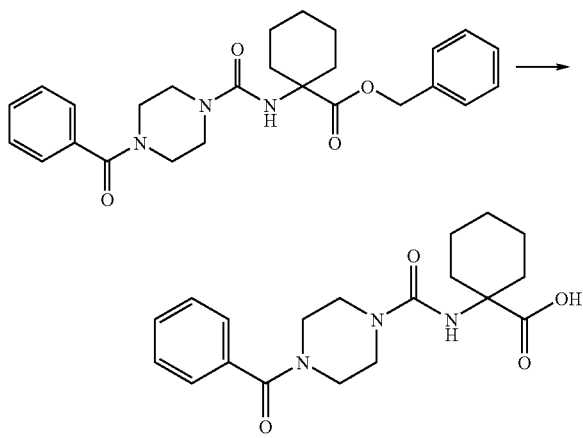

3.60 g (8 mmol) of 1-[[(4-benzoyl-1-piperazinyl)carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 2.88 g (quantitative) of the title compound.

1H-NMR (CDCl$_3$, δ): 1.34-1.42 (2H, m), 1.59-1.74 (2H, m), 1.85-2.10 (6H, m), 3.42-3.58 (6H, m), 3.70-3.87 (2H, m), 4.60 (1H, br-s), 7.39-7.47 (5H, m)

Reference Example 89

1-[[[4-(Phenylmethyl)-1-piperazinyl]carbonyl]amino]cyclohexanecarboxylic acid ethyl ester

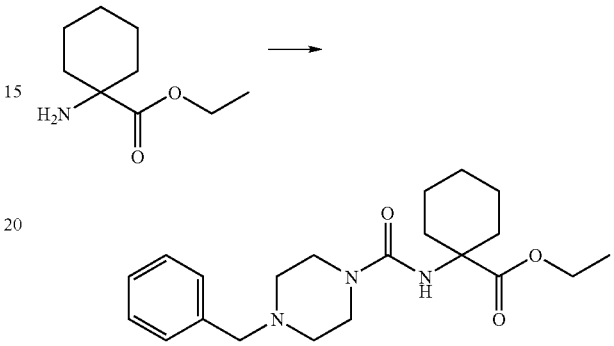

5.82 g (33 mmol) of 4-(phenylmethyl)piperazine was used instead of 1-phenylpiperazine, and 5.14 g (30 mmol) of 1-aminocyclohexanecarboxylic acid ethyl ester was used instead of 1-aminocyclohexanecarboxylic acid phenylmethyl ester in the process according to Reference Example 77 to obtain 7.62 g (68%) of the title compound.

1H-NMR (CDCl$_3$, δ): 1.24 (3H, t, J=7 Hz), 1.24-1.39 (1H, m), 1.40-1.49 (2H, m), 1.55-1.64 (3H, m), 1.80-1.89 (2H, m), 1.97-2.04 (2H, m), 2.44 (4H, t, J=5 Hz), 3.39 (4H, t, J=5 Hz), 3.52 (2H, s), 4.17 (2H, q, J=7 Hz), 4.50 (1H, br-s), 7.23-7.30 (1H, m), 7.30-7.37 (4H, m)

Reference Example 90

1-[[[4-(Phenylmethyl)-1-piperazinyl]carbonyl]amino]cyclohexanecarboxylic acid

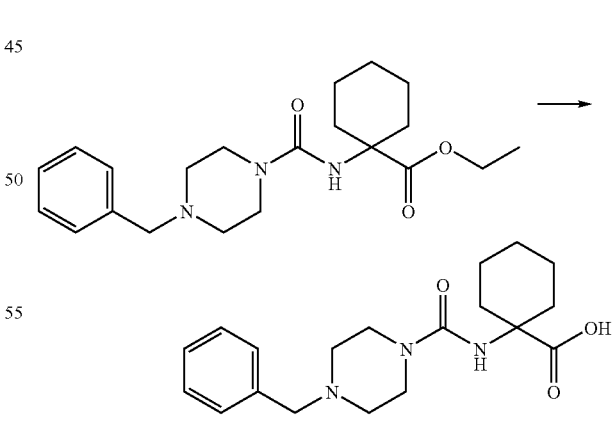

600 ml of 1N aqueous sodium hydroxide solution was added to a solution of 7.62 g (20 mmol) of 1-[[(4-phenylmethyl-1-piperazinyl)carbonyl]amino]cyclohexanecarboxylic acid ethyl ester in 300 ml of ethanol, and the mixture was heated under reflux for 2 hours. Ater ether was added to the reaction solution to wash it, the aqueous layer was neutralized by concentrated hydrochloric acid, and the mixture was extracted with ethyl acetate. After the obtained organic layer was washed with saturated brine, it was dried with anhydrous sodium sulfate. The solvent was distilled off under reduced pressure to obtain 2.90 g (42%) of the title compound.

1H-NMR (CDCl$_3$, δ): 1.28-1.38 (2H, m), 1.60-1.71 (4H, m) 1.88-1.98 (2H, m), 2.01-2.10 (2H, m), 2.49 (4H, t, J=5 Hz), 3.45 (4H, t, J=5 Hz), 3.55 (2H, s), 4.43 (1H, br-s), 7.24-7.34 (5H, m)

Reference Example 91

1-[[4-(1-Oxo-3-phenylpropyl)-1-piperazinyl]carbonyl]amino]cyclohexanecarboxylic acid phenylmethyl ester

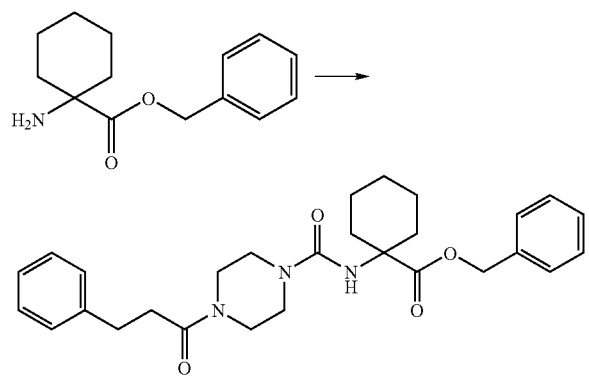

2.40 g (11 mmol) of 1-(1-oxo-3-phenylpropyl)piperazine was used instead of 1-(benzoyl)piperazine in the process according to Reference Example 87 to obtain 3.53 g (74%) of the title compound.

1H-NMR (CDCl$_3$, δ): 1.22-1.39 (1H, m), 1.40-1.49 (2H, m), 1.58-1.67 (3H, m), 1.84-1.93 (2H, m), 2.00-2.07 (2H, m), 2.62 (2H, t, J=6 Hz), 2.98 (2H, t, J=6 Hz), 3.25-3.33 (6H, m), 3.59-3.65 (2H, m), 4.52 (1H, br-s), 5.14 (2H, br-s) 7.18-7.23 (4H, m), 7.28-7.34 (6H, m)

Reference Example 92

1-[[[4-(1-Oxo-3-phenylpropyl)-1-piperazinyl]carbonyl]amino]cyclohexanecarboxylic acid

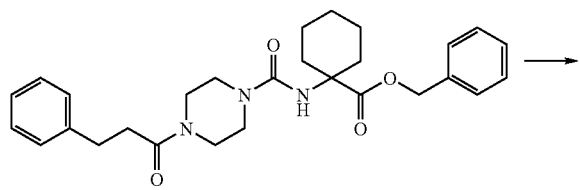

3.53 g (7.4 mmol) of 1-[[[4-(1-oxo-3-phenylpropyl)-1-piperazinyl]carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 2.87 g (quantitative) of the title compound.

1H-NMR (CDCl$_3$, δ): 1.28-1.53 (3H, m), 1.57-1.70 (3H, m) 1.84-1.97 (2H, m), 2.00-2.08 (2H, m), 2.63 (2H, t, J=6 Hz), 2.98 (2H, m, J=6 Hz), 3.33-3.41 (6H, m), 3.67-3.71 (2H, m), 4.78 (1H, br-s), 7.18-7.25 (3H, m), 7.27-7.34 (2H, m)

Reference Example 93

1-[[[4-(Phenylacetyl)-1-piperazinyl]carbonyl]amino]cyclohexanecarboxylic acid phenylmethyl ester

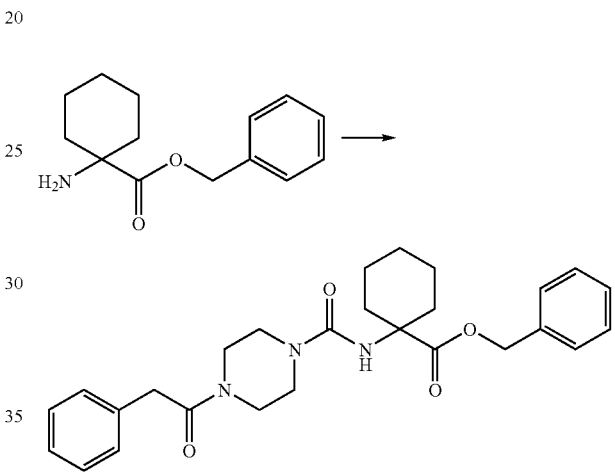

1.23 g (6 mmol) of 1-(phenylacetyl)piperazine was used instead of 1-(1-oxo-3-phenylpropyl)piperazine in the process according to Reference Example 87 to obtain 2.39 g (87%) of the title compound.

1H-NMR (CDCl$_3$, δ): 1.22-1.36 (1H, m), 1.37-2.06 (2H, m), 1.55-1.66 (3H, m), 1.83-1.92 (2H, m), 1.98-2.03 (2H, m), 3.20 (2H, t, J=5 Hz), 3.31 (2H, t, J=5 Hz), 3.41 (2H, t, J=5 Hz), 3.63 (2H, t, J=5 Hz), 3.74 (2H, s), 4.49 (1H, br-s), 5.12 (2H, s), 7.24-7.32 (10H, m)

Reference Example 94

1-[[[4-(Phenylacetyl)-1-piperazinyl]carbonyl]amino]cyclohexanecarboxylic acid

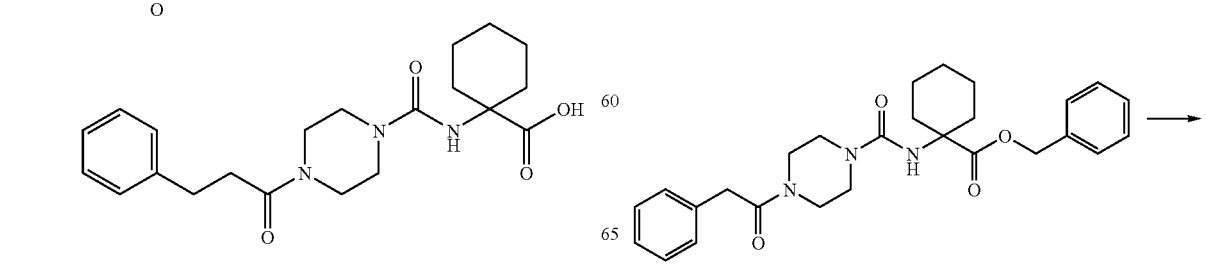

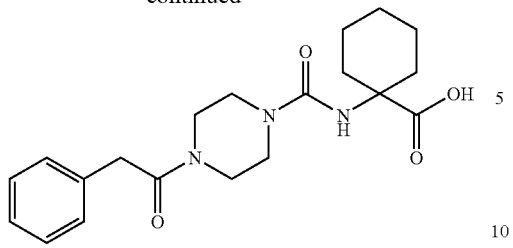

2.39 g (5.2 mmol) of 1-[[[4-(phenylacetyl)-1-piperazinyl]carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 1.94 g (quantitative) of the title compound.

1H-NMR (CDCl$_3$, δ): 1.29-1.39 (3H, m), 1.58-1.70 (3H, m), 1.86-1.96 (2H, m), 1.99-2.07 (2H, m), 3.26 (2H, t, J=5 Hz), 3.38 (2H, t, J=5 Hz), 3.50 (2H, t, J=5 Hz), 3.72 (2H, t, J=5 Hz), 3.76 (2H, s), 4.50 (1H, br-s), 7.23-7.30 (3H, m), 7.30-7.35 (2H, m)

Reference Example 95

1-[(1-Piperidinylcarbonyl)amino]cyclohexanecarboxylic acid phenylmethyl ester

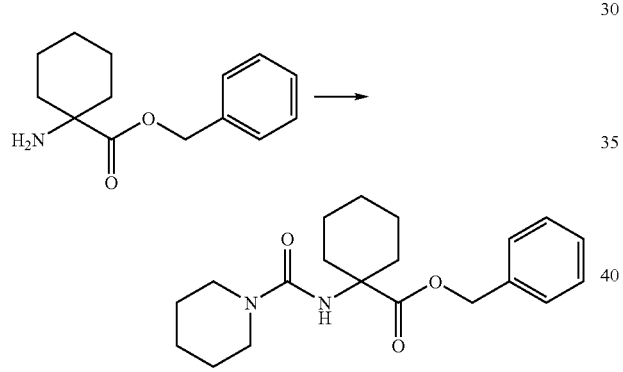

1.34 g (15.8 mmol) of piperidine was used instead of 1-(1-oxo-3-phenylpropyl)piperazine in the process according to Reference Example 87 to obtain 4.59 g (89%) of the title compound.

1H-NMR (CDCl$_3$, δ): 1.22-1.34 (1H, m), 1.40-1.65 (11H, m), 1.82-1.90 (2H, m), 2.02-2.08 (2H, m), 3.32 (4H, t, J=5 Hz), 4.53 (1H, br-s), 5.14 (2H, s), 7.29-7.35 (5H, m)

Reference Example 96

1-[(1-Piperidinylcarbonyl)amino]cyclohexanecarboxylic acid

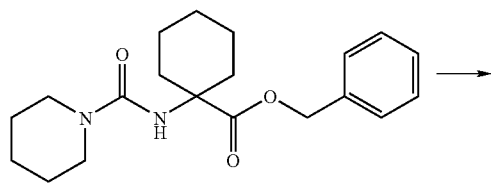

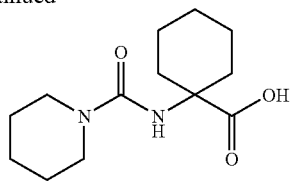

4.59 g (12 mmol) of 1-[(1-piperidinylcarbonyl)amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 3.05 g (quantitative) of the title compound.

1H-NMR (CDCl$_3$, δ): 1.30-1.41 (4H, m), 1.56-1.70 (8H, m), 1.85-1.96 (2H, m), 2.05-2.13 (2H, m), 3.89 (4H, t, J=5 Hz), 4.51 (1H, br-s)

Reference Example 97

1-[(1-Pyrrolidinylcarbonyl)amino]cyclohexanecarboxylic acid phenylmethyl ester

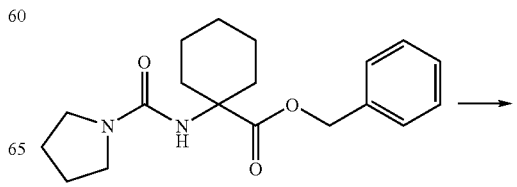

1.12 g (15.8 mmol) of pyrrolidine was used instead of 1-(1-oxo-3-phenylpropyl)piperazine in the process according to Reference Example 87 to obtain 3.23 g (65%) of the title compound.

1H-NMR (CDCl$_3$, δ): 1.23-1.33 (1H, m), 1.42-1.51 (2H, m) 1.51-1.68 (3H, m), 1.82-1.95 (2H, m), 1.89 (4H, t, J=7 Hz), 2.02-2.10 (2H, m), 3.35 (4H, t, J=7 Hz), 4.33 (1H, br-s), 5.16 (2H, s), 7.26-7.36 (5H, m)

Reference Example 98

1-[(1-Pyrrolidinylcarbonyl)amino]cyclohexanecarboxylic acid

-continued

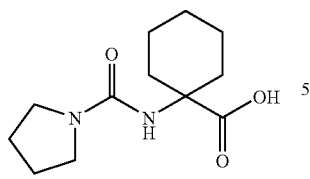

3.23 g (9.8 mmol) of 1-[(1-pyrrolidinylcarbonyl)amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 2.35 g (quantitative) of the title compound.

1H-NMR (CDCl$_3$, δ): 1.29-1.42 (3H, m), 1.58-1.72 (3H, m), 1.88-2.00 (6H, m), 2.05-2.14 (2H, m), 3.40 (4H, t, J=6 Hz), 4.34 (1H, br-s)

Reference Example 99

1-[[(2-Oxo-1-piperidinyl)carbonyl]amino]cyclohexanecarboxylic acid phenylmethyl ester

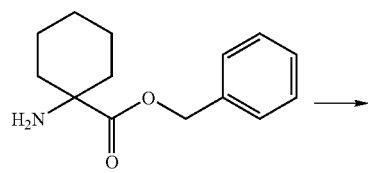

A solution of 183 mg (1.5 mmol) of N,N-dimethylaminopyridine and 3.50 g (15 mmol) of 1-aminocyclohexanecarboxylic acid phenylmethyl ester in toluene was added to a solution of 3.27 g (15 mmol) of di-t-butyl dicarbonate in 60 ml of toluene, and the mixture was stirred at room temperature for 30 minutes. Thereafter, 3.04 g (30 mmol) of triethylamine, 1.83 g (15 mmol) of N,N-dimethylaminopyridine and 1.56 g (15.8 mmol) of 2-piperidone were added and the mixture was heated under reflux overnight. Ethyl acetate was added to the reaction solution, and the mixture was successively washed with water, a 10% aqueous potassium hydrogensulfate solution, a saturated aqueous sodium hydrogencarbonate solution and saturated brine, followed by drying with anhydrous sodium sulfate. The solvent was distilled off under reduced pressure, and the obtained residue was purified by silica gel chromatography to obtain 4.10 g (76%) of the title compound.

1H-NMR (CDCl$_3$, δ): 1.21-1.30 (1H, m), 1.42-1.53 (2H, m) 1.61-1.69 (3H, m), 1.78-1.90 (6H, m), 2.06-2.15 (2H, m), 2.54 (2H, t, J=6 Hz), 3.73 (2H, t, J=6 Hz), 5.16 (2H, s), 7.27-7.35 (5H, m), 9.85 (1H, br-s)

Reference Example 100

1-[[(2-Oxo-1-piperidinyl)carbonyl]amino]cyclohexanecarboxylic acid

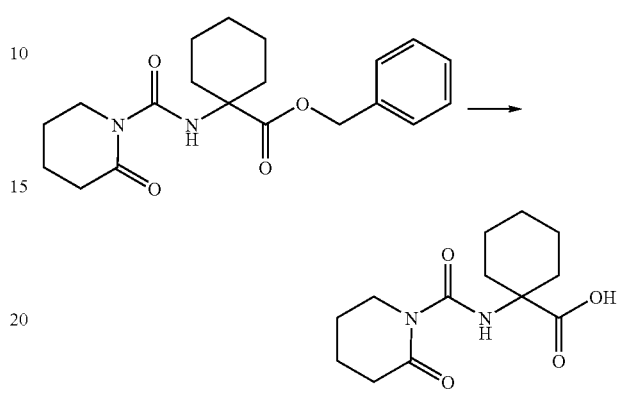

4.10 g (11.4 mmol) of 1-[[1-(2-oxo-1-piperidinyl)carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 2.95 g (96%) of the title compound.

1H-NMR (CDCl$_3$, δ): 1.24-1.35 (1H, m), 1.45-1.64 (2H, m), 1.50-1.71 (3H, m), 1.82-1.92 (6H, m), 2.12-2.16 (2H, m), 2.58 (2H, t, J=6 Hz), 3.80 (2H, t, J=6 Hz), 9.96 (1H, br-s)

Reference Example 101

1-[(1,4-Dioxa-8-azaspiro[4.5]dec-8-ylcarbonyl)amino]cyclohexanecarboxylic acid phenylmethyl ester

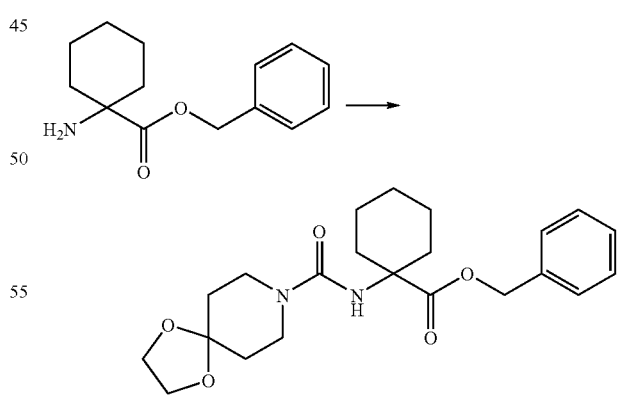

3.00 g (21 mmol) of 1,4-dioxa-8-azaspiro[4.5]decane was used instead of 1-(benzoyl)piperazine in the process according to Reference Example 87 to obtain 5.70 g (71%) of the title compound.

1H-NMR (CDCl$_3$, δ): 1.23-1.34 (1H, m), 1.40-1.48 (2H, m), 1.59-1.67 (3H, m), 1.69 (4H, t, J=6 Hz), 1.84-1.93 (2H, m), 2.00-2.08 (2H, m), 3.47 (4H, t, J=6 Hz), 3.98 (4H, s), 4.59 (1H, br-s), 5.14 (2H, s), 7.27-7.36 (5H, m)

Reference Example 102

1-[(1,4-Dioxa-8-azaspiro[4.5]dec-8-ylcarbonyl)amino]cyclohexanecarboxylic acid

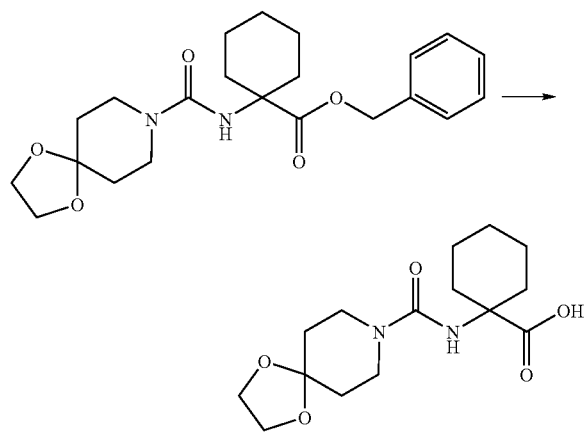

5.70 g (14.2 mmol) of 1-[(1,4-dioxa-8-azaspiro[4.5]dec-8-ylcarbonyl)amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 4.38 g (quantitative) of the title compound.

1H-NMR (CDCl$_3$, δ): 1.30-1.42 (3H, m), 1.60-1.77 (3H, m), 1.75 (4H, t, J=6 Hz), 1.88-2.01 (2H, m), 2.05-2.14 (2H, m), 3.54 (4H, t, J=6 Hz), 3.99 (4H, s), 4.55 (1H, br-s)

Reference Example 103

1-[[[(1,3-Dioxolan-2-ylmethyl)methylamino]carbonyl]amino]cyclohexanecarboxylic acid phenylmethyl ester

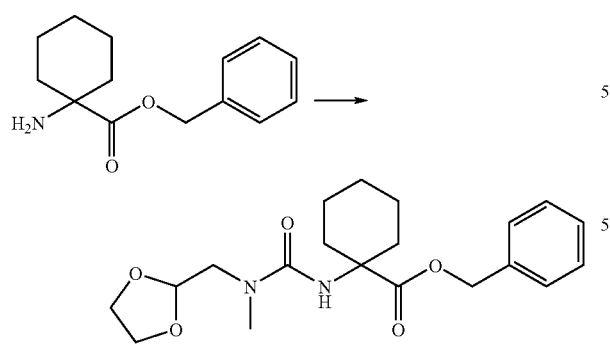

2.46 g (21 mmol) of 2-[(methylamino)methyl]-1,3-dioxolane was used instead of 1-(benzoyl)piperazine in the process according to Reference Example 87 to obtain 6.05 g (80%) of the title compound.

1H-NMR (CDCl$_3$, δ): 1.22-1.34 (1H, m), 1.39-1.50 (2H, m) 1.59-1.68 (2H, m), 1.68-1.74 (3H, m), 1.82-1.91 (2H, m), 2.00-2.08 (2H, m), 3.44-3.50 (4H, m), 3.98 (4H, s), 4.59 (1H, br-s), 5.14 (2H, s), 7.27-7.36 (5H, m)

Reference Example 104

1-[[[(1,3-Dioxolan-2-ylmethyl)methylamino]carbonyl]amino]cyclohexanecarboxylic acid

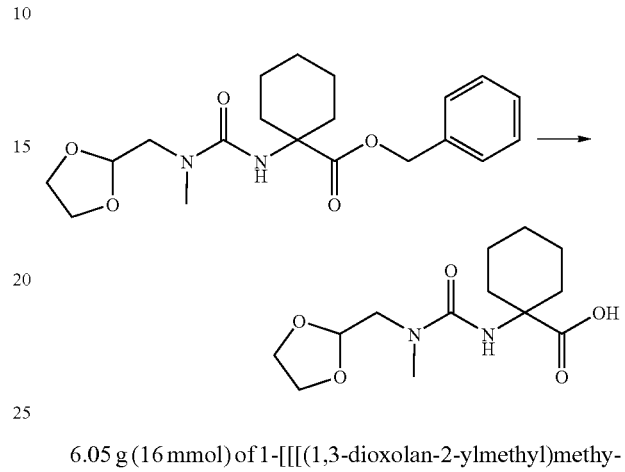

6.05 g (16 mmol) of 1-[[[(1,3-dioxolan-2-ylmethyl)methylamino]carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 4.45 g (97%) of the title compound.

1H-NMR (CDCl$_3$, δ): 1.30-1.41 (3H, m), 1.60-1.75 (5H, m), 1.88-1.97 (2H, m), 2.04-2.13 (2H, m), 3.48-3.59 (4H, m), 3.99 (4H, s), 4.53 (1H, br-s)

Reference Example 105

1-[[(1,3-Dihydro-2H-isoindol-2-yl)carbonyl]amino]cyclohexanecarboxylic acid phenylmethyl ester

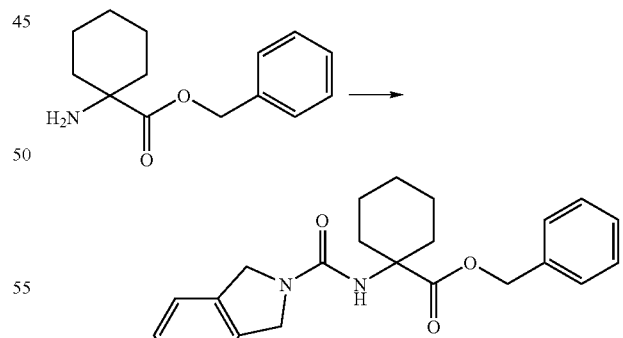

2.50 g (21 mmol) of isoindoline was used instead of 1-(benzoyl)piperazine in the process according to Reference Example 87 to obtain 5.95 g (79%) of the title compound.

1H-NMR (CDCl$_3$, δ): 1.23-1.38 (1H, m), 1.45-1.70 (5H, m), 1.89-1.97 (2H, m), 2.07-2.16 (2H, m), 4.48 (1H, br-s), 4.73 (4H, s), 5.17 (2H, s), 7.25-7.31 (7H, m), 7.31-7.36 (2H, m)

Reference Example 106

1-[[(1,3-Dihydro-2H-isoindol-2-yl)carbonyl]amino]cyclohexanecarboxylic acid

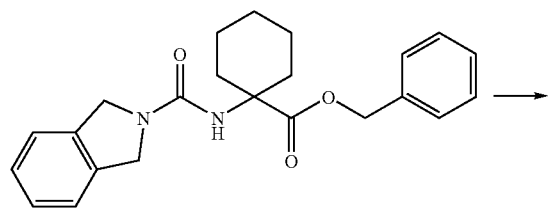

5.95 g (15.8 mmol) of 1-[[(1,3-dihydro-2H-isoindol-2-yl)carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 3.09 g (68%) of the title compound.

1H-NMR (CDCl$_3$, δ): 1.23-1.30 (1H, m), 1.35-1.48 (2H, m), 1.59-1.76 (3H, m), 1.96-2.05 (2H, m), 2.10-2.17 (2H, m), 4.40 (1H, br-s), 4.78 (4H, br-s), 7.24-7.35 (4H, m)

Reference Example 107

1-[[(2-Oxo-1-imidazolidinyl)carbonyl]amino]cyclohexanecarboxylic acid phenylmethyl ester

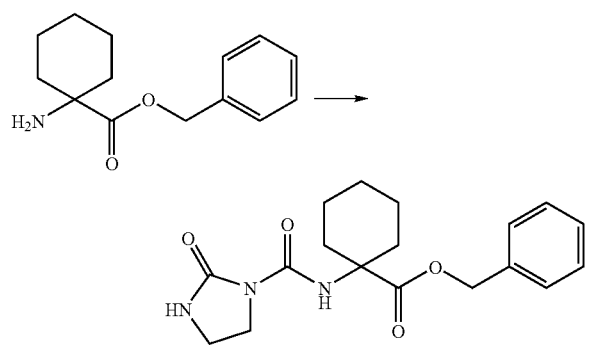

1.38 g (9.3 mmol) of 2-oxo-1-imidazolidinecarbonyl chloride was added to a solution of 2.17 g (9.3 mmol) of 1-aminocyclohexanecarboxylic acid phenylmethyl ester and 1.04 g (10 mmol) of triethylamine in 100 ml of chloroform, and the mixture was stirred at 60° C. for 4 days. The reaction solution was successively washed with water, a 10% aqueous potassium hydrogensulfate solution, a saturated aqueous sodium hydrogencarbonate solution and saturated brine, and it was dried with anhydrous sodium sulfate. The solvent was distilled off under reduced pressure, and the obtained crystal was washed with diethyl ether to obtain 2.64 g (82%) of the title compound.

1H-NMR (CDCl$_3$, δ): 1.22-1.31 (1H, m), 1.44-1.54 (2H, m), 1.60-1.68 (3H, m), 1.81-1.88 (2H, m), 2.08-2.16 (2H, m), 3.48 (2H, t, J=7 Hz), 3.93 (2H, t, J=7 Hz), 4.75 (1H, br-s), 5.17 (2H, s), 7.26-7.36 (5H, m), 8.45 (1H, br-s)

Reference Example 108

1-[[(2-Oxo-1-imidazolidinyl)carbonyl]amino]cyclohexanecarboxylic acid

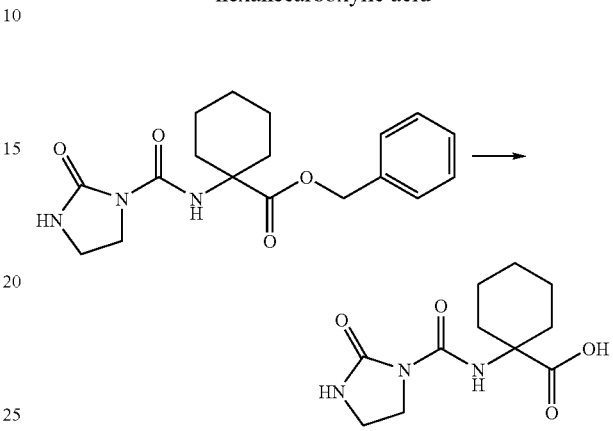

2.64 g (7.6 mmol) of 1-[[(2-oxo-1-imidazolidinyl)carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 1.95 g (quantitative) of the title compound.

1H-NMR (CDCl$_3$, δ): 1.23-1.38 (1H, m), 1.41-1.70 (5H, m) 1.83-1.92 (2H, m), 2.11-2.20 (2H, m), 3.54 (2H, t, J=8 Hz), 4.01 (2H, t, J=8 Hz), 4.92 (1H, br-s), 8.53 (1H, br-s)

Reference Example 109

1-[[(3-Methyl-2-oxo-1-imidazolidinyl)carbonyl]amino]cyclohexanecarboxylic acid phenylmethyl ester

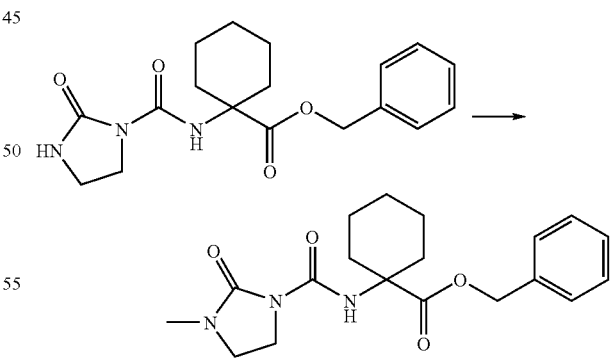

1.83 g (12.9 mmol) of methyl iodide was added to a solution of 1.50 g (4.3 mmol) of 1-[[(2-oxo-1-imidazolidinyl)carbonyl]amino]cyclohexanecarboxylic acid phenylmethyl ester and 1.78 g (12.9 mmol) of potassium carbonate in 100 ml of acetonitrile, and the mixture was heated under reflux overnight. The reaction solution was concentrated, ethyl acetate was added thereto, and the mixture was successively washed with water, a 10% aqueous potassium hydrogensulfate solution, a saturated aqueous sodium hydrogencarbonate solution and saturated brine, followed by drying with anhydrous sodium sulfate. After the solvent was distilled off under reduced pressure, the residue was purified by silica gel chromatography to obtain 710 mg (50%) of the title compound.

1H-NMR (CDCl$_3$, δ): 1.21-1.30 (1H, m), 1.42-1.56 (2H, m), 1.61-1.69 (3H, m), 1.79-1.88 (2H, m), 2.08-2.17 (2H, m), 2.86 (3H, s), 3.40 (2H, t, J=8 Hz), 3.81 (2H, t, J=8 Hz), 5.17 (2H, s), 7.30-7.36 (5H, m), 8.55 (1H, br-s)

Reference Example 110

1-[[(3-Methyl-2-oxo-1-imidazolidinyl)carbonyl]amino]cyclohexanecarboxylic acid

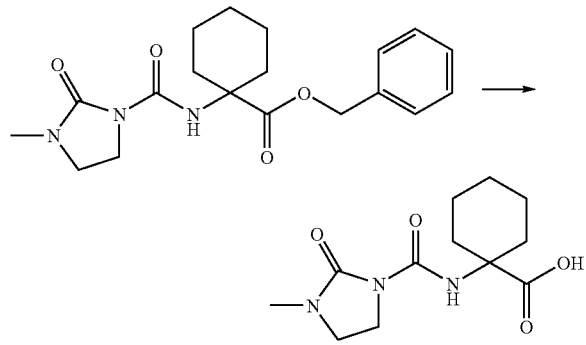

710 mg (2 mmol) of 1-[[(3-methyl-2-oxo-1-imidazolidinyl)carbonyl]amino]cyclohexanecarboxylic acid phenylmethyl ester was used instead of 1-[[(4-phenyl-1-piperazinyl)carbonyl]amino]cyclohexanecarboxylic acid phenylmethyl ester in the process according to Reference Example 78 to obtain 539 mg (quantitative) of the title compound.

1H-NMR (CDCl$_3$, δ): 1.23-1.33 (1H, m), 1.42-1.53 (2H, m), 1.61-1.70 (3H, m), 1.82-1.89 (2H, m), 2.11-2.20 (2H, m), 2.89 (3H, s), 3.46 (2H, dd, J=10 Hz, 8 Hz), 3.91 (2H, dd, J=10 Hz, 8 Hz), 8.66 (1H, br-s)

Reference Example 111

1-[[(2,5-Dihydro-1H-pyrrol-1-yl)carbonyl]amino]cyclohexanecarboxylic acid methyl ester

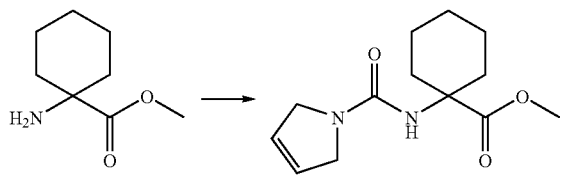 [SMILES: COC(=O)C1(N)CCCCC1 ; COC(=O)C1(NC(=O)N2CC=CC2)CCCCC1]

472 mg (3 mmol) of 1-aminocyclohexanecarboxylic acid methyl ester was used instead of 1-aminocyclohexanecarboxylic acid phenylmethyl ester, and 311 mg (4.5 mmol) of 2,5-dihydropyrrole was used instead of 1-phenylpiperazine in the process according to Reference Example 77 to obtain 698 mg (92%) of the title compound.

1H-NMR (CDCl$_3$, δ): 1.23-1.38 (1H, m), 1.42-1.53 (2H, m), 1.53-1.69 (3H, m), 1.82-1.92 (2H, m), 2.01-2.10 (2H, m), 3.73 (3H, s), 4.18 (4H, s), 4.31 (1H, s), 5.82 (2H, s)

Reference Example 112

1-[[(2,5-Dihydro-1H-pyrrol-1-yl)carbonyl]amino]cyclohexanecarboxylic acid

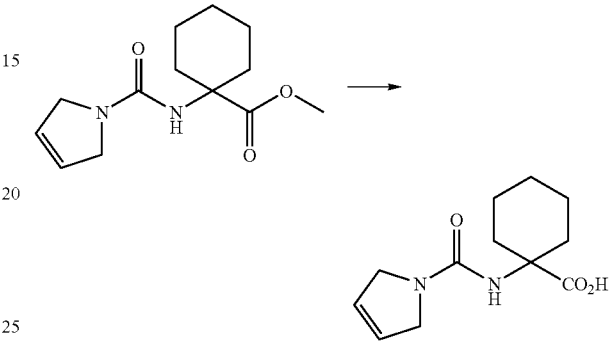

698 mg (2.8 mmol) of 1-[[(2,5-dihydro-1H-pyrrol-1-yl)carbonyl]amino]cyclohexanecarboxylic acid methyl ester was used instead of 1-[[[4-(phenylmethyl)-1-piperazinyl]carbonyl]amino]cyclohexanecarboxylic acid ethyl ester in the process according to Reference Example 90 to obtain 453 mg (69%) of the title compound.

1H-NMR (CDCl$_3$, δ): 1.34-1.73 (6H, m), 1.92-2.22 (2H, m), 2.24-2.36 (2H, m), 4.23 (4H, br-s), 4.23 (1H, br-s), 5.87 (2H, br-s)

Reference Example 113

1-[(1H-Pyrrol-1-ylcarbonyl)amino]cyclohexanecarboxylic acid methyl ester

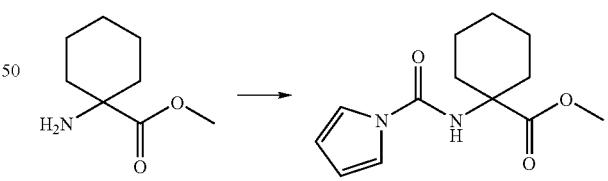

1 g (6.36 mmol) of 1-aminocyclohexanecarboxylic acid methyl ester was used instead of 1-aminocyclohexanecarboxylic acid phenylmethyl ester, and 512 mmol (7.6 mmol) of pyrrole was used instead of 1-phenylpiperazine in the process according to Reference Example 77 to obtain 1.52 g (95%) of the title compound.

1H-NMR (CDCl$_3$, δ): 1.36-1.57 (3H, m), 1.65-1.74 (3H, m), 1.91-2.02 (2H, m), 2.08-2.19 (2H, m), 3.74 (3H, s), 5.58 (1H, s), 6.28 (2H, dd, J=2 Hz, 1 Hz), 7.19 (2H, dd, J=2 Hz, 1 Hz)

Reference Example 114

1-[(1H-Pyrrol-1-ylcarbonyl)amino]cyclohexanecarboxylic acid

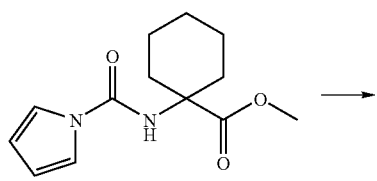

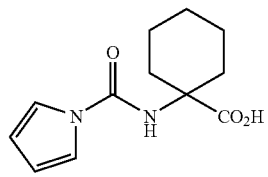

1.52 g (6 mmol) of 1-[[[(1H-pyrrol-1-yl)carbonyl]amino]cyclohexanecarboxylic acid methyl ester was used instead of 1-[[[4-(phenylmethyl)-1-piperazinyl]carbonyl]amino]cyclohexanecarboxylic acid ethyl ester in the process according to Reference Example 90 to obtain 839 mg (58%) of the title compound.

1H-NMR (DMSO-$d_6$, δ): 1.15-1.61 (4H, m), 1.69-1.81 (2H, m), 1.83-1.98 (2H, m), 2.08-2.19 (2H, m), 6.12 (2H, s), 6.21 (1H, d, J=2 Hz), 7.42 (2H, d, J=2 Hz), 7.88 (1H, dr-s)

Reference Example 115

1-[(3-Thiazolidinylcarbonyl)amino]cyclohexanecarboxylic acid

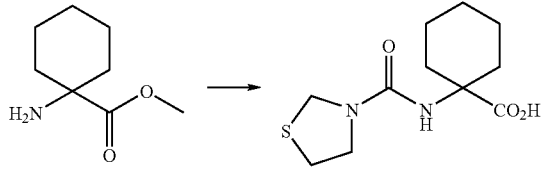 [SMILES: COC(=O)C1(N)CCCCC1 ; O=C(NC1(C(=O)O)CCCCC1)N1CCSC1]

A solution of 78 mg (0.6 mmol) of N,N-dimethylaminopyridine and 1 g (6.36 mmol) of 1-aminocyclohexanecarboxylic acid methyl ester in methylene chloride was added to a solution of 1.39 mg (6.36 mmol) of di-t-butyl dicarbonate in 10 ml of methylene chloride, and the mixture was stirred at room temperature for 30 minutes. Thereafter, a solution of 1.29 g (12.7 mmol) of triethylamine and 680 mg (7.6 mmol) of thiazolidine in methylene chloride was added, and the mixture was stirred at room temperature overnight. After the reaction solution was concentrated, the residue was dissolved in ethyl acetate, and the mixture was washed with water, a 10% aqueous potassium hydrogensulfate solution, a saturated aqueous sodium hydrogencarbonate solution and then saturated brine, followed by drying with anhydrous sodium sulfate. After the solvent was distilled off under reduced pressure, tetrahydrofuran and 1N aqueous sodium hydroxide solution were added to the residue, and the mixture was heated under reflux for 3 hours. After ether was added to the reaction solution to wash it, the aqueous layer was neutralized by concentrated hydrochloric acid, and it was extracted with ethyl acetate. After the obtained organic layer was washed with saturated brine, it was dried with anhydrous sodium sulfate. The solvent was distilled off under reduced pressure to obtain 1.1 g (66%) of the title compound.

1H-NMR (DMSO-$d_6$, δ): 1.08-1.25 (1H, m), 1.36-1.69 (6H, m), 1.82-2.01 (3H, m), 2.93 (2H, t, J=7 Hz), 3.59 (2H, t, J=7 Hz), 4.43 (2H, s), 6.44 (1H, s), 11.99 (1H, br-s)

Reference Example 116

1-[[[(2-Furanylmethyl)methylamino]carbonyl]amino]cyclohexanecarboxylic acid methyl ester

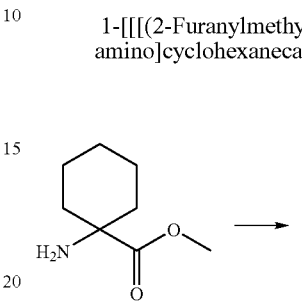

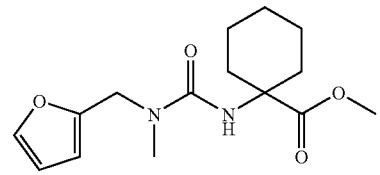

2.83 g (18 mmol) of 1-aminocyclohexanecarboxylic acid methyl ester was used instead of 1-aminocyclohexanecarboxylic acid phenylmethyl ester, and 2.18 g (18 mmol) of (2-furanylmethyl)methylamine was used instead of 1-phenylpiperazine in the process according to Reference Example 77 to obtain 4.27 g (78%) of the title compound.

1H-NMR (CDCl$_3$, δ): 1.25-1.47 (3H, m), 1.57-1.68 (3H, m), 1.80-1.85 (2H, m), 1.97-2.20 (2H, m), 2.94 (3H, s), 3.71 (3H, s), 4.42 (2H, s), 4.74 (1H, s), 6.24 (1H, dd, J=3 Hz, 1 Hz), 6.34 (1H, dd, J=3 Hz, J=3 Hz, 2 Hz), 7.37 (1H, dd, J=2 Hz, 1 Hz)

Reference Example 117

1-[[[(2-Furanylmethyl)methylamino]carbonyl]amino]cyclohexanecarboxylic acid

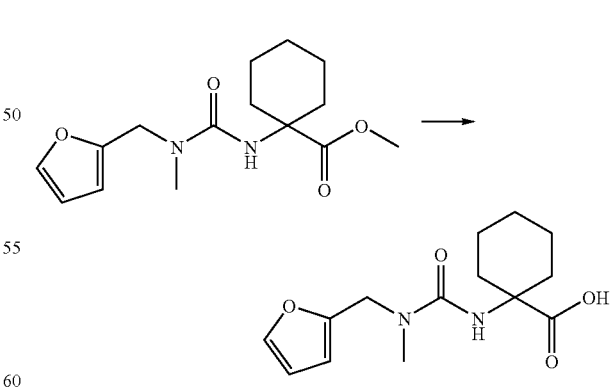

4.27 g (14 mmol) of 1-[[[(2-furanylmethyl)methylamino]carbonyl]amino]cyclohexanecarboxylic acid methyl ester was used instead of 1-[[[4-(phenylmethyl)-1-piperazinyl]carbonyl]amino]cyclohexanecarboxylic acid ethyl ester in the process according to Reference Example 90 to obtain 3.47 g (84%) of the title compound.

1H-NMR (DMSO-d$_6$, δ): 1.12-1.23 (1H, m), 1.38-1.52 (5H, m), 1.58-1.64 (2H, m), 1.80-2.22 (2H, m), 2.81 (3H, s), 4.42 (2H, s), 6.03 (1H, s), 6.24 (1H, dd, J=3 Hz, 1 Hz), 6.40 (1H, dd, J=3 Hz, 2 Hz), 7.57 (1H, dd, J=2 Hz, 1 Hz)

Reference Example 118

1-[[(Methylphenylamino)carbonyl]amino]cyclohexanecarboxylic acid methyl ester

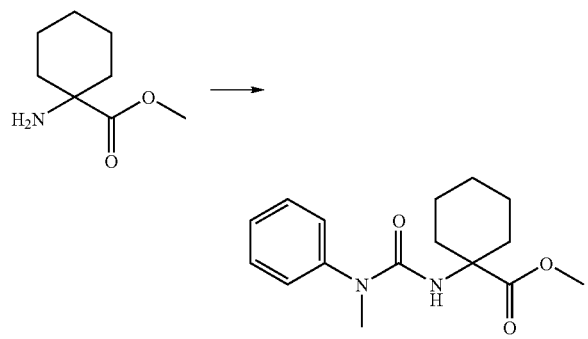

472 mg (3 mmol) of 1-aminocyclohexanecarboxylic acid methyl ester was used instead of 1-aminocyclohexanecarboxylic acid phenylmethyl ester, and 643 mg (6 mmol) of N-methylaniline was used instead of 1-phenylpiperazine in the process according to Reference Example 77 to obtain 834 mg (96%) of the title compound.

1H-NMR (CDCl$_3$, δ): 1.12-1.28 (2H, m), 1.48-1.62 (4H, m), 1.64-1.70 (2H, m), 1.90-1.98 (2H, m), 3.25 (3H, s), 3.74 (3H, s), 4.49 (1H, s), 7.26-7.36 (3H, m), 7.43-7.46 (2H, m)

Reference Example 119

1-[[(Methylphenylamino)carbonyl]amino]cyclohexanecarboxylic acid

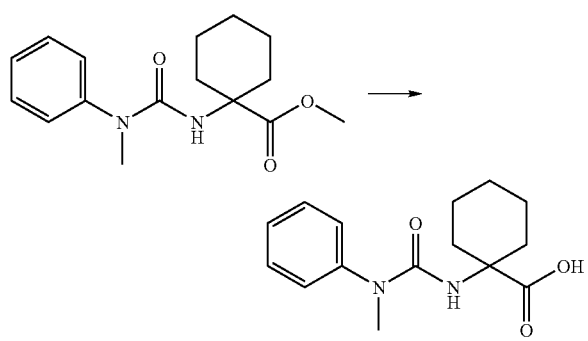

834 mg (2.87 mmol) of 1-[[(methylphenylamino)carbonyl]amino]cyclohexanecarboxylic acid methyl ester was used instead of 1-[[[4-(phenylmethyl)-1-piperazinyl]carbonyl]amino]cyclohexanecarboxylic acid ethyl ester in the process according to Reference Example 90 to obtain 464 mg (59%) of the title compound.

1H-NMR (CDCl$_3$, δ): 0.96-1.05 (2H, m), 1.19-1.30 (1H, m), 1.50-1.60 (3H, m), 1.70-1.81 (2H, m), 1.96-2.02 (2H, m), 3.31 (3H, s), 4.30 (1H, s), 7.26-7.33 (2H, m), 7.44 (1H, t, J=9 Hz), 7.51 (2H, t, J=9 Hz)

Reference Example 120

1-[[[Methyl(phenylmethyl)amino]carbonyl]amino]cyclohexanecarboxylic acid methyl ester

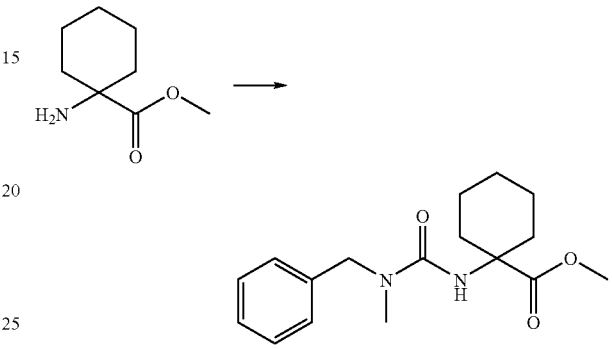

2.83 g (18 mmol) of 1-aminocyclohexanecarboxylic acid methyl ester was used instead of 1-aminocyclohexanecarboxylic acid phenylmethyl ester, and 2.18 g (18 mmol) of N-methylbenzylamine was used instead of 1-phenylpiperazine in the process according to Reference Example 77 to obtain 4.27 g (78%) of the title compound.

1H-NMR (CDCl$_3$, δ): 1.20-1.38 (3H, m), 1.50-1.63 (3H, m), 1.78-1.85 (2H, m), 1.97-2.03 (2H, m), 2.94 (3H, s), 3.73 (3H, s), 4.49 (2H, s), 4.51 (1H, s), 7.25-7.30 (3H, m), 7.35 (2H, dt, J=8 Hz, 1 Hz)

Reference Example 121

1-[[[Methyl(phenylmethyl)amino]carbonyl]amino]cyclohexanecarboxylic acid

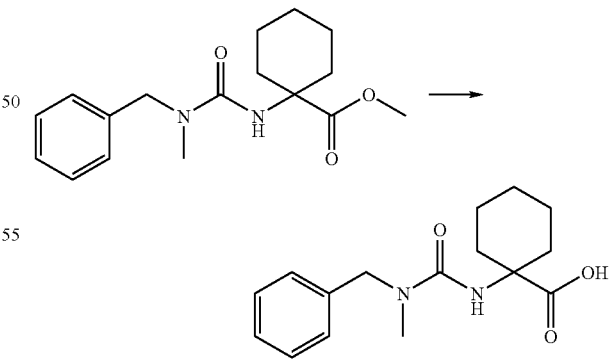

4.27 g (14 mmol) of 1-[[[methyl(phenylmethyl)amino]carbonyl]amino]cyclohexanecarboxylic acid methyl ester was used instead of 1-[[[4-(phenylmethyl)-1-piperazinyl]carbonyl]amino]cyclohexanecarboxylic acid ethyl ester in the process according to Reference Example 90 to obtain 3.54 g (86%) of the title compound.

1H-NMR (DMSO-d$_6$, δ): 1.16-2.04 (1H, m), 1.39-1.47 (5H, m), 1.58-1.65 (2H, m), 1.97-2.22 (2H, m), 2.79 (3H, s), 4.44 (2H, s), 6.00 (1H, s), 7.21-7.34 (5H, m)

Reference Example 122

1-[[(2-Oxo-2H-pyran-5-yl)carbonyl]amino]cyclohexanecarboxylic acid

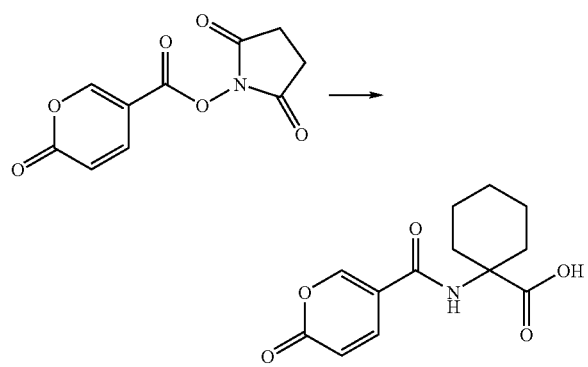

2.37 g (10 mmol) of 5-coumarinecarboxylic acid N-hydroxysuccinimide ester and a solution of 1.43 g (10 mmol) of 1-aminocyclohexanecarboxylic acid and 3.04 g (30 mmol) of triethylamine in 20 ml of dimethylformamide were stirred overnight. Ethyl acetate was added to the reaction solution, and the mixture was washed with a 10% aqueous potassium hydrogensulfate solution and then saturated brine. After it was dried with anhydrous sodium sulfate, the solvent was distilled off under reduced pressure to obtain 1.42 g (60%) of the title compound.

1H-NMR (DMSO-d$_6$, δ): 1.30-1.44 (3H, m), 1.44-1.63 (3H, m), 1.95-2.09 (4H, m), 5.26 (1H, d, J=9 Hz), 7.62 (1H, d, J=9 Hz), 8.28 (1H, d, J=15 Hz), 9.68 (1H, d, J=15 Hz)

Reference Example 123

1-[(4-Fluorobenzoyl)amino]cyclohexanecarboxylic acid

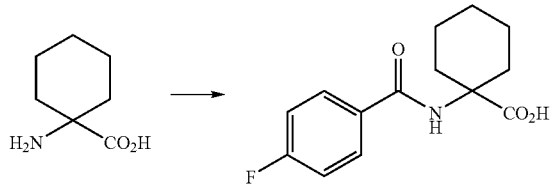 [SMILES: NC1(C(=O)O)CCCCC1 ; O=C(NC1(C(=O)O)CCCCC1)c1ccc(F)cc1]

Under ice-cooling, a solution of 25.0 g (15.8 mmol) of 4-fluorobenzoyl chloride in 30 ml of ether was added dropwise to a mixture solution of 22.6 g (15.8 mmol) of 1-aminocyclohexanecarboxylic acid and 25.0 g (23.7 mmol) of sodium carbonate in 100 ml of ether and 300 ml of water, and the mixture was stirred at room temperature overnight. After the ether layer was separated, the aqueous layer was neutralized by concentrated hydrochloric acid under ice-cooling, and the precipitated crystal was collected by filtration to obtain 27.7 g (66%) of the title compound.

Reference Example 124

1-[[[4-(4-Propylpiperazin-1-yl)phenyl]carbonyl]amino]cyclohexanecarboxylic acid phenylmethyl ester

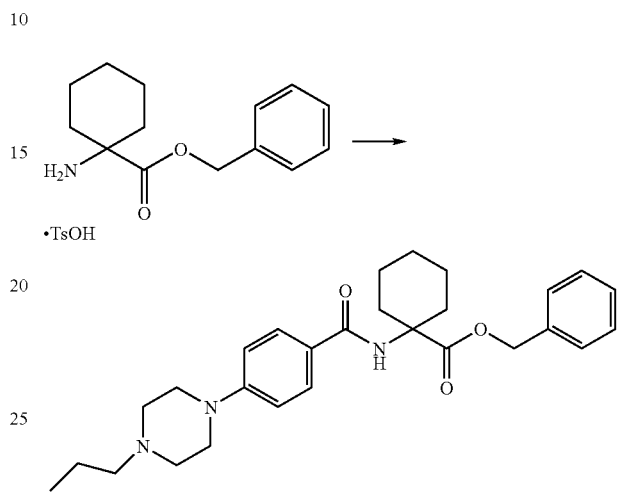

2.36 g (8.44 mmol) of 4-(4-propylpiperazin-1-yl)benzoic acid hydrochloride was used instead of phenylacetyl chloride in the process according to Reference Example 1 to obtain 1.79 g (46%) of the title compound.

1H-NMR (CDCl$_3$, δ): 0.94 (3H, t, J=7 Hz), 1.28-1.40 (1H, m), 1.45-1.61 (4H, m), 1.61-1.72 (3H, m), 1.90-1.98 (2H, m), 2.15-2.23 (2H, m), 2.36 (1H, t, J=6 Hz), 2.37 (1H, t, J=6 Hz), 2.59 (4H, t, J=5 Hz), 3.31 (4H, t, J=5 Hz), 5.16 (2H, s), 6.13 (1H, br-s), 6.89 (2H, d, J=8 Hz), 7.25-7.33 (5H, m), 7.68 (2H, d, J=8 Hz)

Reference Example 125

1-[[[4-(4-Propylpiperazin-1-yl)phenyl]carbonyl]amino]cyclohexanecarboxylic acid

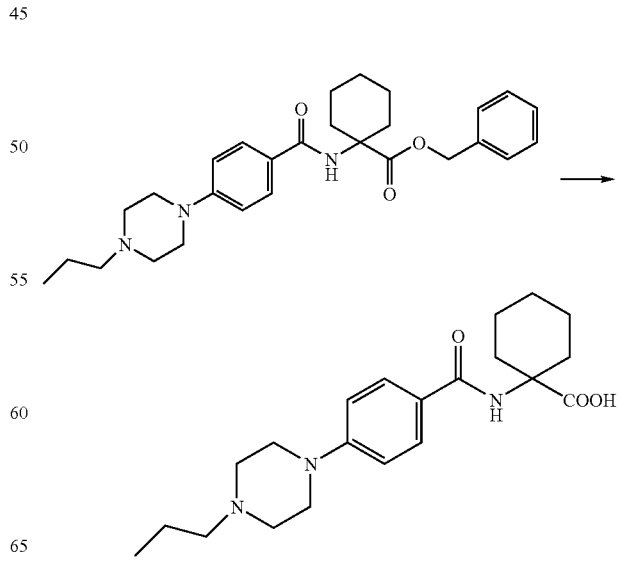

1.79 g (3.86 mmol) of 1-[[[4-(4-propylpiperazin-1-yl)phenyl]carbonyl]amino]cyclohexanecarboxylic acid phenylmethyl ester was used instead of 1-[(phenylacetyl)amino]cyclohexanecarboxylic acid phenylmethyl ester in the process according to Reference Example 2 to obtain 1.43 g (quantitative) of the title compound.

1H-NMR (CDCl$_3$, δ): 0.95 (3H, t, J=8 Hz), 1.39-1.61 (3H, m) 1.65-1.78 (4H, m), 1.94-2.03 (3H, m), 2.21-2.41 (2H, m), 2.45-2.54 (2H, m), 2.65-2.70 (4H, m), 3.27-3.35 (4H, m), 6.06 (1H, br-s), 6.85 (2H, d, J=8 Hz), 7.65 (2H, d, J=8 Hz)

Reference Example 126

1-[[[4-(4-Propylpiperazin-1-yl)phenyl]carbonyl]amino]cyclohexanecarboxylic acid methyl ester

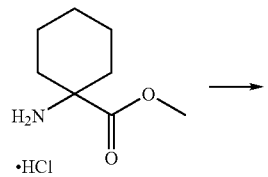

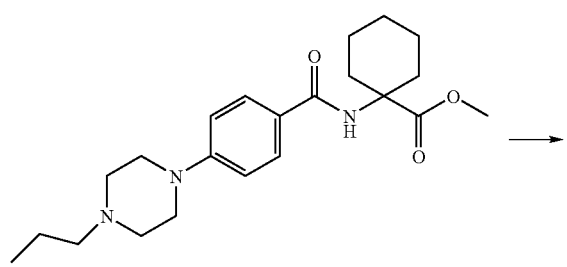

1.00 g (3.57 mmol) of 4-(4-propylpiperazin-1-yl)benzoic acid hydrochloride was used instead of 3-furancarboxylic acid in the process according to Reference Example 15 to obtain 602 g (44%) of the title compound.

NMR (CDCl$_3$, δ): 0.94 (3H, t, J=8 Hz), 1.31-1.40 (1H, m), 1.44-1.58 (4H, m), 1.62-1.74 (3H, m), 1.88-1.96 (2H, m), 2.11-2.19 (2H, m), 2.36 (1H, t, J=6 Hz), 2.37 (1H, t, J=6 Hz), 2.59 (4H, t, J=5 Hz), 3.30 (4H, t, J=5 Hz), 3.72 (3H, s), 6.12 (1H, br-s), 6.89 (2H, dd, J=2 Hz, 7 Hz), 7.69 (2H, dd, J=2 Hz, 7 Hz)

Reference Example 127

1-[[[4-(4-Propylpiperazin-1-yl)phenyl]carbonyl]amino]cyclohexanecarboxylic acid methyl ester hydrochloride

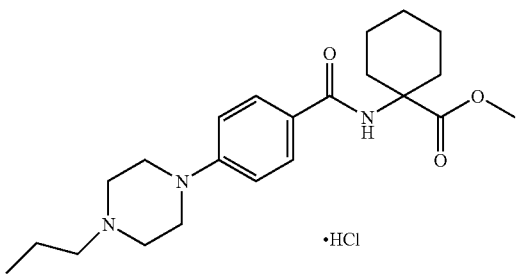

1 ml of 4N hydrochloric acid/ethyl acetate solution was added to a solution of 120 mg (0.31 mmol) of 1-[[[4-(4-propylpiperazin-1-yl)phenyl]carbonyl]amino]cyclohexanecarboxylic acid methyl ester in 10 ml of ethyl acetate, and the mixture was stirred at room temperature for 30 minutes. The precipitated crystal was collected by filtration to obtain 87 mg (66%) of the title compound.

1H-NMR (DMSO-d$_6$, δ): 0.91 (3H, t, J=8 Hz), 1.21-1.35 (1H, m), 1.47-1.62 (5H, m), 1.70-1.81 (4H, m), 2.02-2.10 (2H, m), 3.01-3.14 (4H, m), 3.15-3.28 (2H, m), 3.50-3.58 (2H, m), 3.82-4.02 (5H, m), 7.04 (2H, dd, J=2 Hz, 7 Hz), 7.79 (2H, dd, J=2 Hz, 7 Hz), 8.11 (1H, s)

Reference Example 128

1-[[[4-(4-Propylpiperazin-1-yl)phenyl]carbonyl]amino]cyclohexanecarboxylic acid hydrochloride

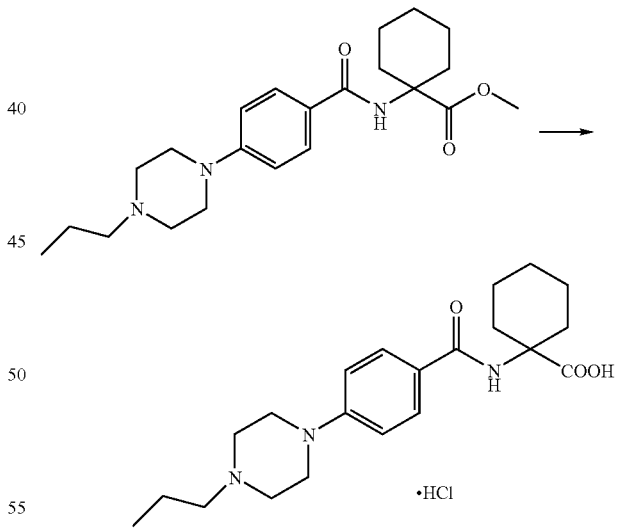

3 ml of 4N hydrochloric acid was added to 600 mg (1.55 mmol) of 1-[[[4-(4-propylpiperazin-1-yl)phenyl]carbonyl]amino]cyclohexanecarboxylic acid methyl ester, and the mixture was heated under reflux for 6 hours. The mixture was cooled to room temperature, and the precipitated crystal was collected by filtration to obtain 258 mg (41%) of the title compound.

1H-NMR (CDCl$_3$, δ): 1.05 (3H, t, J=7 Hz), 1.31-1.43 (1H, m), 1.45-1.56 (2H, m), 1.64-1.78 (3H, m), 1.90-2.02 (4H, m), 2.16-2.25 (2H, m), 2.95-3.28 (5H, m), 3.60-3.75 (4H, m), 3.78-3.89 (2H, m), 6.65 (1H, br-s), 6.92 (2H, d, J=8 Hz), 7.97 (2H, d, J=8 Hz)

Reference Example 129

1-[[[4-(4-Propylpiperazin-1-yl)phenyl]carbonyl]amino]cyclohexanecarboxylic acid ethyl ester

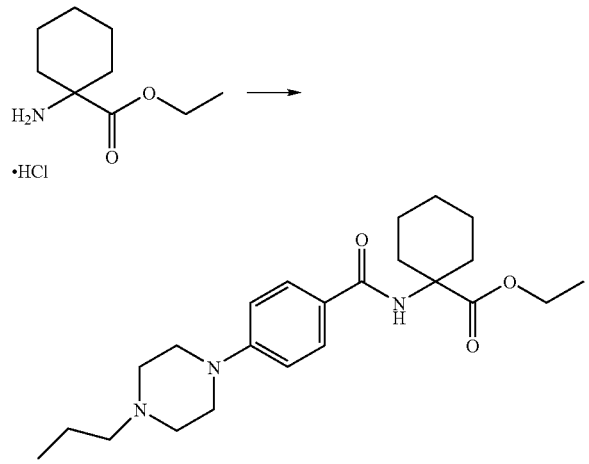 [SMILES: CCOC(=O)C1(N)CCCCC1 ; Cl ; CCCN1CCN(c2ccc(C(=O)NC3(C(=O)OCC)CCCCC3)cc2)CC1]

741 mg (3.57 mmol) of 1-aminocyclohexanecarboxylic acid ethyl ester hydrochloride was used instead of 1-aminocyclohexanecarboxylic acid methyl ester hydrochloride, and 1.00 g (3.57 mmol) of 4-(4-propylpiperazin-1-yl)benzoic acid hydrochloride was used instead of 3-furancarboxylic acid in the process according to Reference Example 15 to obtain 928 mg (65%) of the title compound.

1H-NMR (CDCl$_3$, δ): 0.94 (3H, t, J=8 Hz), 1.24 (3H, t, J=7 Hz), 1.30-1.41 (1H, m), 1.43-1.71 (7H, m), 1.88-1.97 (2H, m), 2.10-2.20 (2H, m), 2.36 (1H, t, J=6 Hz), 2.37 (1H, t, J=6 Hz), 3.31 (4H, t, J=5 Hz), 4.18 (4H, t, J=5 Hz), 4.20 (2H, q, J=7 Hz), 6.10 (1H, br-s), 6.89 (2H, dd, J=2 Hz, 8 Hz), 7.69 (2H, dd, J=2 Hz, 8 Hz)

Reference Example 130

1-[[[4-(4-Propylpiperazin-1-yl)phenyl]carbonyl]amino]cyclohexanecarboxylic acid ethyl ester hydrochloride

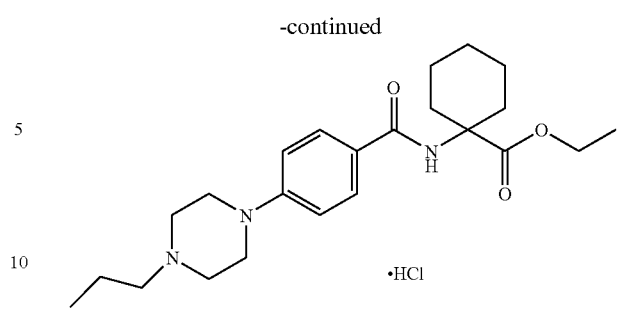

120 mg (0.3 mmol) of 1-[[[4-(4-propylpiperazin-1-yl)phenyl]carbonyl]amino]cyclohexanecarboxylic acid ethyl ester was used instead of 1-[[[4-(4-propylpiperazin-1-yl)phenyl]carbonyl]amino]cyclohexanecarboxylic acid methyl ester in the process according to Reference Example 127 to obtain 114 mg (87%) of the title compound.

1H-NMR (DMSO-d$_6$, δ): 0.93 (3H, t, J=8 Hz), 1.11 (3H, t, J=7 Hz), 1.23-1.32 (1H, m), 1.45-1.55 (5H, m), 1.68-1.80 (4H, m), 2.02-2.10 (2H, m), 3.03-3.18 (6H, m), 3.51-3.62 (2H, m), 3.95-4.04 (2H, m), 4.02 (2H, q, J=7 Hz), 7.04 (2H, d, J=8 Hz), 7.78 (2H, d, J=8 Hz), 8.10 (1H, s)

Reference Example 131

1-[[[4-(4-Propylpiperazin-1-yl)phenyl]carbonyl]amino]cyclohexanecarboxylic acid hydrochloride

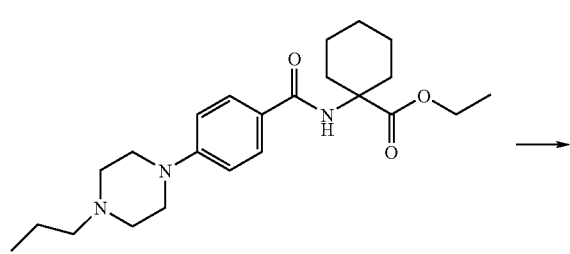

800 mg (1.99 mmol) of 1-[[[4-(4-propylpiperazin-1-yl)phenyl]carbonyl]amino]cyclohexanecarboxylic acid ethyl ester was used instead of 1-[[[4-(4-propylpiperazin-1-yl)phenyl]carbonyl]amino]cyclohexanecarboxylic acid methyl ester in the process according to Reference Example 128 to obtain 197 mg (24%) of the title compound.

1H-NMR (CDCl$_3$, δ): 1.05 (3H, t, J=7 Hz), 1.31-1.43 (1H, m), 1.45-1.56 (2H, m), 1.64-1.78 (3H, m), 1.90-2.02 (4H, m), 2.16-2.25 (2H, m), 2.95-3.28 (5H, m), 3.60-3.75 (4H, m), 3.78-3.89 (2H, m), 6.65 (1H, br-s), 6.92 (2H, d, J=8 Hz), 7.97 (2H, d, J=8 Hz)

Reference Example 132

2-(Phenylmethyl)-3-oxa-1-azaspiro[4.5]dec-1-en-4-one

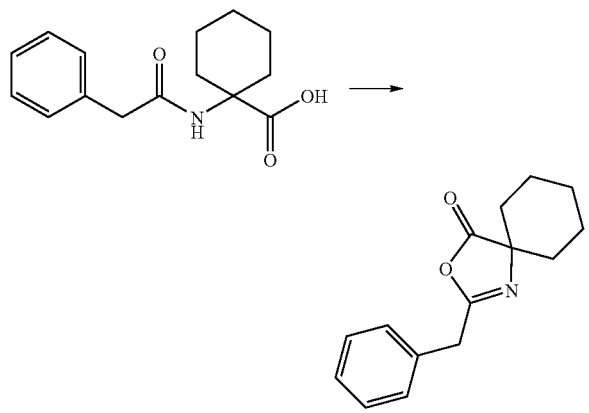 [SMILES: O=C(Cc1ccccc1)NC1(C(=O)O)CCCCC1 ; O=C1OC(Cc2ccccc2)=NC12CCCCC2]

633 mg (3.3 mmol) of 1-ethyl-3-(3-dimethylaminopropyl) carbodiimide hydrochloride was added to a solution of 784 mg (3 mmol) of 1-[(phenylacetyl)amino]cyclohexanecarboxylic acid obtained in Reference Example 2 in 20 ml of methylene chloride. After the mixture was stirred at room temperature for 4 hours, the reaction solution was concentrated under reduced pressure, ethyl acetate was added thereto, and the mixture was successively washed with water, a 10% aqueous potassium hydrogensulfate solution, a saturated aqueous sodium hydrogencarbonate solution and saturated brine, followed by drying with anhydrous sodium sulfate. The solvent was distilled off under reduced pressure to obtain 625 mg (86%) of the title compound.

1H-NMR (CDCl$_3$, δ): 1.48-1.51 (1H, m), 1.56-1.70 (3H, m), 1.70-1.79 (6H, m), 3.79 (2H, s), 7.28-7.36 (5H, m)

Reference Example 133

2-(2-Phenylethyl)-3-oxa-1-azaspiro[4.5]dec-1-en-4-one

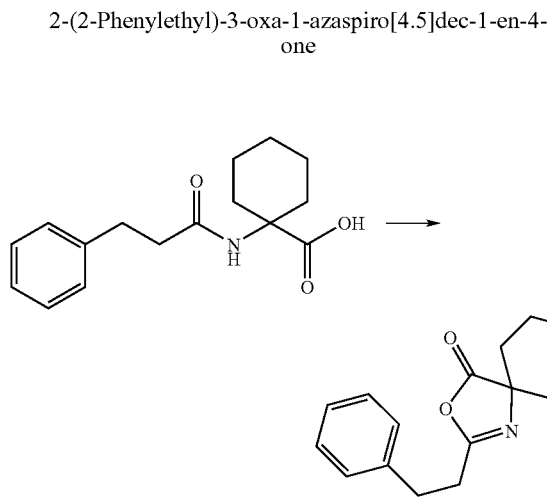

826 mg (3 mmol) of 1-[(1-oxo-3-phenylpropyl)amino]cyclohexanecarboxylic acid was used instead of 1-[(phenylacetyl)amino]cyclohexanecarboxylic acid in the process according to Reference Example 132 to obtain 764 mg (99%) of the title compound.

1H-NMR (CDCl$_3$, δ): 1.47-1.55 (4H, m), 1.57-1.78 (6H, m) 2.79 (2H, t, J=7 Hz), 3.02 (2H, t, J=7 Hz), 7.20-7.23 (3H, m), 7.28-7.31 (2H, m)

Reference Example 134

2-Phenyl-3-oxa-1-azaspiro[4.5]dec-1-en-4-one

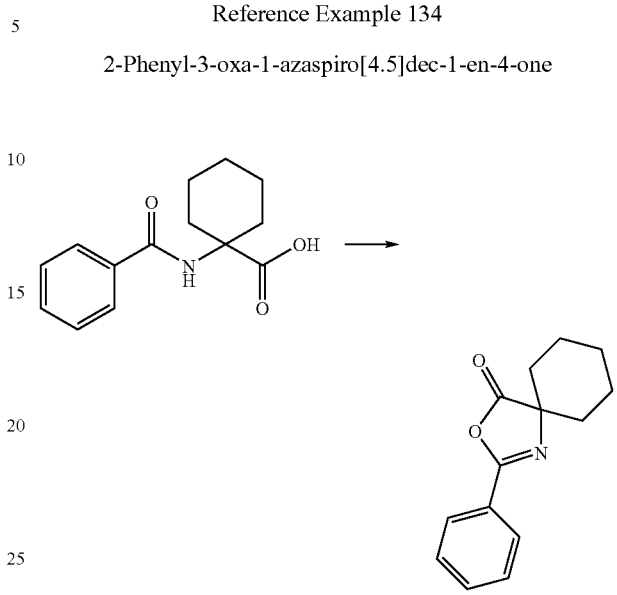

742 mg (3 mmol) of 1-[(benzoyl)amino]cyclohexanecarboxylic acid was used instead of 1-[(phenylacetyl)amino] cyclohexanecarboxylic acid in the process according to Reference Example 132 to obtain 633 mg (92%) of the title compound.

1H-NMR (CDCl$_3$, δ): 1.52-1.58 (1H, m), 1.63-1.78 (3H, m), 1.79-1.89 (6H, m), 7.47 (1H, td, J=7 Hz, 1 Hz), 7.49 (1H, td, J=7 Hz, 1 Hz), 7.56 (1H, td, J=7 Hz, 1 Hz), 8.02 (2H, m)

Reference Example 135

2-(4-Biphenyl)-3-oxa-1-azaspiro[4.5]dec-1-en-4-one

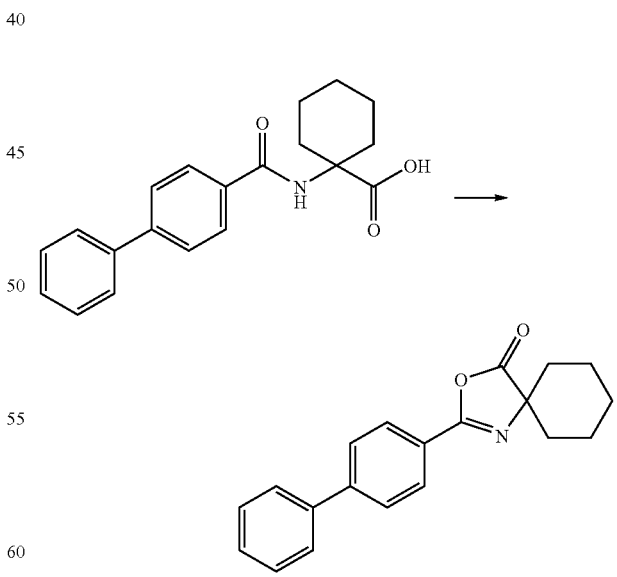

970 mg (3 mmol) of 1-[(4-biphenylcarbonyl)amino]cyclohexanecarboxylic acid was used instead of 1-[(phenylacetyl) amino]cyclohexanecarboxylic acid in the process according to Reference Example 132 to obtain 914 mg (quantitative) of the title compound.

1H-NMR (CDCl₃, δ): 1.52 (2H, m), 1.63-1.71 (1H, m), 1.72-1.80 (2H, m), 1.81-1.90 (5H, m), 7.39-7.42 (1H, m), 7.47-7.50 (2H, m), 7.63 (1H, dd, J=7 Hz, 1 Hz), 7.65 (1H, dd, J=7 Hz, 1 Hz), 7.71 (1H, d, J=7 Hz, 1 Hz), 7.72 (1H, dd, J=7 Hz, 1 Hz), 8.07 (1H, dd, J=7 Hz, 1 Hz), 8.08 (1H, dd, J=7 Hz, 1 Hz)

Reference Example 136

2-(2-Naphthyl)-3-oxa-1-azaspiro[4.5]dec-1-en-4-one

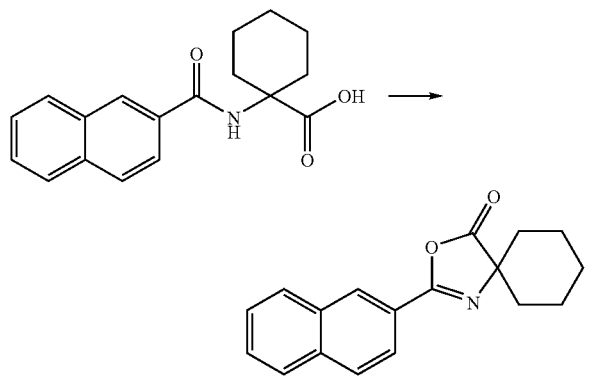

595 mg (2 mmol) of 1-[(2-naphthylcarbonyl)amino]cyclohexanecarboxylic acid was used instead of 1-[(phenylacetyl)amino]cyclohexanecarboxylic acid in the process according to Reference Example 132 to obtain 562 mg (quantitative) of the title compound.

1H-NMR (CDCl₃, δ): 1.54-1.68 (1H, m), 1.69-1.76 (1H, m), 1.78-1.94 (8H, m), 7.26-7.62 (2H, m), 7.89 (1H, d, J=8 Hz), 7.92 (1H, dd, J=8 Hz, 1 Hz), 7.95 (1H, dd, J=8 Hz, 1 Hz), 8.09 (1H, dd, J=8 Hz, 1 Hz), 8.49 (1H, d, J=1 Hz)

Reference Example 137

2-(1-Naphthyl)-3-oxa-1-azaspiro[4.5]dec-1-en-4-one

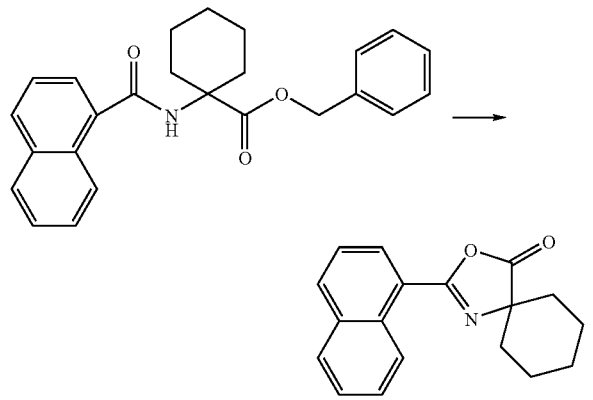

1.35 g (3.5 mmol) of 1-[(1-naphthylcarbonyl)amino]cyclohexanecarboxylic acid phenylmethyl ester obtained in Reference Example 11 was dissolved in 50 ml of methanol, 150 mg of 10% palladium-carbon was added thereto, and the mixture was stirred under a hydrogen atmosphere at room temperature overnight. After the reaction solution was filtered, the filtrate was concentrated under reduced pressure. The obtained residue was dissolved in 30 ml of methylene chloride, and 633 mg (3.3 mmol) of 1-ethyl-3-(3-dimethylaminopropyl)carbodiimide hydrochloride was added thereto. After the mixture was stirred at room temperature for 4 hours, the reaction solution was concentrated under reduced pressure, ethyl acetate was added thereto, and the mixture was successively washed with water, a 10% aqueous potassium hydrogensulfate solution, a saturated aqueous sodium hydrogencarbonate solution and saturated brine, followed by drying with anhydrous sodium sulfate. The solvent was distilled off under reduced pressure to obtain 738 mg (88%) of the title compound.

1H-NMR (CDCl₃, δ): 1.50-1.68 (3H, m), 1.70-2.00 (7H, m), 7.53-7.60 (2H, m), 7.67 (1H, td, 7 Hz, 1 Hz), 7.92 (1H, dd, J=7 Hz, 1 Hz), 8.03 (1H, d, J=7 Hz), 8.17 (1H, dd, J=7 Hz, 1 Hz), 9.33 (1H, dd, J=7 Hz, 1 Hz)

Reference Example 138

2-[(RS)-2,3-Tetrahydrobenzofuran-2-yl]-3-oxa-1-azaspiro[4.5]dec-1-en-4-one

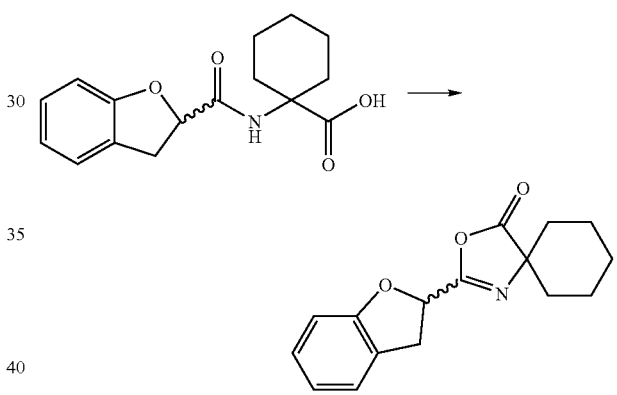

868 mg (3 mmol) of 1-[[[(RS)-2,3-tetrahydrobenzofuran-2-yl]carbonyl]amino]cyclohexanecarboxylic acid was used instead of 1-[(phenylacetyl)amino]cyclohexanecarboxylic acid in the process according to Reference Example 132 to obtain 686 mg (87%) of the title compound.

1H-NMR (CDCl₃, δ): 1.43-1.82 (10H, m), 3.56 (2H, d, J=9 Hz), 5.46 (½H, d, J=10 Hz), 5.48 (½H, d, J=10 Hz), 6.89 (1H, td, 8 Hz, 1 Hz), 6.93 (1H, dd, H=8 Hz, 1 Hz), 7.16 (1H, td, J=8 Hz, 1 Hz), 7.21 (1H, dd, J=8 Hz, 1 Hz)

Reference Example 139

2-(2-Furanyl)-3-oxa-1-azaspiro[4.5]dec-1-en-4-one

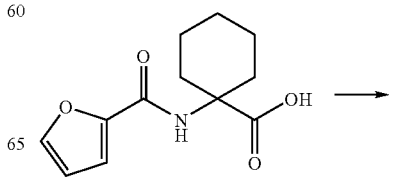

-continued

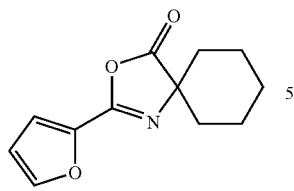

53.2 g (224 mmol) of 1-[(2-furanylcarbonyl)amino]cyclohexanecarboxylic acid was used instead of 1-[(phenylacetyl)amino]cyclohexanecarboxylic acid in the process according to Reference Example 132 to obtain 49.8 g (quantitative) of the title compound.

1H-NMR (CDCl$_3$, δ): 1.53-1.57 (1H, m), 1.66-1.86 (9H, m) 6.58 (1H, dd, J=4 Hz, 2 Hz), 7.09 (1H, dd, J=4 Hz, 1 Hz), 7.65 (1H, dd, J=2 Hz, 1 Hz)

Reference Example 140

2-(3-Furanyl)-3-oxa-1-azaspiro[4.5]dec-1-en-4-one

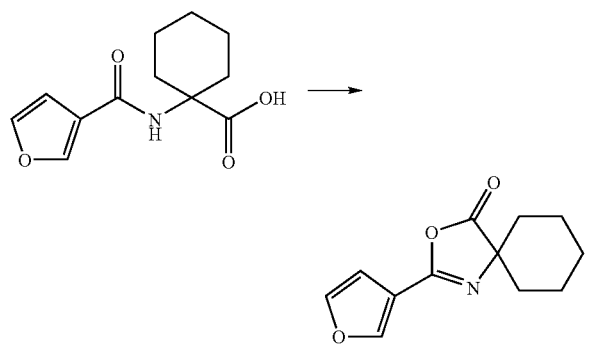

4.48 g (18.9 mmol) of 1-[(3-furanylcarbonyl)amino]cyclohexanecarboxylic acid was used instead of 1-[(phenylacetyl)amino]cyclohexanecarboxylic acid in the process according to Reference Example 132 to obtain 4.02 g (97%) of the title compound.

1H-NMR (CDCl$_3$, δ): 1.54-1.57 (1H, m), 1.63-1.86 (9H, m), 6.86 (1H, dd, J=2 Hz, 1 Hz), 7.51 (1H, t, J=2 Hz), 7.99 (1H, dd, J=2 Hz, 1 Hz)

Reference Example 141

2-[2-(2-Furanyl)ethenyl]-3-oxa-1-azaspiro[4.5]dec-1-en-4-one

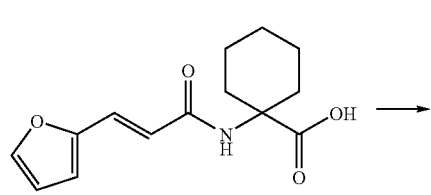

-continued

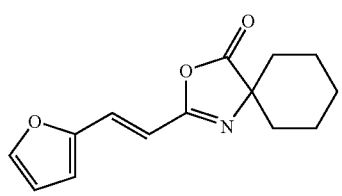

10.0 g (38 mmol) of 1-[[(E)-3-(2-furanyl)-1-oxo-2-propenyl]amino]cyclohexanecarboxylic acid was used instead of 1-[(phenylacetyl)amino]cyclohexanecarboxylic acid in the process according to Reference Example 132 to obtain 8.92 g (96%) of the title compound.

1H-NMR (CDCl$_3$, δ): 1.26-1.54 (2H, m), 1.66-1.84 (8H, m) 6.48 (1H, dd, J=2 Hz, 1 Hz), 6.53 (1H, d, J=16 Hz), 6.60 (1H, d, J=2 Hz), 7.22 (1H, d, J=16 Hz), 7.51 (1H, dd, J=2 Hz, 1 Hz)

Reference Example 142

2-Cyclohexyl-3-oxa-1-azaspiro[4.5]dec-1-en-4-one

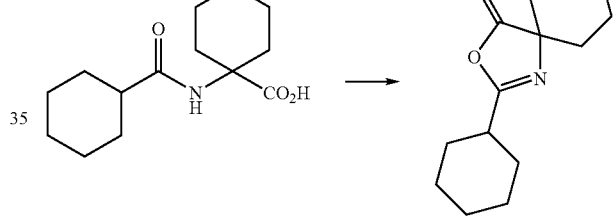

4.15 g (16.3 mmol) of 1-[(cyclohexylcarbonyl)amino]cyclohexanecarboxylic acid was used instead of 1-[(phenylacetyl)amino]cyclohexanecarboxylic acid in the process according to Reference Example 132 to obtain 3.75 g (98%) of the title compound.

1H-NMR (CDCl$_3$, δ): 1.24-1.38 (3H, m), 1.44-1.56 (3H, m), 1.56-1.63 (3H, m), 1.63-1.84 (9H, m), 1.92-2.00 (2H, m), 2.43-2.49 (1H, m)

Reference Example 143

2-(6-Benzothiazolyl)-3-oxa-1-azaspiro[4.5]dec-1-en-4-one

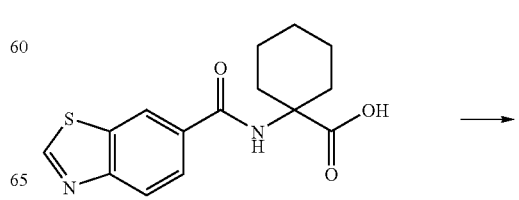

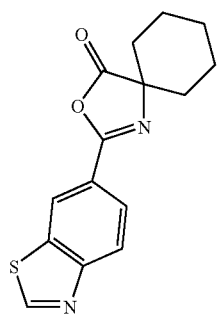

365 mg (1.2 mmol) of 1-[(6-benzothiazolylcarbonyl) amino]cyclohexanecarboxylic acid was used instead of 1-[(phenylacetyl)amino]cyclohexanecarboxylic acid in the process according to Reference Example 132 to obtain 287 mg (83%) of the title compound.

1H-NMR (CDCl₃, δ): 1.53-1.62 (4H, m), 1.68-1.79 (2H, m) 1.81-1.92 (4H, m), 8.19 (1H, dd, J=9 Hz, 2 Hz), 8.22 (1H, dd, J=9 Hz, 1 Hz), 8.65 (1H, dd, J=2 Hz, 1 Hz), 9.15 (1H, s)

Reference Example 144

2-(2-Thienyl)-3-oxa-1-azaspiro[4.5]dec-1-en-4-one

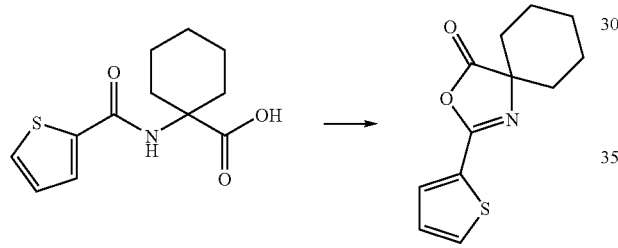

5.0 g (20 mmol) of 1-[(2-thienylcarbonyl)amino]cyclohexanecarboxylic acid was used instead of 1-[(phenylacetyl) amino]cyclohexanecarboxylic acid in the process according to Reference Example 132 to obtain 4.46 g (96%) of the title compound.

1H-NMR (CDCl₃, δ): 1.51-1.59 (1H, m), 1.61-1.69 (1H, m), 1.71-1.88 (8H, m), 7.14 (1H, dd, J=5 Hz, 4 Hz), 7.57 (1H, dd, J=5 Hz, 1 Hz), 7.70 (1H, dd J=4 Hz, 1 Hz)

Reference Example 145

2-(2-Furanyl)-3-oxa-1-azaspiro[4.5]dec-1-en-4-one

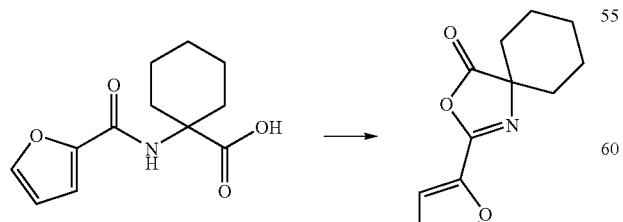

6.0 g (44 mmol) of isobutyl chloroformate was added dropwise to a solution of 10 g (42 mmol) of 1-[(2-furanylcarbonyl) amino]cyclohexanecarboxylic acid obtained in Reference Example 14 and 6.1 ml (44 mmol) of triethylamine in tetrahydrofuran (80 ml), and the mixture was stirred at room temperature for 1 hour. The precipitated crystal was removed by filtration, and the filtrate was concentrated. The obtained crystal was washed with water to obtain 8.95 g (97%) of the title compound.

1H-NMR (CDCl₃, δ): 1.53-1.57 (1H, m), 1.66-1.86 (9H, m), 6.58 (1H, dd, J=4 Hz, 2 Hz), 7.09 (1H, dd, J=4 Hz, 1 Hz), 7.65 (1H, dd, J=2 Hz, 1 Hz)

Reference Example 146

2-(1,3-Benzodioxol-5-yl)-3-oxa-1-azaspiro[4.5]dec-1-en-4-one

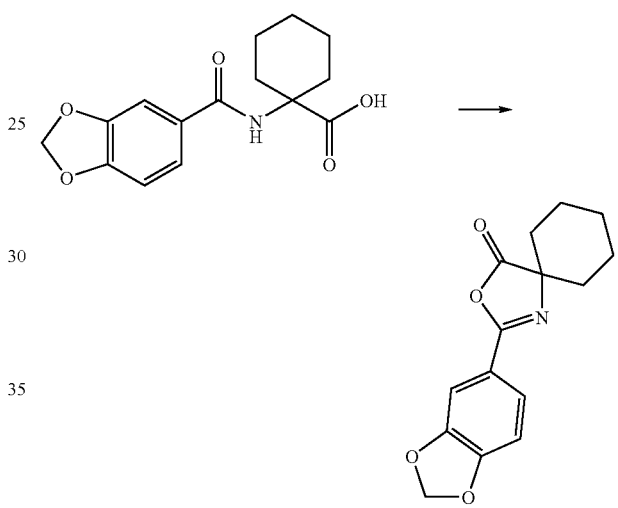

5.8 g (20 mmol) of 1-[[(1,3-benzodioxole)-5-carbonyl] amino]cyclohexanecarboxylic acid was used instead of 1-[(phenylacetyl)amino]cyclohexanecarboxylic acid in the process according to Reference Example 132 to obtain 4.9 g (90%) of the title compound.

1H-NMR (CDCl₃, δ): 1.51-1.57 (1H, m), 1.63-1.75 (3H, m), 1.76-1.88 (6H, m), 6.05 (2H, s), 6.87 (1H, d, J=8 Hz), 7.46 (1H, d, J=2 Hz), 7.55 (1H, dd, J=8 Hz, 2 Hz)

Reference Example 147

2-(2-Benzofuranyl)-3-oxa-1-azaspiro[4.5]dec-1-en-4-one

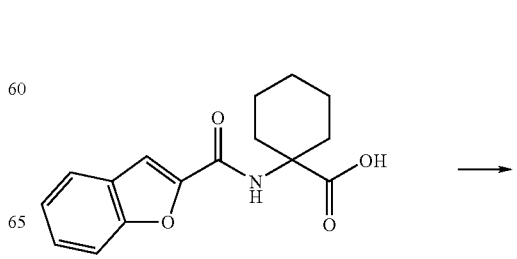

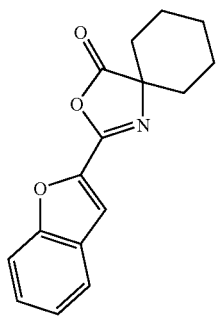

3.8 g (13 mmol) of 1-[[(2-benzofuranyl)carbonyl]amino]cyclohexanecarboxylic acid was used instead of 1-[(phenylacetyl)amino]cyclohexanecarboxylic acid in the process according to Reference Example 132 to obtain 3.4 g (96%) of the title compound.

1H-NMR (CDCl$_3$, δ): 1.51-1.74 (2H, m), 1.78-1.94 (8H, m), 7.33 (1H, ddd, J=8 Hz, 7 Hz, 1 Hz), 7.44 (1H, d, J=1 Hz), 7.46 (1H, ddd, J=8 Hz, 7 Hz, 1 Hz), 7.63 (1H, ddd, J=8 Hz, 2 Hz, 1 Hz), 7.70 (1H, ddd, J=8 Hz, 2 Hz, 1 Hz)

Reference Example 148

2-(2-Pyridinyl)-3-oxa-1-azaspiro[4.5]dec-1-en-4-one 511 mg (2 mmol) of 1-[(2-pyridinylcarbonyl)amino]cyclohexanecarboxylic acid was used instead of 1-[(phenylacetyl)amino]cyclohexanecarboxylic acid in the process according to Reference Example 132 to obtain 405 mg (85%) of the title compound.

1H-NMR (CDCl$_3$, δ): 1.54-1.77 (3H, m), 1.78-1.92 (7H, m), 7.62 (1H, ddd, J=7 Hz, 5 Hz, 2 Hz), 7.87 (1H, dt, J=7 Hz, 2 Hz), 8.04 (1H, dd, J=5 Hz, 2 Hz), 8.82 (1H, dd, J=5 Hz, 2 Hz)

Reference Example 149

2-(3-Thienyl)-3-oxa-1-azaspiro[4.5]dec-1-en-4-one 253 mg (1 mmol) of 1-[(3-thienylcarbonyl)amino]cyclohexanecarboxylic acid was used instead of 1-[(phenylacetyl)amino]cyclohexanecarboxylic acid in the process according to Reference Example 132 to obtain 234 mg (quantitative) of the title compound.

1H-NMR (CDCl$_3$, δ): 1.52-1.87 (10H, m), 7.40 (1H, dd, J=5 Hz, 3 Hz), 7.60 (1H, dd, J=5 Hz, 1 Hz), 8.00 (1H, dd, J=3 Hz, 1 Hz)

Reference Example 150

2-(3-Ethoxy-2-thienyl)-3-oxa-1-azaspiro[4.5]dec-1-en-4-one

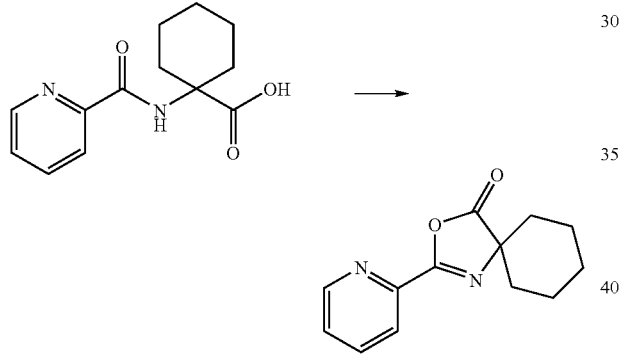

327 mg (1 mmol) of 1-[[(3-ethoxy-2-thienyl)carbonyl]amino]cyclohexanecarboxylic acid was used instead of 1-[(phenylacetyl)amino]cyclohexanecarboxylic acid in the process according to Reference Example 132 to obtain 307 mg (quantitative) of the title compound.

1H-NMR (CDCl$_3$, δ): 1.46 (3H, t, J=7 Hz), 1.49-1.84 (10H, m), 4.22 (2H, q, J=7 Hz), 6.86 (1H, d, J=6 Hz), 7.42 (1H, d, J=6 Hz)

Reference Example 151

2-[2-[(S)-1-Phenylethyl]]-3-oxa-1-azaspiro[4.5]dec-1-en-4-one

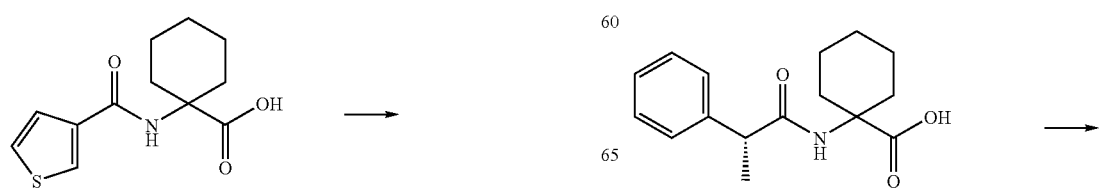

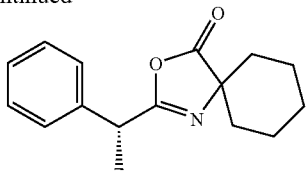

275 mg (1 mmol) of 1-[[(S)-1-oxo-2-phenylpropyl]amino]cyclohexanecarboxylic acid was used instead of 1-[(phenylacetyl)amino]cyclohexanecarboxylic acid in the process according to Reference Example 132 to obtain 257 mg (quantitative) of the title compound.

1H-NMR (CDCl₃, δ): 1.51-1.78 (13H, m), 3.89 (1H, q, J=7 Hz) 7.26-7.35 (5H, m)

Reference Example 152

2-(2-Pyrazinyl)-3-oxa-1-azaspiro[4.5]dec-1-en-4-one

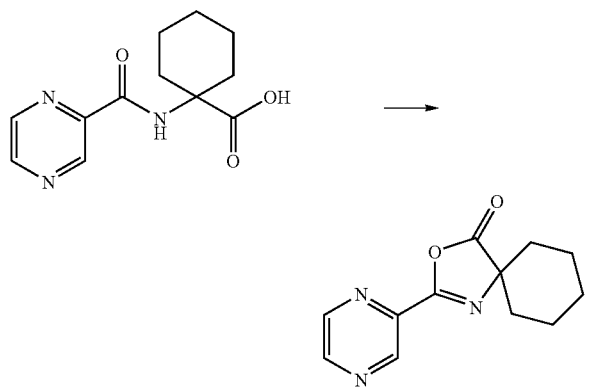

249 mg (1 mmol) of 1-[(2-pyrazinylcarbonyl)amino]cyclohexanecarboxylic acid was used instead of 1-[(phenylacetyl)amino]cyclohexanecarboxylic acid in the process according to Reference Example 132 to obtain 231 mg (quantitative) of the title compound.

1H-NMR (CDCl₃, δ): 1.56-1.93 (10H, m), 8.78 (2H, m), 9.28 (1H, t, J=3 Hz)

Reference Example 153

2-(5-Methylisoxazol-4-yl)-3-oxa-1-azaspiro[4.5]dec-1-en-4-one

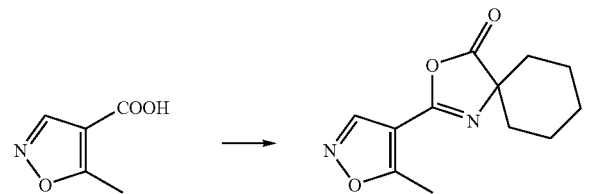

1 g (7.87 mmol) of 5-methylisoxazole-4-carboxylic acid was added to 3 ml of thionyl chloride, and the mixture was stirred overnight. The reaction solution was concentrated under reduced pressure and the obtained residue was added to a solution of 1.13 g (7.87 mmol) of 1-aminocyclohexanecarboxylic acid and 6.6 g (79 mmol) of sodium hydrogencarbonate in 30 ml of toluene-30 ml of water. After the mixture was stirred at room temperature overnight, the toluene layer was separated. The aqueous layer was neutralized by potassium hydrogensulfate, and it was extracted with ethyl acetate. After the obtained organic layer was washed with saturated brine, it was dried with anhydrous sodium sulfate. The solvent was distilled off under reduced pressure, methylene chloride was added thereto, and under ice-cooling, 332 mg (1.73 mmol) of 1-ethyl-3-(3-dimethylaminopropyl)carbodiimide hydrochloride was added. After the mixture was stirred at room temperature overnight, the reaction solution was concentrated under reduced pressure, ethyl acetate was added thereto, and the mixture was successively washed with water, a 10% aqueous potassium hydrogensulfate solution, a saturated aqueous sodium hydrogencarbonate solution and saturated brine, followed by drying with anhydrous sodium sulfate. The solvent was distilled off under reduced pressure to obtain 295 mg (16%) of the title compound.

1H-NMR (CDCl₃, δ): 1.50-1.59 (1H, m), 1.64-1.72 (2H, m), 1.76-1.83 (7H, m), 2.75 (3H, s), 8.55 (1H, s)

Reference Example 154

2-Cyclopentyl-3-oxa-1-azaspiro[4.5]dec-1-en-4-one

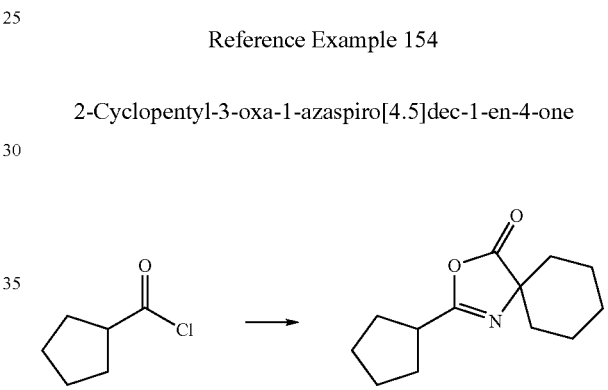

1.98 g (15 mmol) of cyclopentanecarbonyl chloride was added to a solution of 2.16 g (15 mmol) of 1-aminocyclohexanecarboxylic acid and 4.8 g (45 mmol) of sodium carbonate in 50 ml of ethyl acetate-50 ml of water under ice-cooling. After the mixture was stirred at room temperature overnight, ethyl acetate was added thereto, and the mixture was washed with a 10% aqueous potassium hydrogensulfate solution, a saturated aqueous sodium bicarbonate solution and then saturated brine. After the obtained organic layer was washed with saturated brine, it was dried with anhydrous sodium sulfate. The solvent was distilled off under reduced pressure, methylene chloride was added thereto, and under ice-cooling, 1.59 g (8.3 mmol) of 1-ethyl-3-(3-dimethylaminopropyl)carbodiimide hydrochloride was added. After the mixture was stirred at room temperature overnight, the reaction solution was concentrated under reduced pressure, ethyl acetate was added thereto, and the mixture was successively washed with water, a 10% aqueous potassium hydrogensulfate solution, a saturated aqueous sodium hydrogensulfate solution and saturated brine, followed by drying with anhydrous sodium sulfate. The solvent was distilled off under reduced pressure to obtain 1.41 g (42%) of the title compound.

1H-NMR (CDCl₃, δ): 1.53-1.65 (5H, m), 1.67-1.76 (4H, m), 1.86-1.95 (8H, m), 2.80-2.89 (2H, m)

Reference Example 155

2-(5-Methyl-2-thienyl)-3-oxa-1-azaspiro[4.5]dec-1-en-4-one

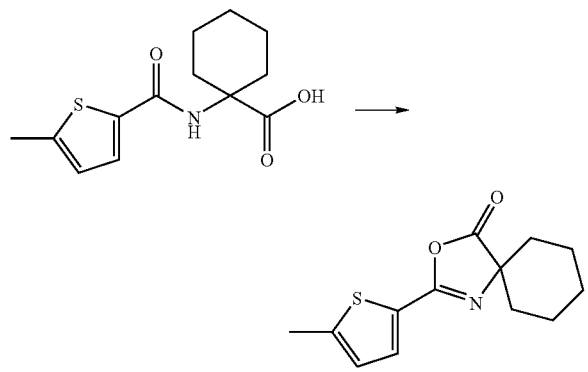

294 mg (1.1 mmol) of 1-[[(5-methyl-2-thienyl)carbonyl]amino]cyclohexanecarboxylic acid was used instead of 1-[(phenylacetyl)amino]cyclohexanecarboxylic acid in the process according to Reference Example 132 to obtain 273 mg (quantitative) of the title compound.

1H-NMR (CDCl$_3$, δ): 1.53-1.62 (3H, m), 1.71-1.84 (7H, m) 2.55 (3H, s), 6.79 (1H, d, J=3 Hz), 7.50 (1H, d, J=3 Hz)

Reference Example 156

2-(4-Methoxyphenyl)-3-oxa-1-azaspiro[4.5]dec-1-en-4-one

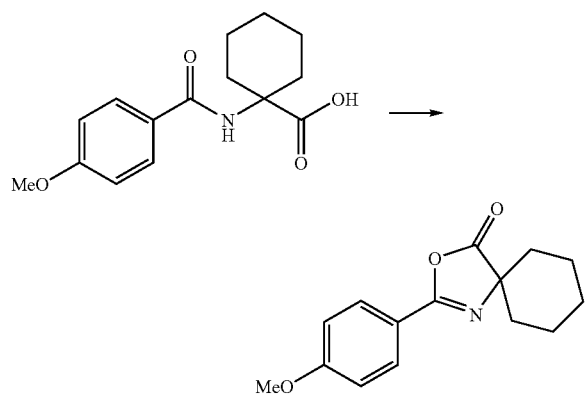

305 mg (1.1 mmol) of 1-[[(4-methoxyphenyl)carbonyl]amino]cyclohexanecarboxylic acid was used instead of 1-[(phenylacetyl)amino]cyclohexanecarboxylic acid in the process according to Reference Example 132 to obtain 288 mg (90%) of the title compound.

1H-NMR (CDCl$_3$, δ): 1.51-1.60 (1H, m), 1.61-1.73 (3H, m), 1.76-1.90 (6H, m), 3.87 (3H, s), 6.96 (2H, dd, J=7 Hz, 2 Hz), 7.94 (2H, dd, J=7 Hz, 2 Hz)

Reference Example 157

2-(3-Methyl-2-thienyl)-3-oxa-1-azaspiro[4.5]dec-1-en-4-one

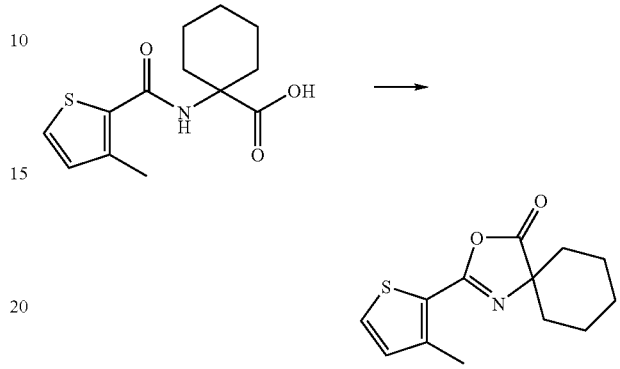

249 mg (1.1 mmol) of 1-[[(3-methyl-2-thienyl)carbonyl]amino]cyclohexanecarboxylic acid was used instead of 1-[(phenylacetyl)amino]cyclohexanecarboxylic acid in the process according to Reference Example 132 to obtain 249 mg (quantitative) of the title compound.

1H-NMR (CDCl$_3$, δ): 1.50-1.60 (1H, m), 1.65-1.78 (3H, m), 1.78-1.90 (6H, m), 2.58 (3H, s), 6.95 (1H, d, J=5 Hz), 7.42 (1H, d, J=5 Hz)

Reference Example 158

2-(3-Methyl-2-furanyl)-3-oxa-1-azaspiro[4.5]dec-1-en-4-one

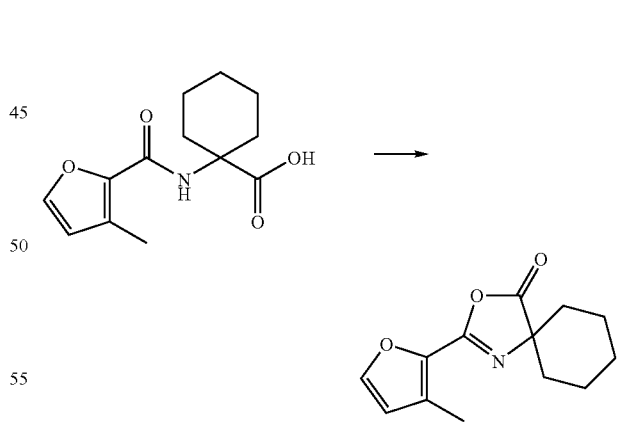

902 mg (3.59 mmol) of 1-[[(3-methyl-2-furanyl)carbonyl]amino]cyclohexanecarboxylic acid was used instead of 1-[(phenylacetyl)amino]cyclohexanecarboxylic acid in the process according to Reference Example 132 to obtain 233 mg (quantitative) of the title compound.

1H-NMR (CDCl$_3$, δ): 1.48-1.61 (1H, m), 1.62-1.89 (9H, m), 2.36 (3H, s), 6.40 (1H, d, J=1 Hz), 7.52 (1H, d, J=1 Hz)

Reference Example 159

2-(3-Pyridinyl)-3-oxa-1-azaspiro[4.5]dec-1-en-4-one

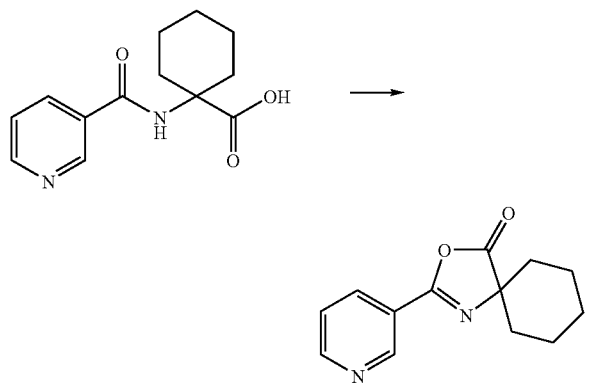

523 mg (2.11 mmol) of 1-[(3-pyridinylcarbonyl)amino]cyclohexanecarboxylic acid was used instead of 1-[(phenylacetyl)amino]cyclohexanecarboxylic acid in the process according to Reference Example 132 to obtain 486 mg (quantitative) of the title compound.

1H-NMR (CDCl$_3$, δ): 1.50-1.90 (10H, m), 7.42 (1H, dd, J=8 Hz, 5 Hz), 8.27 (1H, d, J=8 Hz), 8.78 (1H, d, J=5 Hz), 9.00 (1H, s)

Reference Example 160

2-(1-Methyl-1H-pyrrol-2-yl)-3-oxa-1-azaspiro[4.5]dec-1-en-4-one

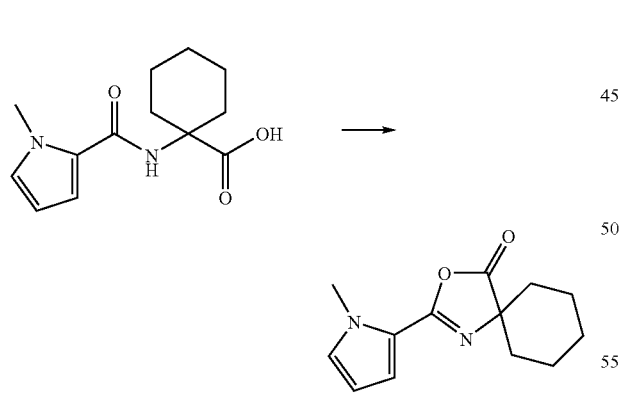

187 mg (0.75 mmol) of 1-[[(1-methyl-1H-pyrrol-2-yl)carbonyl]amino]cyclohexanecarboxylic acid was used instead of 1-[(phenylacetyl)amino]cyclohexanecarboxylic acid in the process according to Reference Example 132 to obtain 172 mg (quantitative) of the title compound.

1H-NMR (CDCl$_3$, δ): 1.44-1.85 (10H, m), 3.40 (3H, s), 6.18 (1H, dd, J=4 Hz, 3 Hz), 6.82-6.86 (2H, m)

Reference Example 161

2-[(R)-1-Phenylethyl]-3-oxa-1-azaspiro[4.5]dec-1-en-4-one

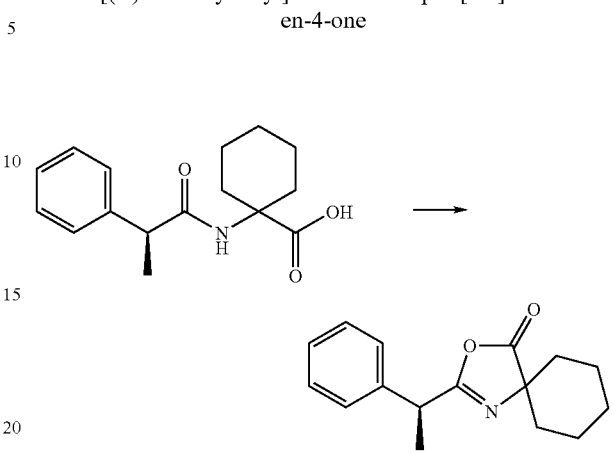

303 mg (1.1 mmol) of 1-[((R)-1-oxo-2-phenylpropyl)amino]cyclohexanecarboxylic acid was used instead of 1-[(phenylacetyl)amino]cyclohexanecarboxylic acid in the process according to Reference Example 132 to obtain 257 mg (90%) of the title compound.

1H-NMR (CDCl$_3$, δ): 1.45-1.65 (7H, m), 1.67-1.80 (6H, m) 3.89 (1H, q, J=7 Hz), 7.26-7.34 (5H, m)

Reference Example 162

2-(1H-Indol-5-ylcarbonyl)-3-oxa-1-azaspiro[4.5]dec-1-en-4-one

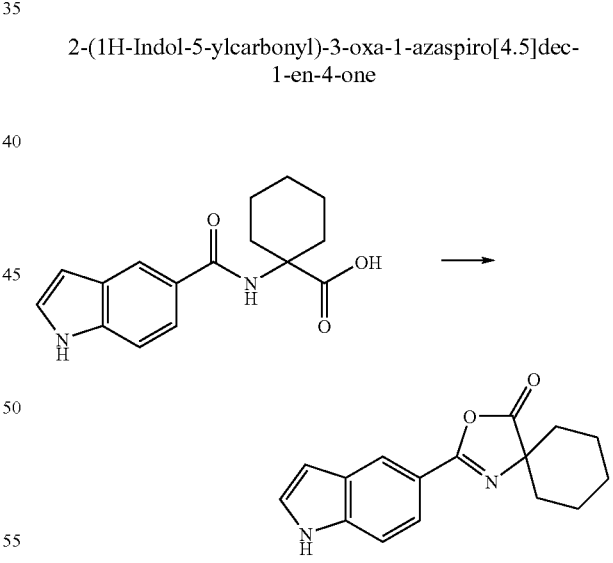

329 mg (1.2 mmol) of 1-[(1H-indol-5-ylcarbonyl)amino]cyclohexanecarboxylic acid was used instead of 1-[(phenylacetyl)amino]cyclohexanecarboxylic acid in the process according to Reference Example 132 to obtain 258 mg (80%) of the title compound.

1H-NMR (CDCl$_3$, δ): 1.56-1.89 (10H, m), 6.65 (1H, dd, J=3 Hz, 2 Hz), 7.26-7.36 (1H, m), 7.46 (1H, d, J=9 Hz), 7.88 (1H, dd, J=9 Hz, 2 Hz), 8.32 (1H, s), 8.35 (1H, br-s)

Reference Example 163

2-(1-Cyclopentenylcarbonyl)-3-oxa-1-azaspiro[4.5]dec-1-en-4-one

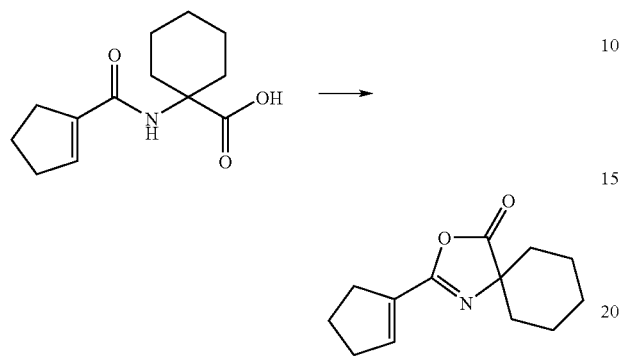

237 mg (1 mmol) of 1-[(1-cyclopentenylcarbonyl)amino]cyclohexanecarboxylic acid was used instead of 1-[(phenylacetyl)amino]cyclohexanecarboxylic acid in the process according to Reference Example 132 to obtain 219 mg (quantitative) of the title compound.

1H-NMR (CDCl$_3$, δ): 1.53-1.82 (10H, m), 1.99-2.10 (2H, m) 2.55-2.69 (2H, m), 2.69-2.80 (2H, m), 6.65-6.67 (1H, m)

Reference Example 164

2-(4-Pyridinyl)-3-oxa-1-azaspiro[4.5]dec-1-en-4-one

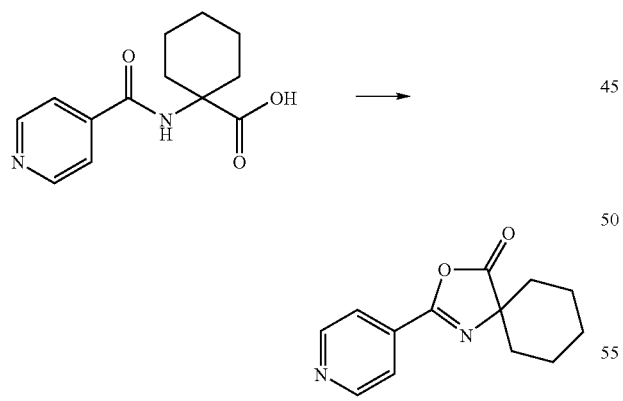

552 mg (2.2 mmol) of 1-[(4-pyridinylcarbonyl)amino]cyclohexanecarboxylic acid was used instead of 1-[(phenylacetyl)amino]cyclohexanecarboxylic acid in the process according to Reference Example 132 to obtain 450 mg (88%) of the title compound.

1H-NMR (CDCl$_3$, δ): 1.50-1.92 (10H, m), 7.85 (2H, dd, J=5 Hz, 2 Hz), 8.80 (2H, dd, J=5 Hz, 2 Hz)

Reference Example 165

2-(1H-Pyrrol-2-yl)-3-oxa-1-azaspiro[4.5]dec-1-en-4-one

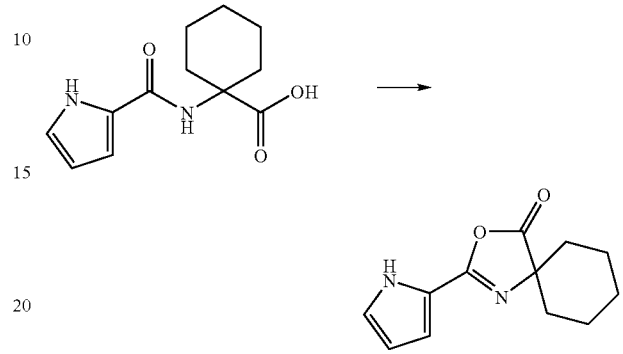

200 mg (0.85 mmol) of 1-[[(1H-pyrrol-2-yl)carbonyl]amino]cyclohexanecarboxylic acid was used instead of 1-[(phenylacetyl)amino]cyclohexanecarboxylic acid in the process according to Reference Example 132 to obtain 184 mg (quantitative) of the title compound.

1H-NMR (CDCl$_3$, δ): 1.51-1.65 (1H, m), 1.65-1.86 (9H, m), 6.32 (1H, dd, J=4 Hz, 2 Hz), 6.87 (1H, dd, J=4 Hz, 2 Hz), 7.01 (1H, dd, J=4 Hz, 2 Hz), 9.37 (1H, br-s)

Reference Example 166

2-(6-Hydroxy-2-pyridinyl)-3-oxa-1-azaspiro[4.5]dec-1-en-4-one

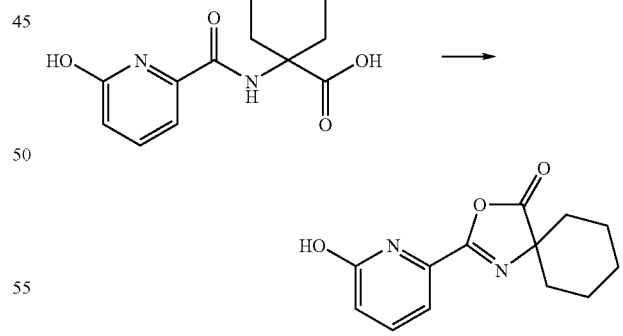

278 mg (1 mmol) of 1-[[(6-hydroxy-2-pyridinyl)carbonyl]amino]cyclohexanecarboxylic acid was used instead of 1-[(phenylacetyl)amino]cyclohexanecarboxylic acid in the process according to Reference Example 132 to obtain 250 mg (97%) of the title compound.

1H-NMR (CDCl$_3$, δ): 1.52 (1H, m), 1.78 (9H, m), 6.85-6.79 (2H, m), 7.50 (1H, dd, J=9 Hz, 7 Hz)

Reference Example 167

2-(2-Hydroxy-3-pyridinyl)-3-oxa-1-azaspiro[4.5]dec-1-en-4-one

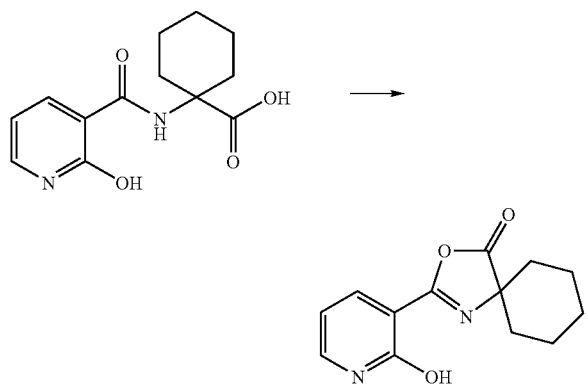

278 mg (1 mmol) of 1-[[(2-hydroxy-3-pyridinyl)carbonyl]amino]cyclohexanecarboxylic acid was used instead of 1-[(phenylacetyl)amino]cyclohexanecarboxylic acid in the process according to Reference Example 132 to obtain 257 mg (quantitative) of the title compound.

1H-NMR (CDCl$_3$, δ): 1.04-2.21 (10H, m), 6.40-6.50 (1H, m) 7.69-7.82 (1H, m), 8.28-8.35 (1H, m)

Reference Example 168

2-(6-Hydroxy-3-pyridinyl)-3-oxa-1-azaspiro[4.5]dec-1-en-4-one

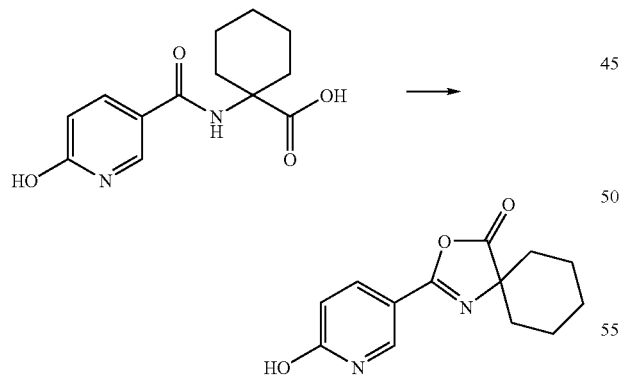

278 mg (1 mmol) of 1-[[(6-hydroxy-3-pyridinyl)carbonyl]amino]cyclohexanecarboxylic acid was used instead of 1-[(phenylacetyl)amino]cyclohexanecarboxylic acid in the process according to Reference Example 132 to obtain 257 mg (quantitative) of the title compound.

1H-NMR (CDCl$_3$, δ): 1.45-1.86 (10H, m), 6.66 (1H, d, J=10 Hz), 8.02 (1H, d, J=2 Hz), 8.05 (1H, dd, J=10 Hz, 2 Hz)

Reference Example 169

2-[2-(2-Furanyl)ethyl]-3-oxa-1-azaspiro[4.5]dec-1-en-4-one

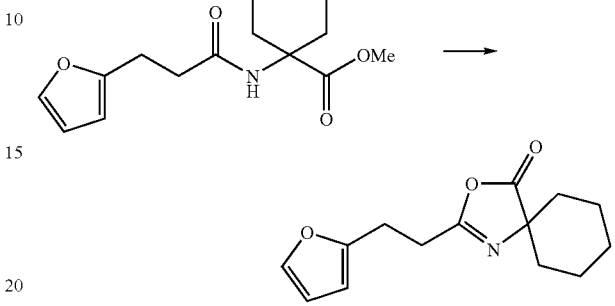

1.7 ml of 2N aqueous NaOH solution was added to a solution of 478 mg (1.7 mmol) of 1-[[1-oxo-3-(2-furanyl)propyl]amino]cyclohexanecarboxylic acid methyl ester obtained in Reference Example 64 in 2 ml of tetrahydrofuran, and the mixture was heated under reflux for 3 hours. Ether was added to the reaction solution to wash it. After the separated aqueous layer was neutralized by concentrated hydrochloric acid, it was extracted with ethyl acetate. After the obtained organic layer was washed with saturated brine, it was dried with anhydrous sodium sulfate, and the solvent was distilled off under reduced pressure. Then, 10 ml of methylene chloride and 377 mg (1.82 mmol) of 1-ethyl-3-(3-dimethylaminopropyl)carbodiimide hydrochloride were added to the residue, and the mixture was stirred at room temperature overnight. The solvent was distilled off under reduced pressure, ethyl acetate was added thereto, and the mixture was washed with water, a 10% aqueous potassium hydrogensulfate solution, a saturated aqueous sodium hydrogencarbonate solution and then saturated brine, followed by drying with anhydrous sodium sulfate. The solvent was distilled off under reduced pressure to obtain 198 mg (47%) of the title compound.

1H-NMR (CDCl$_3$, δ): 1.43-1.60 (4H, m), 1.60-1.80 (6H, m) 2.84 (2H, t, J=7 Hz), 3.05 (2H, t, J=7 Hz), 6.06 (1H, dd, J=2 Hz, 1 Hz), 6.27 (1H, dd, J=2 Hz, 1 Hz), 7.31 (1H, dd, J=2 Hz, 1 Hz)

Reference Example 170

2-[1-[(2-Propoxy)carbonyl]piperidin-4-yl]-3-oxa-1-azaspiro[4.5]dec-1-en-4-one

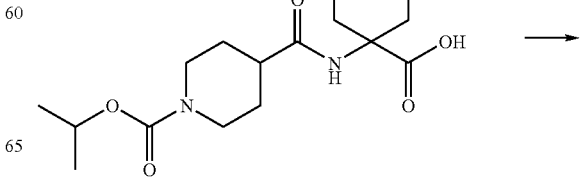

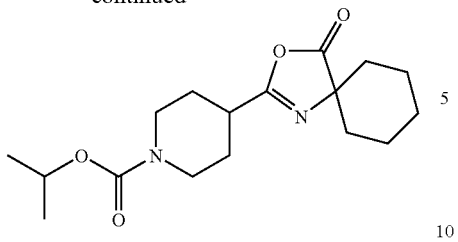

940 mg (2.76 mmol) of 1-[[[1-(2-propoxycarbonyl)piperidin-4-yl]carbonyl]amino]cyclohexanecarboxylic acid was used instead of 1-[(phenylacetyl)amino]cyclohexanecarboxylic acid in the process according to Reference Example 132 to obtain 818 mg (92%) of the title compound.

1H-NMR (CDCl₃, δ): 1.24 (6H, d, J=6 Hz), 1.44-1.79 (12H, m), 1.90-1.98 (2H, m), 2.62-2.69 (1H, m), 2.89-2.99 (2H, m), 4.03-4.19 (2H, m), 4.88-4.97 (1H, m)

Reference Example 171

2-[1-(Ethoxycarbonyl)piperidin-4-yl]-3-oxa-1-azaspiro[4.5]dec-1-en-4-one

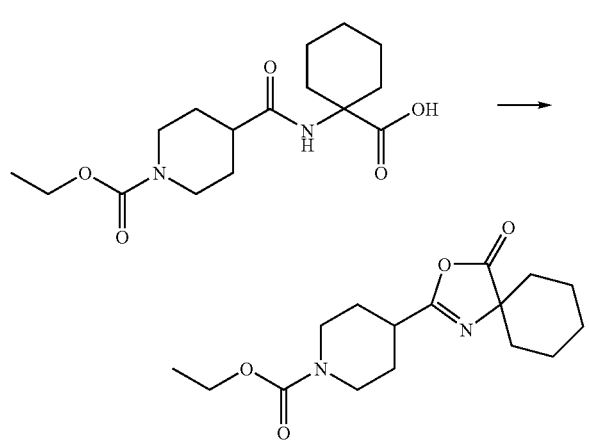

935 mg (2.86 mmol) of 1-[[[1-(ethoxycarbonyl)piperidin-4-yl]carbonyl]amino]cyclohexanecarboxylic acid was used instead of 1-[(phenylacetyl)amino]cyclohexanecarboxylic acid in the process according to Reference Example 132 to obtain 730 mg (83%) of the title compound.

1H-NMR (CDCl₃, δ): 1.26 (3H, t, J=7 Hz), 1.45-1.80 (12H, m) 1.92-1.99 (2H, m), 2.62-2.70 (1H, m), 2.90-3.03 (2H, m), 4.03-4.20 (4H, m)

Reference Example 172

2-[1-(2-Furanylcarbonyl)piperidin-4-yl]-3-oxa-1-azaspiro[4.5]dec-1-en-4-one

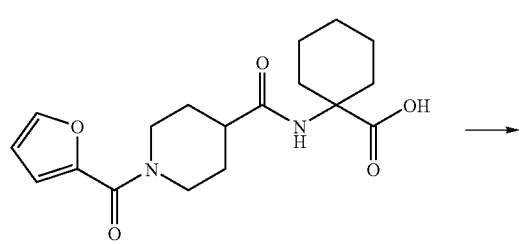

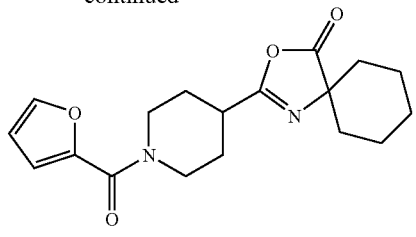

196 mg (0.56 mmol) of 1-[[[1-(2-furanylcarbonyl)piperidin-4-yl]carbonyl]amino]cyclohexanecarboxylic acid was used instead of 1-[(phenylacetyl)amino]cyclohexanecarboxylic acid in the process according to Reference Example 132 to obtain 185 mg (quantitative) of the title compound.

1H-NMR (CDCl₃, δ): 1.49-1.68 (5H, m), 1.68-1.80 (5H, m), 1.80-1.92 (2H, m), 2.03-2.10 (2H, m), 2.75-2.83 (1H, m), 3.05-3.31 (2H, m), 4.28-4.40 (2H, m), 6.48 (1H, dd, J=3 Hz, 1 Hz), 7.00 (1H, dd, J=3 Hz, 1 Hz), 7.48 (1H, dd, J=3 Hz, 1 Hz)

Reference Example 173

2-[[(2-Furanylcarbonyl)amino]methyl]-3-oxa-1-azaspiro[4.5]dec-1-en-4-one

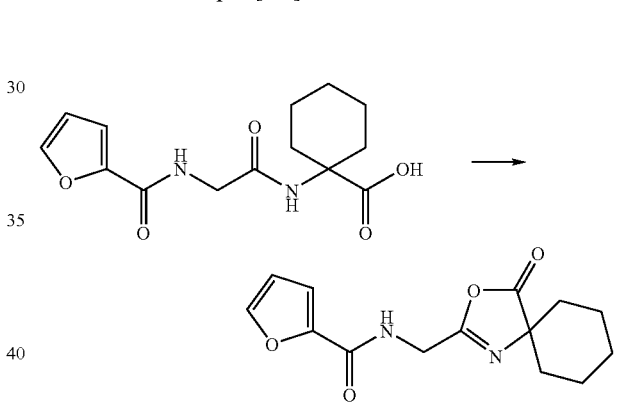

249 mg (1 mmol) of 1-[[[(2-furanylcarbonyl)amino]acetyl]amino]cyclohexanecarboxylic acid was used instead of 1-[(phenylacetyl)amino]cyclohexanecarboxylic acid in the process according to Reference Example 132 to obtain 276 mg (quantitative) of the title compound.

1H-NMR (CDCl₃, δ): 1.50-1.80 (10H, m), 4.45 (2H, d, J=6 Hz) 6.53 (1H, dd, J=3 Hz, 1 Hz), 6.90 (1H, br-s), 7.18 (1H, ddd, J=3 Hz, 2 Hz, 1 Hz), 7.50 (1H, dd, J=2 Hz, 1 Hz)

Reference Example 174

2-[(Benzoylamino)methyl]-3-oxa-1-azaspiro[4.5]dec-1-en-4-one

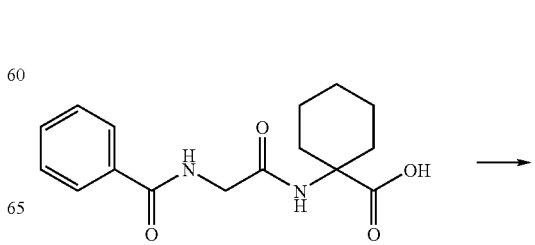

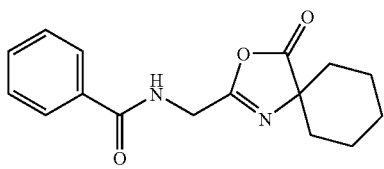

724 mg (2.26 mmol) of 1-[[(benzoylamino)acetyl]amino]cyclohexanecarboxylic acid was used instead of 1-[(phenylacetyl)amino]cyclohexanecarboxylic acid in the process according to Reference Example 132 to obtain 631 mg (97%) of the title compound.

1H-NMR (CDCl$_3$, δ): 1.48-1.58 (1H, m), 1.63-1.80 (9H, m), 4.49 (2H, d, J=5 Hz), 6.76 (1H, br-s), 7.48 (2H, m), 7.55 (1H, m), 7.83 (2H, m)

Reference Example 175

2-(4-Fluorophenyl)-3-oxa-1-azaspiro[4.5]dec-1-en-4-one

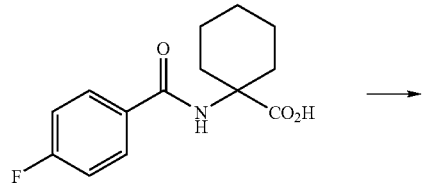

After a suspension of 13.3 g (50 mmol) of 1-[(4-fluorobenzoyl)amino]cyclohexanecarboxylic acid in 30 ml of acetic anhydride was stirred at 100° C. for 30 minutes, the reaction solution was concentrated under reduced pressure. Toluene was added to the residue, and the mixture was washed with water, a saturated aqueous sodium hydrogencarbonate solution and then saturated brine. After the organic layer was dried with anhydrous sodium sulfate, the solvent was distilled off under reduced pressure. The residue was purified by silica gel column chromatography to obtain 8.5 g (69%) of the title compound.

1H-NMR (CDCl$_3$, δ): 1.49-1.60 (1H, m), 1.63-1.90 (9H, m), 7.13-7.20 (2H, m), 8.00-8.05 (2H, m)

Reference Example 176

2-[4-(4-Propylpiperazin-1-yl)phenyl]-3-oxa-1-azaspiro[4.5]dec-1-en-4-one

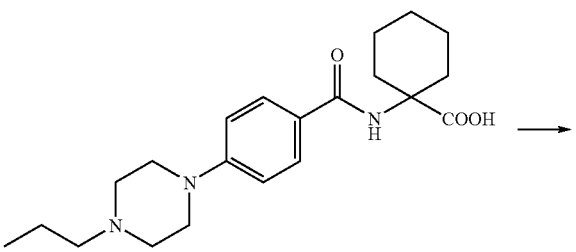

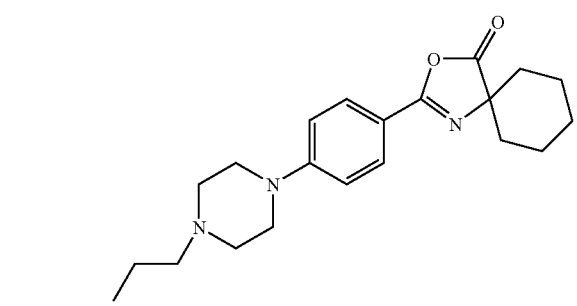

1.43 g (3.86 mmol) of 1-[[[4-(4-propylpiperazin-1-yl)phenyl]carbonyl]amino]cyclohexanecarboxylic acid was used instead of 1-[(phenylacetyl)amino]cyclohexanecarboxylic acid in the process according to Reference Example 132 to obtain 1.33 g (98%) of the title compound.

1H-NMR (CDCl$_3$, δ): 0.94 (3H, t, J=8 Hz), 1.50-1.61 (3H, m), 1.61-1.69 (1H, m), 1.69-1.76 (2H, m), 1.79-1.84 (6H, m), 2.35 (1H, t, J=6 Hz), 2.36 (1H, t, J=6 Hz), 2.59 (4H, t, J=5 Hz), 3.35 (4H, t, J=5 Hz), 6.91 (2H, dd, J=2 Hz, 7 Hz), 7.86 (2H, dd, J=2 Hz, 7 Hz)

Reference Example 177

2-[4-(4-Propylpiperazin-1-yl)phenyl]-3-oxa-1-azaspiro[4.5]dec-1-en-4-one hydrochloride

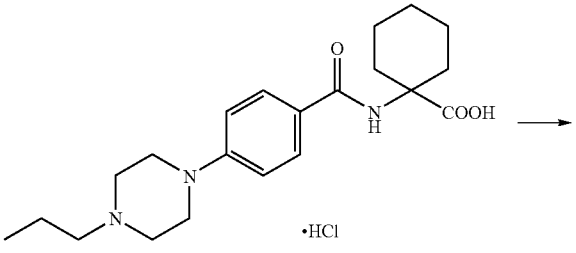

-continued

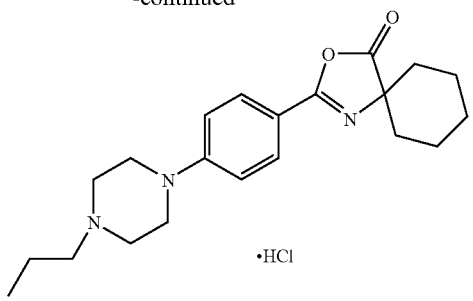

·HCl

After a suspension of 631 mg (1.54 mmol) of 1-[[[4-(4-propylpiperazin-1-yl)phenyl]carbonyl]amino]cyclohexanecarboxylic acid hydrochloride in 18 ml of acetic anhydride was stirred at 100° C. for 1 hour, the reaction solution was concentrated under reduced pressure. Toluene was added to the obtained residue, it was distilled off under reduced pressure three times, and acetic anhydride was removed by azeotropic distillation to obtain 500 mg (83%) of the title compound.

1H-NMR (CDCl$_3$, δ): 1.05 (3H, t, J=8 Hz), 1.50-1.87 (10H, m) 1.95-2.06 (2H, m), 2.86-3.01, (4H, m), 3.59-3.68 (2H, m), 3.79-3.90 (4H, m), 6.91 (2H, dd, 2 Hz, 7 Hz), 7.91 (2H, dd, J=2 Hz, 7 Hz)

Reference Example 178

N-[[1-[[(Phenylmethoxy)carbonyl]amino]cyclohexyl]carbonyl]-L-valinol

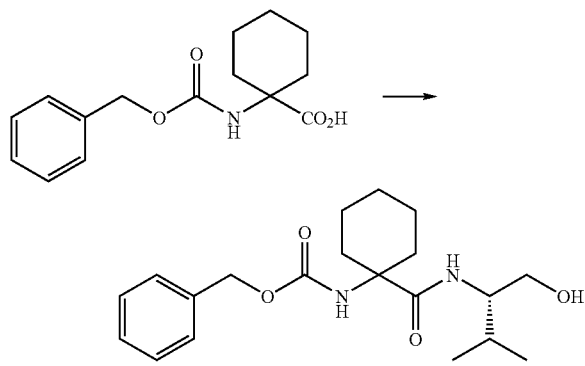

After 422 mg (2.2 mmol) of 1-ethyl-3-(3-dimethylaminopropyl)carbodiimide hydrochloride was added to a solution of 555 mg (2 mmol) of 1-[[(phenylmethoxy)carbonyl]amino] cyclohexanecarboxylic acid, 322 mg (2.1 mmol) of 1-hydroxybenzotriazole and 206 mg (2 mmol) of L-valinol in 20 ml of methylene chloride under ice-cooling, the mixture was stirred at room temperature for 18 hours. The reaction solution was concentrated under reduced pressure, ethyl acetate was added to the residue, and the mixture was washed with water, a 10% aqueous potassium hydrogensulfate solution, a saturated aqueous sodium hydrogencarbonate solution and then saturated brine. The organic layer was dried with anhydrous sodium sulfate and the solvent was distilled off under reduced pressure. The residue was purified by silica gel column chromatography to obtain 662 mg (91%) of the title compound.

1H-NMR (CDCl$_3$, δ): 0.87 (3H, d, J=7 Hz), 0.92 (3H, d, J=7 Hz), 1.28-1.46 (3H, m), 1.52-1.70 (3H, m), 1.73-1.82 (1H, m), 1.85-2.03 (4H, m), 2.76 (1H, br-s), 3.42-4.47 (1H, m), 3.65-3.74 (2H, m), 5.02-5.16 (3H, m), 6.36 (1H, d, J=8 Hz), 7.30-7.40 (5H, m)

Reference Example 179

N-[[1-[[(Phenylmethoxy)carbonyl]amino]cyclohexyl]carbonyl]-L-norleucinol

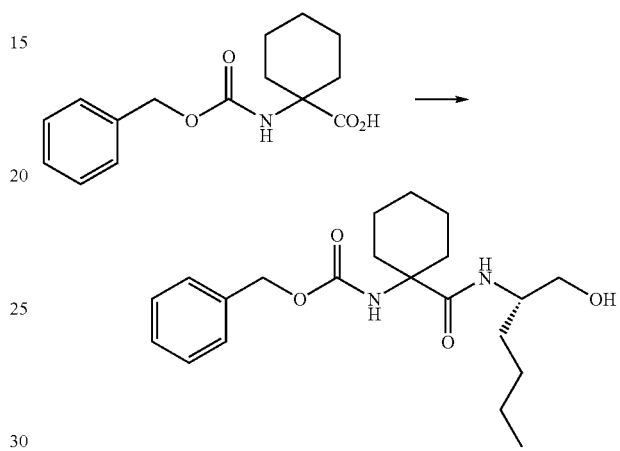

234 mg (2 mmol) of L-norleucinol was used instead of L-valinol in the process according to Reference Example 178 to obtain 350 mg (75%) of the title compound.

1H-NMR (CDCl$_3$, δ): 0.88 (3H, t, J=7 Hz), 1.23-1.52 (9H, m), 1.58-1.70 (3H, m), 1.83-2.04 (4H, m), 2.83 (1H, br-s), 3.34-3.40 (1H, m), 3.70 (1H, br-s), 3.89 (1H, br-s), 5.02-5.13 (3H, m), 6.26 (1H, d, J=8 Hz), 7.31-7.40 (5H, m)

Reference Example 180

N-[[1-[(2-Furanylcarbonyl)amino]cyclohexyl]carbonyl]-L-valinol

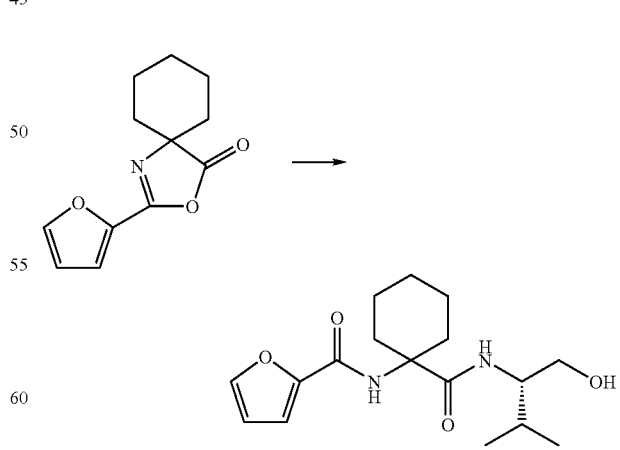

A solution of 8.81 ml (50.6 mmol) of N,N-diisopropylethylamine and 2.09 g (20.2 mmol) of L-valinol in 10 ml of methylene chloride was added to a solution of 3.71 g (16.9 mmol) of 2-(2-furanyl)-3-oxa-1-azaspiro[4.5]dec-1-en-4- one in 100 ml of toluene, and the mixture was heated under reflux for 14 hours. The reaction solution was concentrated under reduced pressure, ethyl acetate was added to the residue, and the mixture was washed with water, a 10% aqueous potassium hydrogensulfate solution, a saturated aqueous sodium hydrogencarbonate solution and then saturated brine. The organic layer was dried with anhydrous sodium sulfate and the solvent was distilled off under reduced pressure. Ethyl acetate was added to the residue and the mixture was stirred overnight. The obtained crystal was collected by filtration to obtain 4.06 g (74.7%) of the title compound.

1H-NMR (CDCl$_3$, δ): 0.93 (3H, d, J=7 Hz), 0.95 (3H, d, J=7 Hz), 1.32-1.56 (3H, m), 1.58-1.76 (3H, m), 1.80-1.90 (1H, m), 1.96-2.08 (2H, m), 2.14-2.24 (2H, m), 3.00-3.06 (1H, m), 3.52-3.58 (1H, m), 3.68-3.78 (2H, m), 6.49 (1H, s), 6.53 (1H, dd, J=4 Hz, 2 Hz), 6.75-6.77 (1H, m), 7.14 (1H, dd, J=4 Hz, 1 Hz), 7.49 (1H, dd, J=2 Hz, 1 Hz)

Reference Example 181

N-[[1-[(2-Furanylcarbonyl)amino]cyclohexyl]carbonyl]-L-valinol

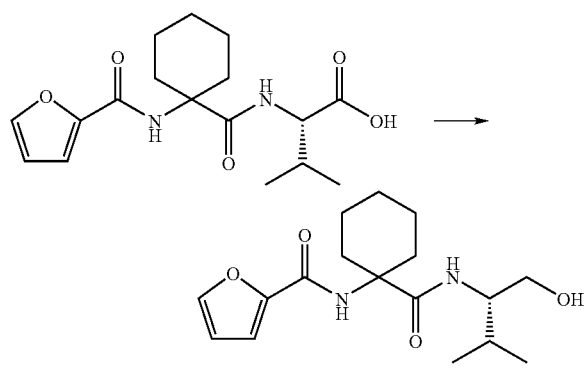

Under an argon atmosphere, 72 mg (0.59 mmol) of isopropyl chlorocarbonate was added to a solution of 200 mg (0.59 mmol) of N-[[1-[(2-furanylcarbonyl)amino]cyclohexyl]carbonyl]-L-valine and 60 mg (0.59 mmol) of triethylamine in 2 ml of tetrahydrofuran under ice-cooling. After the mixture was stirred at 0° C. for 2 hours, the reaction solution was filtered, it was poured to a solution of 45 mg (1.2 mmol) of sodium borohydride in 1 ml of water, and the mixture was stirred overnight. Ethyl acetate was added to the reaction solution, and the mixture was successively washed with a 10% aqueous potassium hydrogensulfate solution, a saturated aqueous sodium hydrogencarbonate solution and saturated brine, followed by drying with sodium sulfate. After the solvent was distilled off under reduced pressure, the obtained crystal was washed with ether to obtain 30 mg (16%) of the title compound.

1H-NMR (CDCl$_3$, δ): 0.93 (3H, d, J=7 Hz), 0.95 (3H, d, J=7 Hz), 1.32-1.56 (3H, m), 1.58-1.76 (3H, m), 1.80-1.90 (1H, m), 1.96-2.08 (2H, m), 2.14-2.24 (2H, m), 3.00-3.06 (1H, m), 3.52-3.58 (1H, m), 3.68-3.78 (2H, m), 6.49 (1H, s), 6.53 (1H, dd, J=4 Hz, 2 Hz), 6.75-6.77 (1H, m), 7.14 (1H, dd, J=4 Hz, 1 Hz), 7.49 (1H, dd, J=2 Hz, 1 Hz)

Reference Example 182

N-[[1-[(2-Furanylcarbonyl)amino]cyclohexyl]carbonyl]-L-valinol

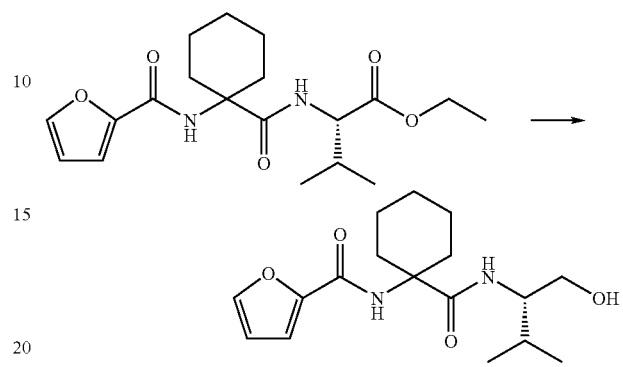

Under an argon atmosphere, 31 mg (0.82 mmol) of lithium aluminum hydride was added to 1 ml of diethyl ether placed in a flask. Under ice-cooling, a solution of 0.3 g (0.82 mmol) of the above compound in 1 ml of tetrahydrofuran was added to the flask, and the mixture was stirred for 1 hour and 30 minutes. Ice-water was added to the reaction solution. Ethyl acetate was added thereto, and the mixture was successively washed with a 10% aqueous potassium hydrogensulfate solution, a saturated aqueous sodium hydrogencarbonate solution and saturated brine. After it was dried with sodium sulfate, the solvent was distilled off under reduced pressure. The obtained crystal was washed with ether to obtain 155 mg (60%) of the title compound.

1H-NMR (CDCl$_3$, δ): 0.93 (3H, d, J=7 Hz), 0.95 (3H, d, J=7 Hz), 1.32-1.56 (3H, m), 1.58-1.76 (3H, m), 1.80-1.90 (1H, m), 1.96-2.08 (2H, m), 2.14-2.24 (2H, m), 3.00-3.06 (1H, m), 3.52-3.58 (1H, m), 3.68-3.78 (2H, m), 6.49 (1H, s), 6.53 (1H, dd, J=4 Hz, 2 Hz), 6.75-6.77 (1H, m), 7.14 (1H, dd, J=4 Hz, 1 Hz), 7.49 (1H, dd, J=2 Hz, 1 Hz)

Reference Example 183

N-[[1-[(4-Morpholinylcarbonyl)amino]cyclohexyl]carbonyl]-L-norleucinol

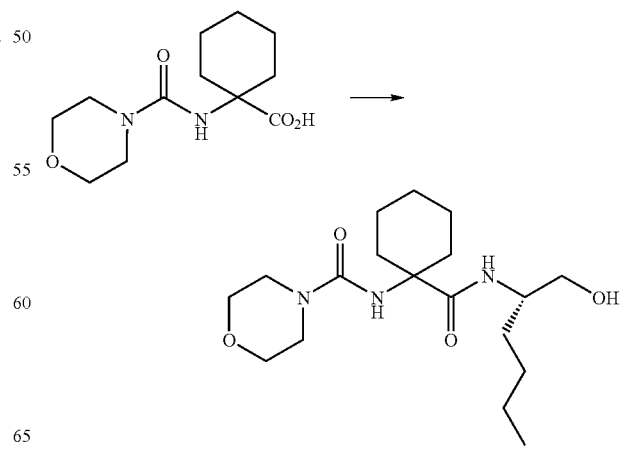

513 mg (2 mmol) of 1-[(4-morpholinylcarbonyl)amino]cyclohexanecarboxylic acid was used instead of 1-[[(phenylmethoxy)carbonyl]amino]cyclohexanecarboxylic acid in the process according to Reference Example 179 to obtain 215 mg (30%) of the title compound.

1H-NMR (CDCl₃, δ): 0.89 (3H, t, J=7 Hz), 1.26-1.56 (9H, m) 1.60-1.73 (3H, m), 1.85-2.05 (4H, m), 3.33-3.43 (5H, m), 3.54 (1H, t, J=7 Hz), 3.66-3.73 (4H, m), 3.76-3.82 (1H, m), 3.83-3.93 (1H, m), 4.64 (1H, br-s), 6.35 (1H, d, J=8 Hz)

Reference Example 184

N—[N-[(Phenylmethoxy)carbonyl]-L-leucyl]-L-valinol

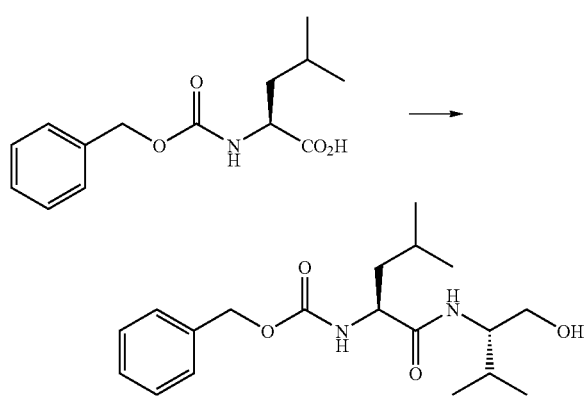

N-[(phenylmethoxy)carbonyl]-L-leucine was used instead of 1-[[(phenylmethoxy)carbonyl]amino]cyclohexanecarboxylic acid in the process according to Reference Example 178 to obtain 659 mg (94%) of the title compound.

1H-NMR (CDCl₃, δ): 0.83-0.99 (12H, m), 1.46-1.74 (3H, m), 1.78-1.90 (1H, m), 2.42 (1H, br-s), 3.57-3.72 (3H, m), 4.10-4.17 (1H, m), 5.04-5.17 (3H, m), 6.22 (1H, d, J=7 Hz), 7.27-7.39 (5H, m)

Reference Example 185

N—[N-[(Phenylmethoxy)carbonyl]-L-leucyl]-L-norleucinol

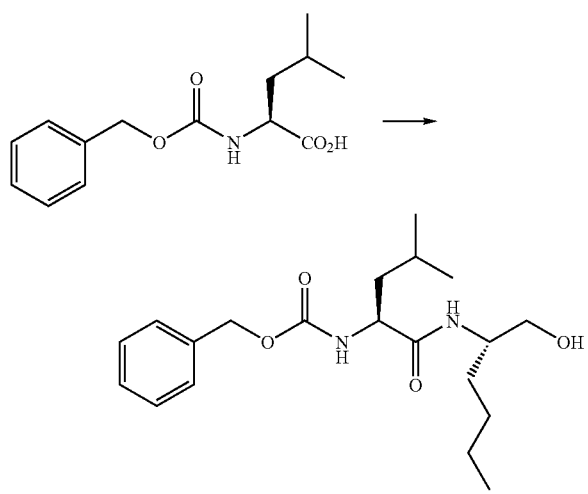

N-[(phenylmethoxy)carbonyl]-L-leucine was used instead of 1-[[(phenylmethoxy)carbonyl]amino]cyclohexanecarboxylic acid, and L-norleucinol was used instead of L-valinol in the process according to Reference Example 178 to obtain 421 mg (58%) of the title compound.

1H-NMR (CDCl₃, δ): 0.88 (3H, t, J=7 Hz), 0.95 (6H, d, J=7 Hz), 1.23-2.72 (9H, m), 2.44 (1H, br-s), 3.47-3.71 (2H, m), 3.89 (1H, br-s), 4.10-4.17 (1H, m), 5.08-5.16 (3H, m), 6.10 (1H, d, J=6 Hz), 7.31-7.39 (5H, m)

Reference Example 186

N—[N-(4-Morpholinylcarbonyl)-L-leucyl]-L-norleucinol

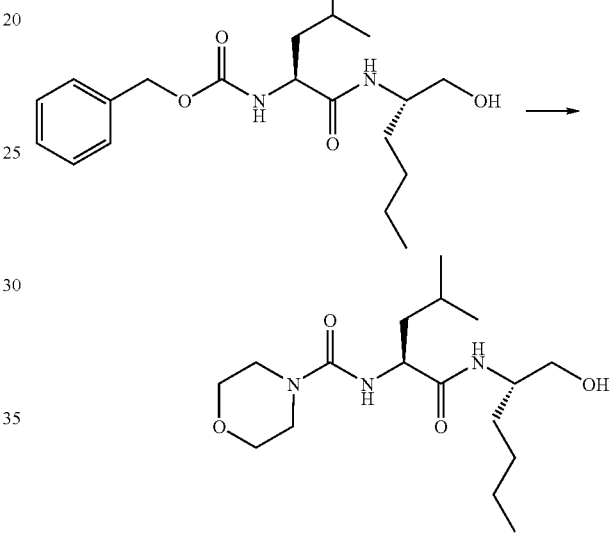

70 mg of 10% palladium-carbon was added to a solution of 700 mg (2 mmol) of N—[N-[(phenylmethoxy)carbonyl]-L-leucyl]-L-norleucinol obtained in Reference Example 185 in 10 ml of methanol, and the mixture was stirred under a hydrogen atmosphere at room temperature overnight. After the reaction solution was filtered, the filtrate was concentrated under reduced pressure. 20 ml of methylene chloride and 404 mg (4 mmol) of triethylamine were added to the residue. A solution of 299 mg (2 mmol) of 4-morpholinecarbonyl chloride in 3 ml of methylene chloride was added to the mixture solution under ice-cooling. The reaction solution was returned to room temperature and stirred overnight. After the reaction solution was washed with water and then saturated brine, it was dried with anhydrous sodium sulfate and the solvent was distilled off under reduced pressure. Ether was added to the residue to wash it to obtain 488 mg (71%) of the title compound.

1H-NMR (CDCl₃, δ): 0.89 (3H, t, J=7 Hz), 0.94 (3H, d, J=7 Hz), 0.96 (3H, d, J=7 Hz), 1.23-1.37 (4H, m), 1.43-1.72 (5H, m), 2.67 (1H, br-s), 3.31-3.44 (4H, m), 3.52-3.60 (1H, m), 3.65-3.73 (5H, m), 3.82-3.89 (1H, m), 4.24-4.32 (1H, m), 4.82 (1H, d, J=8 Hz), 6.31 (1H, d, J=8 Hz)

Reference Example 187

N—[N-(2-Furanylcarbonyl)-L-leucyl]-L-valinol

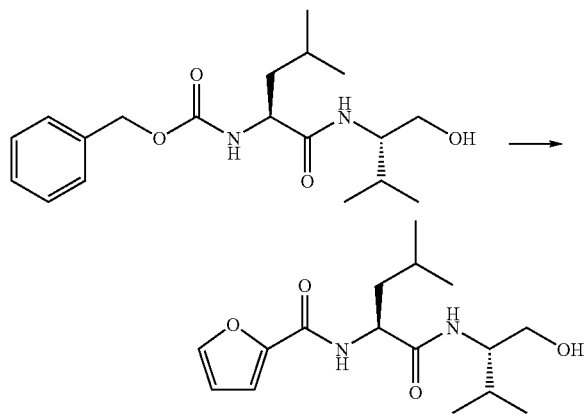

30 mg of 10% palladium-carbon was added to a solution of 350 mg (1 mmol) of N—[N-[(phenylmethoxy)carbonyl]-L-leucyl]-L-valinol obtained in Reference Example 184 in 10 ml of methanol, and the mixture was stirred under a hydrogen atmosphere at room temperature overnight. After the reaction solution was filtered, the filtrate was concentrated under reduced pressure. 10 ml of ethyl acetate, 10 ml of water and further 159 mg (1.5 mmol) of sodium carbonate were added to the residue. Under ice-cooling, a solution of 131 mg (1 mmol) of 2-furancarbonyl chloride in 3 ml of ethyl acetate was added to the mixture solution. The reaction solution was returned to room temperature and stirred overnight. The aqueous layer of the reaction solution was separately collected and it was extracted with ethyl acetate. The organic layer was combined, and after it was washed with a 10% potassium hydrogensulfate and then saturated brine, it was dried with anhydrous sodium sulfate. The solvent was distilled off under reduced pressure and ether was added to the residue to wash the crystal to obtain 268 mg (86%) of the title compound.

1H-NMR (CDCl$_3$, δ): 0.91 (3H, t, J=7 Hz), 0.93 (3H, t, J=7 Hz), 0.97 (3H, t, J=7 Hz), 0.99 (3H, t, J=7 Hz), 1.65-1.94 (4H, m), 2.47 (1H, t, J=5 Hz), 3.63-3.74 (3H, m), 4.54-4.62 (1H, m), 6.42 (1H, d, J=7 Hz), 6.52 (1H, dd, J=4 Hz, 2 Hz), 6.68 (1H, d, J=8 Hz), 7.14 (1H, dd, J=4 Hz, 1 Hz), 7.47 (1H, dd, J=2 Hz, 1 Hz)

Reference Example 188

N-[[1-[(2-Furanylcarbonyl)amino]cyclohexyl]carbonyl]-L-valine ethyl ester

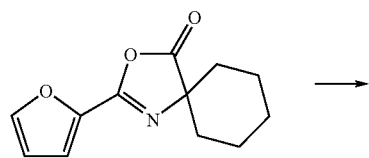

-continued

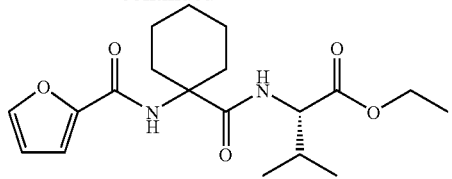

30 ml of dimethylformamide was added to a flask placed with 5 g (27 mmol) of L-valine ethyl ester hydrochloride and 5 g (22.8 mmol) of 2-(2-furanyl)-3-oxa-1-azaspiro[4.5]dec-1-en-4-one. Then, 3.53 g (27.4 mmol) of diisopropylethylamine was added thereto, and the mixture was stirred for 3 days. After the solvent was distilled off under reduced pressure, ethyl acetate was added thereto, and the mixture was successively washed with a 10% aqueous potassium hydrogensulfate solution and saturated brine, followed by drying with sodium sulfate. After the solvent was distilled off under reduced pressure, it was purified by silica gel chromatography to obtain 8.3 g (quantitative) of the title compound.

1H-NMR (CDCl$_3$, δ): 0.89 (3H, d, J=7 Hz), 0.94 (3H, d, J=7 Hz), 1.25 (3H, t, J=7 Hz), 1.35-1.70 (6H, m), 1.98-2.01 (2H, m), 2.19-2.23 (2H, m), 2.31-2.39 (1H, m), 4.11-4.19 (2H, m), 4.49 (1H, dd, J=9 Hz, 5 Hz), 6.34 (1H, s), 6.53 (1H, dd, J=3 Hz, 1 Hz), 7.15 (1H, dd, J=3 Hz, 1 Hz), 7.48 (1H, dd, J=2 Hz, 1 Hz), 7.58 (1H, d, J=9 Hz)

Example 1

N-[[1-[(2-Furanylcarbonyl)amino]cyclohexyl]carbonyl]-L-valine

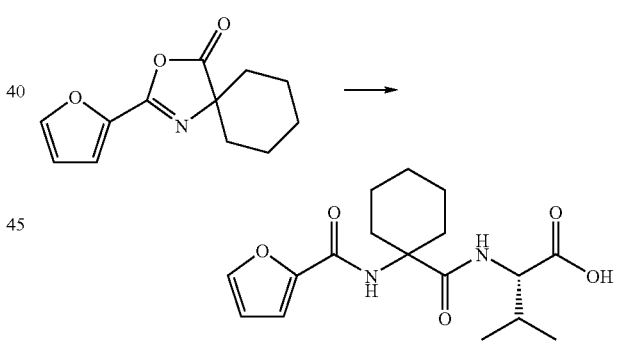

10 ml of N-methylmorpholine was added to 1.0 g (9.1 mmol) of L-valine and 2.0 g (9.1 mmol) of 2-(2-furanyl)-3-oxa-1-azaspiro[4.5]dec-1-en-4-one, and the mixture was stirred and heated under reflux overnight. The reaction solution was distilled off under reduced pressure, ethyl acetate was added thereto, and the mixture was washed with a 10% aqueous potassium hydrogensulfate solution and then saturated brine, followed by drying with anhydrous sodium sulfate. The solvent was distilled off under reduced pressure, and it was purified by silica gel chromatography to obtain 384 mg (12.5%) of the title compound.

1H-NMR (CDCl$_3$, δ): 0.93 (3H, d, J=7 Hz), 0.97 (3H, d, J=7 Hz), 1.33-1.48 (3H, m), 1.64-1.73 (3H, m), 1.98 (2H, dt, J=14 Hz, 4 Hz), 2.22-2.30 (3H, m), 4.46 (1H, m), 6.43 (1H, s), 6.53 (1H, dd, J=3 Hz, 2 Hz), 7.17 (1H, dd, J=3 Hz, 1 Hz), 7.48 (1H, dd, J=2 Hz, 1 Hz), 7.55 (1H, d, J=8 Hz)

Reference Example 189

N-[[1-[[(Phenylmethoxy)carbonyl]amino]cyclohexyl]carbonyl]-L-valinal

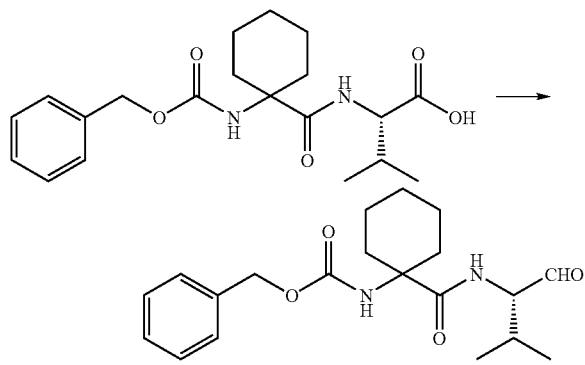

Under an argon gas atmosphere, 1.22 g (9.44 mmol) of N,N-diisopropylethylamine was added dropwise to a solution of 1.50 g (9.44 mmol) of sulfur trioxide-pyridine complex in 10 ml of anhydrous dimethyl sulfoxide and in 5 ml of anhydrous methylene chloride under ice-cooling, and the mixture was stirred for 15 minutes. Further, under ice-cooling, a solution of 570 mg (1.57 mmol) of N-[[1-[[(phenylmethoxy)carbonyl]amino]cyclohexyl]carbonyl]-L-valinol in 3 ml of anhydrous dimethyl sulfoxide was added to the reaction solution, and the mixture was stirred at the same temperature for 2 hours. The reaction solution was poured to ice-water and extracted with ethyl acetate twice. The organic layer was washed with a 10% aqueous citric acid solution, a saturated aqueous sodium hydrogencarbonate solution and then saturated brine, and after it was dried with anhydrous magnesium sulfate, the solvent was distilled off under reduced pressure. 20 ml of diisopropyl ether was added to the residue, and the mixture was stirred at room temperature for 18 hours. The obtained crystal was collected by filtration to obtain 435 mg (77%) of the title compound.

1H-NMR (CDCl$_3$, δ): 0.88 (3H, d, J=7 Hz), 0.97 (3H, d, J=7 Hz), 1.22-1.44 (3H, m), 1.59-1.70 (3H, m), 1.85-2.15 (4H, m), 2.22-2.34 (1H, m), 4.48 (1H, s), 4.96 (1H, s), 5.11 (2H, s), 7.10-7.41 (6H, m), 9.59 (1H, s)

Reference Example 190

N-[[1-[[(Phenylmethoxy)carbonyl]amino]cyclohexyl]carbonyl]-L-norleucinal

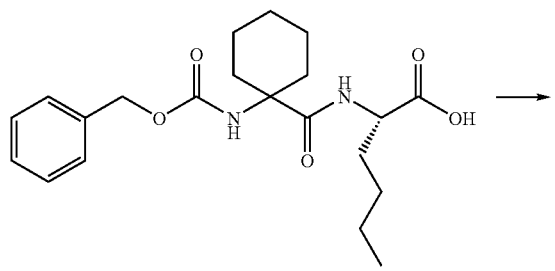

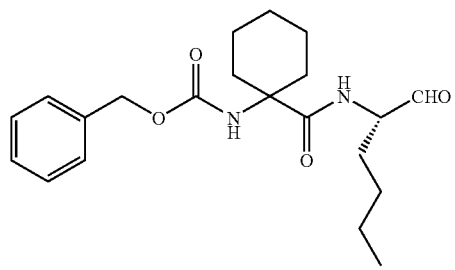

465 mg (1.24 mmol) of N-[[1-[[(phenylmethoxy)carbonyl]amino]cyclohexyl]carbonyl]-L-norleucinol was used instead of N-[[1-[[(phenylmethoxy)carbonyl]amino]cyclohexyl]carbonyl]-L-valinol in the process according to Reference Example 189 to obtain 350 mg (75%) of the title compound.

1H-NMR (CDCl$_3$, δ): 0.88 (3H, d, J=7 Hz), 1.19-1.43 (7H, m), 1.51-1.70 (4H, m), 1.82-2.13 (5H, m), 4.42 (1H, br-s), 4.95 (1H, s), 5.10 (2H, s), 7.10 (1H, br-s), 7.29-7.42 (5H, m), 9.53 (1H, s)

Reference Example 191

N-[[1-[(2-Furanylcarbonyl)amino]cyclohexyl]carbonyl]-L-valinal

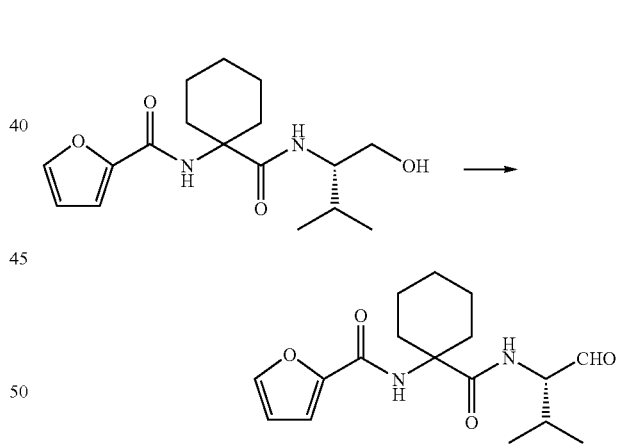

3.50 g (10.9 mmol) of N-[[1-[(2-furanylcarbonyl)amino]cyclohexyl]carbonyl]-L-valinol was used instead of N-[[1-[[(phenylmethoxy)carbonyl]amino]cyclohexyl]carbonyl]-L-valinol in the process according to Reference Example 189 to obtain 3.14 g (90.3%) of the title compound.

1H-NMR (CDCl$_3$, δ): 0.94 (3H, d, J=7 Hz), 1.01 (3H, d, J=7 Hz), 1.30-1.40 (1H, m), 1.41-1.54 (2H, m), 1.62-1.76 (3H, m), 1.95-2.04 (2H, m), 2.20-2.26 (1H, m), 2.28-2.36 (2H, m), 4.44 (1H, dd, J=8 Hz, 5 Hz), 6.38 (1H, br-s), 6.54 (1H, dd, J=4 Hz, 2 Hz), 7.15 (1H, dd, J=4 Hz, 1 Hz), 7.49 (1H, dd, J=2 Hz, 1 Hz), 7.68 (1H, d, J=8 Hz), 9.60 (1H, s)

Reference Example 192

N-[[1-[(4-Morpholinylcarbonyl)amino]cyclohexyl]carbonyl]-L-norleucinal

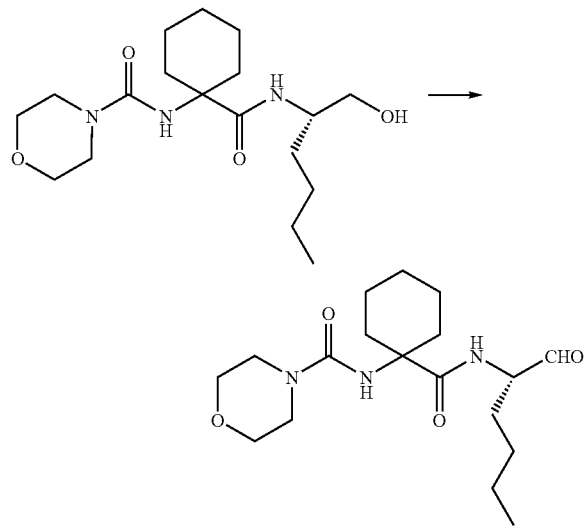

205 mg (0.58 mmol) of N-[[1-[(4-morpholinylcarbonyl)amino]cyclohexyl]carbonyl]-L-norleucinol was used instead of N-[[1-[[(phenylmethoxy)carbonyl]amino]cyclohexyl]carbonyl]-L-valinol in the process according to Reference Example 189 to obtain 125 mg (61%) of the title compound.

1H-NMR (CDCl₃, δ): 0.89 (3H, t, J=7 Hz), 1.23-1.42 (7H, m) 1.52-1.71 (4H, m), 1.83-1.98 (3H, m), 2.05-2.18 (2H, m), 3.34-3.42 (4H, m), 3.65-3.76 (4H, m), 4.37 (1H, dt, J=7 Hz, 7 Hz), 4.48 (1H, s), 7.81 (1H, d, J=7 Hz), 9.55 (1H, s)

Reference Example 193

N—[N-[(Phenylmethoxy)carbonyl]-L-leucyl]-L-valinal

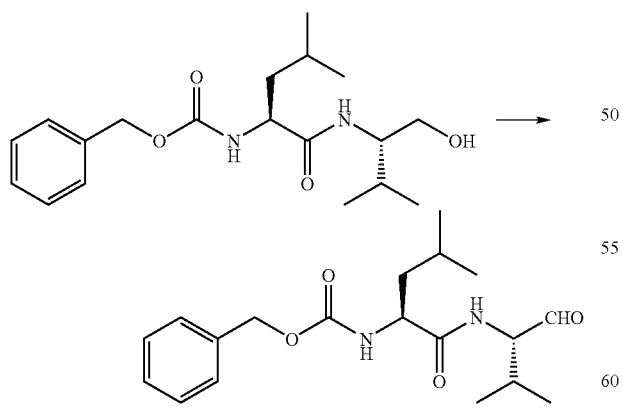

280 mg (0.8 mmol) of N—[N-[(phenylmethoxy)carbonyl]-L-leucyl]-L-valinol was used instead of N-[[1-[[(phenylmethoxy)carbonyl]amino]cyclohexyl]carbonyl]-L-valinol in the process according to Reference Example 189 to obtain 278 mg (quantitative) of the title compound.

1H-NMR (CDCl₃, δ): 0.83-1.01 (12H, m), 1.48-1.59 (1H, m), 1.62-1.74 (2H, m), 2.28-2.37 (1H, m), 4.19-4.28 (1H, m), 4.51-4.56 (1H, m), 5.05-5.17 (3H, m), 6.51 (1H, d, J=7 Hz), 7.27-7.39 (5H, m), 9.64 (1H, s)

Reference Example 194

N—[N-[(Phenylmethoxy)carbonyl]-L-leucyl]-L-norleucinal

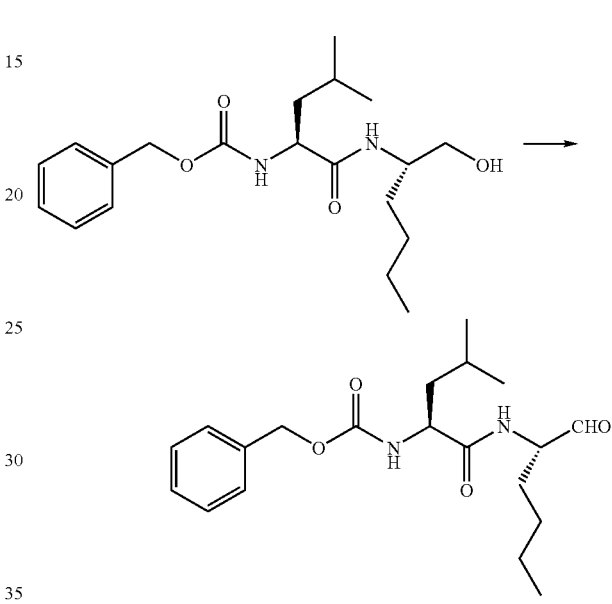

253 mg (0.7 mmol) of N—[N-[(phenylmethoxy)carbonyl]-L-leucyl]-L-norleucinol was used instead of N-[[1-[[(phenylmethoxy)carbonyl]amino]cyclohexyl]carbonyl]-L-valinol in the process according to Reference Example 189 to obtain 195 mg (78%) of the title compound.

1H-NMR (CDCl₃, δ): 0.89 (3H, t, J=7 Hz), 0.95 (6H, d, J=7 Hz), 1.22-1.39 (4H, m), 1.47-1.72 (4H, m), 1.83-1.97 (1H, m), 4.19-4.26 (1H, m), 4.45-4.53 (1H, m), 5.08-5.17 (3H, m), 6.46 (1H, br-s), 7.29-7.39 (5H, m), 9.57 (1H, s)

Reference Example 195

N—[N-(4-Morpholinylcarbonyl)-L-leucyl]-L-norleucinal

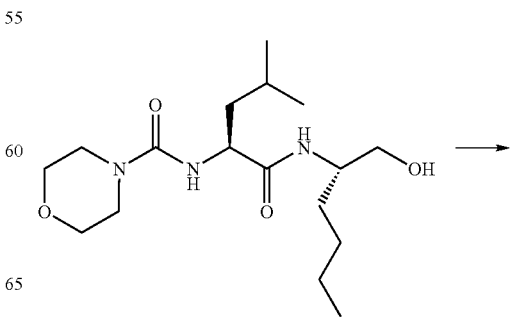

-continued

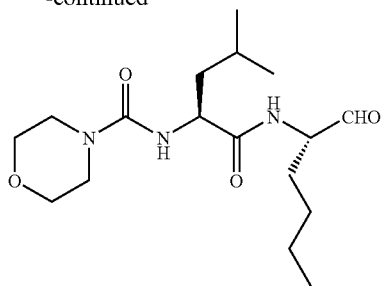

473 mg (1.4 mmol) of N—[N-(4-morpholinylcarbonyl)-L-leucyl]-L-norleucinol was used instead of N-[[1-[[(phenylmethoxy)carbonyl]amino]cyclohexyl]carbonyl]-L-valinol in the process according to Reference Example 189 to obtain 315 mg (67%) of the title compound.

1H-NMR (CDCl$_3$, δ): 0.90 (3H, t, J=7 Hz), 0.96 (3H, d, J=6 Hz), 0.97 (3H, d, J=6 Hz), 1.23-1.39 (4H, m), 1.50-1.76 (4H, m), 1.85-1.96 (1H, m), 3.32-3.43 (4H, m), 3.63-3.72 (4H, m), 4.37-4.46 (2H, m), 4.86 (1H, d, J=8 Hz), 6.69 (1H, d, J=7 Hz), 9.56 (1H, s)

Reference Example 196

N—[N-(2-Furanylcarbonyl)-L-leucyl]-L-valinal

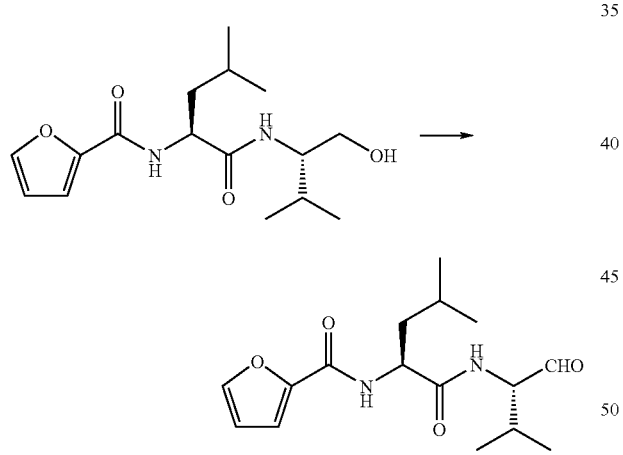

256 mg (0.8 mmol) of N—[N-(2-furanylcarbonyl)-L-leucyl]-L-valinol was used instead of N-[[1-[[(phenylmethoxy)carbonyl]amino]cyclohexyl]carbonyl]-L-valinol in the process according to Reference Example 189 to obtain 175 mg (72%) of the title compound.

1H-NMR (CDCl$_3$, δ): 0.90-1.02 (12H, m), 1.64-1.82 (3H, m) 2.29-2.36 (1H, m), 4.52 (1H, dd, J=8 Hz, 5 Hz), 4.67 (1H, td, J=8 Hz, 6 Hz), 6.51 (1H, dd, J=4 Hz, 2 Hz), 6.67-6.73 (2H, m), 7.14 (1H, dd, J=4 Hz, 1 Hz), 7.46 (1H, dd, J=2 Hz, 1 Hz), 9.65 (1H, s)

Reference Example 197

1-[(2-Benzothienylcarbonyl)amino]cyclohexanecarboxylic acid phenylmethyl ester

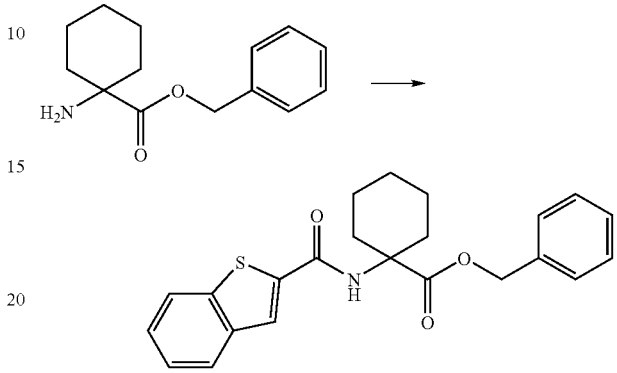

Under ice-cooling, 5.9 g (31 mmol) of 1-ethyl-3-(3-dimethylaminopropyl)carbodiimide hydrochloride was added to a solution of 5 g (28 mmol) of 2-benzothiophenecarboxylic acid, 6.5 g (28 mmol) of 1-aminocyclohexanecarboxylic acid phenylmethyl ester and 4.5 g (29 mmol) of 1-hydroxybenzotriazole in methylene chloride. After the mixture was stirred at room temperature overnight, the reaction solvent was distilled off under reduced pressure. Water was added to the residue and the mixture was extracted with ethyl acetate twice. The obtained organic layer was washed with a 10% aqueous potassium hydrogensulfate solution, a saturated aqueous sodium hydrogencarbonate solution and then saturated brine, and it was dried with anhydrous sodium sulfate. The solvent was distilled off under reduced pressure, diethyl ether was added to the obtained residue, and the mixture was stirred overnight. The crystal was collected by filtration and heated and dried under reduced pressure to obtain 10 g (91%) of the title compound.

1H-NMR (CDCl$_3$, δ): 1.25-1.78 (6H, m), 1.93-2.05 (2H, m), 2.12-2.25 (2H, m), 5.18 (2H, s), 6.24 (1H, s), 7.20-7.38 (5H, m), 7.38-7.51 (2H, m), 7.77 (1H, s), 7.80-7.91 (2H, m)

Reference Example 198

1-[(2-Benzothienylcarbonyl)amino]cyclohexanecarboxylic acid

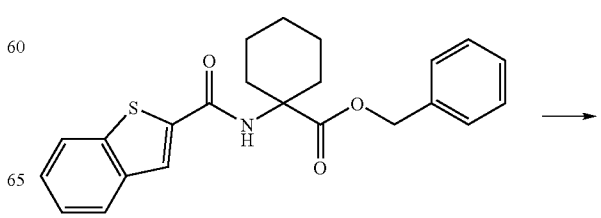

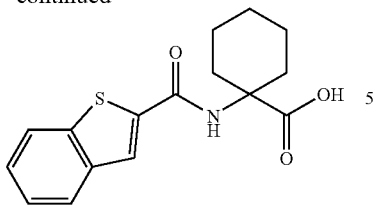

42 ml of 2N aqueous sodium hydroxide solution was added to a solution of 10 g (24 mmol) of 1-[(2-benzothienylcarbonyl)amino]cyclohexanecarboxylic acid phenylmethyl ester in 20 ml of tetrahydrofuran, and the mixture was heated under reflux for 3 days. After ether was added to the reaction solution to wash it, the aqueous layer was neutralized by concentrated hydrochloric acid, and the precipitated crystal was collected by filtration. The obtained crystal was dried under reduced pressure to obtain 6.1 g (80%) of the title compound.

1H-NMR (CDCl$_3$, δ): 1.31-1.85 (6H, m), 1.91-2.08 (2H, m), 2.21-2.35 (2H, m), 6.22 (1H, s), 7.38-7.53 (2H, m), 7.80-7.93 (3H, m)

Reference Example 199

2-(2-Benzothienyl)-3-oxa-1-azaspiro[4.5]dec-1-en-4-one

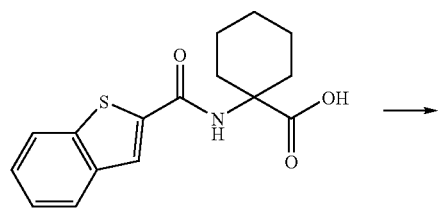

4.1 g (21 mmol) of 1-ethyl-3-(3-dimethylaminopropyl)carbodiimide hydrochloride was added to a solution of 5 g (16 mmol) of 1-[(2-benzothienylcarbonyl)amino]cyclohexanecarboxylic acid in 50 ml of methylene chloride. After the mixture was stirred at room temperature for 4 hours, the reaction solution was concentrated under reduced pressure, ethyl acetate was added thereto, and the mixture was successively washed with water, a 10% aqueous potassium hydrogensulfate solution, a saturated aqueous sodium hydrogencarbonate solution and saturated brine. The organic layer was dried with anhydrous sodium sulfate and the solvent was distilled off under reduced pressure to obtain 3.5 g (75%) of the title compound.

1H-NMR (CDCl$_3$, δ): 1.45-1.98 (10H, m), 7.38-7.51 (2H, m), 7.80-7.91 (2H, m), 7.93 (1H, s)

Reference Example 200

1-[[[4-(Chloromethyl)phenyl]carbonyl]amino]cyclohexanecarboxylic acid methyl ester

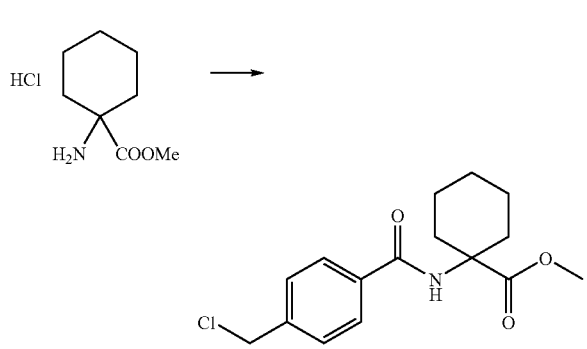

Under ice-cooling, 9.96 g (52 mmol) of 1-ethyl-3-(3-dimethylaminopropyl)carbodiimide hydrochloride was added to a solution of 8.8 g (52 mmol) of 4-(chloromethyl)benzoic acid, 10 g (52 mmol) of 1-aminocyclohexanecarboxylic acid methyl ester hydrochloride, 15 g (152 mmol) of triethylamine and 8.63 g (56 mmol) of 1-hydroxybenzotriazole in methylene chloride. After the mixture was stirred at room temperature overnight, the reaction solvent was distilled off under reduced pressure. Water was added to the residue, and the mixture was extracted with ethyl acetate twice. The obtained organic layer was washed with a 10% aqueous potassium hydrogensulfate solution, a saturated aqueous sodium hydrogencarbonate solution and then saturated brine, and it was dried with anhydrous sodium sulfate. The obtained residue was purified by silica gel column chromatography to obtain 8.5 g (53%) of the title compound.

1H-NMR (CDCl$_3$, δ): 1.25-1.73 (6H, m), 1.83-2.00 (2H, m) 2.08-2.21 (2H, m), 3.71 (3H, s), 5.56 (2H, s), 6.30 (1H, s), 7.44 (2H, dd, J=8 Hz, 2 Hz), 7.75 (2H, dd, J=8 Hz, 2 Hz)

Reference Example 201

1-[[[4-(Hydroxymethyl)phenyl]carbonyl]amino]cyclohexanecarboxylic acid phenylmethyl ester

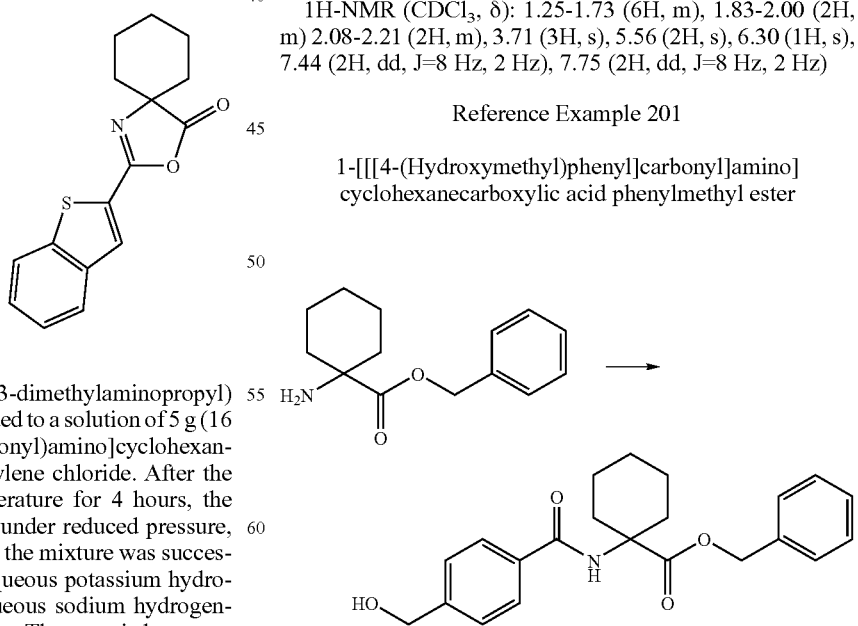

Under ice-cooling, 6.94 g (36 mmol) of 1-ethyl-3-(3-dimethylaminopropyl)carbodiimide hydrochloride was added to a solution of 5 g (33 mmol) of 4-(hydroxymethyl)benzoic acid, 7.7 g (33 mmol) of 1-aminocyclohexanecarboxylic acid phenylmethyl ester and 5.29 g (35 mmol) of 1-hydroxybenzotriazole in methylene chloride. After the mixture was stirred at room temperature overnight, the reaction solvent was distilled off under reduced pressure. Water was added to the residue and the mixture was extracted with ethyl acetate twice. The obtained organic layer was washed with a 10% aqueous potassium hydrogensulfate solution, a saturated aqueous sodium hydrogencarbonate solution and then saturated brine, and it was dried with anhydrous sodium sulfate. The obtained residue was purified by silica gel column chromatography to obtain 6.83 g (56%) of the title compound.

1H-NMR (CDCl$_3$, δ): 1.23-1.79 (6H, m), 1.82-2.23 (4H, m), 4.73 (2H, m), 5.16 (2H, s), 6.25 (1H, s), 7.20-7.32 (5H, m), 7.32-7.43 (2H, m), 7.62-7.79 (2H, m)

Reference Example 202

1-[[[4-[(Dimethylamino)methyl]phenyl]carbonyl]amino]cyclohexanecarboxylic acid methyl ester

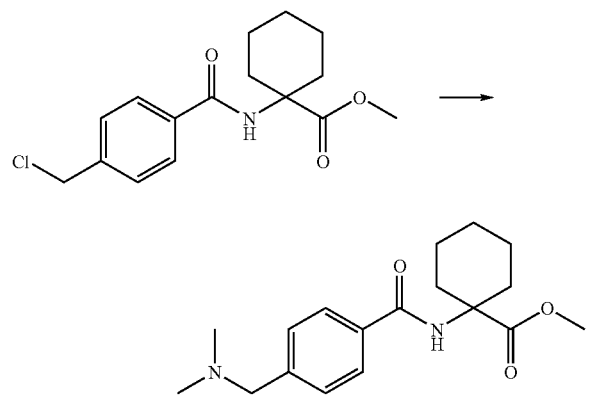

30 ml of 40% aqueous dimethylamine solution was added to 4.5 g (14.5 mmol) of 1-[[[4-(chloromethyl)phenyl]carbonyl]amino]cyclohexanecarboxylic acid methyl ester, and the mixture was heated under reflux for 3 hours. The reaction solution was distilled off under reduced pressure, a saturated aqueous sodium bicarbonate solution was added thereto, and the mixture was extracted with ethyl acetate. The organic layer was washed with saturated brine, and it was dried with anhydrous sodium sulfate. The solvent was distilled off under reduced pressure, diisopropyl ether was added to the residue, and the mixture was stirred overnight. The precipitated solid was collected by filtration to obtain 2.3 g (50%) of the title compound.

1H-NMR (CDCl$_3$, δ): 1.30-2.19 (10H, m), 2.24 (6H, s), 3.46 (2H, s), 3.76 (3H, s), 6.22 (1H, s), 7.38 (2H, d, J=9 Hz), 7.73 (2H, d, J=9 Hz)

Reference Example 203

1-[[[4-[(Dimethylamino)methyl]phenyl]carbonyl]amino]cyclohexanecarboxylic acid phenylmethyl ester

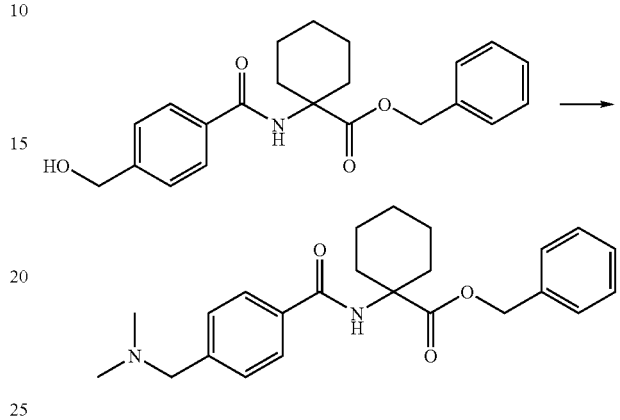

Under ice-cooling, 1 g (9 mmol) of methanesulfonyl chloride was added dropwise to a solution of 3 g (8 mmol) of 1-[[[4-(hydroxymethyl)phenyl]carbonyl]amino]cyclohexanecarboxylic acid phenylmethyl ester and 2.46 g (24 mmol) of triethylamine in methylene chloride. After the mixture was stirred at room temperature for 1 hour, 20 ml of 2N dimethylamine-tetrahydrofuran solution was added, and the mixture was stirred overnight. The reaction solution was distilled off under reduced pressure, a saturated aqueous sodium bicarbonate solution was added thereto, and the mixture was extracted with ethyl acetate. The organic layer was washed with saturated brine, and it was dried with anhydrous sodium sulfate. The solvent was distilled off under reduced pressure and the residue was purified by silica gel column chromatography to obtain 700 mg (22%) of the title compound.

1H-NMR (CDCl$_3$, δ): 1.30-2.01 (9H, m), 2.12-2.28 (1H, m), 2.24 (6H, s), 3.46 (2H, s), 5.17 (2H, s), 6.25 (1H, s), 7.21-7.32 (5H, m), 7.37 (2H, dd, J=9 Hz, 2 Hz), 7.10 (2H, dd, J=9 Hz, 2 Hz)

Reference Example 204

2-[4-[(Dimethylamino)methyl]phenyl]-3-oxa-1-azaspiro[4.5]dec-1-en-4-one

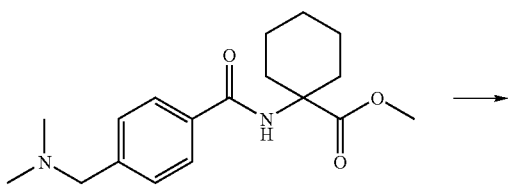

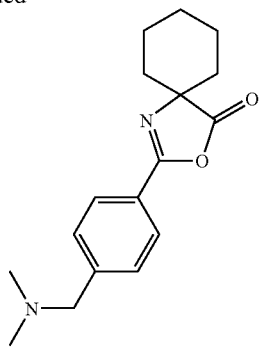

29 ml of 2N aqueous sodium hydroxide solution was added to a solution of 1.85 g (5.8 mmol) of 1-[[[4-[(dimethylamino)methyl]phenyl]carbonyl]amino]cyclohexanecarboxylic acid methyl ester in 29 ml of tetrahydrofuran, and the mixture was heated under reflux overnight. After the mixture was neutralized by concentrated hydrochloric acid, the reaction solution was distilled off under reduced pressure. 30 ml of methylene chloride, 1.76 g (17 mmol) of triethylamine and 1.67 g (8.7 mmol) of 1-ethyl-3-(3-dimethylaminopropyl)carbodiimide hydrochloride were added to the residue, and the mixture was stirred for 1 hour. The reaction solution was distilled off under reduced pressure, a saturated aqueous sodium bicarbonate solution was added thereto, and the mixture was extracted with ethyl acetate. The organic layer was washed with a saturated aqueous sodium bicarbonate solution, and it was dried with anhydrous sodium sulfate. The solvent was distilled off under reduced pressure to obtain 1.33 g (80%) of the title compound.

1H-NMR (CDCl$_3$, δ): 1.50-1.88 (10H, m), 2.25 (6H, s), 3.48 (2H, s), 7.43 (2H, dd, J=9 Hz, 2 Hz), 7.96 (2H, dd, J=9 Hz, 2 Hz)

Reference Example 205

2-[4-[(Dimethylamino)methyl]phenyl]-3-oxa-1-azaspiro[4.5]dec-1-en-4-one

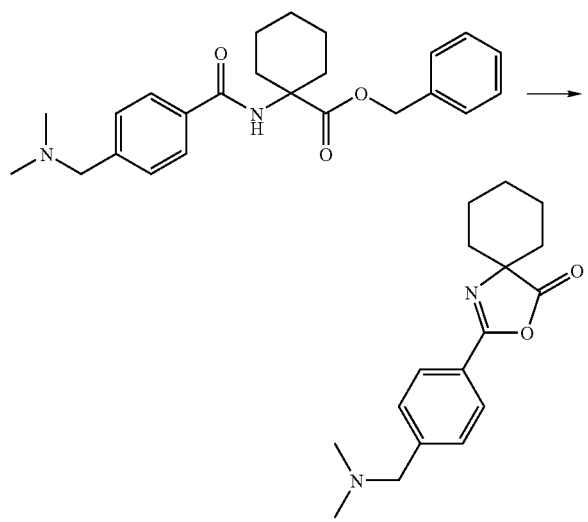

0.7 ml of 2N aqueous sodium hydroxide solution was added to a solution of 100 mg (0.25 mmol) of 1-[[[4-[(dimethylamino)methyl]phenyl]carbonyl]amino]cyclohexanecarboxylic acid phenylmethyl ester in 1 ml of tetrahydrofuran, and the mixture was heated under reflux overnight. After the mixture was neutralized by concentrated hydrochloric acid, the reaction solution was distilled off under reduced pressure. 3 ml of methylene chloride, 126 mg (1.25 mmol) of triethylamine and 96 mg (0.5 mmol) of 1-ethyl-3-(3-dimethylaminopropyl)carbodiimide hydrochloride were added to the residue, and the mixture was stirred for 1 hour. The reaction solution was distilled off under reduced pressure, a saturated aqueous sodium bicarbonate solution was added thereto, and the mixture was extracted with ethyl acetate. The organic layer was washed with a saturated aqueous sodium bicarbonate solution, and it was dried with anhydrous sodium sulfate. The solvent was distilled off under reduced pressure to obtain 52 mg (68%) of the title compound.

1H-NMR (CDCl$_3$, δ): 1.50-1.88 (10H, m), 2.25 (6H, s), 3.48 (2H, s), 7.43 (2H, dd, J=9 Hz, 2 Hz), 7.96 (2H, dd, J=9 Hz, 2 Hz)

Reference Example 206

1-[[[4-(4-Morpholinylmethyl)phenyl]carbonyl]amino]cyclohexanecarboxylic acid phenylmethyl ester

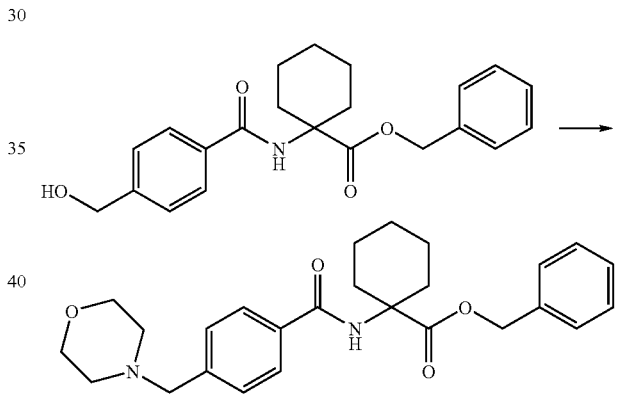

Under ice-cooling, 628 mg (5.5 mmol) of methanesulfonyl chloride was added dropwise to a solution of 1.83 g (5 mmol) of 1-[[[4-(hydroxymethyl)phenyl]carbonyl]amino]cyclohexanecarboxylic acid phenylmethyl ester and 1.52 g (15 mmol) of triethylamine in methylene chloride. After the mixture was stirred at room temperature for 1 hour, 5 ml of morpholine was added thereto, and the mixture was stirred overnight. The reaction solution was distilled off under reduced pressure, a saturated aqueous sodium bicarbonate solution was added thereto, and the mixture was extracted with ethyl acetate. The organic layer was washed with saturated brine, and it was dried with anhydrous sodium sulfate. The solvent was distilled off under reduced pressure and the residue was purified by silica gel column chromatography to obtain 1 g (57%) of the title compound.

1H-NMR (CDCl$_3$, δ): 1.25-1.79 (6H, m), 1.89-2.03 (2H, m), 2.15-2.29 (2H, m), 2.43 (4H, t, J=5 Hz), 3.53 (2H, s), 3.70 (4H, t, J=5 Hz), 5.17 (2H, s), 6.21 (1H, s), 7.21-7.38 (5H, m), 7.39 (2H, d, J=8 Hz), 7.71 (2H, d, J=8 Hz)

Reference Example 207

1-[[[4-(4-Morpholinylmethyl)phenyl]carbonyl]amino]cyclohexanecarboxylic acid methyl ester

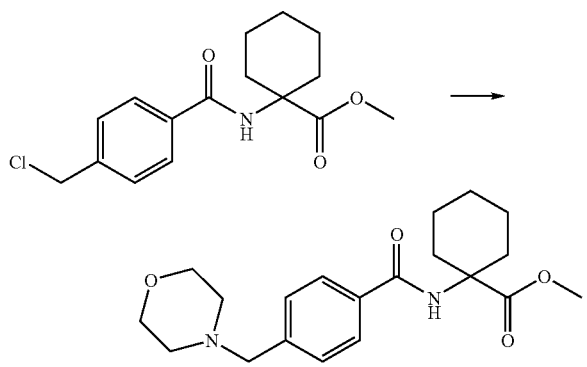

30 ml of morpholine was added to 4 g (13 mmol) of 1-[[[4-(chloromethyl)phenyl]carbonyl]amino]cyclohexanecarboxylic acid methyl ester, and the mixture was heated under reflux for 1 hour. The reaction solution was distilled off under reduced pressure, a saturated aqueous sodium bicarbonate solution was added thereto, and the mixture was extracted with ethyl acetate. The organic layer was washed with saturated brine, and it was dried with anhydrous sodium sulfate. The solvent was distilled off under reduced pressure, diethyl ether was added to the residue, and the mixture was stirred overnight. The precipitated solid was collected by filtration to obtain 3.8 g (83%) of the title compound.

1H-NMR (CDCl$_3$, δ): 1.28-1.80 (6H, m), 1.80-1.99 (2H, m), 2.11-2.21 (2H, m), 2.38-2.49 (4H, m), 3.54 (2H, s), 3.63-3.74 (4H, m), 3.73 (3H, s), 6.22 (1H, s), 7.41 (2H, d, J=8 Hz), 7.73 (2H, d, J=8 Hz)

Reference Example 208

2-[4-(4-Morpholinylmethyl)phenyl]-3-oxa-1-azaspiro[4.5]dec-1-en-4-one

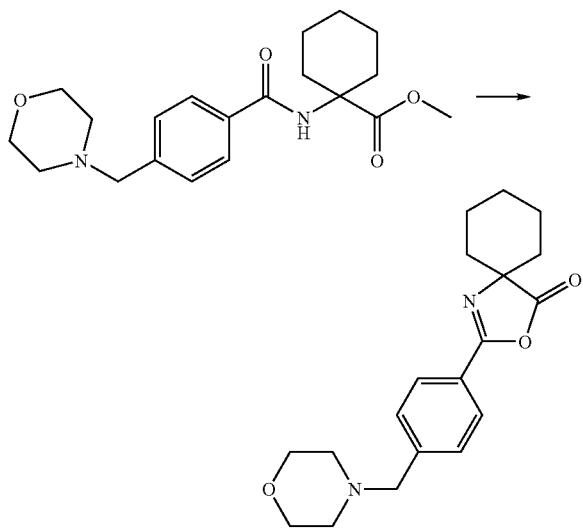

18 ml of 2N aqueous sodium hydroxide solution was added to a solution of 2.07 g (5.7 mmol) of 1-[[[4-(4-morpholinylmethyl)phenyl]carbonyl]amino]cyclohexanecarboxylic acid methyl ester in 18 ml of tetrahydrofuran, and the mixture was heated under reflux overnight. After the mixture was neutralized by concentrated hydrochloric acid, the reaction solution was distilled off under reduced pressure. 30 ml of methylene chloride, 1.74 g (17 mmol) of triethylamine and 1.65 g (8.6 mmol) of 1-ethyl-3-(3-dimethylaminopropyl)carbodiimide hydrochloride were added to the residue, and the mixture was stirred for 1 hour. The reaction solution was distilled off under reduced pressure, a saturated aqueous sodium bicarbonate solution was added thereto, and the mixture was extracted with ethyl acetate. The organic layer was washed with a saturated aqueous sodium bicarbonate solution, and it was dried with anhydrous sodium sulfate. The solvent was distilled off under reduced pressure to obtain 1.27 g (60%) of the title compound.

1H-NMR (CDCl$_3$, δ): 1.42-1.80 (10H, m), 2.44 (4H, t, J=5 Hz), 3.56 (2H, s), 3.71 (4H, t, J=5 Hz), 7.45 (2H, d, J=8 Hz), 7.96 (2H, d, J=8 Hz)

Reference Example 209

2-[4-(4-Morpholinylmethyl)phenyl]-3-oxa-1-azaspiro[4.5]dec-1-en-4-one

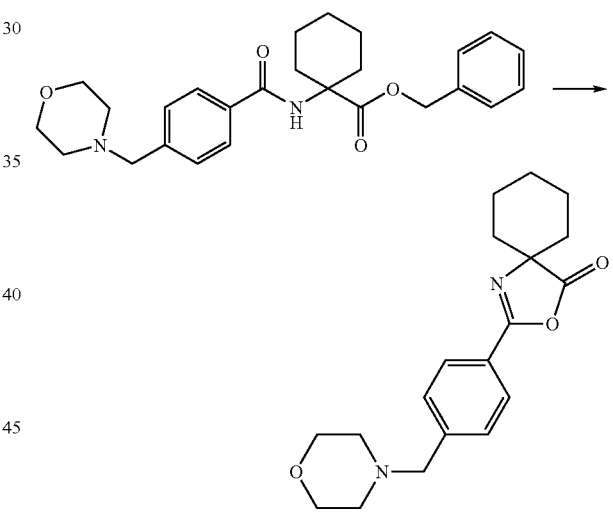

2 ml of 2N aqueous sodium hydroxide solution was added to a solution of 300 mg (0.69 mmol) of 1-[[[4-(4-morpholinylmethyl)phenyl]carbonyl]amino]cyclohexanecarboxylic acid phenylmethyl ester in 2 ml of tetrahydrofuran, and the mixture was heated under reflux overnight. After the mixture was neutralized by concentrated hydrochloric acid, the reaction solution was distilled off under reduced pressure. 3 ml of methylene chloride, 698 mg (6.9 mmol) of triethylamine and 264 mg (1.38 mmol) of 1-ethyl-3-(3-dimethylaminopropyl)carbodiimide hydrochloride were added to the residue, and the mixture was stirred for 1 hour. The reaction solution was distilled off under reduced pressure, a saturated aqueous sodium bicarbonate solution was added thereto, and the mixture was extracted with ethyl acetate. The organic layer was washed with a saturated aqueous sodium bicarbonate solution, and it was dried with anhydrous sodium sulfate. The solvent was distilled off under reduced pressure to obtain 191 mg (80%) of the title compound.

1H-NMR (CDCl₃, δ) 1.42-1.80 (10H, m), 2.44 (4H, t, J=5 Hz), 3.56 (2H, s), 3.71 (4H, t, J=5 Hz), 7.45 (2H, d, J=8 Hz), 7.96 (2H, d, J=8 Hz)

Reference Example 210

1-[[[4-[2-(4-Methyl-1-piperazinyl)-4-thiazolyl]phenyl]carbonyl]amino]cyclohexanecarboxylic acid phenylmethyl ester

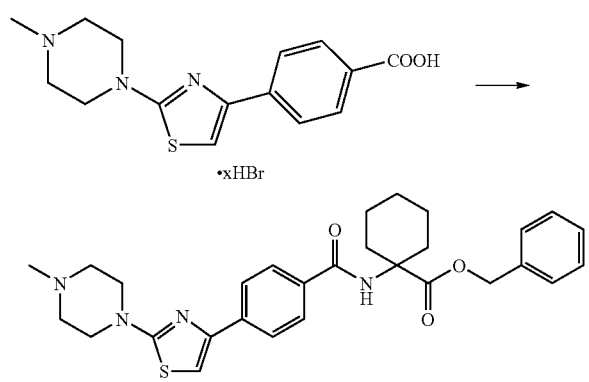

Under ice-cooling, 5.29 g (374 mmol) of 1-ethyl-3-(3-dimethylaminopropyl)carbodiimide hydrochloride was added to a solution of 8.84 g (23.0 mmol) of 4-[2-(4-methyl-1-piperazinyl)-4-thiazolyl]benzoic acid hydrobromide, 4.19 g (27.6 mmol) of 1-hydroxybenzotriazole, 6.44 g (27.6 mmol) of 1-aminocyclohexanecarboxylic acid phenylmethyl ester and 11.9 g (92 mmol) of N,N-diisopropylethylamine in 120 ml of dimethylformamide. After the mixture was stirred at room temperature overnight, under reduced pressure, the reaction solution was concentrated, ethyl acetate was added thereto, and the mixture was successively washed with water, a saturated aqueous sodium hydrogencarbonate solution and saturated brine, followed by drying with anhydrous sodium sulfate. After the solvent was distilled off under reduced pressure, ether was added to the residue and the crystal was washed to obtain 11.8 g (quantitative) of the title compound.

1H-NMR (CDCl₃, δ): 1.30-1.42 (1H, m), 1.45-1.61 (2H, m) 1.62-1.75 (3H, m), 1.91-2.01 (2H, m), 2.18-2.24 (2H, m), 2.37 (3H, s), 2.56 (4H, t, J=5 Hz), 3.59 (4H, t, J=5 Hz), 5.18 (2H, s), 6.23 (1H, br-s), 6.88 (1H, s), 7.25-7.34 (5H, m), 7.76 (2H, dd, J=8 Hz, 2 Hz), 7.90 (2H, dd, J=8 Hz, 2 Hz)

Reference Example 211

1-[[[4-[2-(4-Methyl-1-piperazinyl)-4-thiazolyl]phenyl]carbonyl]amino]cyclohexanecarboxylic acid

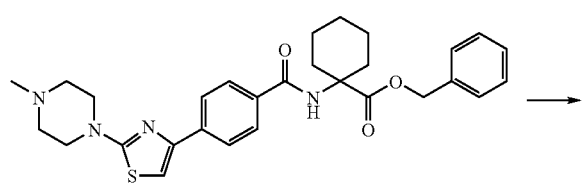

-continued

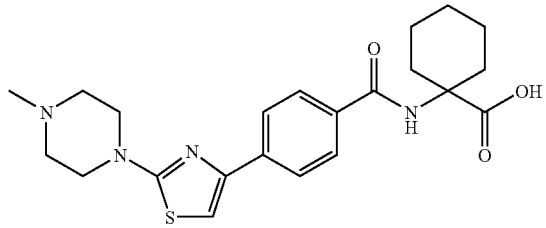

35 ml of 2N aqueous sodium hydroxide solution was added to a solution of 11.8 g (23.0 mmol) of 1-[[[4-[2-(4-methyl-1-piperazinyl)-4-thiazolyl]phenyl]carbonyl]amino]cyclohexanecarboxylic acid phenylmethyl ester in 120 ml of tetrahydrofuran, and the mixture was heated under reflux for 15 hours. Ether was added to the reaction solution to separate the aqueous layer. Concentrated hydrochloric acid was added to the separated aqueous layer to neutralize it, and the precipitated crystal was collected by filtration to obtain 6.60 g (67%) of the title compound.

1H-NMR (CDCl₃, δ): 1.28-1.38 (1H, m), 1.40-1.51 (2H, m), 1.58-1.73 (3H, m), 1.85-2.00 (2H, m), 2.10-2.21 (2H, m), 2.47 (3H, s), 2.66-2.75 (4H, m), 3.54-4.04 (4H, m), 6.38 (1H, br-s), 6.83 (1H, s), 7.69 (2H, d, J=8 Hz), 7.76 (2H, d, J=8 Hz)

Reference Example 212

2-[4-[2-(4-Methyl-1-piperazinyl)-4-thiazolyl]phenyl]-3-oxa-1-azaspiro[4.5]dec-1-en-4-one

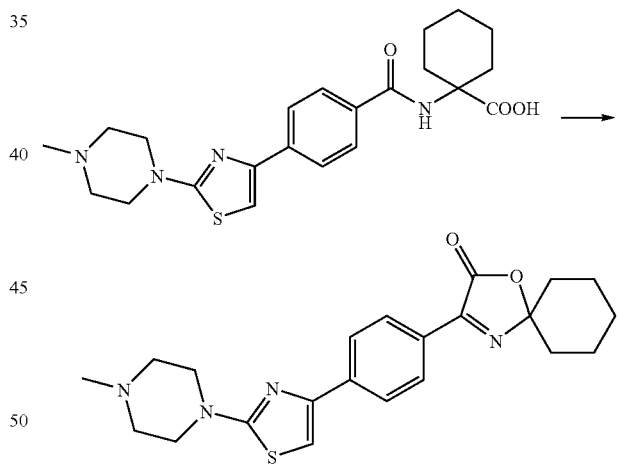

450 mg (2.5 mmol) of 1-ethyl-3-(3-dimethylaminopropyl)carbodiimide hydrochloride was added to a solution of 910 mg (2.1 mmol) of 1-[[[4-[2-(4-methyl-1-piperazinyl)-4-thiazolyl]phenyl]carbonyl]amino]cyclohexanecarboxylic acid in 20 ml of dimethylformamide. After the mixture was stirred at room temperature for 4 hours, the reaction solution was concentrated under reduced pressure, ethyl acetate was added thereto, and the mixture was successively washed with water, a saturated aqueous sodium hydrogencarbonate solution and saturated brine, followed by drying with anhydrous sodium sulfate. The solvent was distilled off under reduced pressure to obtain 577 mg (67%) of the title compound.

1H-NMR (CDCl₃, δ): 1.51-1.62 (1H, m), 1.62-1.71 (1H, m), 1.71-1.78 (2H, m), 1.78-1.90 (6H, m), 2.37 (3H, s), 2.56

(4H, t, J=5 Hz), 3.60 (4H, t, J=5 Hz), 6.92 (1H, s), 7.94 (2H, d, J=8 Hz), 8.00 (2H, d, J=8 Hz)

Reference Example 213

4-[[2-(4-Morpholinyl)-1-piperazinyl]-4-thiazolyl] benzoic acid hydrobromide

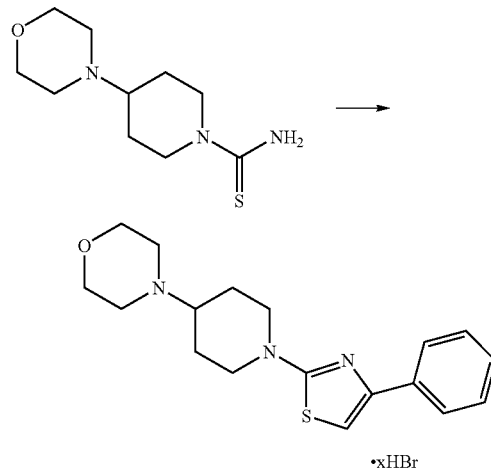

After a solution of 2.47 g (16.9 mmol) of 4-(4-morpholinyl)piperidine-1-thiocarboxamide and 4.08 g (16.9 mmol) of 4-bromoacetyl benzoic acid in 150 ml of ethanol was heated under reflux for 2 hours, the solution was left to cool to room temperature. 150 ml of ether was added to the reaction solution and the mixture was stirred at 4° C. overnight. Thereafter, the precipitated crystal was collected by filtration to obtain 4.64 g (95%) of the title compound.

1H-NMR (DMSO-$d_6$, δ): 1.68-1.80 (2H, m), 2.17-2.25 (2H, m), 3.07-3.20 (4H, m), 3.21-3.63 (5H, m), 3.64-3.78 (1H, m), 3.98-4.10 (1H, m), 4.10-4.18 (2H, m), 7.51 (1H, s), 7.95-7.99 (4H, m)

Reference Example 214

1-[[[4-[2-[4-(4-Morpholinyl)-1-piperazinyl]-4-thiazolyl]phenyl]carbonyl]amino]cyclohexanecarboxylic acid methyl ester

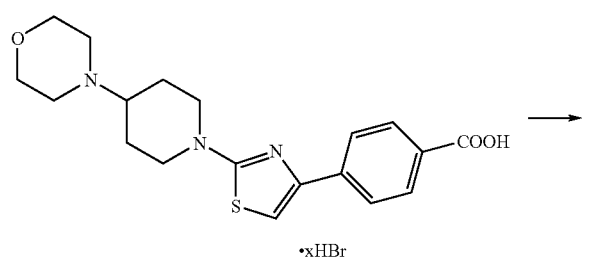

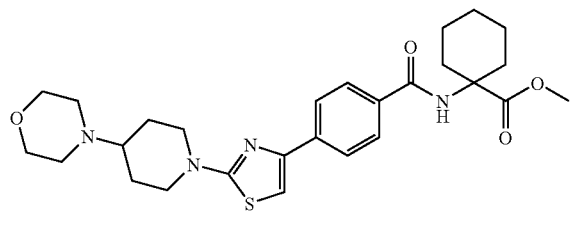

4.50 g (9.90 mmol) of 4-[2-[4-(4-morpholinyl)-1-piperazinyl]-4-thiazolyl]benzoic acid hydrobromide was used instead of 4-[2-(4-methyl-1-piperazinyl)-4-thiazolyl]benzoic acid hydrobromide, and 1.57 g (9.90 mmol) of 1-aminocyclohexanecarboxylic acid methyl ester was used instead of 1-aminocyclohexanecarboxylic acid phenylmethyl ester in the process according to Reference Example 210 to obtain 5.08 g (quantitative) of the title compound.

1H-NMR (CDCl$_3$, δ): 1.32-1.42 (1H, m), 1.45-1.74 (7H, m), 1.93-2.01 (4H, m), 2.14-2.21 (2H, m), 2.41-2.50 (1H, m), 2.58 (4H, t, J=5 Hz), 3.07 (2H, dd, J=13 Hz, 13 Hz), 3.73 (4H, t, J=5 Hz), 3.74 (3H, s), 4.13 (2H, d, J=13 Hz), 6.25 (1H, br-s), 6.86 (1H, s), 7.78 (2H, dd, J=8 Hz, 2 Hz), 7.90 (2H, dd, J=8 Hz, 2 Hz)

Reference Example 215

1-[[[4-[2-[4-(4-Morpholinyl)-1-piperazinyl]-4-thiazolyl]phenyl]carbonyl]amino]cyclohexanecarboxylic acid

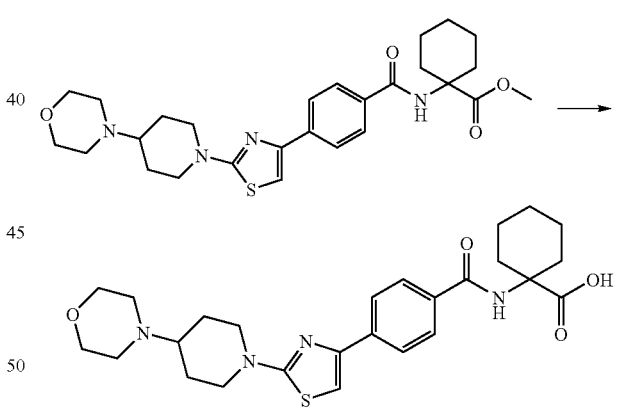

5.08 g (9.90 mmol) of 1-[[[4-[2-[4-(4-morpholinyl)-1-piperazinyl]-4-thiazolyl]phenyl]carbonyl]amino]cyclohexanecarboxylic acid methyl ester was used instead of 1-[[[4-[2-(4-methyl-1-piperazinyl)-4-thiazolyl]phenyl]carbonyl]amino]cyclohexanecarboxylic acid phenylmethyl ester in the process according to Reference Example 211 to obtain 4.93 g (quantitative) of the title compound.

1H-NMR (CDCl$_3$, δ): 1.32-1.45 (1H, m), 1.46-1.60 (2H, m), 1.61-1.77 (5H, m), 1.90-2.03 (4H, m), 2.15-2.25 (2H, m), 2.44-2.52 (1H, m), 2.62 (4H, t, J=5 Hz), 3.08 (2H, dd, J=13 Hz, 13 Hz), 3.78 (4H, t, J=5 Hz), 4.14 (2H, d, J=13 Hz), 6.70 (1H, br-s), 6.88 (1H, s), 7.79 (2H, d, J=8 Hz), 7.90 (2H, d, J=8 Hz)

Reference Example 216

2-[4-[2-[4-(4-Morpholinyl)-1-piperidinyl]-4-thiazolyl]phenyl]-3-oxa-1-azaspiro[4.5]dec-1-en-4-one

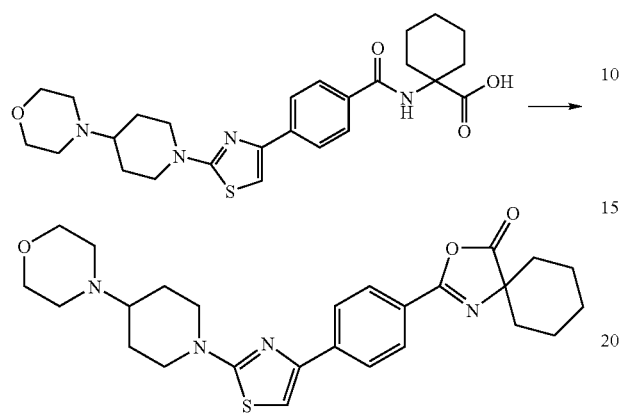

4.93 g (9.90 mmol) of 1-[[[4-[2-[4-(4-morpholinyl)-1-piperazinyl]-4-thiazolyl]phenyl]carbonyl]amino]cyclohexanecarboxylic acid was used instead of 1-[[[4-[2-(4-methyl-1-piperazinyl)-4-thiazolyl]phenyl]carbonyl]amino]cyclohexanecarboxylic acid in the process according to Reference Example 212 to obtain 3.00 g (63%) of the title compound.

1H-NMR (CDCl$_3$, δ): 1.50-1.61 (1H, m), 1.61-1.71 (3H, m), 1.71-1.79 (2H, m), 1.79-1.89 (5H, m), 1.91-2.00 (2H, m), 2.40-2.48 (1H, m), 2.59 (4H, t, J=5 Hz), 3.09 (2H, d, J=12 Hz), 3.74 (4H, t, J=5 Hz), 4.13 (2H, d, J=12 Hz), 6.90 (1H, s), 7.96 (2H, dd, J=7 Hz, 2 Hz), 8.00 (2H, dd, J=7 Hz, 2 Hz)

Reference Example 217

N-[[1-[(2-Benzothienylcarbonyl)amino]cyclohexyl]carbonyl]-L-phenylglycinol

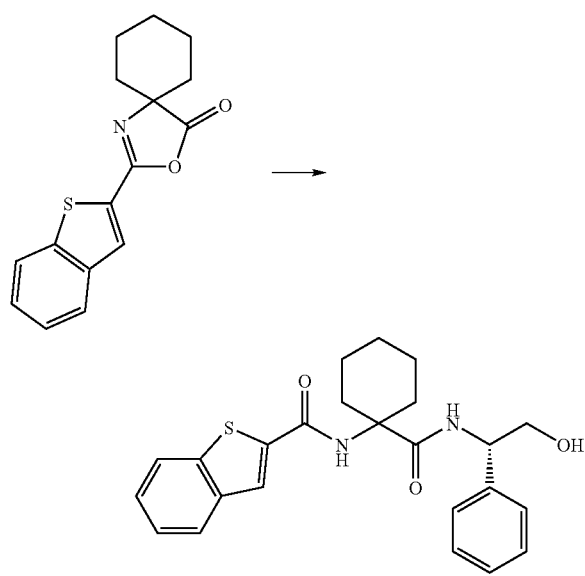

288 mg (2 mmol) of L-phenylglycinol was added to a solution of 500 mg (1.75 mmol) of 2-(2-benzothienyl)-3-oxa-1-azaspiro[4.5]dec-1-en-4-one in 3 ml of N,N-dimethylformamide, and the mixture was stirred overnight. Water was slowly added thereto, and the precipitated crystal was collected by filtration. The obtained crystal was dried under reduced pressure to obtain 730 mg (98%) of the title compound.

1H-NMR (CDCl$_3$, δ): 1.29-1.80 (6H, m), 1.91-2.12 (2H, m) 2.19-2.38 (2H, m), 2.91 (1H, br-s), 3.73-3.83 (1H, m), 3.89-4.02 (1H, m), 5.07-5.20 (1H, m), 6.26 (1H, s), 7.20-7.49 (8H, m), 7.83 (1H, s), 7.84-7.92 (2H, m)

Reference Example 218

N-[[1-[(2-Benzothienylcarbonyl)amino]cyclohexyl]carbonyl]-L-phenylglycinal

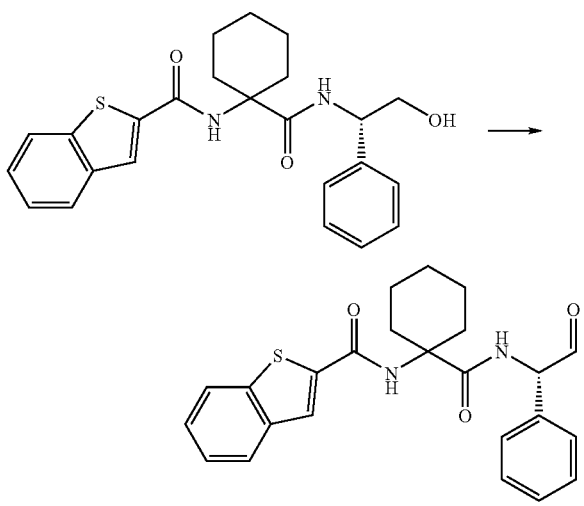

Under ice-cooling, 585 mg (1.38 mmol) of Des Martin periodinane was added to a solution of 100 mg (0.23 mmol) of N-[[1-[(2-benzothienylcarbonyl)amino]cyclohexyl]carbonyl]-L-phenylglycinol in 5 ml of methylene chloride, and the mixture was stirred for 1 hour. At the same temperature, 10 ml of ethyl acetate and 10 ml of saturated aqueous sodium bicarbonate solution were added to the reaction solution. Sodium thiosulfate was added to the reaction solution until the solution became transparent, and the mixture was extracted with ethyl acetate. The organic layer was washed with a saturated aqueous sodium bicarbonate solution and saturated brine, and it was dried with anhydrous sodium sulfate. The solvent was distilled off under reduced pressure, ethyl acetate was added to the obtained residue, and the mixture was stirred for 1 hour. The precipitated solid was collected by filtration to obtain 55 mg (57%) of the title compound.

1H-NMR (CDCl$_3$, δ): 1.21-1.80 (6H, m), 1.83-2.18 (2H, m), 2.23-2.40 (2H, m), 5.51 (1H, d, J=5 Hz), 6.10 (1H, s), 7.21-7.52 (7H, m), 7.83 (1H, s), 7.84-7.96 (2H, m), 8.18 (1H, d, J=5 Hz), 9.55 (1H, s)

Reference Example 219

N-[[1-[(2-Benzothienylcarbonyl)amino]cyclohexyl]carbonyl]-L-methioninol

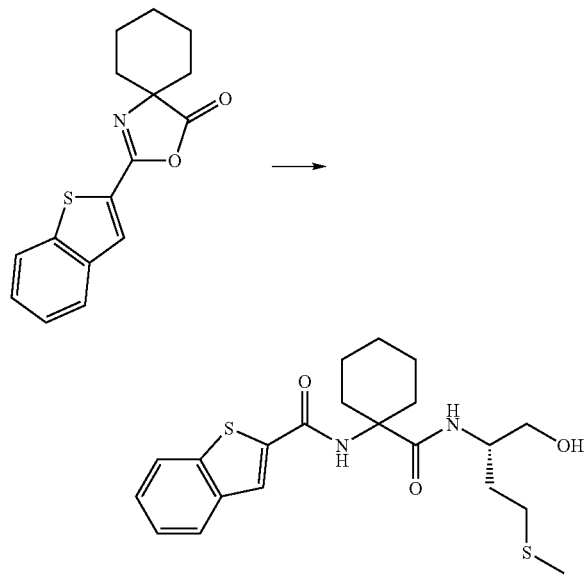

284 mg (2.1 mmol) of L-methioninol was added to a solution of 500 mg (1.75 mmol) of 2-(2-benzothienyl)-3-oxa-1-azaspiro[4.5]dec-1-en-4-one in 3 ml of N,N-dimethylformamide, and the mixture was stirred overnight. Water was slowly added, and the precipitated crystal was collected by filtration. The obtained crystal was dried under reduced pressure to obtain 722 mg (98%) of the title compound.

1H-NMR (CDCl$_3$, δ): 1.31-2.29 (16H, m), 2.45-2.63 (1H, m), 3.06 (1H, br-s), 3.45-3.61 (1H, m), 3.73-3.82 (1H, m), 3.97-4.05 (1H, m), 6.29 (1H, s), 6.85 (1H, br-s), 7.38-7.50 (2H, m), 7.82 (1H, s), 7.83-7.90 (2H, m)

Reference Example 220

N-[[1-[(2-Benzothienylcarbonyl)amino]cyclohexyl]carbonyl]-L-methioninal

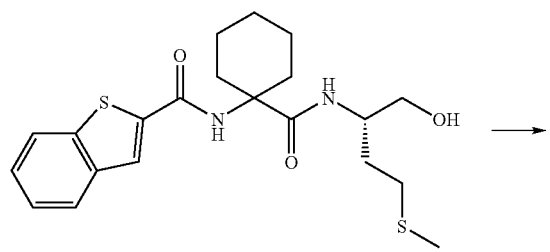

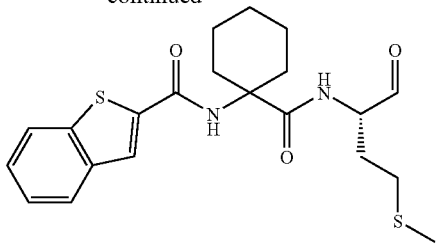

Under an argon gas atmosphere, 245 mg (1.9 mmol) of N,N-diisopropylethylamine was added dropwise to a solution of 297 mg (1.9 mmol) of sulfur trioxide-pyridine complex in 10 ml of dimethyl sulfoxide and 5 ml of anhydrous methylene chloride under ice-cooling, and the mixture was stirred for 15 minutes. Further, under ice-cooling, 100 mg (0.23 mmol) of N-[[1-[(2-benzothienylcarbonyl)amino]cyclohexyl]carbonyl]-L-methioninol was added to the reaction solution, and the mixture was stirred at the same temperature for 2 hours. The reaction solution was poured to ice-water and the mixture was extracted with ethyl acetate twice. The organic layer was washed with a 10% aqueous citric acid solution, a saturated aqueous sodium hydrogencarbonate solution and then saturated brine, and after it was dried with anhydrous magnesium sulfate, the solvent was distilled off under reduced pressure. 20 ml of diisopropyl ether was added to the residue, and the mixture was stirred at room temperature for 18 hours. The obtained crystal was collected by filtration to quantitatively obtain the title compound.

1H-NMR (CDCl$_3$, δ): 1.36-1.80 (9H, m), 1.91-2.09 (5H, m), 2.20-2.35 (2H, m), 2.50-2.63 (1H, m), 4.43-4.59 (1H, m), 6.19 (1H, s), 7.38-7.52 (2H, m), 7.67 (1H, d, J=7 Hz), 7.71 (1H, s), 7.80-7.89 (2H, m), 9.61 (1H, s)

Reference Example 221

N-[[1-[[[4-(4-Morpholinylmethyl)phenyl]carbonyl]amino]cyclohexyl]carbonyl]-L-phenylglycinol

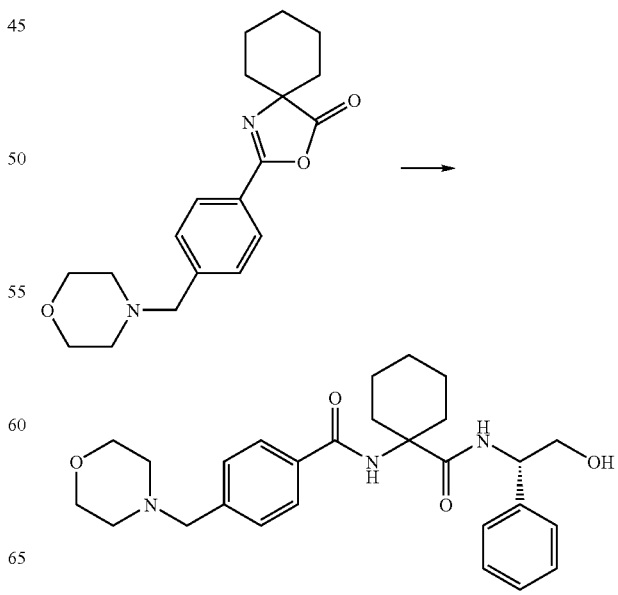

44 mg (0.32 mmol) of L-phenylglycinol was added to a solution of 100 mg (0.29 mmol) of 2-[4-(4-morpholinylmethyl)phenyl]-3-oxa-1-azaspiro[4.5]dec-1-en-4-one in 3 ml of N,N-dimethylformamide, and the mixture was stirred overnight. Water was slowly added, and the precipitated crystal was collected by filtration. The obtained crystal was dried under reduced pressure to obtain 46 mg (34%) of the title compound.

1H-NMR (CDCl$_3$, δ): 1.25-1.80 (6H, m), 1.92-2.10 (2H, m), 2.18-2.32 (2H, m), 2.37-2.50 (4H, m), 2.99 (1H, br-s), 3.55 (2H, s), 3.62-3.71 (4H, m), 3.71-3.83 (1H, m), 3.91-4.02 (1H, m), 5.05-5.18 (1H, m), 6.24 (1H, s), 7.17-7.37 (6H, m), 7.44 (2H, d, J=8 Hz), 7.73 (2H, d, J=8 Hz)

Reference Example 222

N-[[1-[[[4-(4-Morpholinylmethyl)phenyl]carbonyl]amino]cyclohexyl]carbonyl]-L-phenylglycinal

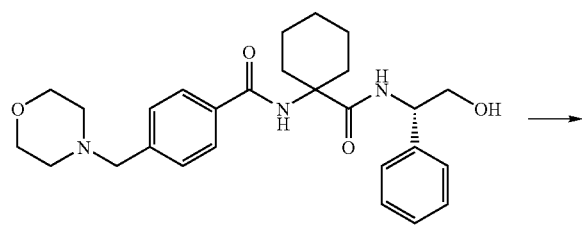

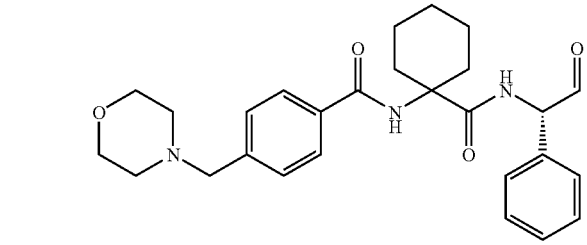

Under ice-cooling, 254 mg (0.6 mmol) of Des Martin periodinane was added to a solution of 46 mg (0.1 mmol) of N-[[1-[[[4-(4-morpholinylmethyl)phenyl]carbonyl]amino]cyclohexyl]carbonyl]-L-phenylglycinol in 5 ml of methylene chloride, and the mixture was stirred for 1 hour. At the same temperature, 10 ml of ethyl acetate and 10 ml of saturated aqueous sodium bicarbonate solution were added to the reaction solution. Sodium thiosulfate was added until the solution became transparent, and the mixture was extracted with ethyl acetate. The organic layer was washed with a saturated aqueous sodium bicarbonate solution and saturated brine, it was dried with anhydrous sodium sulfate. The solvent was distilled off under reduced pressure, ethyl acetate was added to the obtained residue, and the mixture was stirred for 1 hour. The precipitated solid was collected by filtration to obtain 30 mg (60%) of the title compound.

1H-NMR (CDCl$_3$, δ): 1.20-2.37 (10H, m), 2.37-2.60 (4H, m), 3.55 (2H, s), 3.61-3.80 (4H, m), 5.49 (1H, d, J=6 Hz), 6.16 (1H, s), 7.20-7.58 (7H, m), 7.75 (2H, d, J=8 Hz), 8.27 (1H, d, J=6 Hz), 9.54 (1H, s)

Reference Example 223

N-[[1-[[[4-(4-Morpholinylmethyl)phenyl]carbonyl]amino]cyclohexyl]carbonyl]-L-methioninol

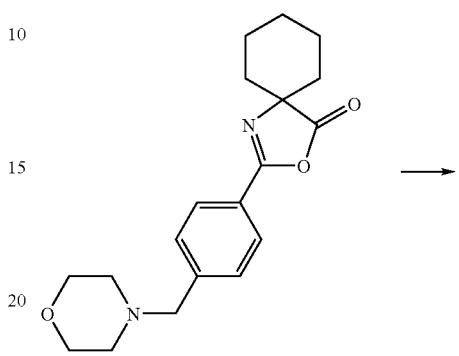

43 mg (0.32 mmol) of L-methioninol was added to a solution of 100 mg (0.29 mmol) of 2-[4-(4-morpholinylmethyl)phenyl]-3-oxa-1-azaspiro[4.5]dec-1-en-4-one in 3 ml of N,N-dimethylformamide, the mixture was stirred overnight. Water was slowly added, and the precipitated crystal was collected by filtration. The obtained crystal was dried under reduced pressure to obtain 65 mg (49%) of the title compound.

1H-NMR (CDCl$_3$, δ): 1.31-2.23 (15H, m), 2.35-2.45 (4H, m) 2.45-2.62 (2H, m), 3.12 (1H, br-s), 3.40-3.60 (3H, m), 3.60-3.82 (5H, m), 3.95-4.05 (1H, m), 6.28 (1H, s), 6.80 (1H, d, J=8 Hz), 7.43 (2H, d, J=8 Hz), 7.72 (2H, d, J=8 Hz)

Reference Example 224

N-[[1-[[[4-(4-Morpholinylmethyl)phenyl]carbonyl]amino]cyclohexyl]carbonyl]-L-methioninal

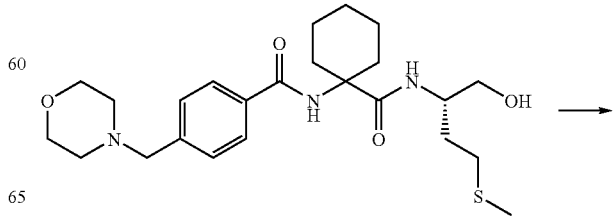

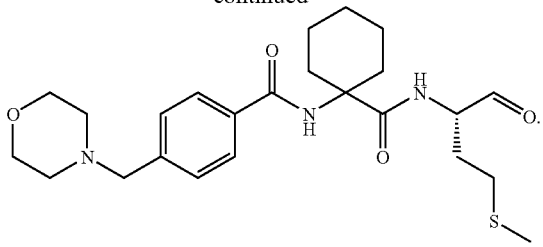

Under ice-cooling, 356 mg (0.84 mmol) of Des Martin periodinane was added to a solution of 65 mg (0.14 mmol) of N-[[1-[[[4-(4-morpholinylmethyl)phenyl]carbonyl]amino]cyclohexyl]carbonyl]-L-methioninol in 5 ml of methylene chloride, and the mixture was stirred for 1 hour. At the same temperature, 10 ml of ethyl acetate and 10 ml of a saturated aqueous sodium bicarbonate solution were added to the reaction solution. Sodium thiosulfate was added to the mixture until the solution became transparent, and the mixture was extracted with ethyl acetate. The organic layer was washed with a saturated aqueous sodium bicarbonate solution and saturated brine, and it was dried with anhydrous sodium sulfate. The solvent was distilled off under reduced pressure to obtain 55 mg (85%) of the title compound.

1H-NMR (CDCl$_3$, δ): 1.20-2.80 (21H, m), 3.56 (2H, s), 3.60-3.81 (4H, m), 4.40-4.58 (1H, m), 5.12 (1H, d, J=7 Hz), 6.18 (1H, s), 7.44 (2H, d, J=8 Hz), 7.73 (2H, d, J=8 Hz), 9.59 (1H, s)

Reference Example 225

N-[[1-[[[4-[2-(4-Methyl-1-piperazinyl)-4-thiazolyl]phenyl]carbonyl]amino]cyclohexyl]carbonyl]-L-methioninol

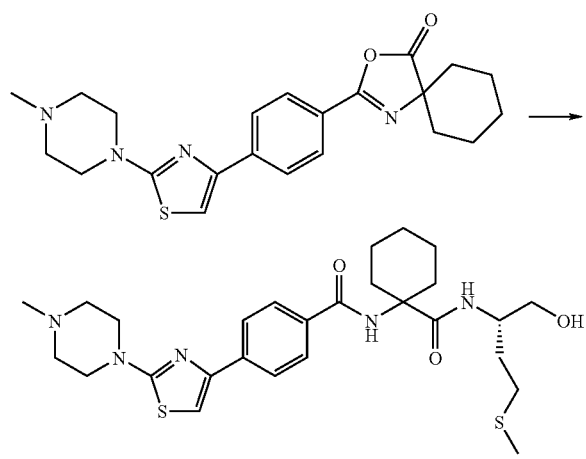

100 mg (0.74 mmol) of L-methioninol was added to a solution of 250 mg (0.68 mmol) of 2-[4-[2-(4-methyl-1-piperazinyl)-4-thiazolyl]phenyl]-3-oxa-1-azaspiro[4.5]dec-1-en-4-one in 20 ml of dimethylformamide. After the mixture was stirred at 80° C. for 15 hours, the reaction solution was concentrated under reduced pressure, ethyl acetate was added thereto, and the mixture was successively washed with water, a saturated aqueous sodium hydrogencarbonate solution and saturated brine, followed by drying with anhydrous sodium sulfate. After the solvent was distilled off under reduced pressure, and diisopropyl ether was added to the residue to wash the crystal to obtain 319 mg (86%) of the title compound.

1H-NMR (CDCl$_3$, δ): 1.37-1.61 (3H, m), 1.65-1.80 (3H, m) 1.80-1.86 (2H, m), 1.96-2.05 (2H, m), 2.07 (3H, s), 2.15-2.29 (2H, m), 2.37 (3H, s), 2.51-2.60 (2H, m), 2.56 (4H, t, J=5 Hz), 3.14-3.21 (1H, m), 3.50-3.56 (1H, m), 3.59 (4H, t, J=5 Hz), 3.77-3.84 (1H, m), 4.00-4.06 (1H, m), 6.30 (1H, br-s), 6.85 (1H, d, J=7 Hz), 6.90 (1H, s), 7.76 (2H, dd, J=8 Hz, 2 Hz), 7.92 (2H, dd, J=8 Hz, 2 Hz)

Reference Example 226

N-[[1-[[[4-[2-(4-Methyl-1-piperazinyl)-4-thiazolyl]phenyl]carbonyl]amino]cyclohexyl]carbonyl]-L-methioninal

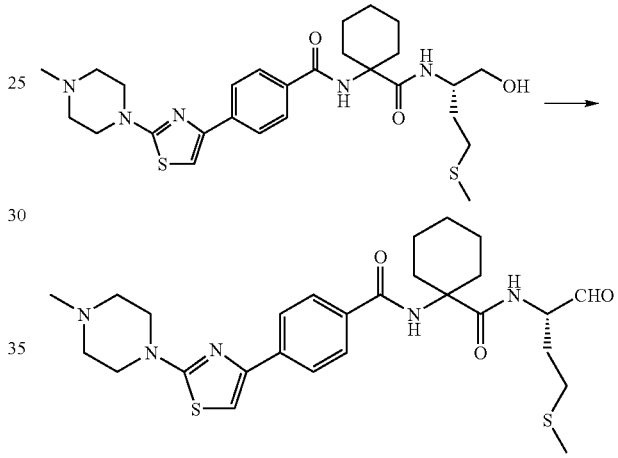

Under an argon gas atmosphere, 453 mg (3.5 mmol) of N,N-diisopropylethylamine was added dropwise to a solution of 658 mg (3.5 mmol) of sulfur trioxide-pyridine complex in 10 ml of anhydrous dimethyl sulfoxide and in 5 ml of anhydrous methylene chloride under ice-cooling, and the mixture was stirred for 15 minutes. Further, under ice-cooling, a solution of 319 mg (0.58 mmol) of N-[[1-[[[4-[2-(4-methyl-1-piperazinyl)-4-thiazolyl]phenyl]carbonyl]amino]cyclohexyl]carbonyl]-L-methioninol in 3 ml of anhydrous dimethyl sulfoxide was added to the reaction solution, and the mixture was stirred at the same temperature for 2 hours. The reaction solution was poured to ice-water and extracted with ethyl acetate twice. The organic layer was washed with a saturated aqueous sodium hydrogencarbonate solution and then saturated brine, after it was dried with anhydrous magnesium sulfate, the solvent was distilled off under reduced pressure. 20 ml of diisopropyl ether was added to the residue, and the mixture was stirred at room temperature for 18 hours. The obtained crystal was collected by filtration to obtain 203 mg (64%) of the title compound.

1H-NMR (CDCl$_3$, δ): 1.36-1.78 (6H, m), 1.98-2.08 (3H, m), 2.02 (3H, s), 2.21-2.57 (3H, m), 2.38 (3H, s), 2.55 (4H, t, J=5 Hz), 2.56 (2H, m), 3.61 (4H, t, J=5 Hz), 4.49 (1H, dt, J=8 Hz, 5 Hz), 6.17 (1H, br-s), 6.90 (1H, s), 7.78 (2H, d, J=8 Hz), 7.84 (1H, d, J=8 Hz), 7.92 (2H, d, J=8 Hz), 9.62 (1H, s)

Reference Example 227

N-[[1-[[[4-[2-(4-Methyl-1-piperazinyl)-4-thiazolyl]phenyl]carbonyl]amino]cyclohexyl]carbonyl]-L-phenylglycinol

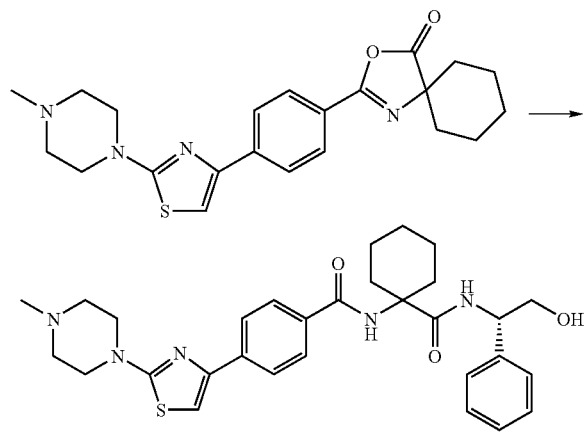

96 mg (0.7 mmol) of L-phenylglycinol was used instead of L-methioninol in the process according to Reference Example 225 to obtain 220 mg (57%) of the title compound.

1H-NMR (CDCl$_3$, δ): 1.34-1.43 (1H, m), 1.42-1.61 (2H, m), 1.61-1.79 (3H, m), 1.96-2.10 (2H, m), 2.20-2.29 (1H, m), 2.30-2.36 (1H, m), 2.37 (3H, s), 2.56 (4H, t, J=5 Hz), 3.01-3.08 (1H, m), 3.60 (4H, t, J=5 Hz), 3.76-3.85 (1H, m), 3.92-4.01 (1H, m), 5.09-5.15 (1H, m), 6.27 (1H, br-s), 6.90 (1H, s), 7.24-7.30 (3H, m), 7.31-7.36 (2H, m), 7.37 (1H, d, J=7 Hz), 7.78 (2H, d, J=8 Hz), 7.92 (2H, d, J=8 Hz)

Reference Example 228

N-[[1-[[[4-[2-(4-Methyl-1-piperazinyl)-4-thiazolyl]phenyl]carbonyl]amino]cyclohexyl]carbonyl]-L-phenylglycinal

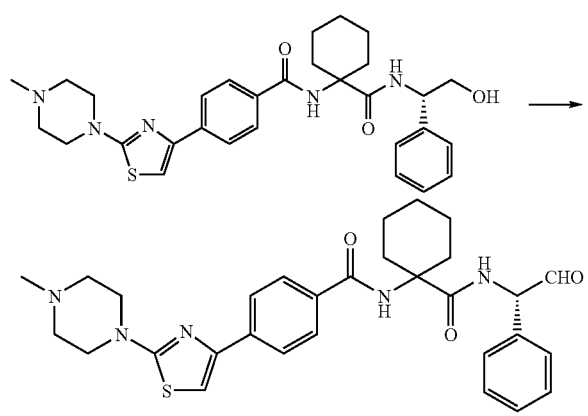

Under an argon gas atmosphere, 310 mg (2.4 mmol) of N,N-diisopropylethylamine was added dropwise to a solution of 382 mg (2.4 mmol) of sulfur trioxide-pyridine complex in 10 ml of anhydrous dimethyl sulfoxide and in 5 ml of anhydrous methylene chloride under ice-cooling, and the mixture was stirred for 15 minutes. Further, under ice-cooling, a solution of 220 mg (0.4 mmol) of N-[[1-[[[4-[2-(4-methyl-1-piperazinyl)-4-thiazolyl]phenyl]carbonyl]amino]cyclohexyl]carbonyl]-L-phenylglycinol in 3 ml of anhydrous dimethyl sulfoxide was added to the reaction solution, and the mixture was stirred at the same temperature for 30 minutes. After the completion of the reaction, under ice-cooling, 200 ml of water was added to the reaction solution, thereafter, the mixture was stirred at room temperature for 3 hours. The precipitated crystal was washed with diethyl ether again to obtain 67 mg (31%) of the title compound.

1H-NMR (CDCl$_3$, δ): 1.35-1.82 (6H, m), 2.25-2.39 (2H, m), 2.50-2.59 (1H, m), 2.62 (3H, s), 2.75 (4H, t, J=5 Hz), 3.06-3.15 (1H, m), 3.72 (4H, t, J=5 Hz), 5.51 (1H, d, J=6 Hz), 6.16 (1H, br-s), 6.91 (1H, s), 7.21-7.38 (5H, m), 7.38 (1H, d, J=6 Hz), 7.79 (2H, d, J=8 Hz), 7.92 (2H, d, J=8 Hz), 9.56 (1H, s)

Reference Example 229

N-[[1-[[[4-[2-[4-(4-Morpholinyl)-1-piperazinyl]-4-thiazolyl]phenyl]carbonyl]amino]cyclohexyl]carbonyl]-L-methioninol

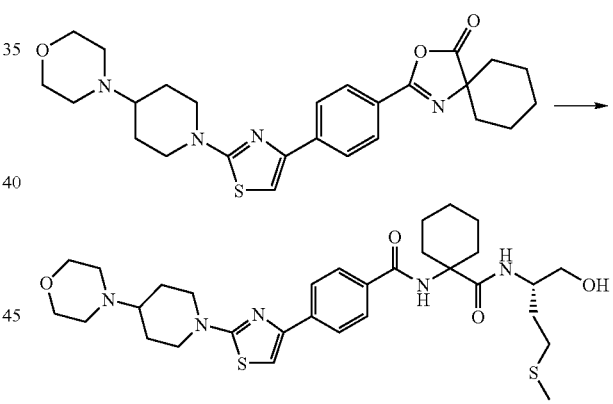

481 mg (1.00 mmol) of 2-[4-[2-[4-(4-morpholinyl)-1-piperidinyl]-4-thiazolyl]phenyl]-3-oxa-1-azaspiro[4.5]dec-1-en-4-one was used instead of 2-[4-[2-(4-methyl-1-piperazinyl)-4-thiazolyl]phenyl]-3-oxa-1-azaspiro[4.5]dec-1-en-4-one in the process according to Reference Example 225 to obtain 501 mg (81%) of the title compound.

1H-NMR (CDCl$_3$, δ): 1.35-1.80 (7H, m), 1.81-1.89 (2H, m), 1.92-2.09 (4H, m), 2.07 (3H, s), 2.15-2.23 (3H, m), 2.41-2.49 (1H, m), 2.54 (2H, t, J=6 Hz), 2.57 (4H, t, J=5 Hz), 3.08 (2H, dd, J=13 Hz, 13 Hz), 3.18 (1H, t, J=7 Hz), 3.50-3.58 (1H, m), 3.74 (4H, t, J=5 Hz), 3.77-3.85 (1H, m), 4.00-4.08 (1H, m), 4.12 (2H, d, J=13 Hz), 6.30 (1H, br-s), 6.83 (1H, d, J=8 Hz), 6.88 (1H, s), 7.77 (2H, d, J=8 Hz), 7.96 (2H, d, J=8 Hz)

Reference Example 230

N-[[1-[[[4-[2-[4-(4-Morpholinyl)-1-piperazinyl]-4-thiazolyl]phenyl]carbonyl]amino]cyclohexyl]carbonyl]-L-methioninal

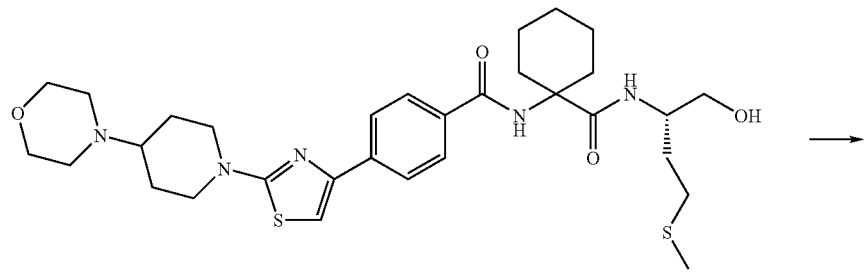

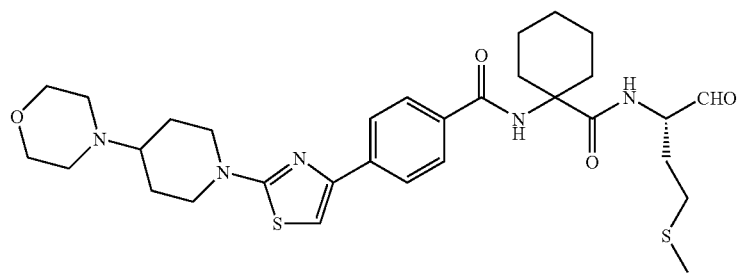

501 mg (0.81 mmol) of N-[[1-[[[4-[2-[(4-morpholinyl)-1-piperazinyl]-4-thiazolyl]phenyl]carbonyl]amino]cyclohexyl]carbonyl]-L-methioninol was used instead of N-[[1-[[[4-[2-(4-methyl-1-piperazinyl)-4-thiazolyl]phenyl]carbonyl]amino]cyclohexyl]carbonyl]-L-methioninol in the process according to Reference Example 226 to obtain 100 mg (20%) of the title compound.

1H-NMR (CDCl$_3$, δ): 1.36-1.56 (3H, m), 1.61-1.79 (6H, m), 1.93-2.07 (5H, m), 2.02 (3H, s), 2.04-2.15 (2H, m), 2.40 (2.49 (1H, m), 2.45 (2H, t, J=6 Hz), 2.58 (4H, t, J=5 Hz), 3.08 (2H, dd, J=12 Hz, 12 Hz), 3.74 (4H, t, J=5 Hz), 4.12 (2H, d, J=12 Hz), 4.49 (1H, dd, J=8 Hz, 5 Hz), 6.15 (1H, br-s), 6.88 (1H, s), 7.78 (2H, d J=8 Hz), 7.85 (1H, d, J=8 Hz), 7.93 (2H, d, J=8 Hz), 9.62 (1H, s)

Reference Example 231

N-[[1-[[[4-[2-[4-(4-Morpholinyl)-1-piperazinyl]-4-thiazolyl]phenyl]carbonyl]amino]cyclohexyl]carbonyl]-L-phenylglycinol

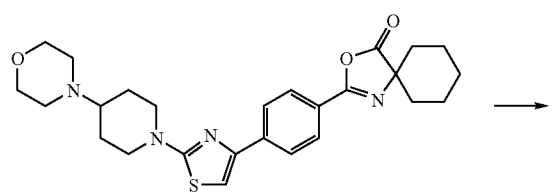

-continued

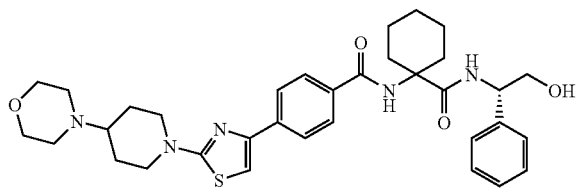

481 mg (1.00 mmol) of 2-[4-[2-[4-(4-morpholinyl)-1-piperidinyl]-4-thiazolyl]phenyl]-3-oxa-1-azaspiro[4.5]dec-1-en-4-one was used instead of 2-[4-[2-(4-methyl-1-piperazinyl)-4-thiazolyl]phenyl]-3-oxa-1-azaspiro[4.5]dec-1-en-4-one, and 137 mg (1.00 mmol) of L-phenylglycinol was used instead of L-methioninol in the process according to Reference Example 225 to obtain 324 mg (52%) of the title compound.

1H-NMR (CDCl$_3$, δ): 1.32-1.78 (9H, m), 1.95-2.11 (4H, m), 2.20-2.27 (1H, m), 2.29-2.36 (1H, m), 2.40-2.49 (1H, m) 2.59 (4H, t, J=5 Hz), 3.09 (2H, dd, J=13 Hz, 13 Hz), 3.74 (4H, t, J=5 Hz), 3.78-3.82 (1H, m), 3.96-4.00 (1H, m), 4.12 (2H, d, J=13 Hz), 5.09-5.14 (1H, m), 6.28 (1H, br-s), 6.88 (1H, s), 7.25-7.30 (1H, m) 7.30-7.35 (4H, m), 7.7-8 (1H, d, J=8 Hz), 7.78 (2H, dd, J=7 Hz, 2 Hz), 7.92 (2H, dd, J=7 Hz, 2 Hz)

Reference Example 232

N-[[1-[[[4-[2-[4-(4-Morpholinyl)-1-piperazinyl]-4-thiazolyl]phenyl]carbonyl]amino]cyclohexyl]carbonyl]-L-phenylglycinal

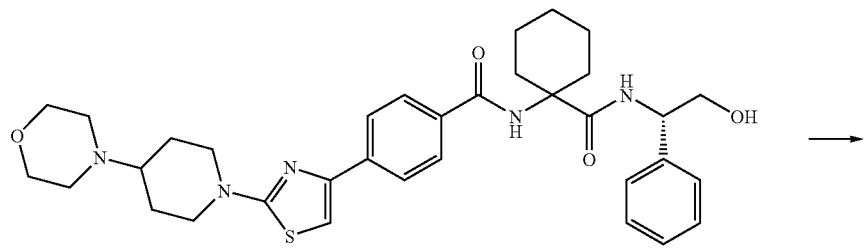

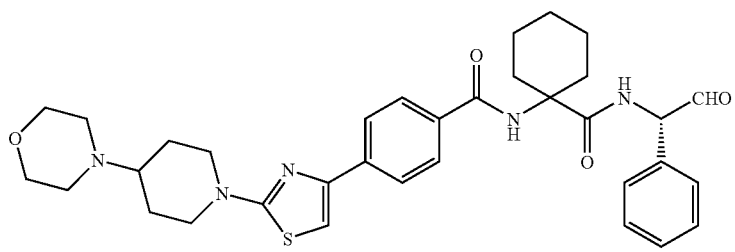

324 mg (0.52 mmol) of N-[[1-[[[4-[2-[4-(4-morpholinyl)-1-piperazinyl]-4-thiazolyl]phenyl]carbonyl]amino]cyclohexyl]carbonyl]-L-phenylglycinol was used instead of N-[[1-[[[4-[2-(4-methyl-1-piperazinyl)-4-thiazolyl]phenyl]carbonyl]amino]cyclohexyl]carbonyl]-L-methioninol in the process according to Reference Example 226 to obtain 128 mg (40%) of the title compound.

1H-NMR (CDCl$_3$, δ): 1.30-1.85 (8H, m), 1.92-2.13 (4H, m), 2.25-2.50 (3H, m), 2.59 (4H, t, J=5 Hz), 3.08 (2H, dd, J=12 Hz, 12 Hz), 3.74 (4H, t, J=5 Hz), 4.13 (2H, d, J=12 Hz), 5.51 (1H, d, J=6 Hz), 6.14 (1H, br-s), 6.88 (1H, s), 7.30-7.41 (5H, m), 7.79 (2H, d, J=8 Hz), 7.93 (2H, d, J=8 Hz), 8.34 (1H, d, J=6 Hz), 9.56 (1H, s)

Reference Example 233

N-[[1-[(2-Benzothienylcarbonyl)amino]cyclohexyl]carbonyl]-L-phenylglycine methyl ester

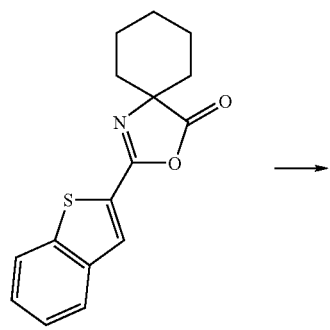

-continued

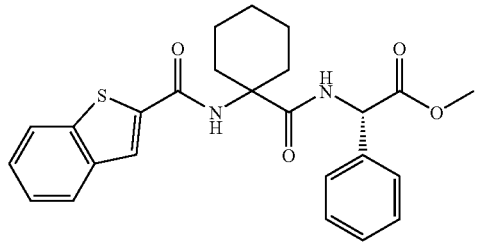

6179 mg (5.3 mmol) of diisopropylethylamine was added to a suspension of 423 mg (2 mmol) of L-phenylglycine methyl ester hydrochloride and 500 mg (1.75 mmol) of 2-(2-benzothienyl)-3-oxa-1-azaspiro[4.5]dec-1-en-4-one in 10 ml of toluene, and the mixture was heated under reflux overnight. After the solvent was distilled off under reduced pressure, ethyl acetate was added thereto, and the mixture was washed with a 10% aqueous potassium hydrogensulfate solution and saturated brine, followed by drying with anhydrous sodium sulfate. After the solvent was distilled off under reduced pressure, diethyl ether was added thereto, and the mixture was stirred overnight. The precipitated solid was collected by filtration and dried under reduced pressure to obtain 670 mg (91%) of the title compound.

1H-NMR (CDCl$_3$, δ): 1.25-1.80 (6H, m), 1.90-2.08 (2H, m) 2.23-2.40 (2H, m), 3.69 (3H, s), 5.53 (1H, d, J=7 Hz), 6.10 (1H, s), 7.23-7.49 (7H, m), 7.81 (1H, s), 7.83-7.91 (2H, m), 8.13 (1H, d, J=7 Hz)

Reference Example 234

N-[[1-[(2-Benzothienylcarbonyl)amino]cyclohexyl]carbonyl]-L-methionine methyl ester

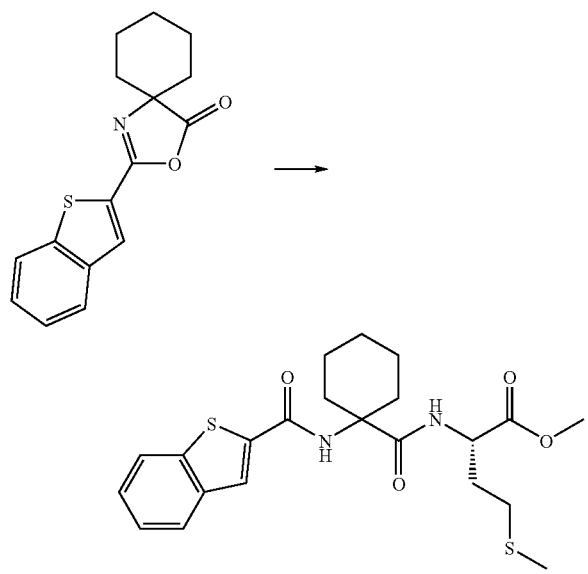

679 mg (5.3 mmol) of diisopropylethylamine was added to a suspension of 419 mg (2 mmol) of L-methionine methyl ester hydrochloride and 500 mg (1.75 mmol) of 2-(2-benzothienyl)-3-oxa-1-azaspiro[4.5]dec-1-en-4-one in 10 ml of toluene, and the mixture was heated under reflux overnight. After the solvent was distilled off under reduced pressure, ethyl acetate was added thereto, and the mixture was washed with a 10% aqueous potassium hydrogensulfate solution and saturated brine, and it was dried with anhydrous sodium sulfate. After the solvent was distilled off under reduced pressure, diethyl ether was added thereto, and the mixture was stirred overnight. The precipitated solid was collected by filtration and dried under reduced pressure to obtain 678 mg (86%) of the title compound.

1H-NMR (CDCl$_3$, δ): 1.30-1.81 (8H, m), 1.95-2.09 (5H, m), 2.11-2.39 (2H, m), 2.43-2.61 (2H, m), 3.71 (3H, s), 4.61-4.73 (1H, m), 6.16 (1H, s), 7.38-7.45 (2H, m), 7.59 (1H, d, J=8 Hz), 7.80 (1H, s), 7.82-7.90 (2H, m)

Reference Example 235

N-[[1-[[[4-[(Dimethylamino)methyl]phenyl]carbonyl]amino]cyclohexyl]carbonyl]-L-phenylglycine methyl ester

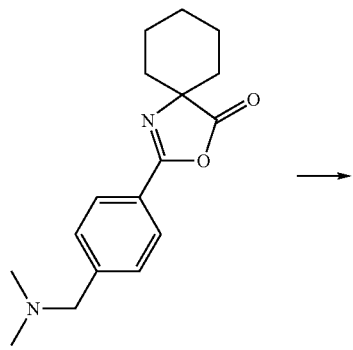

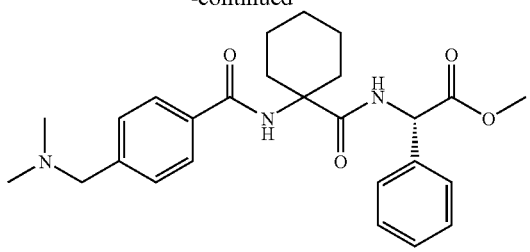

129 mg (1 mmol) of diisopropylethylamine was added to a suspension of 85 mg (0.42 mmol) of L-phenylglycine methyl ester hydrochloride and 100 mg (0.35 mmol) of 2-[4-[(dimethylamino)methyl]phenyl]-3-oxa-1-azaspiro[4.5]dec-1-en-4-one in 3 ml of toluene, and the mixture was heated under reflux overnight. After the solvent was distilled off under reduced pressure, ethyl acetate was added thereto, and the mixture was washed with saturated brine, followed by drying with anhydrous sodium sulfate. After the solvent was distilled off under reduced pressure, diethyl ether was added thereto, and the mixture was stirred overnight. The precipitated solid was collected by filtration and dried under reduced pressure to obtain 62 mg (39%) of the title compound.

1H-NMR (CDCl$_3$, δ): 1.27-1.80 (7H, m), 1.83-2.09 (2H, m), 2.18-2.39 (1H, m), 2.25 (6H, s), 3.47 (2H, s), 3.69 (3H, s), 5.53 (1H, d, J=7 Hz), 6.07 (1H, s), 7.10-7.25 (7H, m), 7.73 (2H, d, J=8 Hz), 8.28 (1H, d, J=7 Hz)

Reference Example 236

N-[[1-[[[4-[(Dimethylamino)methyl]phenyl]carbonyl]amino]cyclohexyl]carbonyl]-L-methionine methyl ester

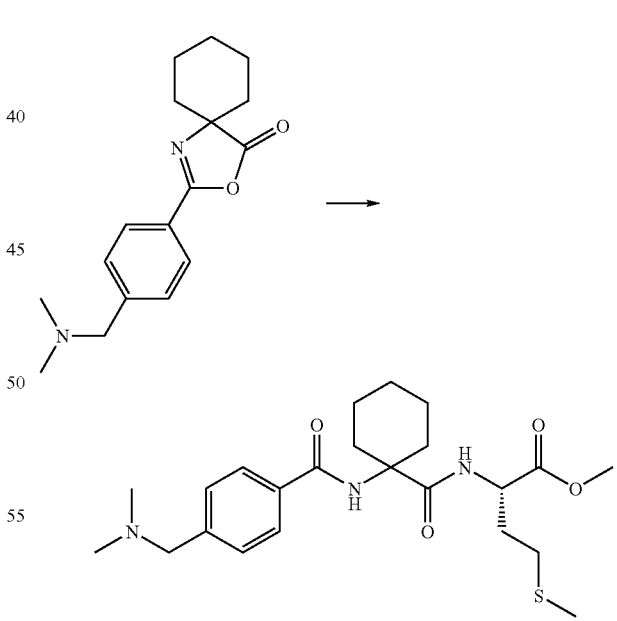

129 mg (1 mmol) of diisopropylethylamine was added to a suspension of 84 mg (0.42 mmol) of L-methionine methyl ester hydrochloride and 100 mg (0.35 mmol) of 2-[4-[(dimethylamino)methyl]phenyl]-3-oxa-1-azaspiro[4.5]dec-1-en-4-one in 3 ml of toluene, and the mixture was heated under reflux overnight. After the solvent was distilled off under reduced pressure, ethyl acetate was added thereto, and the mixture was washed with saturated brine, followed by drying with sodium sulfate. After the solvent was distilled off under reduced pressure, diethyl ether was added thereto, and the mixture was stirred overnight. The precipitated solid was collected by filtration and dried under reduced pressure to obtain 93 mg (59%) of the title compound.

1H-NMR (CDCl$_3$, δ): 1.29-1.58 (4H, m), 1.58-1.79 (4H, m), 1.92-2.35 (7H, m), 2.25 (6H, s), 2.43-2.59 (2H, m), 3.47 (2H, s), 3.71 (3H, s), 4.61-4.72 (1H, m), 6.10 (1H, s), 7.41 (2H, d, J=8 Hz), 7.69 (1H, d, J=8 Hz), 7.73 (2H, d, J=8 Hz)

Reference Example 237

N-[[1-[[[4-[2-(4-Methyl-1-piperazinyl)-4-thiazolyl]phenyl]carbonyl]amino]cyclohexyl]carbonyl]-L-methionine methyl ester

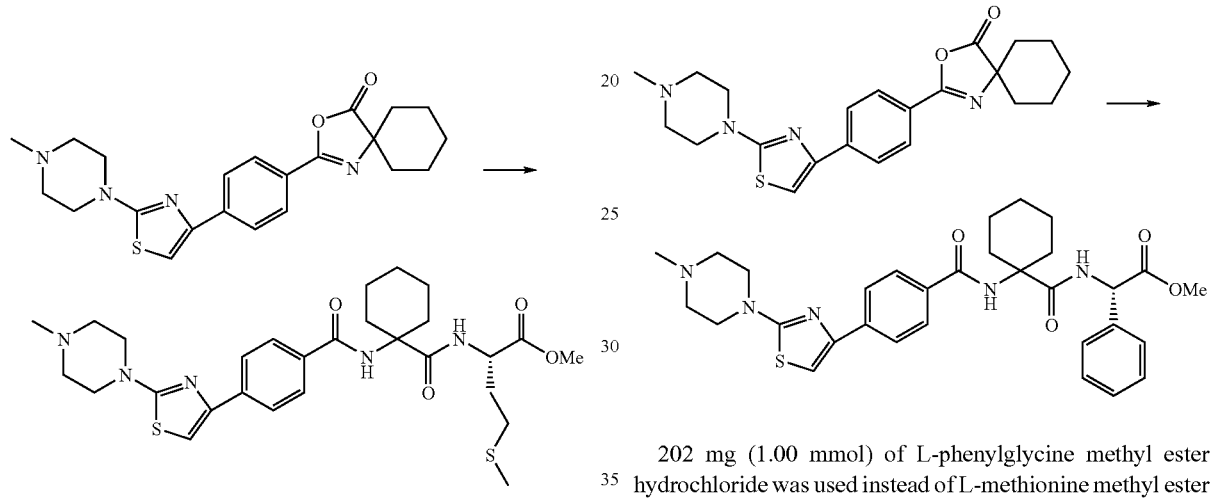

200 mg (1.00 mmol) of L-methionine methyl ester hydrochloride was added to a solution of 411 mg (1.00 mmol) of 2-[4-[2-(4-methyl-1-piperazinyl)-4-thiazolyl]phenyl]-3-oxa-1-azaspiro[4.5]dec-1-en-4-one and 258 mg (2.00 mmol) of N,N-diisopropylethylamine in 20 ml of dimethylformamide. After the mixture was stirred at 80° C. for 15 hours, the reaction solution was concentrated under reduced pressure, ethyl acetate was added thereto, and the mixture was successively washed with water, a saturated aqueous sodium hydrogencarbonate solution and saturated brine, followed by drying with anhydrous sodium sulfate. After the solvent was distilled off under reduced pressure, the residue was purified by silica gel chromatography to obtain 191 mg (33%) of the title compound.

1H-NMR (CDCl$_3$, δ): 1.33-1.60 (3H, m), 1.63-1.78 (3H, m), 1.97-2.05 (3H, m), 2.05 (3H, s), 2.15-2.35 (3H, m), 2.37 (3H, s), 2.50-2.58 (2H, m), 2.56 (4H, t, J=5 Hz), 3.59 (4H, t, J=5 Hz), 3.71 (3H, s), 4.69 (1H, dt, J=7 Hz, 5 Hz), 6.13 (1H, br-s), 6.90 (1H, s), 7.72 (1H, d, J=7 Hz), 7.78 (2H, dd, J=8 Hz, 2 Hz), 7.92 (2H, dd, J=8 Hz, 2 Hz)

Reference Example 238

N-[[1-[[[4-[2-(4-Methyl-1-piperazinyl)-4-thiazolyl]phenyl]carbonyl]amino]cyclohexyl]carbonyl]-L-phenylglycine methyl ester

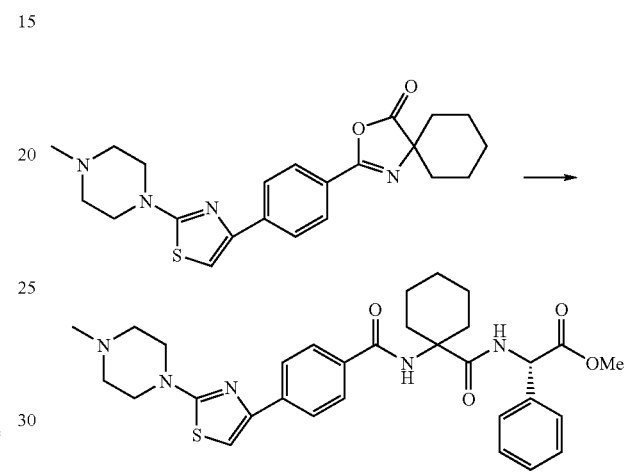

202 mg (1.00 mmol) of L-phenylglycine methyl ester hydrochloride was used instead of L-methionine methyl ester hydrochloride in the process according to Reference Example 237 to obtain 156 mg (24%) of the title compound.

1H-NMR (CDCl$_3$, δ): 1.25-1.41 (1H, m), 1.41-1.55 (2H, m), 1.60-1.76 (3H, m), 1.94-2.05 (2H, m), 2.25-2.40 (2H, m), 2.37 (3H, s), 2.56 (4H, t, J=5 Hz), 3.59 (4H, t, J=5 Hz), 3.69 (3H, s), 5.54 (1H, d, J=7 Hz), 6.08 (1H, br-s), 6.89 (1H, s), 7.26-7.35 (3H, m), 7.38-7.41 (2H, m), 7.78 (2H, d, J=8 Hz), 7.92 (2H, d, J=8 Hz), 8.29 (1H, d, J=7 Hz)

Reference Example 239

N-[[1-[[[4-[2-[4-(4-Morpholinyl)-1-piperidinyl]-4-thiazolyl]phenyl]carbonyl]amino]cyclohexyl]carbonyl]-L-methionine methyl ester

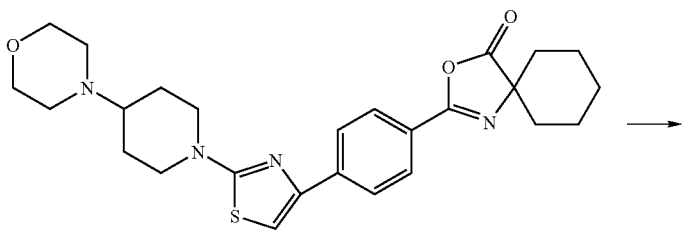

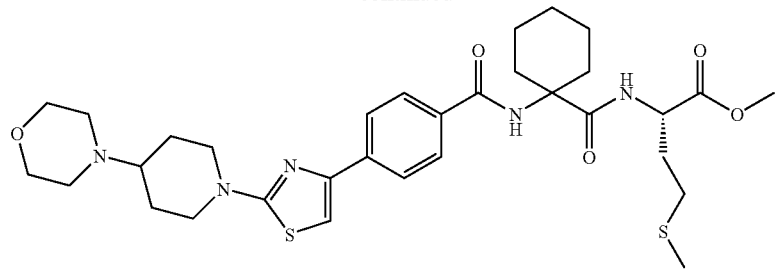

481 mg (1.00 mmol) of 2-[4-[2-[4-(4-morpholinyl)-1-piperidinyl]-4-thiazolyl]phenyl]-3-oxa-1-azaspiro[4.5]dec-1-en-4-one was used instead of 2-[4-[2-(4-methyl-1-piperazinyl)-4-thiazolyl]phenyl]-3-oxa-1-azaspiro[4.5]dec-1-en-4-one in the process according to Reference Example 237 to obtain 439 mg (68%) of the title compound.

1H-NMR (CDCl$_3$, δ): 1.31-1.79 (8H, m), 1.92-2.05 (5H, m), 2.05 (3H, s), 2.15-2.34 (3H, m), 2.40-2.49 (1H, m), 2.53 (2H, t, J=7 Hz), 2.59 (4H, t, J=5 Hz), 3.08 (2H, dd, J=12 Hz, 12 Hz), 3.71 (3H, s), 3.74 (4H, t, J=5 Hz), 4.13 (2H, d, J=12 Hz), 4.69 (1H, dt, J=8 Hz, 5 Hz), 6.12 (1H, br-s), 6.88 (1H, s), 7.72 (1H, d, J=8 Hz), 7.78 (2H, d, J=8 Hz), 7.92 (2H, d, J=8 Hz)

Reference Example 240

N-[[1-[[[4-[2-[4-(4-Morpholinyl)-1-piperidinyl]-4-thiazolyl]phenyl]carbonyl]amino]cyclohexyl]carbonyl]-L-phenylglycine methyl ester

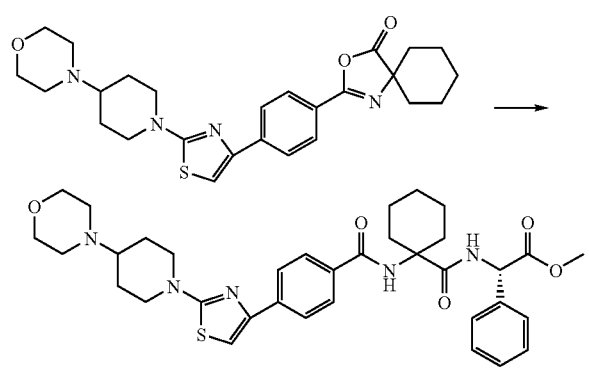

481 mg (1.00 mmol) of 2-[4-[2-[4-(4-morpholinyl)-1-piperidinyl]-4-thiazolyl]phenyl]-3-oxa-1-azaspiro[4.5]dec-1-en-4-one was used instead of 2-[4-[2-(4-methyl-1-piperazinyl)-4-thiazolyl]phenyl]-3-oxa-1-azaspiro[4.5]dec-1-en-4-one, and 202 mg (1.00 mmol) of L-phenylglycine methyl ester hydrochloride was used instead of L-methionine methyl ester hydrochloride in the process according to Reference Example 237 to obtain 156 mg (24%) of the title compound.

1H-NMR (CDCl$_3$, δ): 1.30-1.41 (1H, m), 1.42-1.60 (3H, m) 1.61-1.77 (4H, m), 1.92-2.08 (4H, m), 2.25-2.37 (2H, m), 2.40-2.49 (1H, m), 2.59 (4H, t, J=5 Hz), 3.08 (2H, dd, J=12 Hz, 12 Hz), 3.69 (3H, s), 3.74 (4H, t, J=5 Hz), 4.12 (2H, d, J=12H), 5.54 (1H, d, J=7 Hz), 6.07 (1H, br-s), 6.87 (1H, s), 7.26-7.36 (3H, m), 7.37-7.42 (2H, m), 7.77 (2H, d, J=8 Hz), 7.91 (2H, d, J=8 Hz), 8.30 (1H, d, J=8 Hz)

Example 2

N-[[1-[(2-Benzothienylcarbonyl)amino]cyclohexyl]carbonyl]-L-phenylglycine

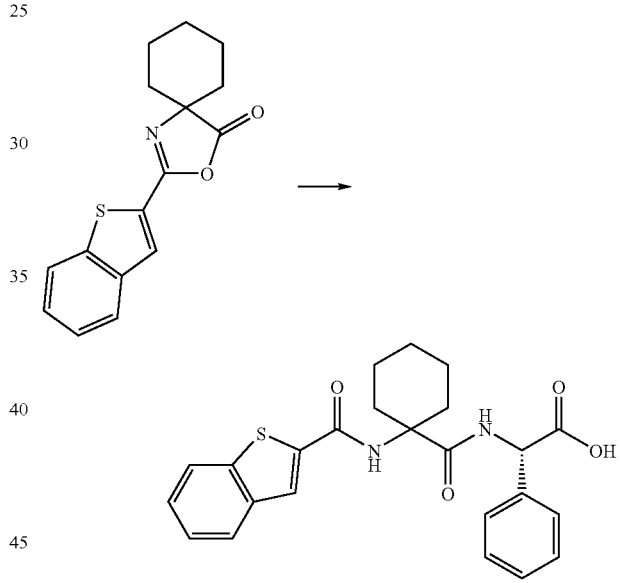

10 ml of N-methylmorpholine was added to 530 mg (3.5 mmol) of L-phenylglycine and 500 mg (1.75 mmol) of 2-(2-benzothienyl)-3-oxa-1-azaspiro[4.5]dec-1-en-4-one, and the mixture was stirred and heated under reflux overnight. The reaction solution was distilled off under reduced pressure, a 10% aqueous potassium hydrogensulfate solution was added thereto, and the mixture was extracted with methylene chloride three times. The obtained organic layer was dried with anhydrous sodium sulfate, and the solvent was distilled off under reduced pressure. Ethyl acetate was added to the obtained residue, and the mixture was stirred overnight. The precipitated solid was collected by filtration and dried under reduced pressure to obtain 259 mg (34%) of the title compound.

1H-NMR (CDCl$_3$, δ): 1.25-1.80 (6H, m), 1.83-2.03 (2H, m), 2.12-2.40 (2H, m), 4.47 (1H, d, J=5 Hz), 6.11 (1H, s), 7.18-7.55 (8H, m), 7.79 (1H, s), 7.80-7.91 (2H, m)

Example 3

N-[[1-[(2-Benzothienylcarbonyl)amino]cyclohexyl]carbonyl]-L-methionine

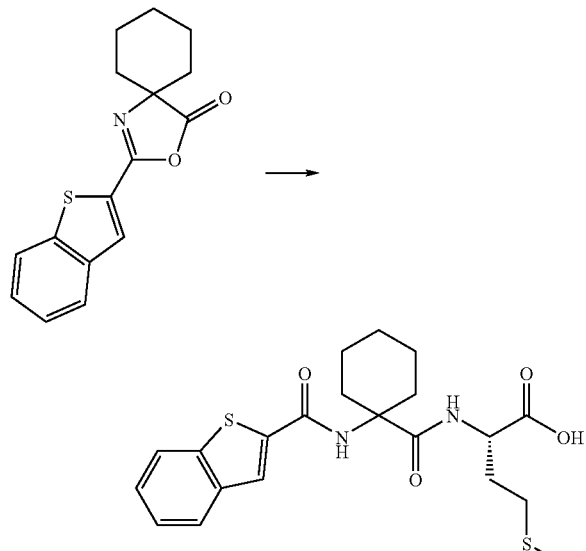

10 ml of N-methylmorpholine was added to 522 mg (3.5 mmol) of L-methionine and 500 mg (1.75 mmol) of 2-(2-benzothienyl)-3-oxa-1-azaspiro[4.5]dec-1-en-4-one, and the mixture was stirred and heated under reflux overnight. The reaction solution was distilled off under reduced pressure, a 10% aqueous potassium hydrogensulfate solution was added thereto, and the mixture was extracted with methylene chloride three times. The obtained organic layer was dried with anhydrous sodium sulfate, and the solvent was distilled off under reduced pressure. Ethyl acetate was added to the obtained residue, and the mixture was stirred overnight. The precipitated solid was collected by filtration and dried under reduced pressure to obtain 170 mg (22%) of the title compound.

1H-NMR (CDCl$_3$, δ): 1.21-2.99 (17H, m), 4.51-4.68 (1H, m) 6.42 (1H, s), 6.75-6.85 (1H, m), 7.32-7.50 (2H, m), 7.74-7.98 (3H, m)

Example 4

N-[[[1-[(1H-Pyrrol-2-yl)carbonyl]amino]cyclohexyl]carbonyl]-L-phenylglycine

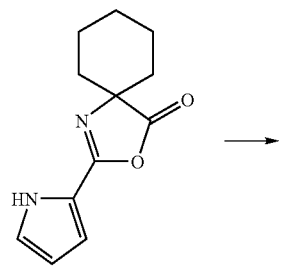

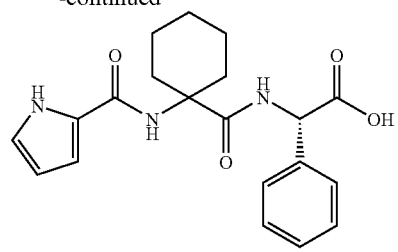

10 ml of N-methylmorpholine was added to 583 mg (3.9 mmol) of L-phenylglycine and 500 mg (1.9 mmol) of 2-(1H-pyrrol-2-yl)-3-oxa-1-azaspiro[4.5]dec-1-en-4-one, and the mixture was stirred and heated under reflux overnight. The reaction solution was distilled off under reduced pressure, a 10% aqueous potassium hydrogensulfate solution was added thereto, and the mixture was extracted with methylene chloride three times. The obtained organic layer was dried with anhydrous sodium sulfate, and the solvent was distilled off under reduced pressure. The obtained residue was purified by silica gel column chromatography to obtain 120 mg (17%) of the title compound.

1H-NMR (CDCl$_3$, δ): 1.18-2.08 (9H, m), 2.18-2.30 (1H, m), 5.63 (1H, d, J=7 Hz), 6.16-6.23 (1H, m), 6.25 (1H, s), 6.61-6.83 (2H, m), 7.17-7.35 (3H, m), 7.41 (2H, d, J=8 Hz), 7.83 (1H, d, J=7 Hz), 10.92 (1H, s)

Example 5

N-[[[1-[(1H-Pyrrol-2-yl)carbonyl]amino]cyclohexyl]carbonyl]-L-methionine

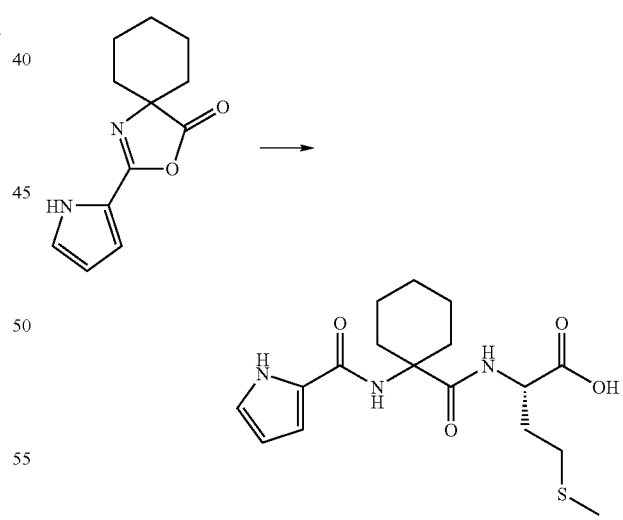

10 ml of N-methylmorpholine was added to 575 mg (3.9 mmol) of L-methionine and 500 mg (1.9 mmol) of 2-(1H-pyrrol-2-yl)-3-oxa-1-azaspiro[4.5]dec-1-en-4-one, and the mixture was stirred and heated under reflux overnight. The reaction solution was distilled off under reduced pressure, a 10% aqueous potassium hydrogensulfate solution was added thereto, and the mixture was extracted with methylene chloride three times. The obtained organic layer was dried with anhydrous sodium sulfate, and the solvent was distilled off under reduced pressure. Ethyl acetate was added to the obtained residue, and the mixture was stirred overnight. The precipitated solid was collected by filtration and dried under reduced pressure to obtain 503 mg (72%) of the title compound.

1H-NMR (CDCl₃, δ): 1.20-2.33 (15H, m), 2.42-2.61 (2H, m), 4.58-4.72 (1H, m), 6.21 (1H, dd, J=5 Hz, 3 Hz), 6.28 (1H, s), 6.69 (1H, d, J=3 Hz), 6.78 (1H, d, J=5 Hz), 7.29 (1H, d, J=8 Hz)

Example 6

N-[[[1-[(4-Methoxyphenyl)carbonyl]amino]cyclohexyl]carbonyl]-L-phenylglycine

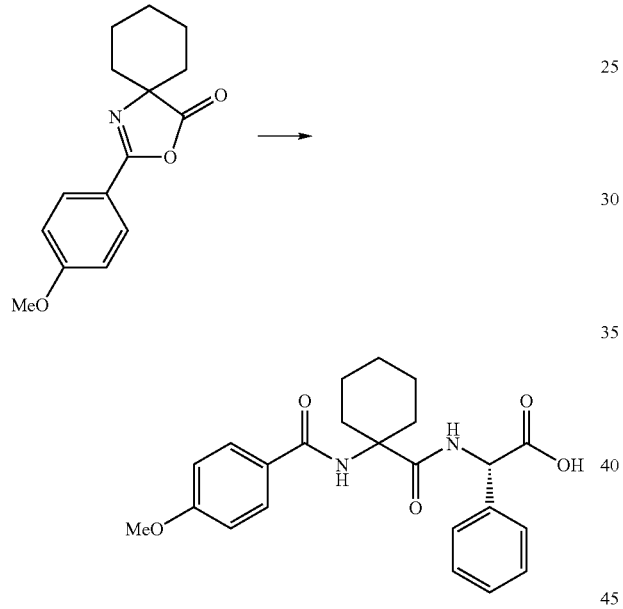

10 ml of N-methylmorpholine was added to 583 mg (3.9 mmol) of L-phenylglycine and 500 mg (1.9 mmol) of 2-(4-methoxyphenyl)-3-oxa-1-azaspiro[4.5]dec-1-en-4-one, and the mixture was stirred and heated under reflux overnight. The reaction solution was distilled off under reduced pressure, a 10% aqueous potassium hydrogensulfate solution was added thereto, and the mixture was extracted with methylene chloride three times. The obtained organic layer was dried with anhydrous sodium hydrogensulfate, and the solvent was distilled off under reduced pressure. The obtained residue was purified by silica gel column chromatography to obtain 92 mg (22%) of the title compound.

1H-NMR (CDCl₃, δ): 1.25-1.58 (3H, m), 1.60-1.81 (3H, m), 1.85-2.05 (2H, m), 2.17-2.39 (2H, m), 3.86 (3H, s), 4.45 (1H, d, J=6 Hz), 6.01 (1H, s), 6.82-7.00 (3H, m), 7.19-7.38 (4H, m), 7.57-7.83 (3H, m)

Example 7

N-[[1-[[(4-Methoxyphenyl)carbonyl]amino]cyclohexyl]carbonyl]-L-methionine 10 ml of N-methylmorpholine was added to 298 mg (2 mmol) of L-methionine and 259 mg (1 mmol) of 2-(4-methoxyphenyl)-3-oxa-1-azaspiro[4.5]dec-1-en-4-one, and the mixture was stirred and heated under reflux overnight. The reaction solution was distilled off under reduced pressure, a 10% aqueous potassium hydrogensulfate solution was added thereto, and the mixture was extracted with methylene chloride three times. The obtained organic layer was dried with anhydrous sodium hydrogensulfate, and the solvent was distilled off under reduced pressure. Ethyl acetate was added to the obtained residue, and the mixture was stirred overnight. The precipitated solid was collected by filtration and dried under reduced pressure to obtain 52 mg (13%) of the title compound.

1H-NMR (CDCl₃, δ): 1.20-2.62 (17H, m), 3.86 (3H, s), 4.56-4.71 (1H, m), 6.27 (1H, s), 6.95 (2H, d, J=9 Hz), 7.75 (2H, d, J=9 Hz), 7.86 (1H, d, J=8 Hz)

Example 8

N-[[1-[[(E)-3-(2-furanyl)-1-oxo-2-Propenyl]amino]cyclohexyl]carbonyl]-L-methionine

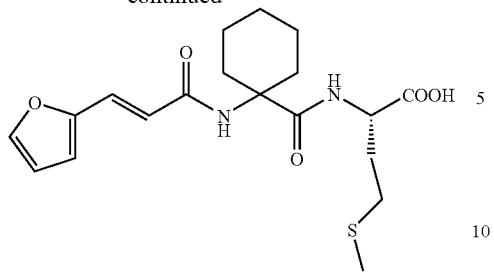

A solution of 491 mg (2 mmol) of 2-[(E)-2-(2-furanyl)ethenyl]-3-oxo-1-azaspiro[4.5]dec-1-en-4-one and 597 mg (4 mmol) of L-methionine in 20 ml of N-methylmorpholine was heated under reflux for 15 hours. After ethyl acetate and water were added to the reaction solution, it was acidified using concentrated hydrochloric acid. The organic layer was separated, it was successively washed with water and saturated brine, and dried with anhydrous sodium sulfate. After the solvent was distilled off under reduced pressure, it was purified by silica gel chromatography to obtain 74 mg (9%) of the title compound.

1H-NMR (CDCl$_3$, δ): 1.24-1.48 (3H, m), 1.59-1.71 (3H, m), 1.87-1.98 (2H, m), 2.00-2.25 (4H, m), 2.05 (3H, s), 2.51-2.63 (2H, m), 4.63 (1H, dt, J=8 Hz, 5H), 6.00 (1H, br-s), 6.40 (1H, d, J=15 Hz), 6.46 (1H, dd, J=3 Hz, 2 Hz), 6.59 (1H, d, J=3 Hz), 7.40 (1H, d, J=15 Hz), 7.45 (1H, d, J=2 Hz), 7.76 (1H, d, J=8 Hz)

Reference Example 241

N-[[1-[[(2-Furanylmethoxy)carbonyl]amino]cyclohexyl]carbonyl]-L-valinol

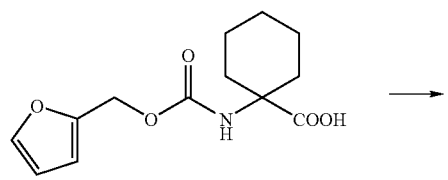

2.00 g (7.48 mmol) of 1-[[(2-furanylmethoxy)carbonyl]amino]cyclohexanecarboxylic acid was used instead of 2-benzothiophenecarboxylic acid, and 772 mg (7.48 mmol) of L-valinol was used instead of 1-aminocyclohexanecarboxylic acid phenylmethyl ester in the process according to Reference Example 197 to obtain 2.67 g (quantitative) of the title compound.

1H-NMR (CDCl$_3$, δ): 0.90 (3H, d, J=7 Hz), 0.95 (3H, d, J=7 Hz), 1.29-1.46 (3H, m), 1.56-1.72 (3H, m), 1.78-1.85 (1H, m), 1.88-1.96 (2H, m), 1.96-2.06 (2H, m), 2.75-2.90 (1H, br-s), 3.48-3.55 (1H, m), 3.68-3.78 (2H, m), 5.06 (1H, br-s), 5.00 (1H, d, J=13 Hz), 5.10 (1H, d, J=13 Hz), 6.35 (1H, br-s), 6.37 (1H, dd, J=3 Hz, 2 Hz), 6.43 (1H, dd, J=3 Hz, 1 Hz), 7.43 (1H, dd, J=2 Hz, 1 Hz)

Reference Example 242

N-[[1-[[(2-Furanylmethoxy)carbonyl]amino]cyclohexyl]carbonyl]-L-valinal

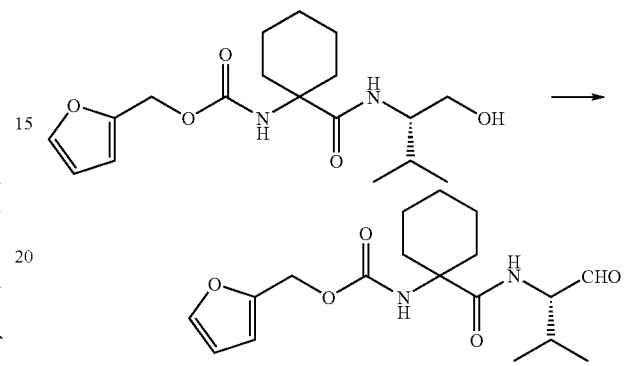

2.67 g of N-[[1-[[(2-furanylmethoxy)carbonyl]amino]cyclohexyl]carbonyl]-L-valinol obtained in above was used instead of N-[[1-[(2-benzothienylcarbonyl)amino]cyclohexyl]carbonyl]-L-methioninol in the process according to Reference Example 220 to obtain 2.08 g (83.7%, 2 steps) of the title compound.

1H-NMR (CDCl$_3$, δ): 0.92 (3H, d, J=7 Hz), 1.00 (3H, d, J=7 Hz), 1.26-1.46 (3H, m), 1.52-1.70 (3H, m), 1.86-1.96 (2H, m), 1.96-2.04 (1H, m), 2.05-2.14 (1H, m), 2.28-2.36 (1H, m), 4.46-4.52 (1H, m), 4.92-4.99 (1H, br-s), 5.04 (1H, d, J=13 Hz), 5.09 (1H, d, J=13 Hz), 6.36 (1H, dd, J=3 Hz, 2 Hz), 6.41 (1H, d, J=3 Hz), 7.04-7.16 (1H, m), 7.42 (1H, d, J=2 Hz), 9.61 (1H, s)

Reference Example 243

N-[[1-[[(E)-3-(2-Furanyl)-1-oxo-2-propenyl]amino]cyclohexyl]carbonyl]-L-valinol

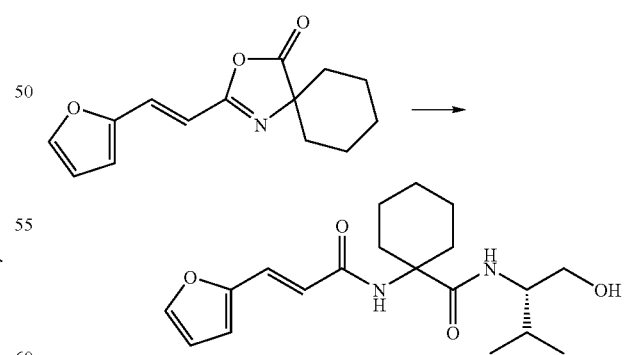

1.07 ml (6.12 mmol) of diisopropylamine was added to a solution of 252 mg (2.45 mmol) of L-valinol and 500 mg (2.04 mmol) of 2-[(E)-2-(2-furanyl)ethenyl]-3-oxo-1-azaspiro[4.5]dec-1-en-4-one in 15 ml of toluene, and the mixture was stirred and heated under reflux for 4 days. The reaction solution was distilled off under reduced pressure, and it was purified by silica gel chromatography to obtain 481 mg (67.7%) of the title compound.

1H-NMR (CDCl$_3$, δ): 0.93 (3H, d, J=7 Hz), 0.95 (3H, d, J=7 Hz), 1.34-1.52 (3H, m), 1.60-1.74 (3H, m), 1.80-1.88 (1H, m), 1.94-2.06 (2H, m), 2.08-2.18 (2H, m), 3.16-3.21 (1H, m), 3.51-3.57 (1H, m), 3.68-3.78 (2H, m), 5.72 (1H, br-s), 6.35 (1H, d, 15 Hz), 6.47 (1H, dd, J=3 Hz, 2 Hz), 6.58 (1H, dd, J=3 Hz, 1 Hz), 6.73 (1H, br-d, J=9 Hz), 7.41 (1H, d, J=15 Hz), 7.46 (1H, dd, J=2 Hz, 1 Hz)

Reference Example 244

N-[[1-[[(E)-3-(2-Furanyl)-1-oxo-2-propenyl]amino]cyclohexyl]carbonyl]-L-valinal

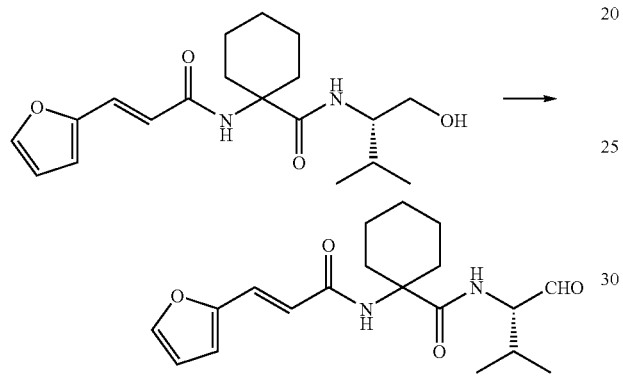

481 mg (1.38 mmol) of N-[[1-[[(E)-3-(2-furanyl)-1-oxo-2-propenyl]amino]cyclohexyl]carbonyl]-L-valinol was used instead of N-[[1-[(2-benzothienylcarbonyl)amino]cyclohexyl]carbonyl]-L-methioninol in the process according to Reference Example 220 to obtain 449 mg (93.9%) of the title compound.

1H-NMR (CDCl$_3$, δ): 0.95 (3H, d, J=7 Hz), 1.01 (3H, d, J=7 Hz), 1.30-1.74 (6H, m), 1.92-2.02 (2H, m), 2.14-2.22 (1H, m), 2.22-2.30 (1H, m), 2.28-2.36 (1H, m), 4.42 (1H, ddd, J=8 Hz, 5 Hz, 1 Hz), 5.55 (1H, br-s), 6.38 (1H, d, J=15 Hz), 6.47 (1H, dd, J=3 Hz, 2 Hz), 6.58 (1H, d, J=3 Hz, 1 Hz), 7.42 (1H, d, J=15 Hz), 7.46 (1H, dd, J=2 Hz, 1 Hz), 7.83 (1H, d, J=8 Hz), 9.59 (1H, d, 1 Hz)

Reference Example 245

N-[[1-[(3-Furanylcarbonyl)amino]cyclohexyl]carbonyl]-L-valinal

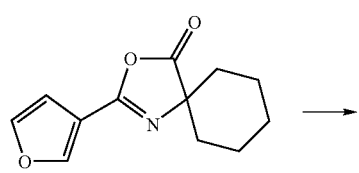

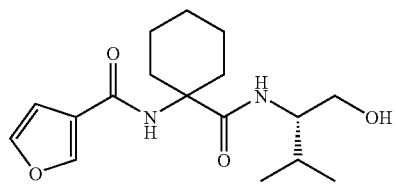

0.52 ml (3.01 mmol) of diisopropylamine was added to a solution of 124 mg (1.20 mmol) of L-valinol and 222 mg (1.00 mmol) of 2-(3-furanyl)-3-oxo-1-azaspiro[4.5]dec-1-en-4-one in 10 mL of toluene, and the mixture was stirred and heated under reflux for 4 days. The reaction solution was distilled off under reduced pressure and the residue was purified by silica gel chromatography to obtain 340 mg (quantitative) of the title compound.

1H-NMR (CDCl$_3$, δ): 0.93 (3H, d, J=7 Hz), 0.96 (3H, d, J=7 Hz), 1.35-1.54 (3H, m), 1.56-1.76 (3H, m), 1.82-1.90 (1H, m), 1.96-2.06 (2H, m), 2.13-2.20 (2H, m), 3.05 (1H, br-s), 3.54-3.59 (1H, m), 3.69-3.78 (2H, m), 5.88 (1H, br-s), 6.60 (1H, dd, J=2 Hz, 1 Hz), 6.80 (1H, br-d, J=8 Hz), 7.46 (1H, dd, J=2 Hz, 2 Hz), 7.96 (1H, dd, J=2 Hz, 1 Hz)

Reference Example 246

N-[[1-[(3-Furanylcarbonyl)amino]cyclohexyl]carbonyl]-L-valinal

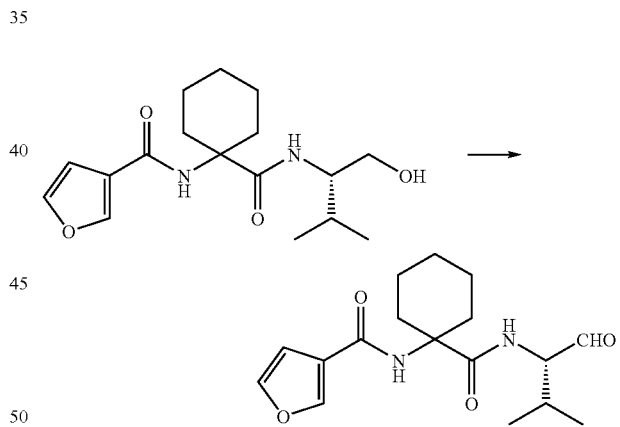

340 mg of N-[[1-[(3-furanylcarbonyl)amino]cyclohexyl]carbonyl]-L-valinol obtained in the above was used instead of N-[[1-[(2-benzothienylcarbonyl)amino]cyclohexyl]carbonyl]-L-methioninol in the process according to Reference Example 220 to obtain 282 g (87.6%, 2 steps) of the title compound.

1H-NMR (CDCl$_3$, δ): 0.95 (3H, d, J=7 Hz), 1.02 (3H, d, J=7 Hz), 1.32-1.52 (3H, m), 1.60-1.76 (3H, m), 1.95-2.06 (2H, m), 2.18-2.24 (1H, m), 2.26-2.36 (2H, m), 4.46 (1H, ddd, J=8 Hz, 5 Hz, 1 Hz), 5.74 (1H, br-s), 6.62 (1H, dd, J=2 Hz, 1 Hz), 7.47 (1H, dd, J=2 Hz, 1 Hz), 7.71 (1H, d, J=8 Hz), 7.97 (1H, dd, J=1 Hz, 1 Hz), 9.61 (1H, d, J=1 Hz)

Reference Example 247

N-[[1-[[(4-Methoxyphenyl)carbonyl]amino]cyclohexyl]carbonyl]-L-valinol

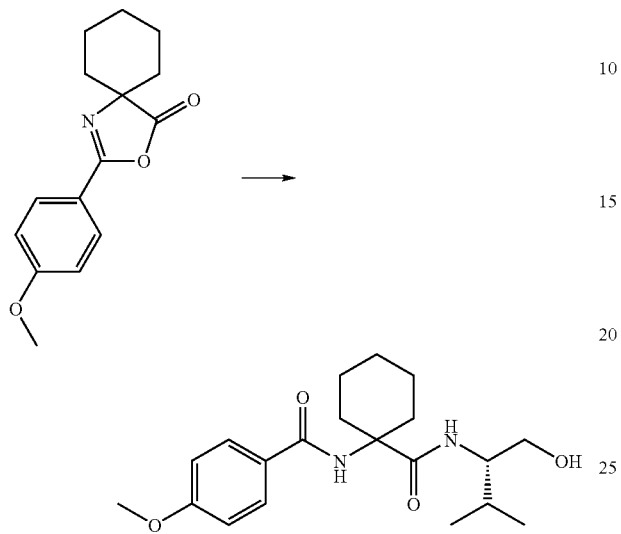

260 mg (1.00 mmol) of 2-(4-methoxyphenyl)-3-oxo-1-azaspiro[4.5]dec-1-en-4-one was added to a solution of 252 mg (2.45 mmol) of L-valinol in 5 mL of ethyl acetate, and the mixture was stirred at room temperature for 4 days. The reaction solution was distilled off under reduced pressure, and the residue was washed with diethyl ether to obtain 243.5 mg (66.7%) of the title compound.

1H-NMR (CDCl$_3$, δ): 0.93 (3H, d, J=7 Hz), 0.96 (3H, d, J=7 Hz), 1.36-1.80 (7H, m), 1.80-1.88 (1H, m), 1.98-2.10 (2H, m), 2.16-2.26 (2H, m), 3.55 (1H, dd, J=11 Hz, 6 Hz), 3.69-3.74 (1H, m), 3.77 (1H, dd, J=11 Hz, 3 Hz), 3.86 (3H, s), 6.17 (1H, br-s), 6.84 (1H, br-d, J=9 Hz), 6.95 (2H, dd, J=7 Hz, 2 Hz), 7.74 (2H, dd, J=7 Hz, 2 Hz)

Reference Example 248

N-[[1-[[(4-Methoxyphenyl)carbonyl]amino]cyclohexyl]carbonyl]-L-valinal

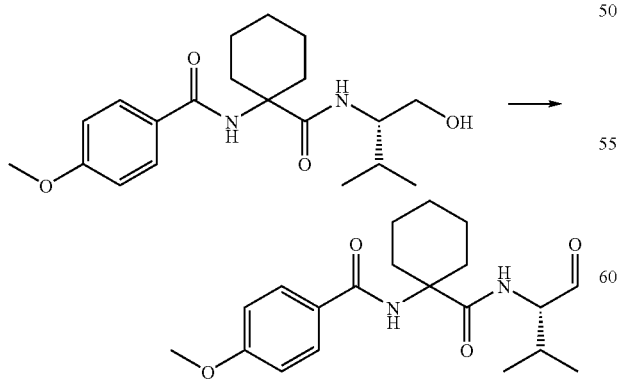

243 mg (0.67 mmol) of N-[[1-[[(4-methoxyphenyl)carbonyl]amino]cyclohexyl]carbonyl]-L-valinol was used instead of N-[[1-[(2-benzothienylcarbonyl)amino]cyclohexyl]carbonyl]-L-methioninol in the process according to Reference Example 220 to obtain 240 mg (98.9%) of the title compound.

1H-NMR (CDCl$_3$, δ): 0.95 (3H, d, J=7 Hz), 1.02 (3H, d, J=7 Hz), 1.34-1.54 (3H, m), 1.63-1.78 (3H, m), 1.96-2.05 (2H, m), 2.24-2.37 (3H, m), 3.87 (3H, s), 4.43 (1H, ddd, J=8 Hz, 5 Hz, 1 Hz), 6.03 (1H, br-s), 6.96 (2H, dd, J=7 Hz, 2 Hz), 7.75 (2H, dd, J=7 Hz, 2 Hz), 7.87 (1H, d, J=8 Hz), 9.60 (1H, s)

Reference Example 249

N-[[1-[[(1H-Pyrrol-2-yl)carbonyl]amino]cyclohexyl]carbonyl]-L-valinol

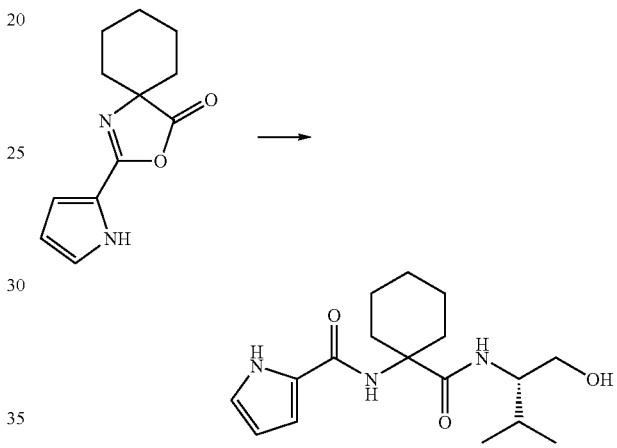

220 mg (1.01 mmol) of 2-(1H-pyrrol-2-yl)-3-oxo-1-azaspiro[4.5]dec-1-en-4-one was added to a solution of 252 mg (2.45 mmol) of L-valinol in 5 mL of ethyl acetate, and the mixture was stirred at room temperature for 4 days. The reaction solution was distilled off under reduced pressure, and it was purified by silica gel chromatography to obtain 247 mg (76.4%) of the title compound.

1H-NMR (CDCl$_3$, δ): 0.93 (3H, d, J=7 Hz), 0.94 (3H, d, J=7 Hz), 1.34-1.52 (3H, m), 1.62-2.14 (8H, m), 2.16-2.22 (1H, m), 3.51 (1H, dd, J=12 Hz, 7 Hz), 3.69-3.76 (2H, m), 6.03 (1H, br-s), 6.27 (1H, ddd, J=4 Hz, 3 Hz, 3 Hz), 6.60-6.66 (2H, m), 6.97 (1H, ddd, J=3 Hz, 3 Hz, 1 Hz), 9.48 (1H, br-s)

Reference Example 250

N-[[1-[[(1H-Pyrrol-2-yl)carbonyl]amino]cyclohexyl]carbonyl]-L-valinal

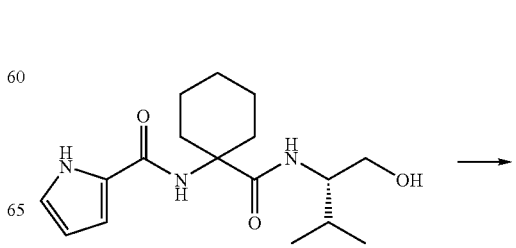

-continued

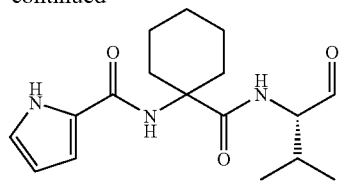

247 mg (0.77 mmol) of N-[[1-[[(1H-pyrrol-2-yl)carbonyl]amino]cyclohexyl]carbonyl]-L-valinol was used instead of N-[[1-[(2-benzothienylcarbonyl)amino]cyclohexyl]carbonyl]-L-methioninol in the process according to Reference Example 220 to obtain 217 mg (88.2%) of the title compound.

1H-NMR (CDCl$_3$, δ): 0.93 (3H, d, J=7 Hz), 1.00 (3H, d, J=7 Hz), 1.32-1.52 (3H, m), 1.60-1.76 (3H, m), 1.94-2.03 (2H, m), 2.18-2.25 (1H, m), 2.26-2.34 (2H, m), 4.45 (1H, dd, J=8 Hz, 5 Hz), 5.84 (1H, br-s), 6.28 (1H, ddd, J=4 Hz, 3 Hz, 3 Hz), 6.63 (1H, ddd, J=4 Hz, 3 Hz, 1 Hz), 6.96 (1H, ddd, J=3 Hz, 3 Hz, 1 Hz), 7.75 (1H, br-d, J=8 Hz), 9.33 (1H, br-s), 9.59 (1H, s)

Test Example 1

Measurement of Cathepsin K Inhibitory Activity

Active enzyme was produced by expressing cathepsin K in the form of a proenzyme in a cell culture from a baculovirus expression system using Sf21 insect cells, followed by incubating for 1 hour at 40° C.[1]. Cathepsin K activity was measured based on decomposition of the fluorescent substrate Z-Gly-Pro-Arg-MCA (Peptide Institute, Inc.) in compliance with the method of Aibe, et al.[2]. Namely, the decomposition of 20 mM Z-Gly-Pro-Arg-MCA by cathepsin K was measured in 100 mM sodium/potassium phosphate, 1 mM EDTA and 8 mM cysteine at pH 6.0. The reaction was carried out for 30 minutes at 37° C., and stopped by the addition of 2×10$^{-5}$ M Calpeptin. After stopping the reaction, fluorescent intensity was measured at an excitation wavelength of 355 nm and measurement wavelength of 460 nm. Inhibition of cathepsin K by the compounds was examined using the reaction system described above. The 50% inhibitory concentrations on cathepsin K of the compounds of the reference examples are shown in Table 1.

Test Example 2

Measurement of Cathepsin B Inhibitory Activity

Human cathepsin B (Calbiochem Corp.) was used for measurement. Activity was measured based on decomposition of the fluorescent substrate Z-Arg-Arg-MCA (Peptide Institute, Inc.) in compliance with the method of Barrett, et al.[3]. Namely, the decomposition of 20 mM Z-Arg-Arg-MCA by cathepsin B was measured in 100 mM sodium/potassium phosphate, 1 mM EDTA, 8 mM cysteine and 0.005% Brij35 at pH 6.0. The reaction was carried out for 30 minutes at 30° C., and stopped by the addition of 2×10$^{-5}$ M Calpeptin. After stopping the reaction, fluorescent intensity was measured at an excitation wavelength of 355 nm and measurement wavelength of 460 nm. Inhibition of cathepsin B by the compounds was examined using the reaction system described above. The 50% inhibitory concentrations on cathepsin B of the compounds of the reference examples are shown in Table 1.

Test Example 3

Measurement of Cathepsin L Inhibitory Activity

Human cathepsin L (Calbiochem Corp.) was used for measurement. Activity was measured based on decomposition of the fluorescent substrate Z-Phe-Arg-MCA (Peptide Institute, Inc.) in compliance with the method of Barrett, et al.[3]. Namely, the decomposition of 20 mM Z-Phe-Arg-MCA by cathepsin L was measured in 100 mM sodium acetate, 5 mM EDTA, 4 mM urea, 8 mM cysteine and 0.005% Brij35 at pH 5.5. The reaction was carried out for 30 minutes at 30° C., and stopped by the addition of 2×10$^{-5}$ M Calpeptin. After stopping the reaction, fluorescent intensity was measured at an excitation wavelength of 355 nm and measurement wavelength of 460 nm. Inhibition of cathepsin L by the compounds was examined using the reaction system described above. The 50% inhibitory concentrations on cathepsin L of the compounds of the reference examples are shown in Table 1.

REFERENCES

Tezuka et al., J. Biol. Chem., 269, 1106-1109 (1994)
Aibe et al., Biol. Pharm. Bull., 19, 1026-1031 (1996)
Barrett, A. J. & Kirschke, H. Methods Enzymol. 80, 535-561 (1981)

TABLE 1

| | | IC$_{50}$ (M) | | |
| --- | --- | --- | --- | --- |
| Compound No. | Structural Formula | human Cathepsin K | human Cathepsin B | human Cathepsin L |
| Reference Example 193 | 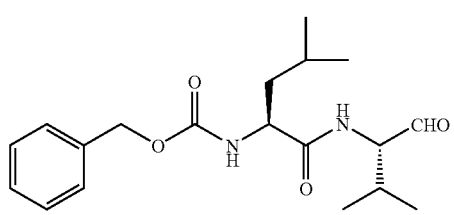 [SMILES: CC(C)C[C@H](NC(=O)OCc1ccccc1)C(=O)N[C@H](C=O)C(C)C] | 1.9 × 10$^{-9}$ | 1.1 × 10$^{-7}$ B/K 58 | 1.4 × 10$^{-7}$ L/K 74 |

TABLE 1-continued

| Compound No. | Structural Formula | Cathepsin K | human Cathepsin B | human Cathepsin L |
|---|---|---|---|---|
| Reference Example 189 | | $1.7 \times 10^{-9}$ | $3.9 \times 10^{-7}$ B/K 230 | $6.8 \times 10^{-7}$ L/K 400 |
| Reference Example 194 | | $3.5 \times 10^{-9}$ | $4.0 \times 10^{-8}$ B/K 11 | $5.3 \times 10^{-8}$ L/K 15 |
| Reference Example 190 | | $4.0 \times 10^{-9}$ | $1.4 \times 10^{-7}$ B/K 35 | $2.0 \times 10^{-7}$ L/K 50 |
| Reference Example 195 | | $3.0 \times 10^{-9}$ | $1.3 \times 10^{-8}$ B/K 4.3 | $2.2 \times 10^{-8}$ L/K 7.3 |
| Reference Example 192 | | $2.2 \times 10^{-8}$ | $2.6 \times 10^{-7}$ B/K 12 | $4.7 \times 10^{-7}$ L/K 21 |
| Reference Example 196 | | $1.9 \times 10^{-9}$ | $5.7 \times 10^{-8}$ B/K 30 | $6.7 \times 10^{-8}$ L/K 35 |

TABLE 1-continued

| | | IC$_{50}$ (M) | | |
|---|---|---|---|---|
| Compound No. | Structural Formula | Cathepsin K | human Cathepsin B | human Cathepsin L |
| Reference Example 191 |  | 5.4 × 10$^{-10}$ | 4.7 × 10$^{-8}$ B/K 87 | 2.0 × 10$^{-7}$ L/K 370 |

The invention claimed is:

1. A cycloalkylcarbonylamino acid derivative represented by formula (I'), or a pharmaceutically acceptable salt thereof:

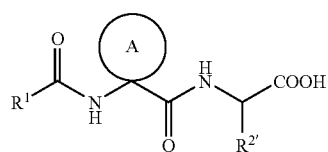

(I')

wherein R$^1$ represents a substituted or unsubstituted aromatic hydrocarbon group, substituted or unsubstituted heterocyclic group, a group R$^4$O—,
wherein R$^4$ is a substituted or unsubstituted alkyl group, substituted or unsubstituted alkenyl group, substituted or unsubstituted alkynyl group, substituted or unsubstituted aromatic hydrocarbon group or substituted or unsubstituted heterocyclic group; wherein an oxazolyl group and a thiazolyl group are excluded from the heterocyclic group of R$^1$,
R$^{2'}$ represents an alkyl group represented by Ra(Rb)CH—
wherein Ra and Rb respectively and independently are a hydrogen atom, substituted or unsubstituted alkyl group, substituted or unsubstituted alkenyl group, substituted or unsubstituted alkynyl group, substituted or unsubstituted aromatic hydrocarbon group or substituted or unsubstituted heterocyclic group; and,
ring A represents a cyclic alkylidene group having 6 carbon atoms;
provided that, in the case R$^{2'}$ is a 2,2-dimethylpropyl group or a 2-(methylthio)ethyl group, R$^4$ is not a t-butyl group, and in the case R$^{2'}$ is a methyl group, R$^4$ is not a benzyl group;
a substituent of an alkyl group in the groups represented by R$^4$, Ra, and Rb is a group selected from a hydroxyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group,
wherein Rx and Ry respectively and independently are a hydrogen atom, alkyl group, alkenyl group, alkynyl group, aromatic hydrocarbon group or heterocyclic group;
a substituent of an alkenyl group or alkynyl group in the groups Ra, Rb and R$^4$ is a group selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group,
wherein Rx and Ry respectively and independently are a hydrogen atom, alkyl group, alkenyl group, alkynyl group, aromatic hydrocarbon group or heterocyclic group; and,
a substituent of an aromatic hydrocarbon group or heterocyclic group in the groups R$^1$ and R$^4$ is selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group,
wherein Rx and Ry respectively and independently are a hydrogen atom, alkyl group, alkenyl group, alkynyl group, aromatic hydrocarbon group or heterocyclic group; and
a substituent of an aromatic hydrocarbon group in the groups Ra and Rb is a group selected from a hydroxyl group, alkyl group, alkenyl group, alkynyl group, halogen atom, aromatic hydrocarbon group, guanidino group, alkylthio group, alkoxycarbonyl group, aryloxy group, arylthio group, acyl group, sulfonyl group, heterocyclyloxy group, heterocyclylthio group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group,
wherein Rx and Ry respectively and independently are a hydrogen atom, alkyl group, alkenyl group, alkynyl group, aromatic hydrocarbon group or heterocyclic group,
a substituent of a heterocyclic group in the groups Ra and Rb is a group selected from a hydroxyl group, alkyl group, alkenyl group, alkynyl group, halogen atom, aromatic hydrocarbon group, heterocyclic group, guanidino group, alkylthio group, alkoxycarbonyl group, aryloxy group, arylthio group, acyl group, sulfonyl group, heterocyclyloxy group, heterocyclylthio group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group wherein Rx and Ry respectively and independently are a hydrogen atom, alkyl group, alkenyl group, alkynyl group, aromatic hydrocarbon group or heterocyclic group.

2. The cycloalkylcarbonylamino acid derivative according to claim 1, or a pharmaceutically acceptable salt thereof, wherein the alkyl of $R^4$, Ra, Rb, Rx and Ry is a linear $C_{1-12}$ alkyl or $C_{3-12}$ branched or cyclic alkyl, the aromatic hydrocarbon of $R^1$, $R^4$, Ra, Rb, Rx and Ry is a monocyclic or polycyclic $C_{6-18}$ aromatic hydrocarbon group, the heterocyclic group of $R^1$, $R^4$, Ra, Rb, Rx and Ry is a 3- to 7-membered ring containing at least one nitrogen atom, oxygen atom or sulfur atom as a ring-constituting hetero atom, the alkenyl group of Ra, Rb, $R^4$, Rx and Ry is a linear $C_{2-12}$ alkenyl group or $C_{3-12}$ branched or cyclic alkenyl group, and the alkynyl group of Ra, Rb, $R^4$, Rx and Ry is a linear $C_{2-12}$ alkynyl group or $C_{3-12}$ branched or cyclic alkynyl group.

3. A cycloalkylcarbonylamino acid derivative represented by formula (I″) or a pharmaceutically acceptable salt thereof:

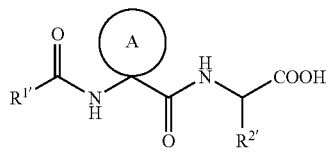

(I″)

wherein $R^{1'}$ is a substituted or unsubstituted aromatic hydrocarbon group or a substituted or unsubstituted heterocyclic group, wherein an oxazolyl group and a thiazolyl group are excluded from the heterocyclic group of $R^{1'}$, $R^{2'}$ represents an alkyl group represented by Ra(Rb)CH— wherein Ra and Rb respectively and independently are a hydrogen atom, substituted or unsubstituted alkyl group, substituted or unsubstituted alkenyl group, substituted or unsubstituted alkynyl group, substituted or unsubstituted aromatic hydrocarbon group, or substituted or unsubstituted heterocyclic group; and ring A represents a cyclic alkylidene group having 6 carbon atoms;

a substituent of an alkyl group of Ra, and Rb is selected from a hydroxyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group, wherein Rx and Ry respectively and independently are a hydrogen atom, alkyl group, alkenyl group, alkynyl group, aromatic hydrocarbon group or heterocyclic group;

a substituent of an alkenyl group or alkynyl group of Ra, Rb, is selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group, wherein Rx and Ry respectively and independently are a hydrogen atom, alkyl group, alkenyl group, alkynyl group, aromatic hydrocarbon group or heterocyclic group;

a substituent of an aromatic hydrocarbon group of $R^{1'}$ is selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group, wherein Rx and Ry respectively and independently are a hydrogen atom, alkyl group, alkenyl group, alkynyl group, aromatic hydrocarbon group or heterocyclic group;

a substituent of an aromatic hydrocarbon group of Ra and Rb is selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group, wherein Rx and Ry respectively and independently are a hydrogen atom, alkyl group, alkenyl group, alkynyl group, aromatic hydrocarbon group or heterocyclic group;

a substituent of a heterocyclic group of $R^{1'}$ is selected from a hydroxyl group, primary or secondary alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group, wherein Rx and Ry respectively and independently are a hydrogen atom, alkyl group, alkenyl group, alkynyl group, aromatic hydrocarbon group or heterocyclic group; and a substituent of a heterocyclic group of Ra and Rb is selected from a hydroxyl group, alkyl group, alkenyl group, alkynyl group, halogen atom, aromatic hydrocarbon group, heterocyclic group, alkoxy group, guanidino group, alkylthio group, alkoxycarbonyl group, aryloxy group, arylthio group, acyl group, sulfonyl group, heterocyclyloxy group, heterocyclylthio group, amido group, ureido group, carboxyl group, carbamoyl group, oxo group, sulfamoyl group, sulfo group, cyano group, nitro group, acyloxy group, azido group, sulfonamido group, mercapto group, alkoxycarbonylamino group and Rx(Ry)N group, wherein Rx and Ry respectively and independently are a hydrogen atom, alkyl group, alkenyl group, alkynyl group, aromatic hydrocarbon group or heterocyclic group.

4. The cycloalkylcarbonylamino acid derivative according to claim 3, or a pharmaceutically acceptable salt thereof, wherein the alkyl group of Ra and Rb is a linear $C_{1-12}$ alkyl or $C_{3-12}$ branched or cyclic alkyl, the aromatic hydrocarbon group of $R^{1'}$, Ra, and Rb is a monocyclic or polycyclic $C_{6-18}$ aromatic hydrocarbon group, the heterocyclic group of $R^{1'}$, Ra, and Rb is a 3- to 7-membered ring containing at least one nitrogen atom, oxygen atom or sulfur atom as a ring-constituting hetero atom, provided that an oxazolyl group and a thiazolyl group are excluded from the heterocyclic group of $R^{1'}$, the alkenyl group of Ra and Rb is a linear $C_{2-12}$ alkenyl group or $C_{3-12}$ branched or cyclic alkenyl group, and the alkynyl group of Ra and Rb is a linear $C_{2-12}$ alkynyl group or $C_{3-12}$ branched or cyclic alkynyl group.

5. The cycloalkylcarbonylamino acid derivative according to claim 1 or 2, or a pharmaceutically acceptable salt thereof, wherein $R^1$ is a substituted or unsubstituted aromatic hydrocarbon group, or substituted or unsubstituted heterocyclic group, provided that an oxazolyl group and a thiazolyl group are excluded from the heterocyclic group of $R^1$, and $R^{2'}$ is an alkyl group represented by Ra(Rb)CH—
 wherein Ra and Rb respectively and independently are a hydrogen atom, substituted or unsubstituted alkyl group, substituted or unsubstituted aromatic hydrocarbon group or substituted or unsubstituted heterocyclic group.

6. A process for producing a cycloalkylcarbonylamino acid derivative represented by formula (I') comprising: condensing an oxazolone derivative represented by formula ($I_0$) with an amino alcohol derivative represented by formula (VII'):

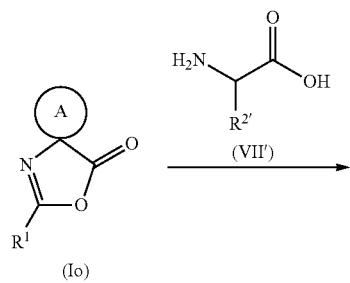

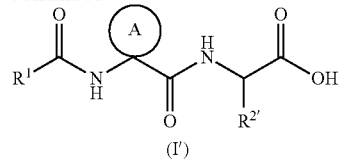

wherein $R^1$, $R^{2'}$ and ring A are the same as defined in claim 1.

7. The cycloalkylcarbonylamino acid derivative according to claim 1 or 2, or a pharmaceutically acceptable salt thereof, wherein $R^{2'}$ is an isopropyl group.

8. The cycloalkylcarbonylamino acid derivative according to claim 3 or 4, or a pharmaceutically acceptable salt thereof, wherein $R^{2'}$ is an isopropyl group.

9. The cycloalkylcarbonylamino acid derivative according to claim 3 or 4, or a pharmaceutically acceptable salt thereof, wherein in the formula (I"), $R^{1'}$ is a substituted or unsubstituted aromatic hydrocarbon group, or substituted or unsubstituted heterocyclic group, provided that an oxazolyl group and a thiazolyl group are excluded from the heterocyclic group of $R^{1'}$, and $R^{2'}$ is an alkyl group of Ra(Rb)CH—
 wherein Ra and Rb respectively and independently are a hydrogen atom, substituted or unsubstituted alkyl group, substituted or unsubstituted aromatic hydrocarbon group or substituted or unsubstituted heterocyclic group.

10. The cycloalkylcarbonylamino acid derivative according to claim 1 or 2, or a pharmaceutically acceptable salt thereof, wherein in the formula (I'), $R^1$ is a 3- to 7-membered heterocyclic group, containing at least one nitrogen atom, oxygen atom or sulfur atom as a ring-constituting hetero atom, provided that an oxazolyl group and a thiazolyl group are excluded from the heterocyclic group of $R^1$, or a substituted aromatic hydrocarbon group, $R^{2'}$ is a $C_{1-4}$ alkyl group, and ring A is a cyclohexylidene group.

11. The cycloalkylcarbonylamino acid derivative according to claim 3 or 4, or a pharmaceutically acceptable salt thereof, wherein in the formula (I"), $R^{1'}$ is a 3- to 7-membered heterocyclic group, containing at least one nitrogen atom, oxygen atom or sulfur atom as a ring-constituting hetero atom, provided that an oxazolyl group and a thiazolyl group are excluded from the heterocyclic group of $R^{1'}$, or a substituted aromatic hydrocarbon group, $R^{2'}$ is a $C_{1-4}$ alkyl group, and ring A is a cyclohexylidene group.

\* \* \* \* \*